United States Patent
Janjic et al.

(12)

(10) Patent No.: US 6,677,146 B1
(45) Date of Patent: Jan. 13, 2004

(54) THERMOPHILIC POLYMERASE III HOLOENZYME

(75) Inventors: Nebojsa Janjic, Boulder, CO (US); James M. Bullard, Longmont, CO (US); Charles S. McHenry, Denver, CO (US); Vladimir Kery, Salt Lake City, UT (US)

(73) Assignee: Replidyne, Inc., Louisville, CO (US)

( * ) Notice: Subject to any disclaimer, the term of this patent is extended or adjusted under 35 U.S.C. 154(b) by 0 days.

(21) Appl. No.: 09/818,780

(22) Filed: Mar. 28, 2001

Related U.S. Application Data
(60) Provisional application No. 60/192,736, filed on Mar. 28, 2000.

(51) Int. Cl.[7] .............................. C12N 9/12; C12N 9/00; C07H 21/04

(52) U.S. Cl. ........................ 435/194; 435/183; 435/195; 435/6; 530/350; 536/23.1; 536/23.2; 536/23.7

(58) Field of Search .................................. 435/183, 195, 435/194, 6; 530/350, 23.1, 23.2, 23.7

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,889,818 A | 12/1989 | Gelfand et al. | 435/194 |
| 4,946,778 A | 8/1990 | Ladner et al. | 435/69 |
| 4,965,188 A | 10/1990 | Mullis et al. | 435/6 |
| 5,322,770 A | 6/1994 | Gelfand | 435/6 |
| 5,948,666 A | 9/1999 | Callen et al. | 435/194 |
| 6,238,905 B1 | 5/2001 | McHenry et al. | 435/252.3 |

FOREIGN PATENT DOCUMENTS

| | | |
|---|---|---|
| JP | 08089259 | 4/1996 |
| WO | WO 94/05797 | 3/1974 |
| WO | WO 91/09950 | 7/1991 |
| WO | WO 93/03367 | 2/1993 |
| WO | WO 93/15115 | 8/1993 |
| WO | WO 98/45452 | 10/1998 |
| WO | WO 99/53074 | 10/1999 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492–495.*
Dong et al., DNA Polymerase III Accessory Proteins, holA and holB Encoding d and d', Journal of Biological Chemistry, vol. 268, No. 16, pp 11758–11765, Jun. 1993.*
Anderson and Young, Quantitative Filter Hybridization, in Nucleic Acid Hybridization (1985).
Ausubel et al, Current Protocols in Molecular Biology, John Wiley & Sons, New York NY (1995), sections 2.9.2 to 2.9.11, 6.1.1–6.1.3 and 6.3.1–6.3.4.

Blinkowa and Walker, Nucl Acids Res., 18:1725–1729 (1990).
Boshart et al., Cell 41:521–530 (1985).
Brush et al., Meth. Enzymol. 262:522–548 (1995).
Chamberlin et al, Nature 228:227–231 (1970).
Chien et al., J. Bacteriol. 127:1550–1557 (1976).
Cull and McHenry, Meth. Enzymol. 262:22–35 (1995).
Dallmann and McHenry, J. BioL Chem. 270:29563–29569 (1995).
Dallmann et al, J. Biol. Chem. 270:29555–29562 (1995).
Dijkema et al., EMBO J. 4(3):761–767 (1985).
Flower and McHenry, Proc. Natl. Acad. Sci. USA 87:3713–3717 (1990).
Gorman et al., Proc. Natl. Acad. Sci. USA 79:6777–6781 (1982).
Hammond and Brown, Protein Expression and Purification 3:65 (1992).
Huse et al, Science 246:1275–1281 (1989).
Kacian et al., Proc. Natl. Acad. Sci USA 69(10):3038–3042 (1972).
Kaledin et al, Biochem. 45:494–501 (1981).
Kim et al., Gene 91:217–223 (1990).
Kim and McHenry, J. Biol. Chem. 271:20681–20689 (1996).
Köhler and Milstein, Nature 256:495–497 (1975).
Kong et al. Cell 69:425–437 (1992).
Kornberg and Baker, DNA Replication, 2nd ed. W.H. Freeman & Company, (1992), pp. 167.
Kornberg and Gefter, J. Biol. Chem. 47:5369–5375 (1972).
LaDuca et al., J. Biol. Chem. 261:7550–7557 (1986).
Lasa et al., Molec. Microbiol. 6:1555–1564 (1992).
Lawyer et at, J. Biol. Chem. 264(11):6427–6437 (1989).
Low et al., J. Biol. Chem. 251:1311 (1976).
Maniatis et al, Science 236:1237–1245 (1987).
McHenry, Ann. Rev. Biochem. 57:519–550 (1988).
McHenry and Komberg, J. Biol. Chem. 252:6478–6484 (1977).
McHenry, J. Biol. Chem. 257:2657–2663 (1982).
Mizushima and S. Nagata, Nucl. Acids. Res. 18(17):5322 (1990).
Mok and Marian, J. Biol. Chem. 262:16644–16654 (1987).
Molineux et at, J. Biol. Chem. 249 6090–6098 (1974).
Mullis et al., Cold Spring Harbor Symposia on Quantitative Biology, vol. LI, pp. 263–273 (1986).

(List continued on next page.)

*Primary Examiner*—Richard Hutson
(74) *Attorney, Agent, or Firm*—Swanson & Bratschun, LLC

(57) ABSTRACT

The present invention relates to gene and amino acid sequences encoding DNA polymerase III holoenzyme subunits and structural genes from thermophilic organisms. In particular, the present invention provides DNA polymerase III holoenzyme subunits and accessory proteins of *T. thermophilus*. The present invention also provides antibodies, primers, probes, and other reagents useful to identify DNA polymerase III molecules.

3 Claims, 63 Drawing Sheets

OTHER PUBLICATIONS

Naktinis et al., J. Biol. Chem. 270:13358–13365 (1995).
Oi and Herzenberg, in Mishell and Shiigi (eds.), Selected Methods in Cellular Immunology, W.H. Freeman & Co., San Francisco (1980), p 351–371.
Sherman et al, Bio essays 3:27–31 (1985).
Studencki and Wallace, DNA 31:1–15 (1984).
Studencki et al., J. Human Genetics 37:42–51 (1985).
Studwell–Vaughan and O'Donnell, J. Biol. Chem. 266:19833–19841 (1991).
Tsuchihashi and Kornberg, Proc. Natl. Acad. Sci USA 87:2516–2520 (1990).
Uetsuki et al., J. Biol. Chem. 264(10):5791–5798 (1989).
Uhlmann et al., Proc. Natl. Acad. Sci. USA 93:6521–6526 (1996).
Voss et al., Trends Biochem. Sci. 11:287–289 (1986).
Wallace et al., Biochimie 67:755–762 (1985).
Wickner, Proc. Natl. Acad. Sci. USA 73:3511–3515 (1976).
Wu et al, J. Biol. Chem. 267:4030; 4044 (1992).
Wu et al., J. Biol. Chem. 259:12117–12122 (1984).
Wu and Wallace, Genomics 4:560–569 (1989).
Yoder and Burgers, J. Biol. Chem. 266:22689–22697 (1991).
Sanjanwala and Ganesan, Proc. Natl. Acad. Sct USA 86:4421–4424 (1989).
Lancy et al., J. Bacteriol., 171:5581–5586 (1989).
Barnes et al, J. Mol. Microbiol., 13:843–854 (1994).
Old et al., Nucleic Acids Res., 21:3323 (1993).
O'Donnell et al., Nucleic Acids Res., 21:1–3 (1993).
Wong et al., J. Bacteriol., 170(6):2668–2675 (1988).
Liao and Dennis, J. Biol. Chem., 267(32):22787–22797 (1992).
Uemori et al., J. Biochem., 113:401–410 (1993).
Ruttimann et al., Eur. J. Biochem., 149:41–46 (1985).
Myers and Gelfand, Biochem., 30:7661–7666. (1991).
Carballeira et al, BioTechn., 9:276–281 (1990).
Glukhov et al., Mol. Cell Probes 4:435.443 (1990).
Sakaguchi and Yajima, Fed. Proc., 33:1519 (1974).
Maki et al, J. Biol. Chem., 263(14):6470–6578 (1988).
Livingston et al, J. Biol. Chem., 250:461–469 (1975).
Sitney et al., Cell, 56:599–605 (1989).
Otto et al., Eur. J. Biochem., 34:440–447 (1973).
McHenry and Johanson, In Proteins Involved in DNA Replication, Plenum Publishing Corporation, pp. 315–319 (1984).
O'Donnell and Studwell, J. Biol. Chem., 265:1179–1187 (1990).
Studwell and O'Donnell, J. Biol. Chem., 265:1171–1178 (1990).
Bauer and Burgers, Proc. Natl. Acad. Sci. USA, 85:7506–7510 (1988).
Hübscher et al., Proc. Natl. Acad. Scl. USA 11:6771–6775 (1981).
Turchi and Bambara, J. Biol. Chem., 268:15136–15141 (1993).
Abramson and Gelfand, Abstr. 72nd Gen. Mtg. Am. Soc. Microbial. p. 200 (1992).
Stenesh and Roe, Biochem. Biophys. Acta 272:156–166 (1972).
Stenesh and McGowan, Biochim Biophys Acta 475: 32–41 (1977).
Kaboev et al., J. Bacteriol, 145:21–26 (1981).
Klimczak et al, Nucleic Acids Res., 13:5269–5282 (1985).
Forterre et al, Can. J. Microbiol, 35:228–233 (1989).
Elie et al, Biochimica Biophysica Acta 951:261–267 (1988).
Rella et al., J. Biochem., 39(2):83–99 (1990).
Rossi et al, System. App. Microblol., 7:337–341 (1986).
Salhi et al., Biochem. Biophys. Res. Commun., 167:1341–1347 (1990).
Salhi et al., J. Mol. Biol., 209:635–644 (1989).
Jannasch et al., Arch Microbiol., 150:103–104 (1988).
Simpson et al, Biochem. Cell Biol., 68:1292–1296 (1990).
Huber el al, Arch Microbiol, 144:324–333 (1986).
Windberger et al, Arch Microbiol., 151:506–512 (1989).
Hamal et al, Eur. J. Biochem., 190:517 (1990).
Sukhanov et al Mikrobiol. Zh., 55:42–45 (1993).
Roditi et al, Nucleic Acids Res., 17:10507 (1989).
Kaledin et al., Biochem., 47:15151521 (1983); translated from Biokhimiya 47: 1785–1791 (1982).
Scalice et al, J. Immunol Meth., 172:147–163 (1994).
Barnes and Brown, Nucleic Acids Res. 6:1203–1219 (1979).
McHenry et al., J. Mol Biol., 272: 178–189 (1997).
Yurieva et al, J. Biol. Chem., 272 :27131–27139 (1997).
Sellman et al., J. Bacteriol., 174:4350–4355 (1992).
Klimczak et al., Biochem., 25:4850–4855 (1986).
Huang and Ito, Nucl. Acids Res., 26:5300–5309 (1998).
Huang and Ito, J. Mol. Evol., 48:756–769 (1999).
Larsen et al., Proc. Natl. Acad. Sci., 97:1683–1688 (2000).
Atlung et al., Mol. Gen. Genet. 200: 442–450 (1985).
Sigma Chemical Company, Catalog, pp. 61 and 62 (1995).
Mitsubishi Chem. Corp. Genbank/Embl Accession No: R98523 (1996).
Deckert et al., PIR 68 Database, Accession No.: G70380, (1998).
Deckert et al. (1998) Nature, 392:353.

* cited by examiner

Column profile of Ni++-NTA purification of *T. thermophilus* α-Subunit

Optimization of expression of pTAC-CCA-TE.

Protein profile of ammonium sulfate precipitation optimization of
*T. thermophilus* α.

SDS-PAGE analysis of ammonium sulfate precipitation optimization of *T. thermophilus* α.

Activity assay analysis of ammonium sulfate precipitation optimization of
*T. thermophilus* α using the gap-filling assay.

SDS-polyacrylamide summary gel of the different purification steps of native
*T. thermophilus* expressed as a translationally coupled protein.

Biotin blot analysis of the growth optimization for expression of N-terminal tagged *T. thermophilus* DnaX subunits from pA1-NB-TX/AP1.L1.

Protein concentration profile of the fractions from the $Ni^{++}$-NTA column purification of N-terminal tagged *T. thermophilus* DnaX.

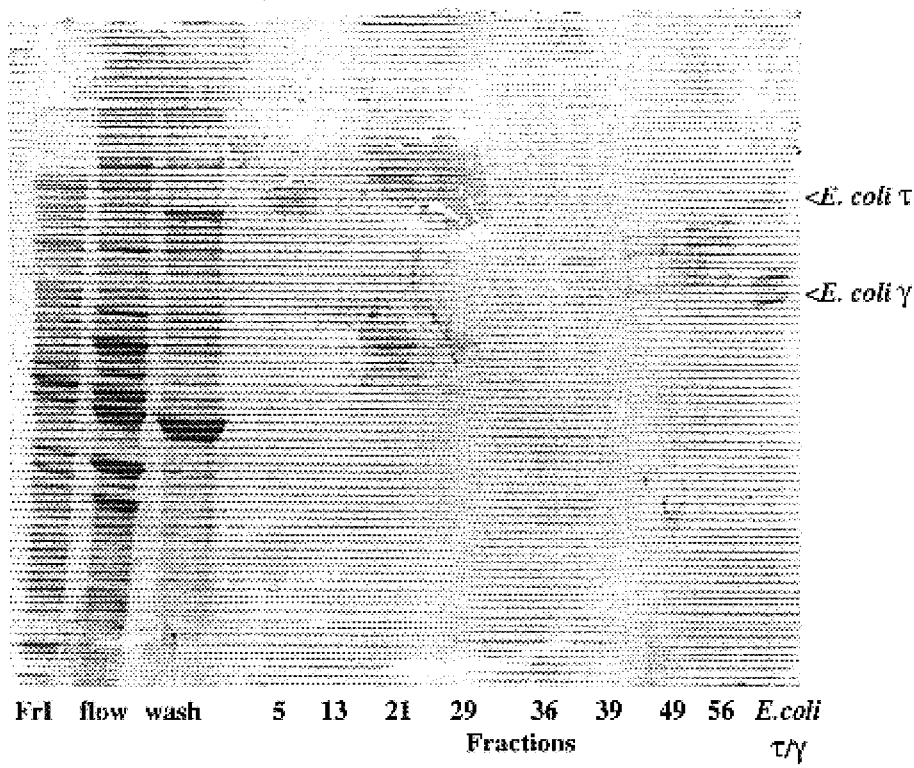
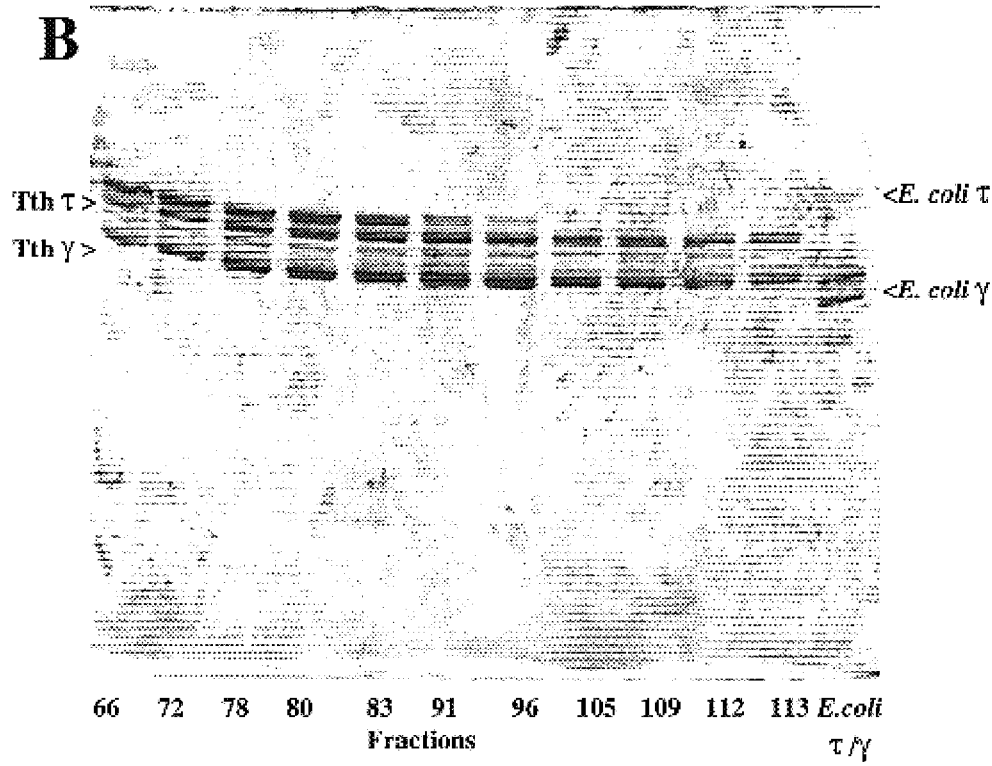
FIG. 9A-B
SDS-PAGE analysis of the fraction from the Ni$^{++}$-NTA column purification of N-terminal tagged *T. thermophilus* DnaX.

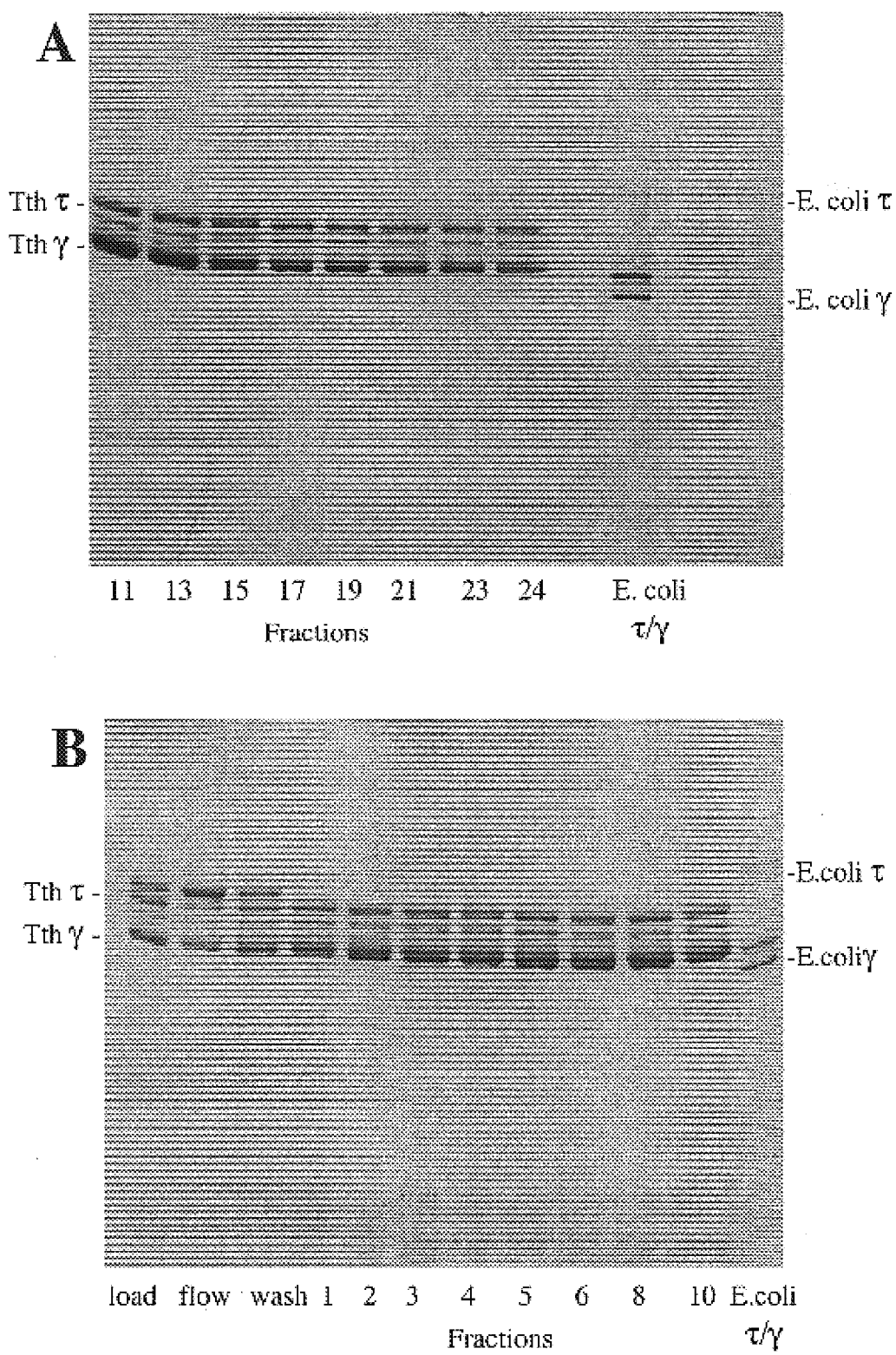
FIG. 10A-B
SDS-PAGE analysis of the fraction from the avidin column purification of N-terminal tagged *T. thermophilus* DnaX.

Western analysis of various antiserum dilutions for determination of dilutions to use in *T. thermophilus* DnaX detection.

Western analysis of various *T. thermophilus* DnaX dilutions for determination of the limit of DnaX detection at antiserum dilution of 1:6400.

SEQ ID NO:9 atggtcatcgccttcaccggggatcccttcctggcgcgggaggccctcttagaggaggca
aggcttaggggcctttcccgcttcaccgagcccaccccggaggccctggcccaggccctc
gccccggggcttttcgggggcggggggcgatgctggacctgagggaggtgggggaggcg
gagtggaaggccctaaagcccctcctggaaagcgtgcccgagggcgtcccgtcctcctc
ctggaccctaagccaagcccctcccgggcggccttctaccggaaccgggaaaggcgggac
ttccccaccccaagggaaaggacctggtgcggcacctggaaaaccgggccaagcgcctg
gggctcaggctcccgggcggggtggcccagtacctggcctccctggaggggggacctcgag
gccctggaacgggagctggagaagcttgccctcctctccctcccctcaccctggagaag
gtggagaaggtggtggccctgaggcccccctcacgggctttgacctggtgcgctccgtc
ctggagaaggaccccaaggaggccctcctgcgcctcaggcgcctcaaggaggagggggag
gagcccctcaggctcctcggggccctctcctggcagttcgccctcctcgcccgggccttc
ttcctcctccgggaaaaccccaggcccaaggaggaggacctcgcccgcctcgaggcccac
ccctacgccgccaaaaaggccctggaggcggcgaggcgccttacggaagaagccctcaag
gaggccctggacgccctcatggaggcggaaaagagggccaagggggggaaagacccatgg
cttgccctggaggcggcggtcctccgcctcgcccgttga

FIG. 13

The DNA coding sequence of the *T. thermophilus* *hol*A gene (SEQ ID NO:9).

SEQ ID NO:10

MVIAFTGDPFLAREALLEEARLRGLSRFTEPTPEALAQALAPGLFGGGGAMLDLREVGEA
EWKALKPLLESVPEGVPVLLLDPKPSPSRAAFYRNRERRDFPTPKGKDLVRHLENRAKRL
GLRLPGGVAQYLASLEGDLEALERELEKLALLSPPLTLEKVEKVVALRPPLTGFDLVRSV
LEKDPKEALLRLRRLKEEGEEPLRLLGALSWQFALLARAFFLLRENPRPKEEDLARLEAH
PYAAKKALEAARRLTEEALKEALDALMEAEKRAKGGKDPWLALEAAVLRLAR

FIG. 14

The amino acid sequence of *T. thermophilus* δ-subunit.

```
                        1                                                50
      Tthdelta     (1)  ------------------MVIAFTGDPFLAREALLEEARLRGLSRFTEP
E. coli delta     (1)  MIRLYPEQLRAQLNEGLRAAYLLLGNDPLLLQESQDAVRQVAAAQGFEEH
     Consensus    (1)                    I   DP L  EA        LA     F E
                       51                                               100
      Tthdelta    (32)  TPEALA-----Q--A---LAPGLFGGGGAMLDLR-EVG--EAEWKALKPL
E. coli delta    (51)  HTFSIDPNTDWNAIFSLCQAMSLFASRQTLLLLLPENGPNAAINEQLLTL
     Consensus   (51)      AI       N      A  LFA     LL L E G  A      L L
                       101                                              150
      Tthdelta    (69)  LESVPEGVPVLLLDPKPSPS--RAAFYRNRERR----DFPTPKGKDLVRH
E. coli delta   (101)  TGLLHDDLLLIVRGNKLSKAQENAAWFTALANRSVQVTCQTPEQAQLPRW
     Consensus  (101)    L D  LIL    K S A   AAFF    R         TP    L R
                       151                                              200
      Tthdelta   (113)  LENRAKRLGLRLPGGVAQYLAS-LEGDLEAIERELEKLALLSP--PLTLE
E. coli delta   (151)  VAARAKQLNLELDDAANQVLCYCYEGNLLALAQALERLSLLWDGKLTLP
     Consensus  (151)  L  RAK L L  A  Q L    EG L AL    LEKLALL P    LTL
                       201                                              250
      Tthdelta   (160)  KVEKVVALRPPLTGEDLVRSVLEKDPKEALLRLRRLKEEGEEPLRLLGAL
E. coli delta   (201)  RVEQAVNDAAHFTPEHWVDALLMGKSKRALHILQQLRLEGSEPVILLRTL
     Consensus  (201)   VE  V        T F V ALL        K AL  L  LK EG EPL LL   L
                       251                                              300
      Tthdelta   (210)  SWQFALLARAFFLLRENPRPKEEDLARLEAHPYAAKKALEAARRLTEEAL
E. coli delta   (251)  QRELLLIVNLKRQSAHTPLRALFDKHRVWQN--RRGMMGEALNRLSQTQL
     Consensus  (251)       LL             P      D  RL          EA   RLS      L
                       301                               345
      Tthdelta   (260)  KEALDALMEAEKRAKG--GKDPWLALEAAVLRLAR----------
E. coli delta   (299)  RQAVQLLTRTELTLKQDYGQSVWAELEGLSLLLCHKPLADVFIDG
     Consensus  (301)  K AL  L    E  K  G    W  LEA   L L
```

FIG. 15

Alignment of the amino acid sequence of δ from *T. thermophilus* and *E. coli*.

```
                          1                                                 50
Aquifex delta       (1)   METTIFQFQKTFFTKPPKERVFVLHGEEQYLIR-TFLSKLKEKYGENYTV
     Tthdelta       (1)   -------------------MVIAFTG DEFLAREALLEEARLRGLSRFTE
B. subtilis delta   (1)   ---MVEDVWKSLKKGE-VHPVYCLYGKETYLLQETVSRIRQTVVDQETKD
    E. coli delta   (1)   -MIRLYPEQLRAQLNEGLRAAVLLLGNDPLLLQESQDAVRQVAAAQGFEE
H. influenzae delta (1)   -MNRIFPEQLNHHLAQGLARVYLLQGQDPLLLSETEDTICQVANLQGFDE
    Consensus       (1)        IF Q       L  VYLL G DPYLL  ET    I QV   Q F E
                          51                                                100
Aquifex delta       (50)  LWGDEISEEEFYTALSET----SIFGGSKEKAVVIYNFGDFLKKLGRKKK
     Tthdelta       (31)  P-----TPEALAQALAP-----GLFGGGG-------AMLDLREVG---EA
B. subtilis delta   (47)  FNLSVFDLEEDPLDQAIADAETFPFMGERR--LVIVKNPYFLTGEKKKEK
    E. coli delta   (50)  HHTFSIDPNTDWNALFSLCQAMSLFASRQ-------TLLLLLPENGPNAA
H. influenzae delta (50)  KNTIQVDSQTDWAQLIESCQSIGLFFSKQ-------ILSLNLPEN-FTAL
    Consensus       (51)        ID E DW ALA        LFGG            L   L
                          101                                               150
Aquifex delta       (96)  EKERLIKVLRNVKS--NYVFLVYDAKLQKQELSSEPLKSVAS--FGGIVV
     Tthdelta       (61)  EWKALKPLLESVPE--GVPVLLLD---PKPSPSRAAEYRNRE------RR
B. subtilis delta   (95)  IEHNVSALESYIQSPAPYTVFVLLAPYEKLDERKKLTKALKK---HAFMM
    E. coli delta   (93)  INEQLLTLTGLLHD--DLLLIVRGNKLSKAQENAAWFTALAN---RSVQV
H. influenzae delta (92)  LQKNLQELISVLHK--DVLLLLQVAKLAKGIEKQTWFITLNQYEPNTLLI
    Consensus       (101) I  NL LL  L       VLLIV  AKL K E     F AL        ILV
                          151                                               200
Aquifex delta       (142) ANRLSK-ERIKQLVLKKFKEKGINVENDALEYLLQLTGYNLMELKLEVEK
     Tthdelta       (100) DFPTPKGKDLVRHLENRAKRLGLRLPGGVAQYLA-SLEGDLEALERELEK
B. subtilis delta   (142) EAKELNAKETTDFTVNLAKTEQKTIGTEAAEHLVLLVNGHLSSIFQEIQK
    E. coli delta   (138) TCQTPEQAQLPRWVAARAKQLNEELDDAANQVLCYCYEGNLIALAQALER
H. influenzae delta (140) NCQTPTVENLPRWVKNRTKAMGLDADNEAIQQLCYSYENNLLALKQALQL
    Consensus       (151)     TP    L RWV NRAK LGL LD EA QYL      EGNLLAL QELEK
                          201                                               250
Aquifex delta       (191) LIDYASEKKILTLDEVKRVAFSVSENVNVFEEVDLLLLKDYEKALKVLDS
     Tthdelta       (149) LALLSE---PLTLEKVEKVVA-LRPPLTGFDLVRSVLEKDPKEALLRLRR
B. subtilis delta   (192) LCTFIGDREELTLDDVKMLVA-RSLEQNIFELINKIVNRKRTESLQIFYD
    E. coli delta   (188) LSLLWPDG-KLTLPRVEQAVN-DAAHFTPFHWVDALLMGKSKRALHILQQ
H. influenzae delta (190) LDLLYPDH-KLNYNRVISVVE-QSSIFTPFQWIDALLVGKANRAKRILKG
    Consensus       (201) L LL  PD   LTLDRV VV   S  T FEWVDALLLKK  RAL IL
                          251                                               300
Aquifex delta       (241) LISFGIHPLQIMKILSSYALKLYTLKRLE-----EKGEDLNKA---MESV
     Tthdelta       (195) LKEEGEEPLRLLGALSWQFALLARAFFLLR----ENPREKEED---LARL
B. subtilis delta   (241) LLKQNEEPIKIMALISNQFRLILQTKYFA-----EQGYGQKQI---ASNL
    E. coli delta   (236) LRLEGSEPVILLRTLQRELLLLVNLKR-Q-----SAHTPLRAL---FDKH
H. influenzae delta (238) LQAEDVQPVILLRTLQRELFTLLELTKPQQRIVTTEKLPIQQIKTEFDRL
    Consensus       (251) L  EG EPL LLR LS     LLL LKR        E   PL  I   DRL
                          301                                               350
Aquifex delta       (283) GIKNNFLKMKFKSYLKANSKEDLKNLILSLQRTDAFSKLYFQDTVQLLRD
     Tthdelta       (238) EAHPYAAKKALEAARRL-TEEALKEALDALMEAEKRAKG--GKDPWIALE
B. subtilis delta   (283) KVHPFRVKLAMDQARLF-SEEELRLLTEQLAVMDYEMKTG-KKDKQLLLE
    E. coli delta   (277) RVWQNRRGMMGEALNRL-SQTQLRQAVQLLTRTELTLKQDYGQSVWAELE
H. influenzae delta (288) KIWQNRRPLFLSAIQRL-TYQTLYETLQELANIERLAKQEFSDEVWIKLA
    Consensus       (301) KI QNR KL LEA      RL S ELK II  L  IE  AK F DVWL LE
                          351              368
Aquifex delta       (333) FLTSRLEREVVKNTSHGG
     Tthdelta       (285) AAVLRLAR----------
B. subtilis delta   (331) LFLLQLLKRNEKNDPHY-
    E. coli delta   (326) GLSLLLCHKPLADVFIDG
H. influenzae delta (337) DLSVKICL----------
    Consensus       (351)  LSLRL R
```

FIG. 16

Alignment of the amino acid sequence of δ-subunit from A. aerolicus,
T. thermophilus, B. subtilis, E. coli and H. influenzae.

Biotin blot analysis of growth/induction time optimization of expression of *T. thermophilus* δ by pA1-NB-TD/AP1.L1.

Optimization of precipitation of *T. thermophilus* δ by ammonium sulfate.

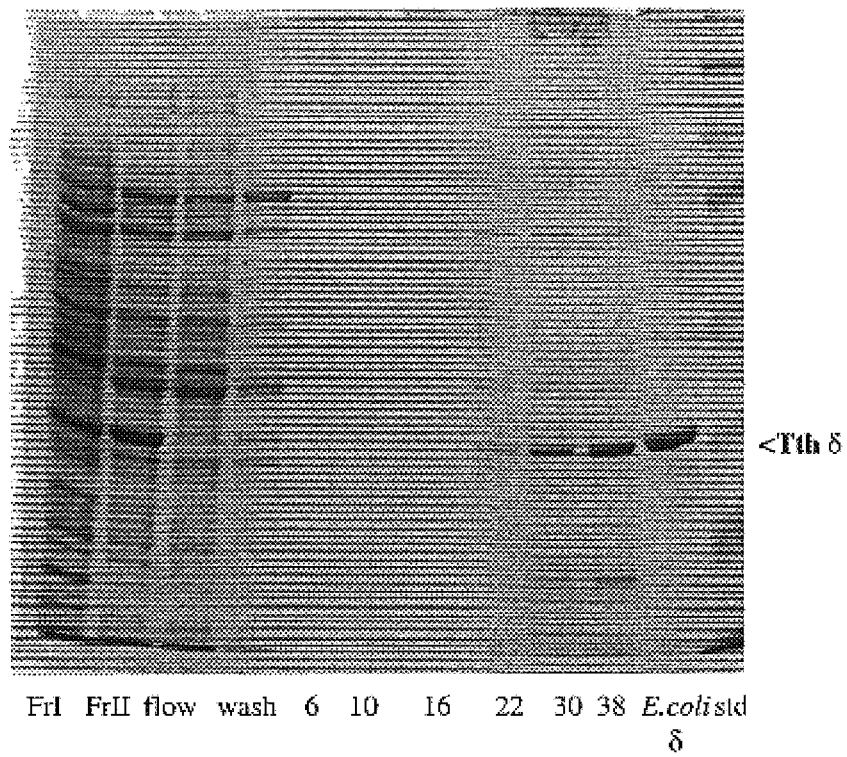
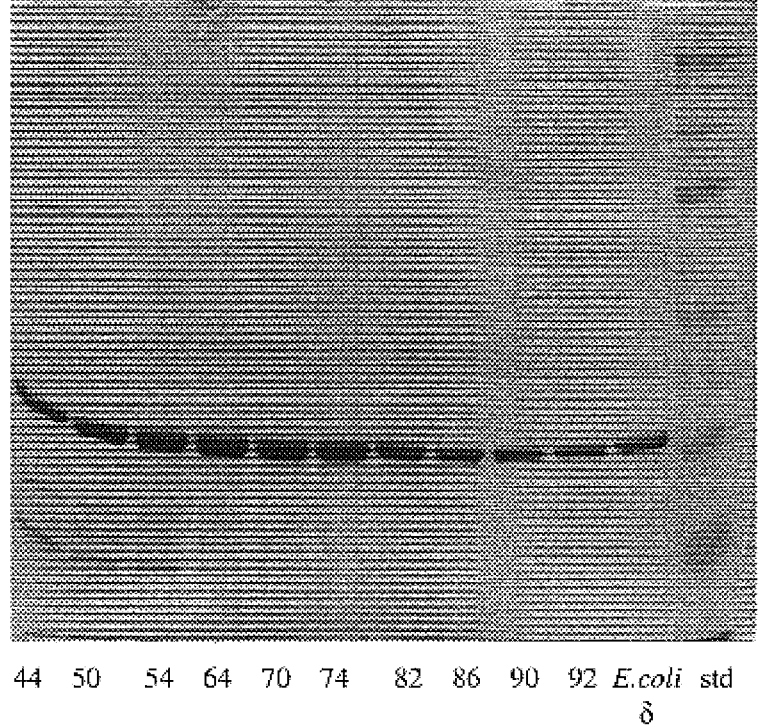
FIG. 19A-B
SDS-PAGE analysis of fractions from the $Ni^{++}$-NTA column purification of
*T. thermophilus* δ.

Protein concentration profile of fractions from the avidin column purification of *T. thermophilus* δ.

SDS-PAGE analysis of fractions from the avidin column purification of *T. thermophilus* δ.

SEQ ID NO:16

```
atggctctacacccggctcaccctggggcaataatcgggcacgaggccgttctcgccctc
cttccccgcctcaccgcccagaccctgctcttctccggccccgaggggggtggggcggcgc
accgtggcccgctggtacgcctgggggctcaaccgcggcttcccccgccctccctgggg
gagcacccggacgtcctcgaggtggggcccaaggcccgggacctccggggccgggccgag
gtgcggctggaggaggtggcgcccctcttggagtggtgctccagccaccccgggagcgg
gtgaaggtggccatcctggactcggcccacctcctcaccgaggccgcggccaacgccctc
ctcaagctcctggaggagccccttcctacgcccgcatcgtcctcatcgccccaagccgc
gccaccctcctccccaccctggcctcccgggccacggaggtggccttcgccccgtgccc
gaggaggccctgcgcgcccttacccaggacccggggctcctccgctacgccgccggggcc
ccgggccgcctccttagggccctccaggaccggaggggtaccgggcccgcatggccagg
gcgcaaagggtcctgaaagccccgccctggagcgcctcgccctgcttcgggagcttttg
gccgaggaggaggggggtccacgccctccacgccgtcctgaagcgcccggagcacctcctt
gccctggagcgggcgcggaggccctggaggggtacgtgagccccgagctggtcctcgcc
cggctggccttagacttagagacatga
```

FIG. 22
The DNA sequence of the T. thermophilus holB gene encoding the δ'-subunit of the T. thermophilus PolIII holoenzyme.

SEQ ID NO:17

MALHPAHPGAIIGHEAVLALLPRLTAQTLLFSGPEGVGRRTVARWYAWGLNRGFPPPSLG
EHPDVLEVGPKARDLRGRAEVRLEEVAPLLEWCSSHPRERVKVAILDSAHLLTEAAANAL
LKLLEEPPSYARIVLIAPSRATLLPTLASRATEVAFAPVPEEALRALTQDPGLLRYAAGA
PGRLLRALQDPEGYRARMARAQRVLKAPPLERLALLRELLAEEEGVHALHAVLKRPEHLL
ALERAREALEGYVSPELVLARLALDLET

FIG. 23

```
                              1                                                   50
E. coli delta prime    (1)   MRWYPWLRPDFEKLVASYQAGRGHLALLIQALPGMGDDAIIYALSRYLLC
   Tth delta prime    (1)   -----------MALHPAHPGAIIGHEAVLALPRLTAQTLLFSGPEGVGR
         Consensus    (1)              L  AH AA   H LI  LP L    LIFA       L
                              51                                                  100
E. coli delta prime   (51)   QQPQGHKSCGHCRGCQLMQAGTHPDYYTLAPEK----GKNTLGVDAPREV
   Tth delta prime   (40)   RTVARWYAWGLNRGFPPPSLGEHPDVLEVGPKARDLRGRAEVRLEEVAPL
         Consensus   (51)              A G RG      G HPD  LAP      GK  L LD V  L
                             101                                                  150
E. coli delta prime   (97)   TEKLNEPARLGGAKVWWTDAALLTDAAANALLKTLFPPPAETWFFLATR
   Tth delta prime   (90)   LPWCSSEPRER-VKVAILDSAHLLTEAAANALLRLLEEPPSYARIVLIAP
         Consensus  (101)     E    H R   KV L A LLTDAAANALLK  LEEPPA         L
                             151                                                  200
E. coli delta prime  (147)   EPERLLATLRSECRLHYLAPPEQYAVTWLSREVTMSQLALLAALRLSAG
   Tth delta prime  (139)   SRATLLPTLASRATEVAFALVPHEALR-------ALTQDP--GLLRYAAG
         Consensus  (151)       LL TL SR    AP PE         LSQD   A LR AAG
                             201                                                  250
E. coli delta prime  (197)   SPGAALALFQ-GDNWQARETLCQALAYSVPSGDWYSLLAALNHEQAPARL
   Tth delta prime  (180)   APGRLLRALCDPEGYRAPMARAQRVLKAPP---------------LERL
         Consensus  (201)   APG  L   Q D W AR      Q L A P                   RL
                             251                                                  300
E. coli delta prime  (246)   HWLATLIMDALKREHGAPQVTNVDVPGLVAELANHLSFSRLQAILGDVCH
   Tth delta prime  (214)   ALLREILAEEEGVHALHAVLK--------------REE----HLLALER
         Consensus  (251)     L  LL D   H A L                  P       L L
                             301                                           339
E. coli delta prime  (296)   IREQLMSVTGINRELLITDLLRIEHYLQPGVVLPVPHL
   Tth delta prime  (245)   AREALEGYVSP--ELVLARLADLGT-------------
         Consensus  (301)    RE L        ELLI  L L IE
```

FIG. 24

**Alignment of the amino acid sequence comparing *E. coli* and *T. thermophilus* δ'.**

```
                          1                                                  50
A. aeolicus delta'   (1)  -------------MEKVFLEKKQ---KTLHIPGGLFYGKEGSGKTKTAF
B. subtillus delta'  (1)  VAISWK---EMNEIQPRVMKLLYNSIEKDRLSHAYLFEGKKGTGKLDAAL
     E. coli delta'  (1)  VR--------WYPWLRPDFEKLVA-SYQAGRGHRALLLQALPGMGDDALIY
H. influenzae delta' (1)  VEIKRKMTALYPWLMPLYHQIAQ-TFDEGLGHRAVLLKADSGLGVESLFN
R. prowazekii delta' (1)  ----------MTILQPLIIELLEFYLKYNKLYNSWLIEAWN---IEQTLQ
          Tth delta' (1)  ----------------MALHP-AHPGAIIGLEAVLALLPRLTAQTLLF
          Consensus  (1)  M         L  PIFM LL  S   GRIHHALLI A  GLG E LLF
                          51                                                 100
A. aeolicus delta'  (35)  EFAKGLLGKE-NVPWGGSGCPSCKHVNELEEAFFKGEIEDFKVYKDKDGK
B. subtillus delta' (48)  LLAKSFFCLE-GGAEPCESCRNGKRI------------------------
     E. coli delta' (43)  ALSRYLLCQQPGGHKSCGHCRGGQLM------------------------
H. influenzae delta'(50)  ALPQKLMCVA-QGDKPCGQCHSCHLM------------------------
R. prowazekii delta'(38)  DLKEFLYIKFFNSNIPLENNPDYYFV------------------------
          Tth delta'(32)  SGPEGVGRRTVARWYAWGLNPGFPPP------------------------
          Consensus (51)  ALAK ILCK   NG  PCG CR C  M
                          101                                                150
A. aeolicus delta'  (84)  KHFVYLMGEHPDFVVIIP-----SGHY-IKIEQIREVKNFAYVKPALSRR
B. subtillus delta' (73)  -----ESCNHPDLHLVQF-----DGLS-LKKAGIQAEGEFSKTGLESHK
     E. coli delta' (69)  -----QAGTHPDYYTLAP----EKGKNTLGVDAVREVTEKLNEHARLGCA
H. influenzae delta'(75)  -----QAHSHPDYHELSP----INGKD-IGVDDINSMVAQEAQQNCN
R. prowazekii delta'(64)  --------ARKLSYTSNA------NN-LSIEGIEKLQDFLNKTSAISGY
          Tth delta'(58)  -----SLGEHPDVLEVGEKARDLRGRAEVRLLEVAPLLEWCSSEPRER-V
          Consensus(101)  AG HPDYH L P       GK  IKIEQIRELQEFLS  HA LSG
                          151                                                200
A. aeolicus delta' (128)  KVVIIDDRHAMISQAANALLKVLFEPPADTFIFTNRRSAILPTLLSF-
B. subtillus delta'(112)  ALYFLSHDQMTANAANSLKRFLEENKDMAVLTEQPQRLLDTIISPC
     E. coli delta' (110)  KVWVTDAALLIDAAANALLSTLEEPPAEMWFLAIREPERLLATLRSRC
H. influenzae delta'(115) KVVYVQGERLLEAAANALLRTLEESRPNETFLQADSSASLLATIYSRC
R. prowazekii delta' (98) KVAVIYSADLMNLHAANACLKILEDTFKNSYIFLITSRAASILSTIRSRC
          Tth delta'(102) KVVALDSRHIFIEAAANALLKILEEPPSYARIVELAPSREIEPTLASF-
          Consensus(151)  KVVII   ADLLTEAAANALLKILEEPPADTYFVLIT    ASLLATI SRC
                          201                                                250
A. aeolicus delta' (177)  --------TFQVELKGFSVKEVMEIAKVDEEIAKLSG--GSLKRAILLKE
B. subtillus delta'(162)  QTLPFQPLQPKAIEDRLIEQDVSPHMARELANMTNNVAEAVELSRN-DEF
     E. coli delta' (160)  RLHYLAPPPEQYAVTWLSREVTMSQDALLAAERLSAGSPQAALALFCGDN
H. influenzae delta'(165) QVWNLSVPNEEIAFEWLKSKSAVENQEILTLAAMNLCRPLLALETLQEGT
R. prowazekii delta'(148) ----------------FKVNIRSPLPNVSNDLYLQFIQEIADNKTL--DF
          Tth delta'(151) -------AT-EVAFAPVPEEALRALTQDPGLLRYAACAPGRLLRALQDPE
          Consensus(201)         VAF  L      VM L  VL AL LNAGAPGA LR LQDDF
                          251                                                300
A. aeolicus delta' (217)  NKDILNKVKEFLENEPLK---------VYKLASFFESWE-PEKQKLFLE
B. subtillus delta'(211)  AESRAKVIKLYEVLHQRKGHAFFFIQDQWMPFFKEKTHQ--EMGLDMLL
     E. coli delta' (210)  WQARETLCQALAYSVESG---------DWYSLLAALNHEQAPARLHWLAT
H. influenzae delta'(215) IEQRKNFLRQFWVFYRRR---------SPLELLPLFDKERYVQQVDWILA
R. prowazekii delta'(180) INRFTTKDRELWLGFIEN---------LFLIMNRILLK--SVNFNIDLL
          Tth delta'(193) GYRARMARAQRVLKAEPL---------ERLAIRRLLAF--EEGVHALHA
          Consensus(251)      R   IK F  L  P K         Y  LL EL KE    L ILL
                          301                                                350
A. aeolicus delta' (256)  IMEELVSQKLTEEKKDNYTYLLDTIRLFKD-GLARGVNEPLWLFTLAVQA
B. subtillus delta'(259)  IYRDVLSIQIGNEDKLIYQDLFQSLKQHALQSTQQSVTNQLL-AVLEAKK
     E. coli delta' (251)  LLMDALKRHHGAAQVTNVL-DVPGLVAELAN-HLSPSRLQALLGDVCHIRE
H. influenzae delta'(256) FLSLCLKHNLEIDSHRQVADLGRGLEQFSDEQTALGELQAFK-IMQKVRS
R. prowazekii delta'(218) DLENKIYNKLINKNPAYLL-QKFTDLKKLIYNTIDYDLDLKTS-YILVVNE
          Tth delta'(232) VLK-RPEHLLALERAREA-LEGYVSPELVLARLALDLET-----------
          Consensus(301)  IL D L  KLG E   NV DL    IK LA   LA  L QI   VL VR
                          351                               387
A. aeolicus delta' (305)  D-----------------------------------
B. subtillus delta'(308)  RLHSN--VNVQGLMEHLVLMLQEG------------
     E. coli delta' (299)  QLMSVTGINRELLITDLLLR-IEHYLQPGVVLPVPHL
H. influenzae delta'(305) DLLTINGVNVELMLLDGLTRLVTEVFETQ--------
R. prowazekii delta'(266) FFTV--------------------------------
          Tth delta'(269) ------------------------------------
          Consensus(351)  L S   VN   LI   L
```

FIG. 25

Biotin blot analysis of growth/induction time optimization of expression of *T. thermophilus* δ' by pA1-NB-TD7/AP1.L1.

SDS-PAGE Analysis of Ni-NTA Column Profile-Tth δ'
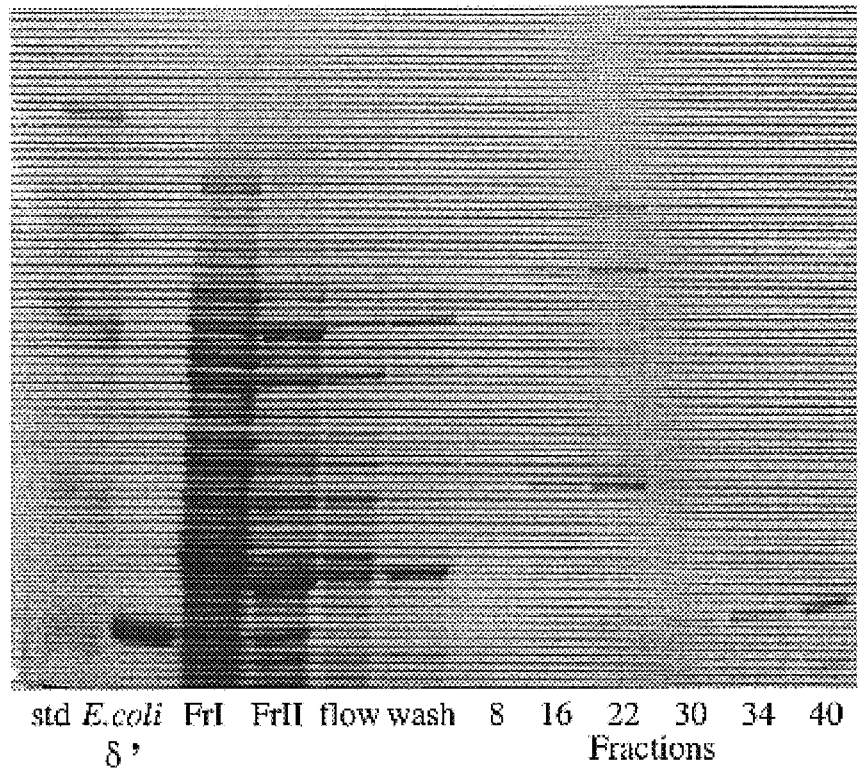
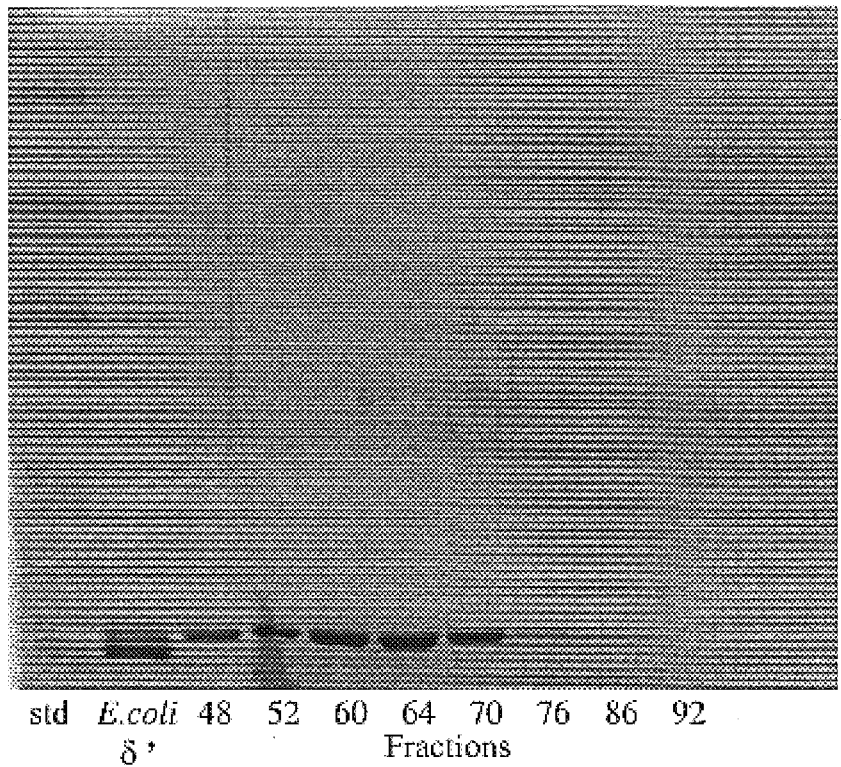
FIG. 27A-B Protein concentration profile of fractions eluting from the Sephacryl S-300 gel filtration column purification of *T. thermophilus* δ'.

SDS-PAGE analysis of fractions from the Sephycryl S-300 column purification of *T. thermophilus* δ'.

SDS-PAGE summary of the purification of *T. thermophilus* δ' as a translationally coupled protein.

Biotin blot analysis of growth/induction time optimization at different temperatures of expression of *T. thermophilus* β by pA1-NB-TN/AP1.L1.

Protein concentration profile of fractions eluting from the $Ni^{++}$-NTA column purification of *T. thermophilus* β.

Primer extension assay to determine stimulation of *T. thermophilus* α by *T. thermophilus* β.

Protein concentration profile of fractions eluting from a Sephacryl S-300 gel filtration column purification of *T. thermophilus* β.

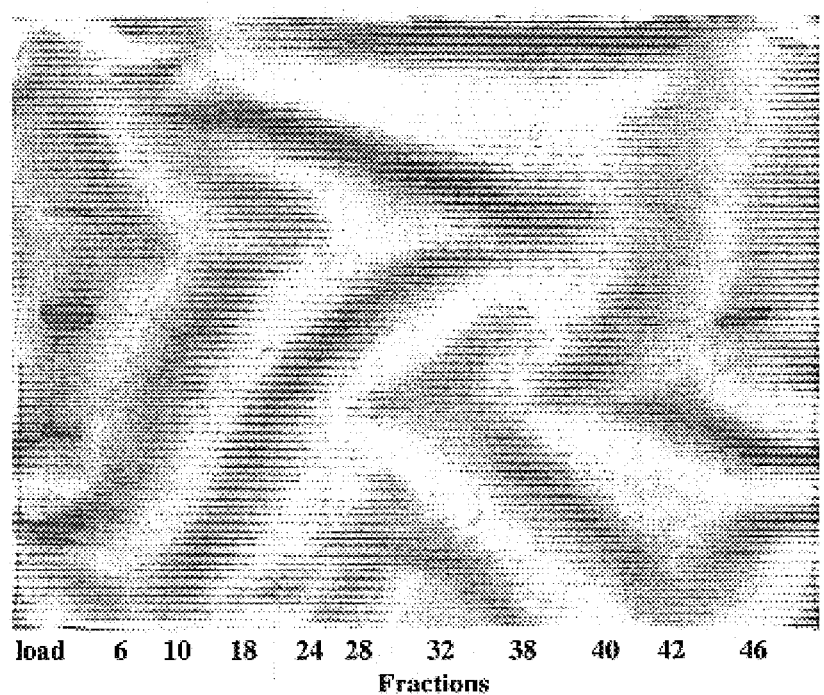
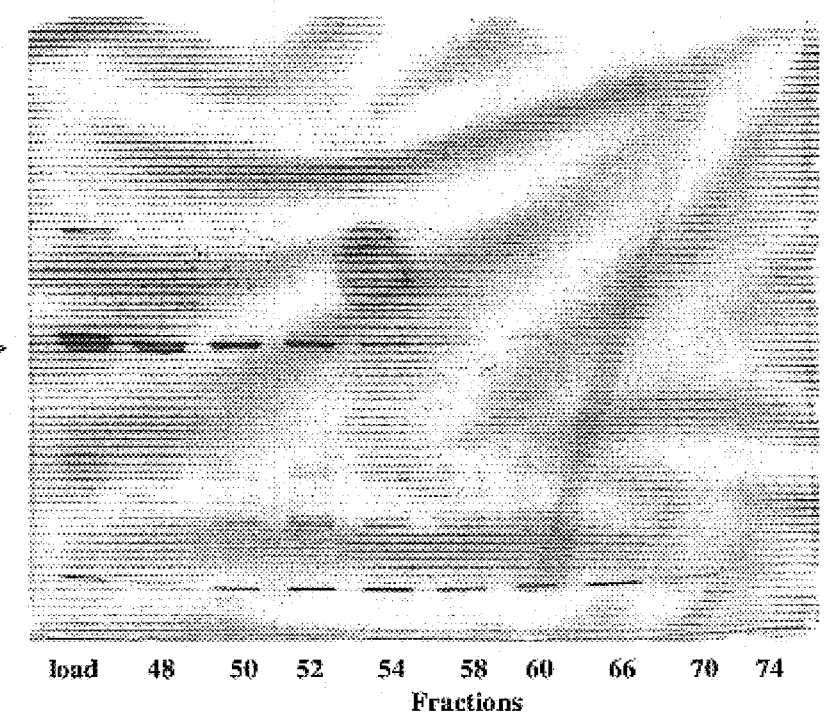
FIG. 35A-B
SDS-PAGE analysis of fractions eluting from a Sephacryl S-300 gel filtration column purification of *T. thermophilus* β.

The pooled fractions of *T. thermophilus* β from the Sepharcry S-300 gel filtration column that was used in production of antibodies directed against β.

Western analysis of various antiserum dilutions for determination of dilutions to use in *T. thermophilus* β detection.

Western analysis of various *T. thermophilus* β dilutions for determination of the limit of β detection at antiserum dilution of 1:6400.

M13gori reconstitution of *T. thermophilus* Pol III subunits.

Temperature dependence for a functional *T. thrmophilus* holoenzyme in the reconstitution assay.

kDa: 440 232 158 67 25

Sephacryl S-200 gel filtration of *T. thermophilus* β.

SEQ ID NO:31:

```
atggctcgaggcctgaaccgcgttttcctcatcggcgccctcgccacccggccggacatg
cgctacaccccggcggggctcgccatttggacctgaccctcgccggtcaggacctgctc
ctttccgataacggggggggagcgggaggtgtcctggtaccaccgggtgaggctcttaggc
cgccaggcggagatgtggggcgacctcttggaccaagggcagctcgtcttcgtggagggc
cgcctggagtaccgccagtgggaaagggagggggagaagcggagcgagctccagatccgg
gccgacttcctggaccccctggacgaccggggggaaggagcgggcggaggacagccgggc
cagcccaggctccgcgccgccctgaaccaggtcttcctcatgggcaacctgacccgggac
ccggaactccgctacaccccccagggcaccgcggtggcccggctgggcctggcggtgaac
gagcgccgccaggggcggaggagcgcacccacttcgtggaggttcaggcctggcgcgac
ctggcggagtgggccgccgagctgaggaagggcgacggccttttcgtgatcggcaggttg
gtgaacgactcctggaccagctccagcggcgagcggcgcttccagacccgtgtggaggcc
ctcaggctggagcgccccacccgtggacctgcccaggccggcggaagcaggtcccgcgaa
gtccagacgggtggggtggacattgacgaaggcttggaagactttccgccggaggaggat
ttgccgttttga
```

FIG. 47

DNA sequence of the gene encoding *T. thermophilus* SSB.

SEQ ID NO:32

MARGLNRVFLIGALATRPDMRYTPAGLAILDLTLAGQDLLLSDNGGEREVSWYHRVRLLG
RQAEMWGDLLDQGQLVFVEGRLEYRQWEREGEKRSELQIRADFLDPLDDRGKERAEDSRG
QPRLRAALNQVFLMGNLTRDPELRYTPQGTAVARLGLAVNERRQGAEERTHFVEVQAWRD
LAEWAAELRKGDGLFVIGRLVNDSWTSSSGERRFQTRVEALRLERPTRGPAQAGGSRSRE
VQTGGVDIDEGLEDFPPEEDLPF

FIG. 48

```
                          1                                                  50
    Aquifex SSB      (1)  ----MLNKVFIIGRLTGDPVITYLPSGTEVVEFTLAYNRRYKNQN-GEFQ
 B. subtilus SSB     (1)  ----MLNRVVLVGRLTKDPEURYTPNGGAVATFTLAVNRIFTNQS-GE-R
    E. coli SSB      (1)  MSARGLNKVILVGRLGNDPEVRYTPNGGAVANLQVATSESWRDKQTGEMR
 H. influenzae SSB   (1)  --MAGLNKVTIVGHLGNDPEIRTMPNGDAVANISVATSESWNDRNTGERR
         TthSSB      (1)  -MARGLNRVFLIGALATRPDMRYTPAGLAILDLTLAGQDLLLSDNGE-R
       Consensus     (1)      GLNKVILVGRLG DPEIRYIPNG AVA LTLA NESW   N GE R
                          51                                                100
    Aquifex SSB     (46)  EESHFFDVKAYGKMAEDWATRFSKGYLVLVEGRLSQEKWEK-EGKKFSKV
 B. subtilus SSB    (45)  E-ADFINGVTWRRQAENVANFLKKGSLAGVGGRLQTRNYENQGQRVFVT
    E. coli SSB     (51)  EQTEWHRVVLFGKLAEVAGEYLRKGAQVYIEGQLRTRSNDD-NGITRYIT
 H. influenzae SSB  (49)  EVTEWHRLVFYRRQAEICGEYLRKGSQVYVEGRLKTRKNQDQNGQDRYTT
         TthSSB     (49)  EVSWYHRVRLLGRQAEMWGDLLDQGQLVWVEGRLEYRQWR-EGEKRSEL
       Consensus    (51)  E SEFHRVV YGRQAEI GEYLRKGSLVYVEGRL TR WE  NG KRY T
                          101                                               150
    Aquifex SSB     (95)  RIIA---ENVR-LINRPKGAELQAEE-----------------EEEVP
 B. subtilus SSB    (94)  EVQAESVQFLEPKNGGGSGSGGYNEG------N---------SGGGQYF
    E. coli SSB    (100)  DILVKTTGTMQ-MLCSAPQQNAQAQP---------------KPQQNGQ
 H. influenzae SSB  (99)  EIQG---DVMQ-MLGGR-NQNAGGYG---------------N-DMGGA
         TthSSB     (98)  QIRADFLDPLD-DRGKERAEDSRGQPRLRAALNQVFLMGNLTRDPELRYT
       Consensus   (101)  EI A    D L  MLG   G  A A                  E
                          151                                               200
    Aquifex SSB    (122)  PIEEEIEKL--------GKEEKPFTDEEDEIPF---------------
 B. subtilus SSB   (128)  GGGQNDNPFGGNQNN--QRRNQGNSFND-DPFANDGKP-IDISDDDIPF-
    E. coli SSB    (132)  PQSADATKKGAKTK---GRERKAAQPEPQPQTEEGED--YGFSDDIPF-
 H. influenzae SSB (126)  PQSSYQAR---QTNN---GNSYQSSRPAPQQAAPQAEPPMDGFDDDIPF-
         TthSSB    (147)  PQGTAVARLGLAVNERRQGAEERTHEVEVGAWRDLAEWAAELRKGDGLFV
       Consensus   (151)  PQ    K G  N     GRE    SF D Q   P AE   D  DDIPF
                          201                                               250
    Aquifex SSB    (148)  --------------------------------------------------
 B. subtilus SSB   (173)  --------------------------------------------------
    E. coli SSB    (176)  --------------------------------------------------
 H. influenzae SSB (169)  --------------------------------------------------
         TthSSB    (197)  IGRLVNDSWTSSSGERRFQTRVEALRLERPTRGPAQAGGSRSREVQTGGV
       Consensus   (201)
                          251           267
    Aquifex SSB    (148)  ----------------
 B. subtilus SSB   (173)  ----------------
    E. coli SSB    (176)  ----------------
 H. influenzae SSB (169)  ----------------
         TthSSB    (247)  DIDEGLEDFPPEEDLPF
       Consensus   (251)
```

FIG. 49

Sequence alignment of *T. thermophilus* SSB compared with SSB amino acid sequences from *Aquifex*, *B. subtilus*, *E. coli* and *H. influenzae*.

```
1                                                   50
C-termTthSSB   (1)  ---ALNQVFLMGNITRDPELRYTEQGTRVARLGERVNERRQ--GAEER--
N-termTthSSB   (1)  MARGLNRVFLGALATRPDMRYTEALLAILDLTLAGQDLLLSDNGGREV
   Consensus   (1)      ALN VFLIG L    PDLRYTP G AI   L  LA ND     A  ER
                    51                                                100
C-termTthSSB  (44)  --TLFLEVQAWRDLAELAAELRKLDGLEVIGRLVNDSLTSSSGERSFQTR
N-termTthSSB  (51)  SWYLRVRELG-RQAEMLGDLLDQGQLVEVELREYRQLERE-GEKRSELQ
   Consensus  (51)      H V L A R    WA  L G  LFV GRL    W     GEKR
                    101                                         147
C-termTthSSB  (92)  VELLRLERP-TRGPAQAGGSRSREVQTGGVDIDEGLEDFPPEEDLPF
N-termTthSSB  (99)  LRLDFLGPLDDRGKERLEDSLGQPRLRA-------------------
   Consensus (101)  I A  LD    RG   A  SR       A
```

FIG. 50

Sequence alignment of the N-terminal region of *T. thermophilus* SSB with the C-terminal region of *T. thermophilus* SSB.

Biotin blot analysis of relevant fractions from the Ni$^{++}$-NTA column purification of *T. thermophilus* SSB.

SEQ ID NO:36

```
gtgcctgcaggtctggaggacgtcaccctggaccagctcctttacaccgcctttgacctg
gagaccacgggcctggacccggagcaagatgccgtggtggccctcgccggggtccatatc
ctgggtcgaagggtcttgcggcaggaggtgttcgaggccctggtgaacccggggcgcccc
atctcccccgcggccacggcggtccacggcctcacggcggagatgctccgggacaagcct
ccctagaggcggtcctccccgccttccgcgccttcgtccaggacacggtgctggtggcc
cacaacggggcctttgacctggcctttctgcgccgggcgggcctggaccagccccccctc
ctggacaccctcctcctcgcccagctcctcttccccgacctcaaggactaccgcctcgag
gccctggcccaccgcttcggcgtccccgccaccgggcggcacaccgccttgggcgatgcg
ctgatgacggcggaggtcttcgtgaggatgcagcccctcctctttgaacgggggcttagg
cggctctgggacgtggtggaggcctgccgccgcctcccttggcccggctcaggtactga
```

FIG. 52

SEQ ID NO:37

```
VPAGLEDVTLDQLLYTAFDLETTGLDPEQDAVVALAGVHILGRRVLRQEVFEALVNPGRP
ISPAATAVHGLTAEMLRDKPPLEAVLPAFRAFVQDTVLVAHNGAFDLAFLRRAGLDQPPL
LDTLLLAQLLFPDLKDYRLEALAHRFGVPATGRHTALGDALMTAEVFVRMQPLLFERGLR
RLWDVVEACRRLPLARLRY
```

FIG. 53

SEQ ID NO:67 gtgcatagcgacgccctcctagccccctcaacgaggcccagcgccaggcggtcctccac
tttgagggccccgccctggtggtggccggggcggggagcgggaagacccgcaccgtggtc
caccgggtggcctacctcgtcgcccgccggggggtcttcccctcggagatcctggccgtc
accttcaccaacaaggccgcggaggagatgcgggagcgcctccggggctggtcccgggg
gcggggaggtctgggtctccaccttccacgccgccgccttgaggatcctccgcgtctac
ggggagcgggtgggcctcaggcccggctttgtggtctacgacgaggacgaccagaccgcc
ctcctcaaggaggtcctgaaggagctcgccctctcggcccggcccggcccatcaaggcc
cttttggaccgggcgaagaaccggggcgtgggccttaaggccctcctcggcgagcttccc
gagtactacgccgggctttcccggggaaggcttggggacgtcctggtgcgctaccaggag
gcccttaaggcccaggggggccttggacttcggggacatcctcctctacgccctgaggctt
ttagaggaggacgaggaggtcctcaggctcgtgcgcaagcgggcccgcttcatccacgtg
gacgagtaccaggacacgagccccgtccagtaccgcttcacccggcttctcgccggggag
gaggccaacctcatggccgtgggcgaccccgaccaggggatctactccttccgggcggcg
gacatcaagaacatcctggacttcacccgggactaccccgaggcccgggtctaccgcctg
gaggagaactaccgctccaccgaggccatcctccgcttcgccaacgccgtgatcgtgaag
aacgccctccgcctggagaaggccctgcgcccggtgaagcggggcggggagcccgtgcgc
ctctaccgggcggaggacgcCgggaggaggcccgcttcgtggccgaggagatcgcccgg
ctcggccccccctgggaccggtacgccgtcctctaccgcaccaacgcccaaagccgcctt
ctggaacaggcgttggcggggcggggatcccggcgcgggtggtgggcggcgtggggttc
tttgaaagggccgaggtcaaggacctcctggcctacgccgcctcgccctcaaccccctg
gacgccgtgagcctgaagcgggtcctgaacaccccctcgggcatcggcccggccacc
tgggccagggtgcagctcctcgcccaggagaagggggcttcctccctgggaggccctgaag
gaggcggccaggaccttccccgcgccgagcccctgaggcacttcgtggccctggtggag
gagcttcaggacctggtcttcggccccgccgaggccttcttccgccacctcctcgaggcc
accgactacccgcctacctccgggaggcctaccccgaggacgccgaggaccgcctggag
aacgtggaggagctcctcagggcggccaaggaggcggaggacctgcaggacttcctggac
cgggtggccctcaccgccaaggcggaggagcccgccgaggcggaggggagggtcgccctc
atgaccctgcacaacgccaagggctggagttccccgtggtcttcctcgtgggggtggag
gaggggcttctgccccaccgcaactccgtgagcaccctcgagggcctggaggaggagcgc
cgcctcttctacgtgggcatcacccgggcccaggagaggctctacctctccacgccgag
gagcgggaggtctacggcaggcgggagcccgccggccgagccgcttcctggaggaggtg
gaggaggggctttacgaggtgtacgaccctaccggcgcccgccctccccgcccccccat
cgcccgaggcccggggccttccggggcggggagcgggtggtccaccccgcttcggcccc
ggcaccgtggtggcggcccaggggacgaggtcacggtccactttgaggggtttgggctc
aagcgcctttccctcaagtacgcggagcttaagccggcatga

FIG. 54

SEQ ID NO:68

VHSDALLAPLNEAQRQAVLHFEGPALVVAGAGSGKTRTVVHRVAYLVARRGVF
PSEILAVTFTNKAAEEMRERLRGLVPGAGEVWVSTFHAAALRILRVYGERVGLR
PGFVVYDEDDQTALLKEVLKELALSARPGPIKALLDRAKNRGVGLKALLGELPE
YYAGLSRGRLGDVLVRYQEALKAQGALDFGDILLYALRLLEEDEEVLRLVRKRA
RFIHVDEYQDTSPVQYRFTRLLAGEEANLMAVGDPDQGIYSFRAADIKNILDFTR
DYPEARVYRLEENYRSTEAILRFANAVIVKNALRLEKALRPVKRGGEPVRLYRA
EDAREEARFVAEEIARLGPPWDRYAVLYRTNAQSRLLEQALAGRGIPARVVGGV
GFFERAEVKDLLAYARLALNPLDAVSLKRVLNTPPRGIGPATWARVQLLAQEKG
LPPWEALKEAARTFPRAEPLRHFVALVEELQDLVFGPAEAFFRHLLEATDYPAYL
REAYPEDAEDRLENVEELLRAAKEAEDLQDFLDRVALTAKAEEPAEAEGRVAL
MTLHNAKGLEFPVVFLVGVEEGLLPHRNSVSTLEGLEEERRLFYVGITRAQERLY
LSHAEEREVYGRREPARPSRFLEEVEEGLYEVYDPYRRPPSPPPHRPRPGAFRGGE
RVVHPRFGPGTVVAAQGDEVTVHFEGFGLKRLSLKYAELKPA

Fig. 55

SEQ ID NO:71

```
atggacgcgggccaggcggtggagctgatcaagtcccgcctctccttgcgggaggtggtc
tcccgctacgtggccctgaagccggcgggccgcggccgctggaagggcctctgccccttc
caccaggagaagaccccctcttcctacgtggacgaggagaagggcctcttctactgcttc
gggtgcaaggccgggggcgacctcttcgccttcgtccaaagggcggagggcgctggacttc
cccgaggccctggaaaggctcgcggaggaggcgggggtggagcttccccggcggaaggcc
ccggaaaggcgccgggagctcctcgaggtcctggccctggcccagacctacttcctggag
cacctccacgcccaccccgaggccctggcctacctgaggaagcggggcctcacggaggag
agcgtggcccgcttcggcctgggctacgccccgcccaagggggacgggctcgtggccttc
ctcgcccggcacggggtggccccggaggagggcgtgcgggccggggtgctggcggagcgg
caggggcgcttcgtggaccgcctccgccaccgcatcaccttccccatcaaggacgccttc
gggcgcgtcgtggccttcaccgggagggccctggggaggacgggcccaagtacctgaac
accccgaaaccccctttccgcaagcaggaggtcctcttcgcctaccccgaggcccgg
cccgccttgagggagggccgggccatcgtggtggagggctctttgacgccatcgccctc
caccagctgggcttcccggagacggtggccgtgctgggctcgggcctctccgagggacag
gccctcctcctcaagaaggcgggggtcctggaggtctacctggcctttgacgccgacgag
gccgggcagaaggccaccttgcagagcctgaacctggagctcgcccccaggttcctcttc
tacgccgtccgcctccccgccaaggacccgggggagctcctcctccaccccgagggaagg
gccctcttccagaaggccctggaggaggccctccccgaggtggccttccgctttgaggag
gcgagccgggggctggacctctcccggcccgagcacaagcggaaggtcctcgaggccctc
acccccaggatgctcaccccggagccctttgatcccgtggccgagcggctcaaggccctg
gtggtggagcgcctggcctttccccaagagcctcgaggactacctggcgagccttagg
acccgggggcggcccgcccctccccaccgcccccaccccacccccggcaacaagacc
ctccttctggagctggacgccatcgccctcctcctctccgccccggaggagcgcttcctg
gagcttgtggactacgtggagacccaggtctggcccccggagggttccttcctcggggag
ttcctggccctggcccggaaggagccccggcgggaccacctccgccgcacccctaagccag
cgggaggaaggaggaaggctctttgagcgcctgctcctcgcgccccggggggaggatccc
aggctccaggagaagctggaccacacctggcccgcctgcgggaagcctacctccaggag
cggctcgccaaggtcaaggcggccctcgcccaaaaccccgacccccccaccctggagcgc
ctccttaaggagtaccaggagatccgggtggccatagaggcggagcgccgcctctacaag
cggcgcccccctccttcgggctggtccacctag
```

Fig. 56

SEQ ID NO:72

```
MDAGQAVELIKSRLSLREVVSRYVALKPAGRGRWKGLCPFHQEKTPSFYVDEEKGLFYCF
GCKAGGDLFAFVQRAEGLDFPEALERLAEEAGVELPRRKAPERRRELLEVLALAQTYFLE
HLHAHPEALAYLRKRGLTEESVARFGLGYAPPKGDGLVAFLARHGVAPEEGVRAGVLAER
QGRFVDRLRHRITFPIKDAFGRVVAFTGRALGEDGPKYLNTPETPLFRKQEVLFAYPEAR
PALREGRAIVVEGLFDAIALHQLGFPETVAVLGSGLSEGQALLLKKAGVLEVYLAFDADE
AGQKATLQSLNLELAPRFLFYAVRLPAKDPGELLLHPEGRALFQKALEEALPEVAFRFEE
ASRGLDLSRPEHKRKVLEALTPRMLTPEPFDPVAERLKALVVERLGLSPKSLEDYLASLR
TRGRPAPPPPPPPLTPGNKTLLLELDAIALLLSAPEERFLELVDYVETQVWPPEGSFLGE
FLALARKEPRRDHLRRTLSQREEGGRLFERLLLAPRGEDPRLQEKLDHTLARLREAYLQE
RLAKVKAALAQNPDPPTLERLLKEYQEIRVAIEAERRLYKRRPPPSGWST
```

Fig. 57

SEQ ID NO:75 gtgcgggtgcttcaggtggcccttccctgccgcttccgcccatgagctacctccctccc
ttggggcaggagggagaggaggccttggggcggcgggtggccgttccttttcgggggag
gtccaggtgggggtggtggtgggggaagggggcggccctccctgaacctccgccacgcc
atcgcctacctggaccccgcccctacctgcgcccggaggagatcctcttttggaagag
gcggcccgctacctttcgcccccctgggccaggtcctggcggacttcctcccccctttt
cccccttgcgccaccgggtccgcctctaccggggcggacccgaaggtcctgcccccg
gggctcggggccttggtggactggcgggaggcccggggctttgacccaagcttttggac
ctcctgcgggaggcggggatgctggaggaggagctcgccttcgggaggcgcggggggtg
ctggtgcccctgaagcccgcccacccgatcccagctggaccgcgtccttcaggtcctg
cgggagctgggctttgccgaaagccaggcggccctggcccgggcggcggggggtggggtg
ggccgggtgcgccgcctcgtccaggagggtacatcggcaccgcgtcccccgaggaggcc
gccccgccccggcggacggggtggacgtggcgcccctccacctccccgagaggcccgag
cgggtcaacggcggggaggtttctggaacgcgttcgggtgctcaaggggcttttgggggag
ggggaccacctggtcctcttccccgaggtgagcctcttggagcggtttctcgcccacttc
cccggggccacgccctaccacggggggctttccggcccggtccgggagcggttttccgg
aggccgcgcggcgtggtcttcgccacctacggcgggctcctcctcccttcaccccccgc
tctttggtggtggtggaggaggggagcgagagctacaagcttcctcggggagccgggcc
ttcgtcccccgcttgcggagcttagggcccggctcctcggggtgcccctcacctacctc
tccctggtgcccgcggtggaggttttggagcgaaaaggcttcgccctgcccgtgcccaag
ccccgccttctcctcttggacctccggcgggagcggggctttcccgtcacggggcgggcc
ctcgccctcctccgccaggtggaggagcgggggcggcaggccgtggtcctctccgcccgc
aagggtacagcgccctcctcctctgccaggactgcggcttccggcccatgtgccccgac
tgcgccttgcccctgcggtaccaccgggaggggaaggggcgctcgtctgccaccagtgc
ggccaccgcgaggacccgcccctcctctgccccggtgcggctcccccctcctcgccccc
aaggggcccggggtggactggatccgggaggccctggcggagaggcttcccttcccgtc
taccgctacgccggcgacgggaaggacgacctcaccccctcctcgagggccggccgggg
gtggtggtggggaccacggccctcctcagggggcctaggcttcccgacctcgccctcgtc
ctcctcccttggcggacggcttcctcctggagtcggacttccgggcggcggagcggtac
caccgccttctctgggccctcacggagctcaggcccgggcggaggcccctcctcgtcctc
cagaccttcaccccgagcaccccgtgcaccgggccctcgaggcggggaggtggaggcc
tacctgtggcaggagaaggccctgcgggaggccctcaactacccgccgggtgcgcatg
gtaaagctggaggtgcgccaccgaaaggaagagcgggcccgggaaaaggccttcgccctc
ctggaggccttgcgggccgaggcggaggaggggaggtcctgggccccgccccgctccc
gtgccccgggtgaaggggcattacgtcttccacctcctcctccggggggagcacggagcgg
ctcgcccgcctcctcggcctcctggaccggcggcagttcaggctggaccccgacccttc
cacttcgtggggcttttggaggactag

Fig. 58

SEQ ID NO:76

```
VRVLQVALPLPLPPMSYLPPLGQEGEEALGRRVAVPFRGEVQVGVVVGEGGRPSLNLRHA
IAYLDPAPYLRPEEILFLEEAARYLFAPLGQVLADFLPPFPPLRHRVRLYPGADPKVLPP
GLGALVDWREARGFDPKLLDLLREAGMLEEELAFREARGVLVPLKPAHPDPQLDRVLQVL
RELGFAESQAALARAAGVGVGRVRRLVQEGYIGTASPEEAAPPPADGVDVAPLHLPERPE
RVNGGRFLERVRVLKGLLGEGDHLVLFPEVSLLERFLAHFPGATPYHGGLSGPVRERFFR
RPRGVVFATYGGLLLPFTPRSLVVVEEGSESYKLPSGSRAFVPPLAELRARLLGVPLTYL
SLVPAVEVLERKGFALPVPKPRLLLLDLRRERGFPVTGRALALLRQVEERGRQAVVLSAR
KGYSALLLCQDCGFRPMCPDCALPLRYHREGKGALVCHQCGHREDPPLLCPRCGSPLLAP
KGPGVDWIREALAERLSLPVYRYAGDGKDDLTPLLEGRPGVVVGTTALLRGPRLPDLALV
LLPLADGFLLESDFRAAERYHRLLWALTELRPGRRPLLVLQTFTPEHPVHRALEAGEVEA
YLWQEKALREALNYPPRVRMVKLEVRHRKEERAREKAFALLEALRAEAEEGEVLGPAPAP
VPRVKGHYVFHLLLRGSTERLARLLGLLDRRQFRLDPDPFHFVGLLED
```

Fig. 59

SEQ ID NO: 81 gtggagcgggtggtgcggccccttctggacgggaggttcctcctggaggaggggg ctttgggagtggcgctaccccttt ccctggagggggagtgtggtcctggacct gagaccacggggcttgccccgggcctggacgaggtgattgaggtgggcctcctc gagggggggaggcgcctcccttccagagcctcgtccgccttcccgcccgccg ttcgtggagcgcctcaccggcatccccgggaggccctggaggaggccccctcc gaggttctggagaaggcctacccctcctcgccgacgccaccttggtgatccac gcctttgacctgggcttcctccgcccggccctggagggcctgggctaccgcctg cccgtggtggactccctgcgcttggccagacggggcttaccaggccttaggcgc ctggacgccctctccgaggtcctggagcttccccgaaggacctgccaccgggcc gacgtggagcgcaccctcgccgtggtgcacgaggtgtactatatgcttacgtcc ccccgcacgctttgggaactcgggaggtag

Fig. 60

SEQ ID NO: 82

VERVVRPLLDGRFLLEEGVGLWEWRYPFPLEGEAVVVLDLETTGLAPGLDEVIE
VGLLRLEGGRRLPFQSLVRPSRPPSPFVERLTGIPREALEEAPSLEEVLEKAYPLLA
DATLVIHNAAFDLGFLRPALEGLGYRLENPVVDSLRLARRGLPGLRRYGLDALS
EVLELPRRTCHRALEDVERTLAVVHEVYYMLTSGRPRTLWELGR

Fig. 61

SEQ ID NO: 22

5' UTR
gtgaccgggcccccctcgaggtcgacggtatcgataagcttgatatcgaaaaagagagtcgtaatagccgt
taaaggaggcgtcgggca ATGAACATAACGGTTCCCAAGAAACTCCTCTCGGACCAGCTTTCCCTCCTGGAGCGCATCGTCCCC*TCTAG*
*AAGCGCCAACCCCCTCTACACCTACCTGGGGCTTTACGCCGAGGAAGGGGCCTTG*
ATCCTCTTCGGGACCAACGGGGAGGTGGACCTCGAGGTCCGCCTCCCCGCCGAGGCCCAAAGC
CTTCCCCGGGTGCTCGTCCCCGCCCAGCCCTTCTTCCAGCTGGTGCGGAGCCTTCCTGGGGAC
CTCGTGGCCCTCGGCCTCGCCTCGGAGCCGGGCCAGGGGGGGCAGCTGGAGCTCTCCTCCGGG
CGCTTCCGCACCCGGCTCAGCCTGGCCCCTGCCGAGGGCTACCCCGAGCTTCTGGTGCCCGAG
GGGGAGGACAAGGGGGCCTTCCCCCTGCGGACGCGGATGCCCTCCGGGGAGCTCGTCAAGGCC
TTGACCCACGTGCGCTACGCCGCGAGCAACGAGGAGTACCGGGCCATCTTCCGCGGGGTGCAG
CTGGAGTTCTCCCCCCAGGGCTTCCGGGCGGTGGCCTCCGACGGGTACCGCCTCGCCCTCTACGACCTGCC
CCTGCCCCAAGGGTTCCAGGCCAAGGCCGTGGTCCCCGCCCGGAGCGTGGACGAGATGGTGCGGGTCCTGA
AGGGGGCGGACGGGGCCGAGGCCGACCTCGCCCTGGGCGAGGGGGTGTTGGCCCTGGCCCTCGAGGGCGGA
AGCGGGGTCCGGATGGCCCTCCGCCTCATGGAAGGGGAGTTCCCCGACTACCAGAGGGTCATCCCCCAGGA
GTTCGCCCTCAGGGTCCAGGTGGAGGGGGAGGCCCTCAGGGAGGCGGTGCGCCGGGTGAGCGTCCTCTCCG
ACCGGCAGAACCACCGGGTGGACCTCCTTTTGGAGGAGGGCCGGATCCTCCTTTCCGCCGAGGGGACTAC
GGCAAGGGGCAGGAGGAGGTGCCCGCCCAGGTGGAGGGGCCGGGCATGGCCGTGGCCTACAACGCCCGCTA
CCTCCTCGAGGCCCTCGCCCCCGTGGGGGACCGGGCCCACCTGGGCATCTCCGGGCCCACGAGTCCGAGCC
TCATCTGGGGGACGGGGAGGGGTACCGGGCGGTGGTGGTGCCCCTCAGGGTCTAG 3' UTR
ggggtagtatggggcggggagcgtgaagcgcttccacaagggaggttgggcatgaccaccatcgtcggcg
tccgggcacgcgaggttttggattccaggggctttcccacggtagaggcggaggtggagctggaaggcggg
gccaggggccgggccatggtgccctccggggcctccaccggaacccacgaggccctggagctcagggacgg
cggcaagcgctacctgggcaaggggtgcgccgggcggtggagaacgtcaacgagcgcatcgcccccgagc
tcgtcggcatggacgccctggaccaggaaggggtggaccgggccatgctggagctggacggcaccccaac
aaggccaacctgggagcgaacgccgtcctcgcggtctccctggccgtggcccgggcggcggccgaggccct
gggcctgccccttaccgctacctgggcggggtccaggggtcaccctgcccgtgccctcatgaacgtca
tcaacggggggaagcacgccgacaaccgggtggacttccaggagttcatgctggtgcccgcggggcggga
agcttcgccgaggccttgaggatcggggccgaggtcttccacaccctcaaggccgtcctcaaggagaaggg
ctacagcaccaacgtggggacgagggaggcttcgccccccgacctcaggagcaacgaggaggcggtggagc
ttttgctcctcgccattgagcgggcggggtacaccccgggccaggaggtctccctggccctggacccggcc
acgagcgagctttaccgggacgggaagtaccacctggaaggggagggcaaggtcctctcctcggaggagat
ggtggccttctggggaggcctgggtggagaagtacccatccgctccattgaggacggccttgccgaggacg
actgggaggggtggcggcttctcaccgagcgcctgggggggaaggtccagctcgtggggacgacctcttc
gtcaccaacccggaaaggctccgggcggggattgagcggggggtggccaacgccatcctggtcaaggtgaa
ccagatcgggaccctctcggaaaccctcgaggccatccgcctggcccagcgctcggggtacagggcggtga
tcgagaattc

Fig. 62

SEQ ID NO: 23 amino acid sequence

MNITVPKKLLSDQLSLLERIVPSRSANPLYTYLGLYAEEGALILFGTNGEVDLEVRLPA
EAQSLPRVLVPAQPFFQLVRSLPGDLVALGLASEPGQGGQLELSSGRFRTRLSLAPAEG
YPELLVPEGEDKGAFPLRTRMPSGELVKALTHVRYAASNEEYRAIFRGVQLEFSPQGFR
AVASDGYRLALYDLPLPQGFQAKAVVPARSVDEMVRVLKGADGAEADLALGEGVLALAL
EGGSGVRMALRLMEGEFPDYQRVIPQEFALRVQVEGEALREAVRRVSVLSDRQNHRVDL
LLEEGRILLSAEGDYGKGQEEVPAQVEGPGMAVAYNARYLLEALAPVGDRAHLGISGPT
SPSLIWGDGEGYRAVVVPLRV

Fig. 63

SEQUENCE LISTING

<160> NUMBER OF SEQ ID NOS: 98

<210> SEQ ID NO 1
<211> LENGTH: 34
<212> TYPE: DNA
<213> ORGANISM: Artificial Sequence
<220> FEATURE:
<223> OTHER INFORMATION: ATG linker/adaptor

<400> SEQUENCE: 1
cgataaaaaa aaaggccggc cgctagcggt acca                    34

<210> SEQ ID NO 2
<211> LENGTH: 57
<212> TYPE: DNA
<213> ORGANISM: Artificial Sequence
<220> FEATURE:
<223> OTHER INFORMATION: ATG linker/adaptor

<400> SEQUENCE: 2
ctagaggagg ttaattaacc atggaaaaaa aaaggtacca aaaaaaagg ccggcca    57

<210> SEQ ID NO 3
<211> LENGTH: 24
<212> TYPE: DNA
<213> ORGANISM: Artificial Sequence
<220> FEATURE:
<223> OTHER INFORMATION: ATG linker/adaptor

<400> SEQUENCE: 3
ttaaatgcat aaaaaaaaag gtac                    24

<210> SEQ ID NO 4
<211> LENGTH: 39
<212> TYPE: DNA
<213> ORGANISM: Artificial Sequence
<220> FEATURE:
<223> OTHER INFORMATION: ATG linker/adaptor

<400> SEQUENCE: 4
taacatatga aaaaaaaac caggttgcta gcggtacca                    39

<210> SEQ ID NO 5
<211> LENGTH: 44
<212> TYPE: DNA
<213> ORGANISM: Artificial Sequence
<220> FEATURE:
<223> OTHER INFORMATION: ATG linker/adaptor

<400> SEQUENCE: 5
ctaggaaaaa aaaggtacc aaaaaaaag gccggccact agtg                    44

<210> SEQ ID NO 6
<211> LENGTH: 44
<212> TYPE: DNA
<213> ORGANISM: Artificial Sequence
<220> FEATURE:
<223> OTHER INFORMATION: ATG linker/adaptor

<400> SEQUENCE: 6
ggtaccaaaa atgcatgagc tcgctagcaa gcttaaaaaa aaaa                    44

<210> SEQ ID NO 7
<211> LENGTH: 41

<212> TYPE: DNA
<213> ORGANISM: Artificial Sequence
<220> FEATURE:
<223> OTHER INFORMATION: ATG linker/adaptor

<400> SEQUENCE: 7
gaaaaaaaaa accggtggat ccgcggaaaa aaaaccatgg a            41

<210> SEQ ID NO 8
<211> LENGTH: 45
<212> TYPE: DNA
<213> ORGANISM: Artificial Sequence
<220> FEATURE:
<223> OTHER INFORMATION: ATG linker/adaptor

<400> SEQUENCE: 8
ttgaggaggt atcgataaaa aaaccggtcc taggctagct cgaga        45

<210> SEQ ID NO 9
<211> LENGTH: 879
<212> TYPE: DNA
<213> ORGANISM: Thermus thermophilus

<400> SEQUENCE: 9
atggtcatcg ccttcaccgg ggatcccttc ctggcgcggg aggccctctt agaggaggca    60
aggcttaggg gcctttcccg cttcaccgag cccacccccgg aggccctggc ccaggccctc   120
gccccggggc ttttcggggg cggggggggcg atgctggacc tgaggaggt ggggggaggcg   180
gagtggaagg ccctaaagcc cctcctggaa agcgtgcccg agggcgtccc cgtcctcctc   240
ctggacccta agccaagccc ctcccggggcg gccttctacc ggaaccggga aaggcgggac   300
ttccccaccc ccaagggaaa ggacctggtg cggcacctgg aaaaccgggc caagcgcctg   360
gggctcaggc tcccgggcgg ggtggcccag tacctggcct ccctggaggg ggacctcgag   420
gccctggaac gggagctgga agcttgcc ctcctctccc ctcccctcac cctggagaag     480
gtggagaagg tggtggcct gaggcccccc ctcacgggct tgacctggt gcgctccgtc     540
ctggagaagg accccaagga ggccctcctg cgcctcaggc gcctcaagga ggaggggggag  600
gagcccctca ggctcctcgg ggccctctcc tggcagttcg ccctcctcgc ccgggccttc   660
ttcctcctcc gggaaaaccc caggcccaag gaggaggacc tcgcccgcct cgaggcccac   720
ccctacgccg ccaaaaaggc cctggaggcg gcgaggcgcc ttacggaaga agccctcaag   780
gaggccctgg acgccctcat ggaggcggaa aagagggcca aggggggggaa agacccatgg   840
cttgccctgg aggcggcggt cctccgcctc gcccgttga                          879

<210> SEQ ID NO 10
<211> LENGTH: 292
<212> TYPE: PRT
<213> ORGANISM: Thermus thermophilus

<400> SEQUENCE: 10

Met Val Ile Ala Phe Thr Gly Asp Pro Phe Leu Ala Arg Glu Ala Leu
1               5                   10                  15

Leu Glu Glu Ala Arg Leu Arg Gly Leu Ser Arg Phe Thr Glu Pro Thr
            20                  25                  30

Pro Glu Ala Leu Ala Gln Ala Leu Ala Pro Gly Leu Phe Gly Gly Gly
        35                  40                  45

Gly Ala Met Leu Asp Leu Arg Glu Val Gly Glu Ala Glu Trp Lys Ala
    50                  55                  60

```
Leu Lys Pro Leu Leu Glu Ser Val Pro Glu Gly Val Pro Val Leu Leu
 65                  70                  75                  80

Leu Asp Pro Lys Pro Ser Pro Ser Arg Ala Ala Phe Tyr Arg Asn Arg
                 85                  90                  95

Glu Arg Arg Asp Phe Pro Thr Pro Lys Gly Lys Asp Leu Val Arg His
            100                 105                 110

Leu Glu Asn Arg Ala Lys Arg Leu Gly Leu Arg Leu Pro Gly Gly Val
        115                 120                 125

Ala Gln Tyr Leu Ala Ser Leu Glu Gly Asp Leu Glu Ala Leu Glu Arg
    130                 135                 140

Glu Leu Glu Lys Leu Ala Leu Leu Ser Pro Pro Leu Thr Leu Glu Lys
145                 150                 155                 160

Val Glu Lys Val Val Ala Leu Arg Pro Pro Leu Thr Gly Phe Asp Leu
                165                 170                 175

Val Arg Ser Val Leu Glu Lys Asp Pro Lys Glu Ala Leu Leu Arg Leu
            180                 185                 190

Arg Arg Leu Lys Glu Glu Gly Glu Pro Leu Arg Leu Leu Gly Ala
        195                 200                 205

Leu Ser Trp Gln Phe Ala Leu Leu Ala Arg Ala Phe Phe Leu Leu Arg
    210                 215                 220

Glu Asn Pro Arg Pro Lys Glu Glu Asp Leu Ala Arg Leu Glu Ala His
225                 230                 235                 240

Pro Tyr Ala Ala Lys Lys Ala Leu Glu Ala Ala Arg Arg Leu Thr Glu
                245                 250                 255

Glu Ala Leu Lys Glu Ala Leu Asp Ala Leu Met Glu Ala Glu Lys Arg
            260                 265                 270

Ala Lys Gly Gly Lys Asp Pro Trp Leu Ala Leu Glu Ala Ala Val Leu
        275                 280                 285

Arg Leu Ala Arg
    290

<210> SEQ ID NO 11
<211> LENGTH: 27
<212> TYPE: DNA
<213> ORGANISM: Artificial Sequence
<220> FEATURE:
<223> OTHER INFORMATION: ATG primer P134-S592pst

<400> SEQUENCE: 11
gaattctgca ggtcatcgcc ttcaccg                                  27

<210> SEQ ID NO 12
<211> LENGTH: 21
<212> TYPE: DNA
<213> ORGANISM: Artificial Sequence
<220> FEATURE:
<223> OTHER INFORMATION: ATG primer P139-S181

<400> SEQUENCE: 12
gggggaccgg atcgccttct a                                       21

<210> SEQ ID NO 13
<211> LENGTH: 31
<212> TYPE: DNA
<213> ORGANISM: Artificial Sequence
<220> FEATURE:
<223> OTHER INFORMATION: ATG primer P139-A1082

<400> SEQUENCE: 13
```

```
gtacgcccac ggtcatgtct ctaagtctaa g                                    31

<210> SEQ ID NO 14
<211> LENGTH: 29
<212> TYPE: DNA
<213> ORGANISM: Artificial Sequence
<220> FEATURE:
<223> OTHER INFORMATION: ATG primer P139-S91

<400> SEQUENCE: 14 ctcccccct cggtgcgggc cctggtgaa                                         29

<210> SEQ ID NO 15
<211> LENGTH: 22
<212> TYPE: DNA
<213> ORGANISM: Artificial Sequence
<220> FEATURE:
<223> OTHER INFORMATION: ATG primer P139-A1407

<400> SEQUENCE: 15
ctcggcgctg tagtggatga cg                                               22

<210> SEQ ID NO 16
<211> LENGTH: 807
<212> TYPE: DNA
<213> ORGANISM: Thermus thermophilus

<400> SEQUENCE: 16
atggctctac acccggctca ccctggggca ataatcgggc acgaggccgt tctcgccctc      60
cttccccgcc tcaccgccca gaccctgctc ttctccggcc ccgagggggt ggggcggcgc     120
accgtggccc gctggtacgc ctgggggctc aaccgcggct ccccccgcc ctccctgggg      180 gagcacccgg acgtcctcga ggtggggccc aaggcccggg acctccgggg ccgggccgag     240
gtgcggctgg aggaggtggc gcccctcttg gagtggtgct ccagccaccc ccgggagcgg     300
gtgaaggtgg ccatcctgga ctcggcccac ctcctcaccg aggccgcggc caacgccctc     360
ctcaagctcc tggaggagcc ccttcctac gcccgcatcg tcctcatcgc cccaagccgc     420 gccacccctcc tccccacccct ggcctcccgg ccacggagg tggccttcgc ccccgtgccc    480
gaggaggccc tgcgcgccct tacccaggac ccgggggctcc tccgctacgc cgccggggcc    540
ccgggccgcc tccttagggc cctccaggac ccggagggggt accgggcccg catggccagg    600
gcgcaaaggg tcctgaaagc cccgcccctg gagcgcctcg ccctgcttcg ggagcttttg     660
gccgaggagg aggggggtcca cgccctccac gccgtcctga agcgcccgga gcacctcctt    720
gccctggagc gggcgcggga ggccctggag gggtacgtga gccccgagct ggtcctcgcc    780
cggctggcct tagacttaga gacatga                                          807

<210> SEQ ID NO 17
<211> LENGTH: 268
<212> TYPE: PRT
<213> ORGANISM: Thermus thermophilus

<400> SEQUENCE: 17

Met Ala Leu His Pro Ala His Pro Gly Ala Ile Ile Gly His Glu Ala
1               5                   10                  15

Val Leu Ala Leu Leu Pro Arg Leu Thr Ala Gln Thr Leu Leu Phe Ser
            20                  25                  30

Gly Pro Glu Gly Val Gly Arg Arg Thr Val Ala Arg Trp Tyr Ala Trp
        35                  40                  45
```

```
Gly Leu Asn Arg Gly Phe Pro Pro Ser Leu Gly Glu His Pro Asp
        50                  55                  60

Val Leu Glu Val Gly Pro Lys Ala Arg Asp Leu Arg Gly Arg Ala Glu
 65                  70                  75                  80

Val Arg Leu Glu Glu Val Ala Pro Leu Leu Glu Trp Cys Ser Ser His
                 85                  90                  95

Pro Arg Glu Arg Val Lys Val Ala Ile Leu Asp Ser Ala His Leu Leu
                100                 105                 110

Thr Glu Ala Ala Ala Asn Ala Leu Leu Lys Leu Leu Glu Glu Pro Pro
                115                 120                 125

Ser Tyr Ala Arg Ile Val Leu Ile Ala Pro Ser Arg Ala Thr Leu Leu
        130                 135                 140

Pro Thr Leu Ala Ser Arg Ala Thr Glu Val Ala Phe Ala Pro Val Pro
145                 150                 155                 160

Glu Glu Ala Leu Arg Ala Leu Thr Gln Asp Pro Gly Leu Leu Arg Tyr
                165                 170                 175

Ala Ala Gly Ala Pro Gly Arg Leu Leu Arg Ala Leu Gln Asp Pro Glu
                180                 185                 190

Gly Tyr Arg Ala Arg Met Ala Arg Ala Gln Arg Val Leu Lys Ala Pro
            195                 200                 205

Pro Leu Glu Arg Leu Ala Leu Leu Arg Glu Leu Leu Ala Glu Glu Glu
        210                 215                 220

Gly Val His Ala Leu His Ala Val Leu Lys Arg Pro Glu His Leu Leu
225                 230                 235                 240

Ala Leu Glu Arg Ala Arg Glu Ala Leu Glu Gly Tyr Val Ser Pro Glu
                245                 250                 255

Leu Val Leu Ala Arg Leu Ala Leu Asp Leu Glu Thr
                260                 265

<210> SEQ ID NO 18
<211> LENGTH: 31
<212> TYPE: DNA
<213> ORGANISM: Artificial Sequence
<220> FEATURE:
<223> OTHER INFORMATION: ATG primer P139-S254pst

<400> SEQUENCE: 18
gaattctgca ggctctacac ccggctcacc c                              31

<210> SEQ ID NO 19
<211> LENGTH: 31
<212> TYPE: DNA
<213> ORGANISM: Artificial Sequence
<220> FEATURE:
<223> OTHER INFORMATION: ATG primer P139-A1081stopspe

<400> SEQUENCE: 19
ggacactagt tcatcatgtc tctaagtcta a                              31

<210> SEQ ID NO 20
<211> LENGTH: 44
<212> TYPE: DNA
<213> ORGANISM: Artificial Sequence
<220> FEATURE:
<223> OTHER INFORMATION: forward ATG primer P69-S541

<400> SEQUENCE: 20
ggatatgcat tgaggaggat cgattaatgg gccgcaaact ccgc                44
```

```
<210> SEQ ID NO 21
<211> LENGTH: 21
<212> TYPE: DNA
<213> ORGANISM: Artificial Sequence
<220> FEATURE:
<223> OTHER INFORMATION: reverse ATG primer P69-A971

<400> SEQUENCE: 21
cggctcgcca ggcgcaccag g                                              21

<210> SEQ ID NO 22
<211> LENGTH: 2363
<212> TYPE: DNA
<213> ORGANISM: Thermus thermophilus
<220> FEATURE:
<221> NAME/KEY: misc_feature
<223> OTHER INFORMATION: Includes 5' UTR and 3' UTR

<400> SEQUENCE: 22
ggtaccgggc cccctcgag gtcgacggta tcgataagct tgatatcgaa aaagagagtc       60
gtaatagccg ttaaggagg cgtcgggcaa tgaacataac ggttcccaag aaactcctct      120
cggaccagct ttcctcctg gagcgcatcg tccctctag aagcgccaac cccctctaca      180
cctacctggg gctttacgcc gaggaagggg ccttgatcct cttcgggacc aacggggagg     240
tggacctcga ggtccgcctc cccgccgagg cccaaagcct tccccgggtg ctcgtccccg     300
cccagccctt cttccagctg gtgcggagcc ttcctgggga cctcgtggcc ctcggcctcg     360
cctcggagcc gggccagggg gggcagctgg agctctcctc cgggcgcttc cgcacccggc     420
tcagcctggc ccctgccgag ggctaccccg agcttctggt gcccgagggg gaggacaagg     480
gggccttccc cctgcggacg cggatgccct ccggggagtc cgtcaaggcc ttgacccacg     540
tgcgctacgc cgcgagcaac gaggagtacc gggccatctt ccgcggggtg cagctggagt     600 tctccccca gggcttccgg gcggtggcct ccgacgggta ccgcctcgcc ctctacgacc     660 tgccctgcc ccaagggttc caggccaagg ccgtggtccc cgcccggagc gtggacgaga     720
tggtgcgggt cctgaagggg gcggacgggg ccgaggccga cctcgccctg gcgagggg     780 tgttggccct ggccctcgag ggcggaagcg gggtccggat ggccctccgc ctcatggaag     840
gggagttccc cgactaccag aggtcatcc cccaggagtt cgccctcagg gtccaggtgg     900 aggggaggc cctcagggag gcggtgcgcc gggtgagcgt cctctccgac cggcagaacc     960
accgggtgga cctccttttg gaggaggcc ggatcctcct ttccgccgag ggggactacg    1020
gcaaggggca ggaggaggtg cccgcccagg tggagggcc gggcatggcc gtggcctaca    1080
acgcccgcta cctcctcgag gccctcgccc cgtggggga ccgggcccac ctgggcatct    1140
ccgggcccac gagtccgagc ctcatctggg gggacgggga ggggtaccgg gcggtggtgg    1200 tgccctcag gtctaggg gtagtatggg gcggggagc gtgaagcgct tccacaaggg    1260
aggttgggca tgaccaccat cgtcggcgtc cgggcacgcg aggttttgga ttccaggggc    1320
tttcccacgg tagaggcgga ggtggagctg aaggcgggg ccaggggccg ggccatggtg    1380
ccctccgggg cctccaccgg aacccacgag gccctggagc tcaggacgg cggcaagcgc    1440 tacctgggca ggggggtgcg ccgggcggtg gagaacgtca cgagcgcat cgcccccgag    1500 ctcgtcggca tggacgccct ggaccaggaa gggtggacc gggccatgct ggagctggac    1560
ggcaccccca acaaggccaa cctgggagcg aacgccgtcc tcgcggtctc cctggccgtg    1620
gcccgggcgg cggccgaggc cctgggcctg ccccttacc gctacctggg cggggtccag    1680
ggggtcaccc tgcccgtgcc cctcatgaac gtcatcaacg gggggaagca cgccgacaac    1740
```

-continued

```
cgggtggact tccaggagtt catgctggtg cccgcggggg cgggaagctt cgccgaggcc    1800
ttgaggatcg gggccgaggt cttccacacc ctcaaggccg tcctcaagga agggctac      1860 agcaccaacg tggggacga gggaggcttc gcccccgacc tcaggagcaa cgaggaggcg     1920
gtggagcttt tgctcctcgc cattgagcgg gcggggtaca ccccgggcca ggaggtctcc    1980
ctggccctgg acccggccac gagcgagctt taccgggacg ggaagtacca cctggaaggg    2040
gagggcaagg tcctctcctc ggaggagatg gtggccttct gggaggcctg ggtggagaag    2100
taccccatcc gctccattga ggacggcctt gccgaggacg actgggaggg gtggcggctt    2160
ctcaccgagc gcctgggggg gaaggtccag ctcgtggggg acgacctctt cgtcaccaac    2220
ccggaaaggc tccgggcggg gattgagcgg ggggtggcca cgccatcct ggtcaaggtg     2280 aaccagatcg ggaccctctc ggaaaccctc gaggccatcc gcctggccca gcgctcgggg   2340
tacagggcgg tgatcgagaa ttc                                           2363
```

<210> SEQ ID NO 23
<211> LENGTH: 375
<212> TYPE: PRT
<213> ORGANISM: Thermus thermophilus

<400> SEQUENCE: 23

```
Met Asn Ile Thr Val Pro Lys Lys Leu Leu Ser Asp Gln Leu Ser Leu
1               5                   10                  15

Leu Glu Arg Ile Val Pro Ser Arg Ser Ala Asn Pro Leu Tyr Thr Tyr
            20                  25                  30

Leu Gly Leu Tyr Ala Glu Glu Gly Ala Leu Ile Leu Phe Gly Thr Asn
        35                  40                  45

Gly Glu Val Asp Leu Glu Val Arg Leu Pro Ala Glu Ala Gln Ser Leu
    50                  55                  60

Pro Arg Val Leu Val Pro Ala Gln Pro Phe Phe Gln Leu Val Arg Ser
65                  70                  75                  80

Leu Pro Gly Asp Leu Val Ala Leu Gly Leu Ala Ser Glu Pro Gly Gln
                85                  90                  95

Gly Gly Gln Leu Glu Leu Ser Ser Gly Arg Phe Arg Thr Arg Leu Ser
            100                 105                 110

Leu Ala Pro Ala Glu Gly Tyr Pro Glu Leu Leu Val Pro Glu Gly Glu
        115                 120                 125

Asp Lys Gly Ala Phe Pro Leu Arg Thr Arg Met Pro Ser Gly Glu Leu
    130                 135                 140

Val Lys Ala Leu Thr His Val Arg Tyr Ala Ala Ser Asn Glu Glu Tyr
145                 150                 155                 160

Arg Ala Ile Phe Arg Gly Val Gln Leu Glu Phe Ser Pro Gln Gly Phe
                165                 170                 175

Arg Ala Val Ala Ser Asp Gly Tyr Arg Leu Ala Leu Tyr Asp Leu Pro
            180                 185                 190

Leu Pro Gln Gly Phe Gln Ala Lys Ala Val Pro Ala Arg Ser Val
        195                 200                 205

Asp Glu Met Val Arg Val Leu Lys Gly Ala Asp Gly Ala Glu Ala Asp
    210                 215                 220

Leu Ala Leu Gly Glu Gly Val Leu Ala Leu Leu Glu Gly Gly Ser
225                 230                 235                 240

Gly Val Arg Met Ala Leu Arg Leu Met Glu Gly Glu Phe Pro Asp Tyr
                245                 250                 255
```

-continued

Gln Arg Val Ile Pro Gln Glu Phe Ala Leu Arg Val Gln Val Glu Gly
            260                 265                 270

Glu Ala Leu Arg Glu Ala Val Arg Arg Val Ser Val Leu Ser Asp Arg
        275                 280                 285

Gln Asn His Arg Val Asp Leu Leu Glu Glu Gly Arg Ile Leu Leu
    290                 295                 300

Ser Ala Glu Gly Asp Tyr Gly Lys Gly Gln Glu Glu Val Pro Ala Gln
305                 310                 315                 320

Val Glu Gly Pro Gly Met Ala Val Ala Tyr Asn Ala Arg Tyr Leu Leu
                325                 330                 335

Glu Ala Leu Ala Pro Val Gly Asp Arg Ala His Leu Gly Ile Ser Gly
            340                 345                 350

Pro Thr Ser Pro Ser Leu Ile Trp Gly Asp Gly Glu Gly Tyr Arg Ala
        355                 360                 365

Val Val Val Pro Leu Arg Val
            370         375

<210> SEQ ID NO 24
<211> LENGTH: 33
<212> TYPE: DNA
<213> ORGANISM: Artificial Sequence
<220> FEATURE:
<223> OTHER INFORMATION: ATG forward primer P118-S85

<400> SEQUENCE: 24
aactgcagaa cataacggtt cccaagaaac tcc          33

<210> SEQ ID NO 25
<211> LENGTH: 22
<212> TYPE: DNA
<213> ORGANISM: Artificial Sequence
<220> FEATURE:
<223> OTHER INFORMATION: ATG reverse primer P118-A731

<400> SEQUENCE: 25
gacccgcacc atctcgtcca cg          22

<210> SEQ ID NO 26
<211> LENGTH: 147
<212> TYPE: PRT
<213> ORGANISM: Aquifex

<400> SEQUENCE: 26

Met Leu Asn Lys Val Phe Ile Ile Gly Arg Leu Thr Gly Asp Pro Val
1               5                   10                  15

Ile Thr Tyr Leu Pro Ser Gly Thr Pro Val Val Glu Phe Thr Leu Ala
            20                  25                  30

Tyr Asn Arg Arg Tyr Lys Asn Gln Asn Gly Glu Phe Gln Glu Glu Ser
        35                  40                  45

His Phe Phe Asp Val Lys Ala Tyr Gly Lys Met Ala Glu Asp Trp Ala
    50                  55                  60

Thr Arg Phe Ser Lys Gly Tyr Leu Val Leu Glu Gly Arg Leu Ser
65                  70                  75                  80

Gln Glu Lys Trp Glu Lys Glu Gly Lys Lys Phe Ser Lys Val Arg Ile
                85                  90                  95

Ile Ala Glu Asn Val Arg Leu Ile Asn Arg Pro Lys Gly Ala Glu Leu
            100                 105                 110

Gln Ala Glu Glu Glu Glu Val Pro Pro Ile Glu Glu Ile Glu
        115                 120                 125

-continued

```
Lys Leu Gly Lys Glu Glu Lys Pro Phe Thr Asp Glu Glu Asp Glu
        130                 135                 140
Ile Pro Phe
145

<210> SEQ ID NO 27
<211> LENGTH: 172
<212> TYPE: PRT
<213> ORGANISM: Bacillus subtilis

<400> SEQUENCE: 27

Met Leu Asn Arg Val Val Leu Val Gly Arg Leu Thr Lys Asp Pro Glu
1               5                   10                  15
Leu Arg Tyr Thr Pro Asn Gly Ala Ala Val Ala Thr Phe Thr Leu Ala
            20                  25                  30
Val Asn Arg Thr Phe Thr Asn Gln Ser Gly Glu Arg Glu Ala Asp Phe
        35                  40                  45
Ile Asn Cys Val Thr Trp Arg Arg Gln Ala Glu Asn Val Ala Asn Phe
    50                  55                  60
Leu Lys Lys Gly Ser Leu Ala Gly Val Asp Gly Arg Leu Gln Thr Arg
65                  70                  75                  80
Asn Tyr Glu Asn Gln Gln Gly Gln Arg Val Phe Val Thr Glu Val Gln
                85                  90                  95
Ala Glu Ser Val Gln Phe Leu Glu Pro Lys Asn Gly Gly Ser Gly
            100                 105                 110
Ser Gly Gly Tyr Asn Glu Gly Asn Ser Gly Gly Gln Tyr Phe Gly
        115                 120                 125
Gly Gly Gln Asn Asp Asn Pro Phe Gly Gly Asn Gln Asn Gln Arg
    130                 135                 140
Arg Asn Gln Gly Asn Ser Phe Asn Asp Asp Pro Phe Ala Asn Asp Gly
145                 150                 155                 160
Lys Pro Ile Asp Ile Ser Asp Asp Leu Pro Phe
                165                 170

<210> SEQ ID NO 28
<211> LENGTH: 20
<212> TYPE: DNA
<213> ORGANISM: Artificial Sequence
<220> FEATURE:
<223> OTHER INFORMATION: allows detection of stimulation by b

<400> SEQUENCE: 28
tgcaaatcgc gttagcttag                                               20

<210> SEQ ID NO 29
<211> LENGTH: 26
<212> TYPE: DNA
<213> ORGANISM: Artificial Sequence
<220> FEATURE:
<223> OTHER INFORMATION: forward/sense ATG primer P138-S540

<400> SEQUENCE: 29
gatccatggc tcgaggcctg aaccgc                                        26

<210> SEQ ID NO 30
<211> LENGTH: 30
<212> TYPE: DNA
<213> ORGANISM: Artificial Sequence
<220> FEATURE:
<223> OTHER INFORMATION: reverse/antisense primer P138-A1348
```

<400> SEQUENCE: 30

```
gacggtacct catcaaaacg gcaaatcctc                                    30
```

<210> SEQ ID NO 31
<211> LENGTH: 792
<212> TYPE: DNA
<213> ORGANISM: Thermus thermophilus

<400> SEQUENCE: 31

```
atggctcgag gcctgaaccg cgttttcctc atcggcgccc tcgccacccg gccggacatg   60
cgctacaccc cggcggggct cgccattttg gacctgaccc tcgccggtca ggacctgctc  120
cttttccgata acgggggga gcgggaggtg tcctggtacc accgggtgag gctcttaggc  180
cgccaggcgg agatgtgggg cgacctcttg gaccaagggc agctcgtctt cgtggagggc  240
cgcctggagt accgccagtg ggaagggag ggagcgagct ccagatccgg               300
gccgacttcc tggaccccct ggacgaccgg ggaaggagc gggcggagga cagccggggc   360
cagcccaggc tccgcgccgc cctgaaccag gtcttcctca tgggcaacct gacccgggac   420
ccggaactcc gctacacccc ccagggcacc gcggtggccc ggctgggcct ggcggtgaac   480
gagcgccgcc aggggggcgga ggagcgcacc cacttcgtgg aggttcaggc ctggcgcgac   540
ctggcggagt gggccgccga gctgaggaag ggcgacggcc ttttcgtgat cggcaggttg   600
gtgaacgact cctggaccag ctccagcggc gagcggcgct tccagacccg tgtgaggcc   660
ctcaggctgg agcgccccac ccgtggacct gcccaggccg gcggaagcag gtcccgcgaa   720
gtccagacgg gtggggtgga cattgacgaa ggcttggaag actttccgcc ggaggaggat   780
ttgccgtttt ga                                                       792
```

<210> SEQ ID NO 32
<211> LENGTH: 263
<212> TYPE: PRT
<213> ORGANISM: Thermus thermophilus

<400> SEQUENCE: 32

```
Met Ala Arg Gly Leu Asn Arg Val Phe Leu Ile Gly Ala Leu Ala Thr
1               5                   10                  15

Arg Pro Asp Met Arg Tyr Thr Pro Ala Gly Leu Ala Ile Leu Asp Leu
                20                  25                  30

Thr Leu Ala Gly Gln Asp Leu Leu Leu Ser Asp Asn Gly Gly Glu Arg
            35                  40                  45

Glu Val Ser Trp Tyr His Arg Val Arg Leu Leu Gly Arg Gln Ala Glu
        50                  55                  60

Met Trp Gly Asp Leu Leu Asp Gln Gly Gln Leu Val Phe Val Glu Gly
65                  70                  75                  80

Arg Leu Glu Tyr Arg Gln Trp Glu Arg Glu Gly Lys Arg Ser Glu
                85                  90                  95

Leu Gln Ile Arg Ala Asp Phe Leu Asp Pro Leu Asp Arg Gly Lys
            100                 105                 110

Glu Arg Ala Glu Asp Ser Arg Gly Gln Pro Arg Leu Arg Ala Ala Leu
        115                 120                 125

Asn Gln Val Phe Leu Met Gly Asn Leu Thr Arg Asp Pro Glu Leu Arg
    130                 135                 140

Tyr Thr Pro Gln Gly Thr Ala Val Ala Arg Leu Gly Leu Ala Val Asn
145                 150                 155                 160
```

```
Glu Arg Arg Gln Gly Ala Glu Glu Arg Thr His Phe Val Glu Val Gln
                165                 170                 175

Ala Trp Arg Asp Leu Ala Glu Trp Ala Ala Glu Leu Arg Lys Gly Asp
            180                 185                 190

Gly Leu Phe Val Ile Gly Arg Leu Val Asn Asp Ser Trp Thr Ser Ser
            195                 200                 205

Ser Gly Glu Arg Arg Phe Gln Thr Arg Val Glu Ala Leu Arg Leu Glu
        210                 215                 220

Arg Pro Thr Arg Gly Pro Ala Gln Ala Gly Ser Arg Ser Arg Glu
225                 230                 235                 240

Val Gln Thr Gly Gly Val Asp Ile Asp Glu Gly Leu Glu Asp Phe Pro
                245                 250                 255

Pro Glu Glu Asp Leu Pro Phe
            260

<210> SEQ ID NO 33
<211> LENGTH: 29
<212> TYPE: DNA
<213> ORGANISM: Artificial Sequence
<220> FEATURE:
<223> OTHER INFORMATION: ATG primer P138-A1343spe

<400> SEQUENCE: 33
gacgactagt aaacggcaaa tcctcctcc                                      29

<210> SEQ ID NO 34
<211> LENGTH: 36
<212> TYPE: DNA
<213> ORGANISM: Artificial Sequence
<220> FEATURE:
<223> OTHER INFORMATION: Tth probe

<400> SEQUENCE: 34
cctcgaacac ctcctgccgc aagacccttc gaccca                              36

<210> SEQ ID NO 35
<211> LENGTH: 36
<212> TYPE: DNA
<213> ORGANISM: Artificial Sequence
<220> FEATURE:
<223> OTHER INFORMATION: probe

<400> SEQUENCE: 35
cctcgaacac ctcctgccgc aagacccttc gaccca                              36

<210> SEQ ID NO 36
<211> LENGTH: 600
<212> TYPE: DNA
<213> ORGANISM: Thermus thermophilus

<400> SEQUENCE: 36
gtgcctgcag gtctggagga cgtcaccctg gaccagctcc tttacaccgc ctttgacctg     60
gagaccacgg gcctggaccc ggagcaagat gccgtggtgg ccctcgccgg ggtccatatc    120
ctgggtcgaa gggtcttgcg gcaggaggtg ttcgaggccc tggtgaaccc ggggcgcccc    180 atctccccg cggccacggc ggtccacggc ctcacggcgg agatgctccg ggacaagcct    240
cccctagagg cggtcctccc cgccttccgc gccttcgtcc aggacacggt gctggtggcc    300
cacaacgggg cctttgacct ggcctttctg cgccgggcgg cctgaccag ccccccctc    360 ctggacaccc tcctcctcgc ccagctcctc ttccccgacc tcaaggacta ccgcctcgag    420
```

```
gccctggccc accgcttcgg cgtccccgcc accgggcggc acaccgcctt gggcgatgcg    480
ctgatgacgg cggaggtctt cgtgaggatg cagcccctcc tctttgaacg ggggcttagg    540
cggctctggg acgtggtgga ggcctgccgc cgcctcccct tggcccggct caggtactga    600
```

<210> SEQ ID NO 37
<211> LENGTH: 199
<212> TYPE: PRT
<213> ORGANISM: Thermus thermophilus

<400> SEQUENCE: 37

Val Pro Ala Gly Leu Glu Asp Val Thr Leu Asp Gln Leu Leu Tyr Thr
1               5                   10                  15

Ala Phe Asp Leu Glu Thr Thr Gly Leu Asp Pro Glu Gln Asp Ala Val
            20                  25                  30

Val Ala Leu Ala Gly Val His Ile Leu Gly Arg Arg Val Leu Arg Gln
        35                  40                  45

Glu Val Phe Glu Ala Leu Val Asn Pro Gly Arg Pro Ile Ser Pro Ala
    50                  55                  60

Ala Thr Ala Val His Gly Leu Thr Ala Glu Met Leu Arg Asp Lys Pro
65                  70                  75                  80

Pro Leu Glu Ala Val Leu Pro Ala Phe Arg Ala Phe Val Gln Asp Thr
                85                  90                  95

Val Leu Val Ala His Asn Gly Ala Phe Asp Leu Ala Phe Leu Arg Arg
            100                 105                 110

Ala Gly Leu Asp Gln Pro Pro Leu Leu Asp Thr Leu Leu Leu Ala Gln
        115                 120                 125

Leu Leu Phe Pro Asp Leu Lys Asp Tyr Arg Leu Glu Ala Leu Ala His
    130                 135                 140

Arg Phe Gly Val Pro Ala Thr Gly Arg His Thr Ala Leu Gly Asp Ala
145                 150                 155                 160

Leu Met Thr Ala Glu Val Phe Val Arg Met Gln Pro Leu Leu Phe Glu
                165                 170                 175

Arg Gly Leu Arg Arg Leu Trp Asp Val Val Glu Ala Cys Arg Arg Leu
            180                 185                 190

Pro Leu Ala Arg Leu Arg Tyr
        195

<210> SEQ ID NO 38
<211> LENGTH: 25
<212> TYPE: DNA
<213> ORGANISM: Artificial Sequence
<220> FEATURE:
<223> OTHER INFORMATION: forward/sense ATG primer P140-S96cla

<400> SEQUENCE: 38

```
ccatcgatgc ctgcaggtct ggagg                                           25
```

<210> SEQ ID NO 39
<211> LENGTH: 33
<212> TYPE: DNA
<213> ORGANISM: Artificial Sequence
<220> FEATURE:
<223> OTHER INFORMATION: reverse/antisense ATG primer P140-A713kpn

<400> SEQUENCE: 39

```
gacggtacct catcagtacc tgagccgggc caa                                  33
```

<210> SEQ ID NO 40

```
<211> LENGTH: 28
<212> TYPE: DNA
<213> ORGANISM: Artificial Sequence
<220> FEATURE:
<223> OTHER INFORMATION: reverse/antisense ATG primer P140-A708Spe

<400> SEQUENCE: 40
cctcactagt gtacctgagc cgggccaa                                                28

<210> SEQ ID NO 41
<211> LENGTH: 39
<212> TYPE: DNA
<213> ORGANISM: Artificial Sequence
<220> FEATURE:
<223> OTHER INFORMATION: ATG primer P118-S74

<400> SEQUENCE: 41
ggatccaagc ttcatatgaa cataacggtt cccaagaaa                                    39

<210> SEQ ID NO 42
<211> LENGTH: 35
<212> TYPE: DNA
<213> ORGANISM: Artificial Sequence
<220> FEATURE:
<223> OTHER INFORMATION: ATG primer P118-1231

<400> SEQUENCE: 42
gagcagctag cctactagac cctgaggggc accac                                        35

<210> SEQ ID NO 43
<211> LENGTH: 29
<212> TYPE: DNA
<213> ORGANISM: Artificial Sequence
<220> FEATURE:
<223> OTHER INFORMATION: ATG primer P134-A1486spe

<400> SEQUENCE: 43
gaggactagt acgggcgagg cggaggacc                                               29

<210> SEQ ID NO 44
<211> LENGTH: 24
<212> TYPE: DNA
<213> ORGANISM: Artificial Sequence
<220> FEATURE:
<223> OTHER INFORMATION: forward/sense ATG primer P139-S253

<400> SEQUENCE: 44
ctttccccca tggctctaca cccg                                                    24

<210> SEQ ID NO 45
<211> LENGTH: 38
<212> TYPE: DNA
<213> ORGANISM: Artificial Sequence
<220> FEATURE:
<223> OTHER INFORMATION: reverse/antisense ATG primer P139-A1085

<400> SEQUENCE: 45
ggatccggcc ggcctcatca tgtctctaag tctaaggc                                     38

<210> SEQ ID NO 46
<211> LENGTH: 28
<212> TYPE: DNA
<213> ORGANISM: Artificial Sequence
<220> FEATURE:
<223> OTHER INFORMATION: ATG primer P139-A1075

<400> SEQUENCE: 46
```

```
gaggactagt tgtctctaag tctaaggc                                        28

<210> SEQ ID NO 47
<211> LENGTH: 22
<212> TYPE: DNA
<213> ORGANISM: Artificial Sequence
<220> FEATURE:
<223> OTHER INFORMATION: forward ATG primer P38-S1586

<400> SEQUENCE: 47
aactgcagag cgccctctac cg                                              22

<210> SEQ ID NO 48
<211> LENGTH: 22
<212> TYPE: DNA
<213> ORGANISM: Artificial Sequence
<220> FEATURE:
<223> OTHER INFORMATION: reverse ATG primer P38-A2050

<400> SEQUENCE: 48
cggtggtggc gaagacgaag ag                                              22

<210> SEQ ID NO 49
<211> LENGTH: 30
<212> TYPE: DNA
<213> ORGANISM: Artificial Sequence
<220> FEATURE:
<223> OTHER INFORMATION: forward/sense ATG primer P38-S1cla2

<400> SEQUENCE: 49
acttatcgat aatgagcgcc ctctaccgcc                                      30

<210> SEQ ID NO 50
<211> LENGTH: 35
<212> TYPE: DNA
<213> ORGANISM: Artificial Sequence
<220> FEATURE:
<223> OTHER INFORMATION: reverse/antisence ATG primer P38-A1603STOPspe

<400> SEQUENCE: 50
gaggactagt ttattatata ccagtacccc ctatc                                35

<210> SEQ ID NO 51
<211> LENGTH: 24
<212> TYPE: DNA
<213> ORGANISM: Artificial Sequence
<220> FEATURE:
<223> OTHER INFORMATION: forward/sense ATG primer P134-S415

<400> SEQUENCE: 51
cgggagggtg aagcgcaaga tgtc                                            24

<210> SEQ ID NO 52
<211> LENGTH: 21
<212> TYPE: DNA
<213> ORGANISM: Artificial Sequence
<220> FEATURE:
<223> OTHER INFORMATION: reverse/antisense ATG primer P134-A2099

<400> SEQUENCE: 52
gccgcacccc cgccccgtag t                                               21

<210> SEQ ID NO 53
<211> LENGTH: 32
<212> TYPE: DNA
```

<213> ORGANISM: Artificial Sequence
<220> FEATURE:
<223> OTHER INFORMATION: forward/sense ATG primer P134-S585de

<400> SEQUENCE: 53
ggatccaagc ttcatatggt catcgccttc ac                          32

<210> SEQ ID NO 54
<211> LENGTH: 33
<212> TYPE: DNA
<213> ORGANISM: Artificial Sequence
<220> FEATURE:
<223> OTHER INFORMATION: reverse/antisense ATG primer P134-A1493kpn

<400> SEQUENCE: 54
agatctggta cctcatcaac gggcgaggcg gag                         33

<210> SEQ ID NO 55
<211> LENGTH: 28
<212> TYPE: DNA
<213> ORGANISM: Artificial Sequence
<220> FEATURE:
<223> OTHER INFORMATION: forward/sense ATG primer P134-S588cla2

<400> SEQUENCE: 55
actgatcgat aatggtcatc gccttcac                               28

<210> SEQ ID NO 56
<211> LENGTH: 33
<212> TYPE: DNA
<213> ORGANISM: Artificial Sequence
<220> FEATURE:
<223> OTHER INFORMATION: reverse/antisence ATG primer P134-A1491stopspe

<400> SEQUENCE: 56
gaggtactag tcatcaacgg gcgaggcgga gga                         33

<210> SEQ ID NO 57
<211> LENGTH: 34
<212> TYPE: DNA
<213> ORGANISM: Artificial Sequence
<220> FEATURE:
<223> OTHER INFORMATION: forward/sense ATG primer P139-S250cla2

<400> SEQUENCE: 57
actgatcgat aatggctcta cacccggctc accc                        34

<210> SEQ ID NO 58
<211> LENGTH: 31
<212> TYPE: DNA
<213> ORGANISM: Artificial Sequence
<220> FEATURE:
<223> OTHER INFORMATION: reverse/antisence ATG primer P139-A1081stopspe

<400> SEQUENCE: 58
ggacactagt tcatcatgtc tctaagtcta a                           31

<210> SEQ ID NO 59
<211> LENGTH: 35
<212> TYPE: DNA
<213> ORGANISM: Artificial Sequence
<220> FEATURE:
<223> OTHER INFORMATION: forward/sense ATG primer P118-S78cla2

<400> SEQUENCE: 59
agtcatcgat aatgaacata acggttccca agaaa                       35

<210> SEQ ID NO 60
<211> LENGTH: 34
<212> TYPE: DNA
<213> ORGANISM: Artificial Sequence
<220> FEATURE:
<223> OTHER INFORMATION: reverse/antisence ATG primer P118-A1230spe

<400> SEQUENCE: 60
gaggactagt ctactagacc ctgaggggca ccac        34

<210> SEQ ID NO 61
<211> LENGTH: 34
<212> TYPE: DNA
<213> ORGANISM: Artificial Sequence
<220> FEATURE:
<223> OTHER INFORMATION: forward/sense ATG primer P138-S539pst

<400> SEQUENCE: 61
aaactgcagg ctcgaggcct gaaccgcgtt ttcc        34

<210> SEQ ID NO 62
<211> LENGTH: 31
<212> TYPE: DNA
<213> ORGANISM: Artificial Sequence
<220> FEATURE:
<223> OTHER INFORMATION: reverse/antisense ATG primer P138-A1348stopspe

<400> SEQUENCE: 62
gacaactagt catcaaaacg gcaaatcctc c        31

<210> SEQ ID NO 63
<211> LENGTH: 32
<212> TYPE: DNA
<213> ORGANISM: Artificial Sequence
<220> FEATURE:
<223> OTHER INFORMATION: forward/sense ATG primer P138-S533cla2

<400> SEQUENCE: 63
actgatcgat aatggctcga ggcctgaacc gc        32

<210> SEQ ID NO 64
<211> LENGTH: 31
<212> TYPE: DNA
<213> ORGANISM: Artificial Sequence
<220> FEATURE:
<223> OTHER INFORMATION: reverse/antisence ATG primer P138-A1348stopspe

<400> SEQUENCE: 64
gacaactagt catcaaaacg gcaaatcctc c        31

<210> SEQ ID NO 65
<211> LENGTH: 37
<212> TYPE: DNA
<213> ORGANISM: Artificial Sequence
<220> FEATURE:
<223> OTHER INFORMATION: forward/sense ATG primer P159-S1689

<400> SEQUENCE: 65
gactatgcat agcgacgccc tcctagcccc cctcaac        37

<210> SEQ ID NO 66
<211> LENGTH: 35
<212> TYPE: DNA
<213> ORGANISM: Artificial Sequence
<220> FEATURE:

<223> OTHER INFORMATION: reverse/antisense ATG primer P159-A3786

<400> SEQUENCE: 66
gactactagt ctatcatgcc ggcttaagct ccgcg         35

<210> SEQ ID NO 67
<211> LENGTH: 2082
<212> TYPE: DNA
<213> ORGANISM: Thermus thermophilus

<400> SEQUENCE: 67

| | | |
|---|---|---|
| gtgcatagcg acgccctcct agccccctc aacgaggccc agcgccaggc ggtcctccac | 60 |
| tttgaggggc cgccctggt ggtggccggg gcggggagcg ggaagacccg caccgtggtc | 120 |
| caccgggtgg cctacctcgt cgcccgccgg ggggtcttcc cctcggagat cctggccgtc | 180 |
| accttcacca acaaggccgc ggaggagatg cgggagcgcc tccgggggct ggtcccgggg | 240 |
| gcggggagg tctgggtctc caccttccac gccgccgcct tgaggatcct ccgcgtctac | 300 |
| ggggagcggg tgggcctcag gcccggcttt gtggtctacg acgaggacga ccagaccgcc | 360 |
| ctcctcaagg aggtcctgaa ggagctcgcc ctctcggccc ggcccggccc catcaaggcc | 420 |
| cttttggacc gggcgaagaa ccgggccgtg ggccttaagg ccctcctcgg cgagcttccc | 480 |
| gagtactacg ccgggctttc ccggggaagg cttggggacg tcctggtgcg ctaccaggag | 540 |
| gcccttaagg cccaggggc cttggacttc ggggacatcc tcctctacgc cctgaggctt | 600 |
| ttagaggagg acgaggaggt cctcaggctc gtgcgcaagc gggcccgctt catccacgtg | 660 |
| gacgagtacc aggacacgag ccccgtccag taccgcttca cccggcttct cgccggggag | 720 |
| gaggccaacc tcatggccgt gggcgacccc gaccagggga tctactcctt ccgggcggcg | 780 |
| gacatcaaga acatcctgga cttcacccgg gactaccccg aggcccgggt ctaccgcctg | 840 |
| gaggagaact accgctccac cgaggccatc ctccgcttcg ccaacgccgt gatcgtgaag | 900 |
| aacgccctcc gcctggagaa ggccctgcgc ccggtgaagc ggggcgggga gcccgtgcgc | 960 |
| ctctaccggg cggaggacgc ccgggaggag gcccgcttcg tggccgagga gatcgcccgg | 1020 |
| ctcggccccc cctgggaccg gtacgccgtc ctctaccgca ccaacgccca agccgccttt | 1080 |
| ctggaacagg cgttggcggg gcgggggatc ccggcgcggg tggtgggcgg cgtgggggttc | 1140 |
| tttgaaaggg ccgaggtcaa ggacctcctg gcctacgccc gcctcgccct caacccccttg | 1200 |
| gacgccgtga gcctgaagcg ggtcctgaac accccccctc ggggcatcgg cccggccacc | 1260 |
| tgggccaggg tgcagctcct cgcccaggag aaggggcttc ctccctggga ggccctgaag | 1320 |
| gaggcggcca ggaccttccc ccgcgccgag cccctgaggc acttcgtggc cctggtggag | 1380 |
| gagcttcagg acctggtctt cggccccgcc gaggccttct tccgccacct cctcgaggcc | 1440 |
| accgactacc ccgcctacct ccgggaggcc taccccgagg acgccgagga ccgcctggag | 1500 |
| aacgtggagg agctcctcag gcggccaag gaggcggagg acctgcagga cttcctggac | 1560 |
| cgggtggccc tcaccgccaa ggcggaggag ccgccgaggc ggaggggag ggtcgccctc | 1620 |
| atgaccctgc acaacgccaa ggggctggag ttccccgtgg tcttcctcgt gggggtggag | 1680 |
| gagggcttc tgccccaccg caactccgtg agcaccctcg agggcctgga ggaggagcgc | 1740 |
| cgcctcttct acgtgggcat caccccgggcc caggagaggc tctacctctc ccacgccgag | 1800 |
| gagcgggagg tctacggcag gcgggagccc gccggccga ccgcttcct ggaggaggtg | 1860 |
| gaggaggggc tttacgaggt gtacgacccc taccggcgcc cgccctcccc gccccccat | 1920 |
| cgcccgaggc ccgggcgctt ccggggcggg gagcgggtgg tccacccccg cttcggcccc | 1980 |

```
ggcaccgtgg tggcggccca gggggacgag gtcacggtcc actttgaggg gtttgggctc    2040
aagcgccttt ccctcaagta cgcggagctt aagccggcat ga                       2082
```

<210> SEQ ID NO 68
<211> LENGTH: 693
<212> TYPE: PRT
<213> ORGANISM: Thermus thermophilus

<400> SEQUENCE: 68

```
Val His Ser Asp Ala Leu Leu Ala Pro Leu Asn Glu Ala Gln Arg Gln
1               5                   10                  15

Ala Val Leu His Phe Glu Gly Pro Ala Leu Val Val Ala Gly Ala Gly
            20                  25                  30

Ser Gly Lys Thr Arg Thr Val His Arg Val Ala Tyr Leu Val Ala
        35                  40                  45

Arg Arg Gly Val Phe Pro Ser Glu Ile Leu Ala Val Thr Phe Thr Asn
50                  55                  60

Lys Ala Ala Glu Glu Met Arg Glu Arg Leu Arg Gly Leu Val Pro Gly
65                  70                  75                  80

Ala Gly Glu Val Trp Val Ser Thr Phe His Ala Ala Leu Arg Ile
                85                  90                  95

Leu Arg Val Tyr Gly Glu Arg Val Gly Leu Arg Pro Gly Phe Val Val
                100                 105                 110

Tyr Asp Glu Asp Asp Gln Thr Ala Leu Leu Lys Glu Val Leu Lys Glu
            115                 120                 125

Leu Ala Leu Ser Ala Arg Pro Gly Pro Ile Lys Ala Leu Leu Asp Arg
130                 135                 140

Ala Lys Asn Arg Gly Val Gly Leu Lys Ala Leu Leu Gly Glu Leu Pro
145                 150                 155                 160

Glu Tyr Tyr Ala Gly Leu Ser Arg Gly Arg Leu Gly Asp Val Leu Val
                165                 170                 175

Arg Tyr Gln Glu Ala Leu Lys Ala Gln Gly Ala Leu Asp Phe Gly Asp
            180                 185                 190

Ile Leu Leu Tyr Ala Leu Arg Leu Leu Glu Glu Asp Glu Glu Val Leu
        195                 200                 205

Arg Leu Val Arg Lys Arg Ala Arg Phe Ile His Val Asp Glu Tyr Gln
210                 215                 220

Asp Thr Ser Pro Val Gln Tyr Arg Phe Thr Arg Leu Leu Ala Gly Glu
225                 230                 235                 240

Glu Ala Asn Leu Met Ala Val Gly Asp Pro Asp Gln Gly Ile Tyr Ser
                245                 250                 255

Phe Arg Ala Ala Asp Ile Lys Asn Ile Leu Asp Phe Thr Arg Asp Tyr
            260                 265                 270

Pro Glu Ala Arg Val Tyr Arg Leu Glu Glu Asn Tyr Arg Ser Thr Glu
        275                 280                 285

Ala Ile Leu Arg Phe Ala Asn Ala Val Ile Val Lys Asn Ala Leu Arg
290                 295                 300

Leu Glu Lys Ala Leu Arg Pro Val Lys Arg Gly Gly Glu Pro Val Arg
305                 310                 315                 320

Leu Tyr Arg Ala Glu Asp Ala Arg Glu Ala Arg Phe Val Ala Glu
                325                 330                 335

Glu Ile Ala Arg Leu Gly Pro Pro Trp Asp Arg Tyr Ala Val Leu Tyr
            340                 345                 350
```

```
Arg Thr Asn Ala Gln Ser Arg Leu Leu Glu Gln Ala Leu Ala Gly Arg
        355                 360                 365

Gly Ile Pro Ala Arg Val Val Gly Val Gly Phe Phe Glu Arg Ala
        370                 375                 380

Glu Val Lys Asp Leu Leu Ala Tyr Ala Arg Leu Ala Leu Asn Pro Leu
385                 390                 395                 400

Asp Ala Val Ser Leu Lys Arg Val Leu Asn Thr Pro Arg Gly Ile
                405                 410                 415

Gly Pro Ala Thr Trp Ala Arg Val Gln Leu Leu Ala Gln Glu Lys Gly
            420                 425                 430

Leu Pro Pro Trp Glu Ala Leu Lys Glu Ala Ala Arg Thr Phe Pro Arg
            435                 440                 445

Ala Glu Pro Leu Arg His Phe Val Ala Leu Val Glu Glu Leu Gln Asp
        450                 455                 460

Leu Val Phe Gly Pro Ala Glu Ala Phe Phe Arg His Leu Leu Glu Ala
465                 470                 475                 480

Thr Asp Tyr Pro Ala Tyr Leu Arg Glu Ala Tyr Pro Glu Asp Ala Glu
                485                 490                 495

Asp Arg Leu Glu Asn Val Glu Leu Leu Arg Ala Ala Lys Glu Ala
                500                 505                 510

Glu Asp Leu Gln Asp Phe Leu Asp Arg Val Ala Leu Thr Ala Lys Ala
            515                 520                 525

Glu Glu Pro Ala Glu Ala Glu Gly Arg Val Ala Leu Met Thr Leu His
            530                 535                 540

Asn Ala Lys Gly Leu Glu Phe Pro Val Val Phe Leu Val Gly Val Glu
545                 550                 555                 560

Glu Gly Leu Leu Pro His Arg Asn Ser Val Ser Thr Leu Glu Gly Leu
                565                 570                 575

Glu Glu Glu Arg Arg Leu Phe Tyr Val Gly Ile Thr Arg Ala Gln Glu
            580                 585                 590

Arg Leu Tyr Leu Ser His Ala Glu Glu Arg Glu Val Tyr Gly Arg Arg
            595                 600                 605

Glu Pro Ala Arg Pro Ser Arg Phe Leu Glu Glu Val Glu Glu Gly Leu
        610                 615                 620

Tyr Glu Val Tyr Asp Pro Tyr Arg Arg Pro Ser Pro Pro His
625                 630                 635                 640

Arg Pro Arg Pro Gly Ala Phe Arg Gly Gly Glu Arg Val Val His Pro
                645                 650                 655

Arg Phe Gly Pro Gly Thr Val Val Ala Ala Gln Gly Asp Glu Val Thr
            660                 665                 670

Val His Phe Glu Gly Phe Gly Leu Lys Arg Leu Ser Leu Lys Tyr Ala
        675                 680                 685

Glu Leu Lys Pro Ala
        690

<210> SEQ ID NO 69
<211> LENGTH: 35
<212> TYPE: DNA
<213> ORGANISM: Artificial Sequence
<220> FEATURE:
<223> OTHER INFORMATION: forward/sense ATG primer P161-S1922

<400> SEQUENCE: 69
gactctgcag gacgcgggcc aggcggtgga gctga                           35
```

<210> SEQ ID NO 70
<211> LENGTH: 35
<212> TYPE: DNA
<213> ORGANISM: Artificial Sequence
<220> FEATURE:
<223> OTHER INFORMATION: reverse/antisense ATG primer P161-A3714

<400> SEQUENCE: 70

| gactactagt ctactaggtg gaccagcccg aagga | 35 |
|---|---|

<210> SEQ ID NO 71
<211> LENGTH: 1773
<212> TYPE: DNA
<213> ORGANISM: Thermus thermophilus

<400> SEQUENCE: 71

| atggacgcgg gccaggcggt ggagctgatc aagtcccgcc tctccttgcg ggaggtggtc | 60 |
|---|---|
| tcccgctacg tggccctgaa gccggcgggc cgcggccgct ggaagggcct ctgcccttc | 120 |
| caccaggaga agacccctc tttctacgtg gacgaggaga agggcctctt ctactgcttc | 180 |
| gggtgcaagg ccgggggcga cctcttcgcc ttcgtccaaa gggcggaggg gctggacttc | 240 |
| cccgaggccc tggaaaggct cgcggaggag gcgggggtgg agcttcccg gcggaaggcc | 300 |
| ccggaaaggc gccgggagct cctcgaggtc ctggccctgg cccagaccta cttcctggag | 360 |
| cacctccacg cccaccccga ggccctggcc tacctgagga agcggggcct cacggaggag | 420 |
| agcgtggccc gcttcggcct gggctacgcc ccgcccaagg gggacgggct cgtggccttc | 480 |
| ctcgcccggc acggggtggc cccggaggag ggcgtgcggg ccggggtgct ggcggagcgg | 540 |
| cagggggcgct tcgtggaccg cctccgccac cgcatcacct ccccatcaa ggacgccttc | 600 |
| gggcgcgtcg tggccttcac cgggagggcc ctggggagg acgggcccaa gtacctgaac | 660 |
| acccccgaaa ccccccttt ccgcaagcag gaggtcctct tcgcctaccc cgaggcccgg | 720 |
| cccgccttga gggagggccg ggccatcgtg gtggagggggc tctttgacgc catcgccctc | 780 |
| caccagctgg gcttcccgga gacggtggcc gtgctgggct cgggcctctc cgagggacag | 840 |
| gccctcctcc tcaagaaggc ggggggtcctg gaggtctacc tggcctttga cgccgacgag | 900 |
| gccgggcaga aggccacctt gcagagcctg aacctggagc tcgcccccag gttcctcttc | 960 |
| tacgccgtcc gcctccccgc caaggacccg ggggagctcc tcctccaccc cgagggaagg | 1020 |
| gccctcttcc agaaggccct ggaggaggcc ctccccgagg tggccttccg ctttgaggag | 1080 |
| gcgagccggg ggctggacct ctcccggcc gagcacaagc ggaaggtcct cgaggccctc | 1140 |
| accccaggga tgctcacccc ggagccctt gatcccgtgg ccgagcggct caaggccctg | 1200 |
| gtggtggagc gcctgggcct ttcccccaag agcctcgagg actacctggc gagccttagg | 1260 |
| acccgggggc ggccccgccc tcccccaccg ccccacccc tcaccccgg caacaagacc | 1320 |
| ctccttctgg agctggacgc catcgccctc ctcctctccg ccccgaggga gcgcttcctg | 1380 |
| gagcttgtgg actacgtgga gacccaggtc tggccccgg agggttcctt cctcggggag | 1440 |
| ttcctggccc tggcccggaa ggagcccggg cggaccacc tccgccgcac cctaagccag | 1500 |
| cgggaggaag gaggaaggct ctttgagcgc ctgctcctcg cgccccgggg ggaggatccc | 1560 |
| aggctccagg agaagctgga ccacaccctg gcccgcctgc gggaagccta cctcaggag | 1620 |
| cggctcgcca aggtcaaggc ggccctcgcc caaaacccg acccccccac cctggagcgc | 1680 |
| ctccttaagg agtaccagga gatcgggtg gccatagagg cggagcgccg cctctacaag | 1740 |
| cggcgccccc ctccttcggg ctggtccacc tag | 1773 |

-continued

```
<210> SEQ ID NO 72
<211> LENGTH: 590
<212> TYPE: PRT
<213> ORGANISM: Thermus thermophilus

<400> SEQUENCE: 72
```

| | | | | | | | | | | | | | | | |
|---|---|---|---|---|---|---|---|---|---|---|---|---|---|---|---|
| Met | Asp | Ala | Gly | Gln | Ala | Val | Glu | Leu | Ile | Lys | Ser | Arg | Leu | Ser | Leu |
| 1 | | | | 5 | | | | | 10 | | | | | 15 | |
| Arg | Glu | Val | Val | Ser | Arg | Tyr | Val | Ala | Leu | Lys | Pro | Ala | Gly | Arg | Gly |
| | | | 20 | | | | | 25 | | | | | 30 | | |
| Arg | Trp | Lys | Gly | Leu | Cys | Pro | Phe | His | Gln | Glu | Lys | Thr | Pro | Ser | Phe |
| | | 35 | | | | | 40 | | | | | 45 | | | |
| Tyr | Val | Asp | Glu | Glu | Lys | Gly | Leu | Phe | Tyr | Cys | Phe | Gly | Cys | Lys | Ala |
| | 50 | | | | | 55 | | | | | 60 | | | | |
| Gly | Gly | Asp | Leu | Phe | Ala | Phe | Val | Gln | Arg | Ala | Glu | Gly | Leu | Asp | Phe |
| 65 | | | | | 70 | | | | | 75 | | | | | 80 |
| Pro | Glu | Ala | Leu | Glu | Arg | Leu | Ala | Glu | Glu | Ala | Gly | Val | Glu | Leu | Pro |
| | | | | 85 | | | | | 90 | | | | | 95 | |
| Arg | Arg | Lys | Ala | Pro | Glu | Arg | Arg | Glu | Leu | Leu | Glu | Val | Leu | Ala | |
| | | | 100 | | | | | 105 | | | | | 110 | | |
| Leu | Ala | Gln | Thr | Tyr | Phe | Leu | Glu | His | Leu | His | Ala | His | Pro | Glu | Ala |
| | | | 115 | | | | | 120 | | | | | 125 | | |
| Leu | Ala | Tyr | Leu | Arg | Lys | Arg | Gly | Leu | Thr | Glu | Glu | Ser | Val | Ala | Arg |
| | 130 | | | | | 135 | | | | | 140 | | | | |
| Phe | Gly | Leu | Gly | Tyr | Ala | Pro | Pro | Lys | Gly | Asp | Gly | Leu | Val | Ala | Phe |
| 145 | | | | | 150 | | | | | 155 | | | | | 160 |
| Leu | Ala | Arg | His | Gly | Val | Ala | Pro | Glu | Glu | Gly | Val | Arg | Ala | Gly | Val |
| | | | | 165 | | | | | 170 | | | | | 175 | |
| Leu | Ala | Glu | Arg | Gln | Gly | Arg | Phe | Val | Asp | Arg | Leu | Arg | His | Arg | Ile |
| | | | 180 | | | | | 185 | | | | | 190 | | |
| Thr | Phe | Pro | Ile | Lys | Asp | Ala | Phe | Gly | Arg | Val | Val | Ala | Phe | Thr | Gly |
| | | | 195 | | | | | 200 | | | | | 205 | | |
| Arg | Ala | Leu | Gly | Glu | Asp | Gly | Pro | Lys | Tyr | Leu | Asn | Thr | Pro | Glu | Thr |
| | 210 | | | | | 215 | | | | | 220 | | | | |
| Pro | Leu | Phe | Arg | Lys | Gln | Glu | Val | Leu | Phe | Ala | Tyr | Pro | Glu | Ala | Arg |
| 225 | | | | | 230 | | | | | 235 | | | | | 240 |
| Pro | Ala | Leu | Arg | Glu | Gly | Arg | Ala | Ile | Val | Val | Glu | Gly | Leu | Phe | Asp |
| | | | | 245 | | | | | 250 | | | | | 255 | |
| Ala | Ile | Ala | Leu | His | Gln | Leu | Gly | Phe | Pro | Glu | Thr | Val | Ala | Val | Leu |
| | | | 260 | | | | | 265 | | | | | 270 | | |
| Gly | Ser | Gly | Leu | Ser | Glu | Gly | Gln | Ala | Leu | Leu | Lys | Lys | Ala | Gly | |
| | | 275 | | | | | 280 | | | | | 285 | | | |
| Val | Leu | Glu | Val | Tyr | Leu | Ala | Phe | Asp | Ala | Asp | Glu | Ala | Gly | Gln | Lys |
| | 290 | | | | | 295 | | | | | 300 | | | | |
| Ala | Thr | Leu | Gln | Ser | Leu | Asn | Leu | Glu | Leu | Ala | Pro | Arg | Phe | Leu | Phe |
| 305 | | | | | 310 | | | | | 315 | | | | | 320 |
| Tyr | Ala | Val | Arg | Leu | Pro | Ala | Lys | Asp | Pro | Gly | Glu | Leu | Leu | Leu | His |
| | | | | 325 | | | | | 330 | | | | | 335 | |
| Pro | Glu | Gly | Arg | Ala | Leu | Phe | Gln | Lys | Ala | Leu | Glu | Glu | Ala | Leu | Pro |
| | | | 340 | | | | | 345 | | | | | 350 | | |
| Glu | Val | Ala | Phe | Arg | Phe | Glu | Glu | Ala | Ser | Arg | Gly | Leu | Asp | Leu | Ser |
| | | | 355 | | | | | 360 | | | | | 365 | | |
| Arg | Pro | Glu | His | Lys | Arg | Lys | Val | Leu | Glu | Ala | Leu | Thr | Pro | Arg | Met |
| | 370 | | | | | 375 | | | | | 380 | | | | |

-continued

```
Leu Thr Pro Glu Pro Phe Asp Pro Val Ala Glu Arg Leu Lys Ala Leu
385                 390                 395                 400

Val Val Glu Arg Leu Gly Leu Ser Pro Lys Ser Leu Glu Asp Tyr Leu
            405                 410                 415

Ala Ser Leu Arg Thr Arg Gly Arg Pro Ala Pro Pro Pro Pro
            420                 425                 430

Pro Leu Thr Pro Gly Asn Lys Thr Leu Leu Glu Leu Asp Ala Ile
        435                 440                 445

Ala Leu Leu Leu Ser Ala Pro Glu Glu Arg Phe Leu Glu Leu Val Asp
    450                 455                 460

Tyr Val Glu Thr Gln Val Trp Pro Pro Glu Gly Ser Phe Leu Gly Glu
465                 470                 475                 480

Phe Leu Ala Leu Ala Arg Lys Glu Pro Arg Arg Asp His Leu Arg Arg
            485                 490                 495

Thr Leu Ser Gln Arg Glu Glu Gly Gly Arg Leu Phe Glu Arg Leu Leu
            500                 505                 510

Leu Ala Pro Arg Gly Glu Asp Pro Arg Leu Gln Glu Lys Leu Asp His
        515                 520                 525

Thr Leu Ala Arg Leu Arg Glu Ala Tyr Leu Gln Glu Arg Leu Ala Lys
    530                 535                 540

Val Lys Ala Ala Leu Ala Gln Asn Pro Asp Pro Thr Leu Glu Arg
545                 550                 555                 560

Leu Leu Lys Glu Tyr Gln Glu Ile Arg Val Ala Ile Glu Ala Glu Arg
            565                 570                 575

Arg Leu Tyr Lys Arg Arg Pro Pro Pro Ser Gly Trp Ser Thr
            580                 585                 590

<210> SEQ ID NO 73
<211> LENGTH: 37
<212> TYPE: DNA
<213> ORGANISM: Artificial Sequence
<220> FEATURE:
<223> OTHER INFORMATION: forward/sense ATG primer P162-S963

<400> SEQUENCE: 73
ccgaagagcc tctccaggag ggggaggagg ggaacca                              37

<210> SEQ ID NO 74
<211> LENGTH: 30
<212> TYPE: DNA
<213> ORGANISM: Artificial Sequence
<220> FEATURE:
<223> OTHER INFORMATION: reverse/antisense ATG primer P162-A3625

<400> SEQUENCE: 74
ggggcagccg caagggggtaa gggtagaaaa                                     30

<210> SEQ ID NO 75
<211> LENGTH: 2127
<212> TYPE: DNA
<213> ORGANISM: Thermus thermophilus

<400> SEQUENCE: 75
gtgcgggtgc ttcaggtggc ccttcccctg ccgcttccgc ccatgagcta cctccctccc      60
ttggggcagg aggagagga ggccttgggg cggcgggtgg ccgttccttt tcggggggag     120
gtccaggtgg gggtggtggt gggggaaggg gggcggccct ccctgaacct ccgccacgcc    180
atcgcctacc tggaccccgc cccctacctg cgcccggagg agatcctctt tttggaagag    240
```

-continued

```
gcggcccgct accttttcgc cccctgggc caggtcctgg cggacttcct cccccctttt      300
cccccttgc gccaccgggt ccgcctctac ccggggcgg acccgaaggt cctgcccccg       360
gggctcgggg ccttggtgga ctggcgggag gcccggggct tgaccccaa gcttttggac      420
ctcctgcggg aggcgggat gctggaggag gagctcgcct tccggaggc gcggggggtg       480
ctggtgcccc tgaagcccgc ccaccccgat ccccagctgg accgcgtcct tcaggtcctg     540
cgggagctgg gctttgccga aagccaggcg gccctggccc gggcggcggg ggtggggggtg    600
ggccgggtgc gccgcctcgt ccaggagggg tacatcggca ccgcgtcccc cgaggaggcc    660
gccccgcccc ggcggacgg ggtggacgtg gcgcccctcc acctcccga gaggcccgag       720
cgggtcaacg gcgggaggtt tctggaacgc gttcgggtgc tcaagggct tttgggggag      780
ggggaccacc tggtcctctt ccccgaggtg agcctcttgg agcggtttct cgcccacttc     840
cccggggcca cgcccctacca cggggggctt tccggcccgg tccgggagcg ttttttccgg    900
aggccgcgcg gcgtggtctt cgccacctac ggcgggctcc tcctccccttt cacccccgc    960
tctttggtgg tggtggagga ggggagcgag agctacaagc ttccctcggg gagccgggcc    1020
ttcgtccccc cgcttgcgga gcttagggcc cggctcctcg gggtgcccct cacctacctc    1080
tccctggtgc ccgcggtgga ggttttggag cgaaaaggct tcgccctgcc cgtgcccaag    1140
ccccgccttc tcctcttgga cctccggcgg gagcggggct ttcccgtcac ggggcgggcc    1200
ctcgccctcc tccgccaggt ggaggagcgg gggcggcagg ccgtggtcct ctccgcccgc    1260
aagggggtaca gcgccctcct cctctgccag gactgcggct tccggcccat gtgccccgac   1320
tgcgccttgc ccctgcggta ccaccgggag gggaagggg cgctcgtctg ccaccagtgc    1380
ggccaccgcg aggacccgcc cctcctctgc ccccggtgcg gctccccct cctcgccccc    1440
aagggggcccg ggtggactg gatccgggag gccctggcgg agaggctttc ccttcccgtc   1500
taccgctacg ccggcgacgg gaaggacgac ctcacccccc tcctcgaggg ccggccgggg   1560
gtggtggtgg ggaccacggc cctcctcagg gggcctaggc ttcccgacct cgccctcgtc   1620
ctcctcccctt tggcggacgg cttcctcctg gagtcggact ccgggcggc ggagcggtac   1680
caccgccttc tctgggccct cacggagctc aggcccgggc ggaggcccct cctcgtcctc   1740
cagaccttca cccccgagca ccccgtgcac cgggccctcg aggcggggga ggtggaggcc   1800
tacctgtggc aggagaaggc cctgcgggag gccctcaact acccgccgcg ggtgcgcatg   1860
gtaaagctgg aggtgcgcca ccgaaaggaa gagcgggccc gggaaaaggc cttcgccctc   1920
ctggaggcct gcggggccga ggcggaggag gggaggtcc tgggccccgc ccccgctccc   1980
gtgccccggg tgaaggggca ttacgtcttc cacctcctcc tccggggggag cacggagcgg   2040
ctcgcccgcc tcctcggcct cctggaccgg cggcagttca ggctggaccc cgaccccttc   2100
cacttcgtgg ggcttttgga ggactag                                        2127
```

<210> SEQ ID NO 76
<211> LENGTH: 708
<212> TYPE: PRT
<213> ORGANISM: Thermus thermophilus

<400> SEQUENCE: 76

Val Arg Val Leu Gln Val Ala Leu Pro Leu Pro Leu Pro Pro Met Ser
1               5                   10                  15

Tyr Leu Pro Pro Leu Gly Gln Glu Gly Glu Glu Ala Leu Gly Arg Arg
            20                  25                  30

-continued

```
Val Ala Val Pro Phe Arg Gly Glu Val Gln Val Gly Val Val Gly
         35                  40                  45
Glu Gly Gly Arg Pro Ser Leu Asn Leu Arg His Ala Ile Ala Tyr Leu
 50                  55                  60
Asp Pro Ala Pro Tyr Leu Arg Pro Glu Glu Ile Leu Phe Leu Glu Glu
 65                  70                  75                  80
Ala Ala Arg Tyr Leu Phe Ala Pro Leu Gly Gln Val Leu Ala Asp Phe
                 85                  90                  95
Leu Pro Pro Phe Pro Pro Leu Arg His Arg Val Arg Leu Tyr Pro Gly
                100                 105                 110
Ala Asp Pro Lys Val Leu Pro Pro Gly Leu Gly Ala Leu Val Asp Trp
             115                 120                 125
Arg Glu Ala Arg Gly Phe Asp Pro Lys Leu Leu Asp Leu Leu Arg Glu
         130                 135                 140
Ala Gly Met Leu Glu Glu Leu Ala Phe Arg Glu Ala Arg Gly Val
145                 150                 155                 160
Leu Val Pro Leu Lys Pro Ala His Pro Asp Pro Gln Leu Asp Arg Val
                165                 170                 175
Leu Gln Val Leu Arg Glu Leu Gly Phe Ala Glu Ser Gln Ala Ala Leu
                180                 185                 190
Ala Arg Ala Gly Val Gly Val Gly Arg Val Arg Arg Leu Val Gln
         195                 200                 205
Glu Gly Tyr Ile Gly Thr Ala Ser Pro Glu Glu Ala Ala Pro Pro Pro
210                 215                 220
Ala Asp Gly Val Asp Val Ala Pro Leu His Leu Pro Glu Arg Pro Glu
225                 230                 235                 240
Arg Val Asn Gly Gly Arg Phe Leu Glu Arg Val Arg Val Leu Lys Gly
                245                 250                 255
Leu Leu Gly Glu Gly Asp His Leu Val Leu Phe Pro Glu Val Ser Leu
                260                 265                 270
Leu Glu Arg Phe Leu Ala His Phe Pro Gly Ala Thr Pro Tyr His Gly
            275                 280                 285
Gly Leu Ser Gly Pro Val Arg Glu Arg Phe Phe Arg Arg Pro Arg Gly
        290                 295                 300
Val Val Phe Ala Thr Tyr Gly Gly Leu Leu Leu Pro Phe Thr Pro Arg
305                 310                 315                 320
Ser Leu Val Val Glu Glu Gly Ser Glu Ser Tyr Lys Leu Pro Ser
                325                 330                 335
Gly Ser Arg Ala Phe Val Pro Pro Leu Ala Glu Leu Arg Ala Arg Leu
            340                 345                 350
Leu Gly Val Pro Leu Thr Tyr Leu Ser Leu Val Pro Ala Val Glu Val
        355                 360                 365
Leu Glu Arg Lys Gly Phe Ala Leu Pro Val Pro Lys Pro Arg Leu Leu
    370                 375                 380
Leu Leu Asp Leu Arg Arg Glu Arg Gly Phe Pro Val Thr Gly Arg Ala
385                 390                 395                 400
Leu Ala Leu Leu Arg Gln Val Glu Glu Arg Gly Arg Gln Ala Val Val
                405                 410                 415
Leu Ser Ala Arg Lys Gly Tyr Ser Ala Leu Leu Leu Cys Gln Asp Cys
            420                 425                 430
Gly Phe Arg Pro Met Cys Pro Asp Cys Ala Leu Pro Leu Arg Tyr His
        435                 440                 445
Arg Glu Gly Lys Gly Ala Leu Val Cys His Gln Cys Gly His Arg Glu
```

```
                450             455             460
Asp Pro Pro Leu Leu Cys Pro Arg Cys Gly Ser Pro Leu Leu Ala Pro
465                 470                 475                 480

Lys Gly Pro Gly Val Asp Trp Ile Arg Glu Ala Leu Ala Glu Arg Leu
                485                 490                 495

Ser Leu Pro Val Tyr Arg Tyr Ala Gly Asp Gly Lys Asp Asp Leu Thr
            500                 505                 510

Pro Leu Leu Glu Gly Arg Pro Gly Val Val Gly Thr Thr Ala Leu
            515                 520             525

Leu Arg Gly Pro Arg Leu Pro Asp Leu Ala Leu Val Leu Leu Pro Leu
    530                 535                 540

Ala Asp Gly Phe Leu Leu Glu Ser Asp Phe Arg Ala Ala Glu Arg Tyr
545                 550                 555                 560

His Arg Leu Leu Trp Ala Leu Thr Glu Leu Arg Pro Gly Arg Arg Pro
                565                 570                 575

Leu Leu Val Leu Gln Thr Phe Thr Pro Glu His Pro Val His Arg Ala
            580                 585                 590

Leu Glu Ala Gly Glu Val Glu Ala Tyr Leu Trp Gln Glu Lys Ala Leu
            595                 600                 605

Arg Glu Ala Leu Asn Tyr Pro Pro Arg Val Arg Met Val Lys Leu Glu
    610                 615                 620

Val Arg His Arg Lys Glu Glu Arg Ala Arg Glu Lys Ala Phe Ala Leu
625                 630                 635                 640

Leu Glu Ala Leu Arg Ala Glu Ala Glu Glu Gly Glu Val Leu Gly Pro
                645                 650                 655

Ala Pro Ala Pro Val Pro Arg Val Lys Gly His Tyr Val Phe His Leu
            660                 665                 670

Leu Leu Arg Gly Ser Thr Glu Arg Leu Ala Arg Leu Leu Gly Leu Leu
    675                 680                 685

Asp Arg Arg Gln Phe Arg Leu Asp Pro Asp Pro Phe His Phe Val Gly
690                 695                 700

Leu Leu Glu Asp
705

<210> SEQ ID NO 77
<211> LENGTH: 32
<212> TYPE: DNA
<213> ORGANISM: Artificial Sequence
<220> FEATURE:
<223> OTHER INFORMATION: forward/sense ATG primer P162-S1052

<400> SEQUENCE: 77
gactctgcag cgggtgcttc aggtggccct tc                                32

<210> SEQ ID NO 78
<211> LENGTH: 33
<212> TYPE: DNA
<213> ORGANISM: Artificial Sequence
<220> FEATURE:
<223> OTHER INFORMATION: reverse/antisense ATG primer P162-A3180

<400> SEQUENCE: 78
cagtactagt ctagtcctcc aaaagcccca cga                               33

<210> SEQ ID NO 79
<211> LENGTH: 17
<212> TYPE: DNA
<213> ORGANISM: Artificial Sequence
```

-continued

<220> FEATURE:
<223> OTHER INFORMATION: forward/sense ATG primer #P133-S150

<400> SEQUENCE: 79
tgggggcgaa cctcacg                                                  17

<210> SEQ ID NO 80
<211> LENGTH: 19
<212> TYPE: DNA
<213> ORGANISM: Artificial Sequence
<220> FEATURE:
<223> OTHER INFORMATION: reverse/antisense ATG primer #P133-A1237

<400> SEQUENCE: 80
accccggcct tccagtcca                                                19

<210> SEQ ID NO 81
<211> LENGTH: 620
<212> TYPE: DNA
<213> ORGANISM: Thermus thermophilus

<400> SEQUENCE: 81
gtggagcggg tggtgcggcc ccttctggac gggaggttcc tcctgaggga ggggtgggc    60
tttgggagtg gcgctacccc tttcccctgg aggggaggc ggtggtggtc ctggacctga  120
gaccacgggg cttgccccgg gcctggacga ggtgattgag gtgggcctcc tccgcctgag  180
ggggggaggc gcctcccctt ccagagcctc gtccgcccct cccgcccgcc gagcccttcg  240
tggagcgcct caccggcatc cccgggagg ccctggagga ggccccctcc ctggagaggt   300
tctggagaag gcctaccccc tcctcgccga cgccaccttg gtgatccaca cgcgccttt   360
gacctgggct tcctccgccc ggccctggag ggcctgggct accgcctgga aaacccgtgg  420
tggactccct gcgcttggcc agacgggct taccaggcct taggcgctac ggctggacgc  480
cctctccgag gtcctggagc ttccccgaag gacctgccac cgggccctcg agacgtggag  540
cgcaccctcg ccgtggtgca cgaggtgtac tatatgctta cgtccggccg ccccgcacgc  600
tttgggaact cgggaggtag                                              620

<210> SEQ ID NO 82
<211> LENGTH: 209
<212> TYPE: PRT
<213> ORGANISM: Thermus thermophilus

<400> SEQUENCE: 82

Val Glu Arg Val Val Arg Pro Leu Leu Asp Gly Arg Phe Leu Leu Glu
1               5                   10                  15

Glu Gly Val Gly Leu Trp Glu Trp Arg Tyr Pro Phe Pro Leu Glu Gly
            20                  25                  30

Glu Ala Val Val Leu Asp Leu Glu Thr Thr Gly Leu Ala Pro Gly
        35                  40                  45

Leu Asp Glu Val Ile Glu Val Gly Leu Arg Leu Glu Gly Gly Arg
    50                  55                  60

Arg Leu Pro Phe Gln Ser Leu Val Arg Pro Ser Arg Pro Ser Pro
65                  70                  75                  80

Phe Val Glu Arg Leu Thr Gly Ile Pro Arg Glu Ala Leu Glu Glu Ala
                85                  90                  95

Pro Ser Leu Glu Glu Val Leu Glu Lys Ala Tyr Pro Leu Leu Ala Asp
            100                 105                 110

Ala Thr Leu Val Ile His Asn Ala Ala Phe Asp Leu Gly Phe Leu Arg

```
                  115                 120                 125
Pro Ala Leu Glu Gly Leu Gly Tyr Arg Leu Glu Asn Pro Val Val Asp
        130                 135                 140

Ser Leu Arg Leu Ala Arg Arg Gly Leu Pro Gly Leu Arg Arg Tyr Gly
145                 150                 155                 160

Leu Asp Ala Leu Ser Glu Val Leu Glu Leu Pro Arg Arg Thr Cys His
                165                 170                 175

Arg Ala Leu Glu Asp Val Glu Arg Thr Leu Ala Val Val His Glu Val
            180                 185                 190

Tyr Tyr Met Leu Thr Ser Gly Arg Pro Arg Thr Leu Trp Glu Leu Gly
        195                 200                 205

Arg

<210> SEQ ID NO 83
<211> LENGTH: 33
<212> TYPE: DNA
<213> ORGANISM: Artificial Sequence
<220> FEATURE:
<223> OTHER INFORMATION: forward/sense ATG primer #P133-S442nc0

<400> SEQUENCE: 83
ggatccatgg agcgggtggt gcggcccctt ctg                              33

<210> SEQ ID NO 84
<211> LENGTH: 35
<212> TYPE: DNA
<213> ORGANISM: Artificial Sequence
<220> FEATURE:
<223> OTHER INFORMATION: reverse/antisense ATG primer #P133-A109kpn

<400> SEQUENCE: 84
aagctaggta cctactacct cccgagttcc caaag                            35

<210> SEQ ID NO 85
<211> LENGTH: 31
<212> TYPE: DNA
<213> ORGANISM: Artificial Sequence
<220> FEATURE:
<223> OTHER INFORMATION: reverse/antisense ATG primer #P133-A1084Spe

<400> SEQUENCE: 85
cctcactagt cctcccgagt tcccaaagcg t                                31

<210> SEQ ID NO 86
<211> LENGTH: 175
<212> TYPE: PRT
<213> ORGANISM: Escherichia coli

<400> SEQUENCE: 86

Met Ser Ala Arg Gly Ile Asn Lys Val Ile Leu Val Gly Arg Leu Gly
1               5                   10                  15

Asn Asp Pro Glu Val Arg Tyr Ile Pro Asn Gly Gly Ala Val Ala Asn
            20                  25                  30

Leu Gln Val Ala Thr Ser Glu Ser Trp Arg Asp Lys Gln Thr Gly Glu
        35                  40                  45

Met Arg Glu Gln Thr Glu Trp His Arg Val Val Leu Phe Gly Lys Leu
    50                  55                  60

Ala Glu Val Ala Gly Glu Tyr Leu Arg Lys Gly Ala Gln Val Tyr Ile
65                  70                  75                  80

Glu Gly Gln Leu Arg Thr Arg Ser Trp Asp Asp Asn Gly Ile Thr Arg
```

```
                         85                  90                  95
Tyr Ile Thr Glu Ile Leu Val Lys Thr Thr Gly Thr Met Gln Met Leu
                    100                 105                 110
Gly Ser Ala Pro Gln Gln Asn Ala Gln Ala Gln Pro Lys Pro Gln Gln
                115                 120                 125
Asn Gly Gln Pro Gln Ser Ala Asp Ala Thr Lys Lys Gly Gly Ala Lys
    130                 135                 140
Thr Lys Gly Arg Glu Arg Lys Ala Ala Gln Pro Glu Pro Gln Pro Gln
145                 150                 155                 160
Thr Pro Glu Gly Glu Asp Tyr Gly Phe Ser Asp Ile Pro Phe
                165                 170                 175

<210> SEQ ID NO 87
<211> LENGTH: 168
<212> TYPE: PRT
<213> ORGANISM: Haemophilus influenzae

<400> SEQUENCE: 87

Met Ala Gly Ile Asn Lys Val Ile Ile Val Gly His Leu Gly Asn Asp
1               5                   10                  15
Pro Glu Ile Arg Thr Met Pro Asn Gly Asp Ala Val Ala Asn Ile Ser
                20                  25                  30
Val Ala Thr Ser Glu Ser Trp Asn Asp Arg Asn Thr Gly Glu Arg Arg
            35                  40                  45
Glu Val Thr Glu Trp His Arg Ile Val Phe Tyr Arg Arg Gln Ala Glu
        50                  55                  60
Ile Cys Gly Glu Tyr Leu Arg Lys Gly Ser Gln Val Tyr Val Glu Gly
65                  70                  75                  80
Arg Leu Lys Thr Arg Lys Trp Gln Asp Gln Asn Gly Gln Asp Arg Tyr
                85                  90                  95
Thr Thr Glu Ile Gln Gly Asp Val Met Gln Met Leu Gly Gly Arg Asn
                100                 105                 110
Gln Asn Ala Gly Gly Tyr Gly Asn Asp Met Gly Gly Ala Pro Gln Ser
            115                 120                 125
Ser Tyr Gln Ala Arg Gln Thr Asn Asn Gly Asn Ser Tyr Gln Ser Ser
        130                 135                 140
Arg Pro Ala Pro Gln Gln Ala Ala Pro Gln Ala Glu Pro Pro Met Asp
145                 150                 155                 160
Gly Phe Asp Asp Asp Ile Pro Phe
                165

<210> SEQ ID NO 88
<211> LENGTH: 263
<212> TYPE: PRT
<213> ORGANISM: Thermus thermophilus

<400> SEQUENCE: 88

Met Ala Arg Gly Leu Asn Arg Val Phe Leu Ile Gly Ala Leu Ala Thr
1               5                   10                  15
Arg Pro Asp Met Arg Tyr Thr Pro Ala Gly Leu Ala Ile Leu Asp Leu
                20                  25                  30
Thr Leu Ala Gly Gln Asp Leu Leu Ser Asp Asn Gly Gly Glu Arg
            35                  40                  45
Glu Val Ser Trp Tyr His Arg Val Arg Leu Leu Gly Arg Gln Ala Glu
        50                  55                  60
Met Trp Gly Asp Leu Leu Asp Gln Gly Gln Leu Val Phe Val Glu Gly
```

-continued

```
                65                  70                  75                  80
Arg Leu Glu Tyr Arg Gln Trp Glu Arg Glu Gly Lys Arg Ser Glu
                    85                  90                  95

Leu Gln Ile Arg Ala Asp Phe Leu Asp Pro Leu Asp Asp Arg Gly Lys
            100                 105                 110

Glu Arg Ala Glu Asp Ser Arg Gly Gln Pro Arg Leu Arg Ala Ala Leu
            115                 120                 125

Asn Gln Val Phe Leu Met Gly Asn Leu Thr Arg Asp Pro Glu Leu Arg
        130                 135                 140

Tyr Thr Pro Gln Gly Thr Ala Val Ala Arg Leu Gly Leu Ala Val Asn
145                 150                 155                 160

Glu Arg Arg Gln Gly Ala Glu Arg Thr His Phe Val Glu Val Gln
                165                 170                 175

Ala Trp Arg Asp Leu Ala Glu Trp Ala Ala Glu Leu Arg Lys Gly Asp
                180                 185                 190

Gly Leu Phe Val Ile Gly Arg Leu Val Asn Asp Ser Trp Thr Ser Ser
                195                 200                 205

Ser Gly Glu Arg Arg Phe Gln Thr Arg Val Glu Ala Leu Arg Leu Glu
        210                 215                 220

Arg Pro Thr Arg Gly Pro Ala Gln Ala Gly Gly Ser Arg Ser Arg Glu
225                 230                 235                 240

Val Gln Thr Gly Gly Val Asp Ile Asp Glu Gly Leu Glu Asp Phe Pro
                245                 250                 255

Pro Glu Glu Asp Leu Pro Phe
            260
```

<210> SEQ ID NO 89
<211> LENGTH: 305
<212> TYPE: PRT
<213> ORGANISM: Aquifex aeolicus

<400> SEQUENCE: 89

```
Met Glu Lys Val Phe Leu Glu Lys Leu Gln Lys Thr Leu His Ile Pro
1               5                   10                  15

Gly Gly Leu Leu Phe Tyr Gly Lys Glu Gly Ser Gly Lys Thr Lys Thr
            20                  25                  30

Ala Phe Glu Phe Ala Lys Gly Ile Leu Cys Lys Glu Asn Val Pro Trp
        35                  40                  45

Gly Cys Gly Ser Cys Pro Ser Cys Lys His Val Asn Glu Leu Glu Glu
    50                  55                  60

Ala Phe Phe Lys Gly Glu Ile Glu Asp Phe Lys Val Tyr Lys Asp Lys
65                  70                  75                  80

Asp Gly Lys Lys His Phe Val Tyr Leu Met Gly Glu His Pro Asp Phe
                85                  90                  95

Val Val Ile Ile Pro Ser Gly His Tyr Ile Lys Ile Glu Gln Ile Arg
            100                 105                 110

Glu Val Lys Asn Phe Ala Tyr Val Lys Pro Ala Leu Ser Arg Arg Lys
        115                 120                 125

Val Ile Ile Ile Asp Asp Ala His Ala Met Thr Ser Gln Ala Ala Asn
    130                 135                 140

Ala Leu Leu Lys Val Leu Glu Glu Pro Pro Ala Asp Thr Thr Phe Ile
145                 150                 155                 160

Leu Thr Thr Asn Arg Arg Ser Ala Ile Leu Pro Thr Ile Leu Ser Arg
                165                 170                 175
```

```
Thr Phe Gln Val Glu Phe Lys Gly Phe Ser Val Lys Glu Val Met Glu
            180                 185                 190

Ile Ala Lys Val Asp Glu Glu Ile Ala Lys Leu Ser Gly Gly Ser Leu
            195                 200                 205

Lys Arg Ala Ile Leu Leu Lys Glu Asn Lys Asp Ile Leu Asn Lys Val
        210                 215                 220

Lys Glu Phe Leu Glu Asn Glu Pro Leu Lys Val Tyr Lys Leu Ala Ser
225                 230                 235                 240

Glu Phe Glu Lys Trp Glu Pro Glu Lys Gln Lys Leu Phe Leu Glu Ile
                245                 250                 255

Met Glu Glu Leu Val Ser Gln Lys Leu Thr Glu Lys Lys Asp Asn
            260                 265                 270

Tyr Thr Tyr Leu Leu Asp Thr Ile Arg Leu Phe Lys Asp Gly Leu Ala
            275                 280                 285

Arg Gly Val Asn Glu Pro Leu Trp Leu Phe Thr Leu Ala Val Gln Ala
            290                 295                 300

Asp
305

<210> SEQ ID NO 90
<211> LENGTH: 329
<212> TYPE: PRT
<213> ORGANISM: Bacillus subtilis

<400> SEQUENCE: 90

Met Ala Ile Ser Trp Lys Glu Met Asn Glu Leu Gln Pro Arg Val Met
1               5                   10                  15

Lys Leu Leu Tyr Asn Ser Ile Glu Lys Asp Arg Leu Ser His Ala Tyr
            20                  25                  30

Leu Phe Glu Gly Lys Lys Gly Thr Gly Lys Leu Asp Ala Ala Leu Leu
        35                  40                  45

Leu Ala Lys Ser Phe Phe Cys Leu Glu Gly Gly Ala Glu Pro Cys Glu
    50                  55                  60

Ser Cys Arg Asn Cys Lys Arg Ile Glu Ser Gly Asn His Pro Asp Leu
65                  70                  75                  80

His Leu Val Gln Pro Asp Gly Leu Ser Ile Lys Lys Ala Gln Ile Gln
                85                  90                  95

Ala Leu Gln Glu Glu Phe Ser Lys Thr Gly Leu Glu Ser His Lys Lys
            100                 105                 110

Leu Tyr Ile Ile Ser His Ala Asp Gln Met Thr Ala Asn Ala Ala Asn
        115                 120                 125

Ser Leu Leu Lys Phe Leu Glu Glu Pro Asn Lys Asp Thr Met Ala Val
    130                 135                 140

Leu Ile Thr Glu Gln Pro Gln Arg Leu Leu Asp Thr Ile Ile Ser Arg
145                 150                 155                 160

Cys Gln Thr Leu Pro Phe Gln Pro Leu Gln Pro Lys Ala Ile Glu Asp
                165                 170                 175

Arg Leu Ile Glu Gln Asp Val Ser Pro His Met Ala Arg Leu Leu Ala
            180                 185                 190

Asn Met Thr Asn Asn Val Ala Glu Ala Val Glu Leu Ser Arg Asn Asp
        195                 200                 205

Glu Phe Ala Glu Ser Arg Ala Lys Val Ile Lys Leu Tyr Glu Val Leu
    210                 215                 220

His Gln Arg Lys Gly His Ala Phe Phe Ile Gln Asp Gln Trp Met
225                 230                 235                 240
```

```
Pro Phe Phe Lys Glu Lys Thr His Gln Glu Met Gly Leu Asp Met Leu
                245                 250                 255

Leu Leu Ile Tyr Arg Asp Val Leu Ser Ile Gln Ile Gly Asn Glu Asp
            260                 265                 270

Lys Leu Ile Tyr Gln Asp Leu Phe Gln Ser Ile Lys Gln His Ala Leu
            275                 280                 285

Gln Ser Thr Gln Gln Ser Val Thr Asn Gln Ile Leu Ala Val Leu Glu
        290                 295                 300

Ala Lys Lys Arg Leu His Ser Asn Val Asn Val Gln Gly Leu Met Glu
305                 310                 315                 320

His Leu Val Leu Met Leu Gln Glu Gly
                325

<210> SEQ ID NO 91
<211> LENGTH: 334
<212> TYPE: PRT
<213> ORGANISM: Escherichia coli

<400> SEQUENCE: 91

Met Arg Trp Tyr Pro Trp Leu Arg Pro Asp Phe Glu Lys Leu Val Ala
1               5                   10                  15

Ser Tyr Gln Ala Gly Arg Gly His His Ala Leu Leu Ile Gln Ala Leu
            20                  25                  30

Pro Gly Met Gly Asp Asp Ala Leu Ile Tyr Ala Leu Ser Arg Tyr Leu
        35                  40                  45

Leu Cys Gln Gln Pro Gln Gly His Lys Ser Cys Gly His Cys Arg Gly
    50                  55                  60

Cys Gln Leu Met Gln Ala Gly Thr His Pro Asp Tyr Tyr Thr Leu Ala
65                  70                  75                  80

Pro Glu Lys Gly Lys Asn Thr Leu Gly Val Asp Ala Val Arg Glu Val
                85                  90                  95

Thr Glu Lys Leu Asn Glu His Ala Arg Leu Gly Gly Ala Lys Val Val
            100                 105                 110

Trp Val Thr Asp Ala Ala Leu Leu Thr Asp Ala Ala Ala Asn Ala Leu
        115                 120                 125

Leu Lys Thr Leu Glu Glu Pro Pro Ala Glu Thr Trp Phe Phe Leu Ala
    130                 135                 140

Thr Arg Glu Pro Glu Arg Leu Leu Ala Thr Leu Arg Ser Arg Cys Arg
145                 150                 155                 160

Leu His Tyr Leu Ala Pro Pro Glu Gln Tyr Ala Val Thr Trp Leu
                165                 170                 175

Ser Arg Glu Val Thr Met Ser Gln Asp Ala Leu Leu Ala Ala Leu Arg
                180                 185                 190

Leu Ser Ala Gly Ser Pro Gly Ala Ala Leu Ala Leu Phe Gln Gly Asp
            195                 200                 205

Asn Trp Gln Ala Arg Glu Thr Leu Cys Gln Ala Leu Ala Tyr Ser Val
        210                 215                 220

Pro Ser Gly Asp Trp Tyr Ser Leu Leu Ala Ala Leu Asn His Glu Gln
225                 230                 235                 240

Ala Pro Ala Arg Leu His Trp Leu Ala Thr Leu Leu Met Asp Ala Leu
                245                 250                 255

Lys Arg His His Gly Ala Ala Gln Val Thr Asn Val Asp Val Pro Gly
            260                 265                 270

Leu Val Ala Glu Leu Ala Asn His Leu Ser Pro Ser Arg Leu Gln Ala
```

```
            275                 280                 285
Ile Leu Gly Asp Val Cys His Ile Arg Glu Gln Leu Met Ser Val Thr
        290                 295                 300
Gly Ile Asn Arg Glu Leu Leu Ile Thr Asp Leu Leu Arg Ile Glu
305                 310                 315                 320
His Tyr Leu Gln Pro Gly Val Val Leu Pro Val Pro His Leu
                    325                 330

<210> SEQ ID NO 92
<211> LENGTH: 333
<212> TYPE: PRT
<213> ORGANISM: Haemophilus influenzae

<400> SEQUENCE: 92

Met Glu Ile Lys Arg Lys Met Thr Ala Leu Tyr Pro Trp Leu Met Pro
1               5                   10                  15
Ile Tyr His Gln Ile Ala Gln Thr Phe Asp Glu Gly Leu Gly His His
                20                  25                  30
Ala Val Leu Ile Lys Ala Asp Ser Gly Leu Gly Val Glu Ser Leu Phe
            35                  40                  45
Asn Ala Leu Ala Gln Lys Ile Met Cys Val Ala Gln Gly Asp Lys Pro
        50                  55                  60
Cys Gly Gln Cys His Ser Cys His Leu Met Gln Ala His Ser His Pro
65                  70                  75                  80
Asp Tyr His Glu Leu Ser Pro Ile Asn Gly Lys Asp Ile Gly Val Asp
                85                  90                  95
Gln Val Arg Asp Ile Asn Glu Met Val Ala Gln His Ala Gln Gln Asn
            100                 105                 110
Gly Asn Lys Val Val Tyr Val Gln Gly Ala Glu Arg Leu Thr Glu Ala
        115                 120                 125
Ala Ala Asn Ala Leu Leu Lys Thr Leu Glu Glu Pro Arg Pro Asn Thr
130                 135                 140
Tyr Phe Leu Leu Gln Ala Asp Ser Ser Ala Ser Leu Leu Ala Thr Ile
145                 150                 155                 160
Tyr Ser Arg Cys Gln Val Trp Asn Leu Ser Val Pro Asn Glu Glu Ile
                165                 170                 175
Ala Phe Glu Trp Leu Lys Ser Lys Ser Ala Val Glu Asn Gln Glu Ile
            180                 185                 190
Leu Thr Ala Leu Ala Met Asn Leu Gly Arg Pro Leu Leu Ala Leu Glu
        195                 200                 205
Thr Leu Gln Glu Gly Phe Ile Glu Gln Arg Lys Asn Phe Leu Arg Gln
    210                 215                 220
Phe Trp Val Phe Tyr Arg Arg Ser Pro Leu Glu Leu Leu Pro Leu
225                 230                 235                 240
Phe Asp Lys Glu Arg Tyr Val Gln Gln Val Asp Trp Ile Leu Ala Phe
                245                 250                 255
Leu Ser Asp Cys Leu Lys His Lys Leu Glu Ile Asp Ser His Arg Gln
            260                 265                 270
Val Ala Asp Leu Gly Arg Gly Ile Glu Gln Phe Ser Asp Glu Gln Thr
        275                 280                 285
Ala Leu Gly Leu Leu Gln Ala Ile Lys Ile Met Gln Lys Val Arg Ser
    290                 295                 300
Asp Leu Leu Thr Ile Asn Gly Val Asn Val Glu Leu Met Leu Leu Asp
305                 310                 315                 320
```

```
Gly Leu Thr Arg Leu Val Thr Glu Val Phe Glu Thr Gln
                325                 330
```

<210> SEQ ID NO 93
<211> LENGTH: 269
<212> TYPE: PRT
<213> ORGANISM: Rickettsia prowazekii

<400> SEQUENCE: 93

```
Met Thr Ile Leu Gln Pro Leu Ile Ile Glu Leu Leu Glu Phe Tyr Leu
1               5                   10                  15

Lys Tyr Asn Lys Leu Tyr Asn Ser Trp Leu Ile Glu Ala Trp Asn Ile
            20                  25                  30

Glu Gln Thr Leu Gln Asp Leu Lys Glu Phe Ile Tyr Ile Lys Phe Phe
        35                  40                  45

Asn Ser Asn Ile Pro Leu Glu Asn Asn Pro Asp Tyr Tyr Phe Val Ala
    50                  55                  60

Arg Lys Asp Ser Tyr Thr Ser Asn Ala Lys Asn Ile Ser Ile Glu Gln
65                  70                  75                  80

Ile Arg Lys Leu Gln Asp Phe Leu Asn Lys Thr Ser Ala Ile Ser Gly
                85                  90                  95

Tyr Lys Val Ala Val Ile Tyr Ser Ala Asp Leu Met Asn Leu His Ala
            100                 105                 110

Ala Asn Ala Cys Leu Lys Ile Leu Glu Asp Thr Pro Lys Asn Ser Tyr
        115                 120                 125

Ile Phe Leu Ile Thr Ser Arg Ala Ala Ser Ile Ile Ser Thr Ile Arg
    130                 135                 140

Ser Arg Cys Phe Lys Val Asn Ile Arg Ser Pro Leu Pro Asn Val Ser
145                 150                 155                 160

Asn Asp Leu Tyr Leu Gln Phe Ile Gln Pro Ile Ala Asp Asn Lys Thr
                165                 170                 175

Leu Asp Phe Ile Asn Arg Phe Thr Thr Lys Asp Arg Glu Leu Trp Leu
            180                 185                 190

Gly Phe Ile Glu Asn Leu Phe Leu Met Asn Arg Ile Leu Lys Lys
        195                 200                 205

Ser Val Asn Phe Asn Ile Asp Leu Leu Asp Leu Glu Asn Lys Ile Tyr
    210                 215                 220

Asn Lys Leu Asn Lys Asn Pro Ala Tyr Leu Leu Gln Lys Phe Thr Asp
225                 230                 235                 240

Ile Lys Lys Leu Ile Tyr Asn Thr Ile Asp Tyr Asp Leu Asp Leu Lys
                245                 250                 255

Thr Ser Tyr Ile Leu Val Val Asn Glu Phe Phe Thr Val
            260                 265
```

<210> SEQ ID NO 94
<211> LENGTH: 268
<212> TYPE: PRT
<213> ORGANISM: Thermus thermophilus

<400> SEQUENCE: 94

```
Met Ala Leu His Pro Ala His Pro Gly Ala Ile Ile Gly His Glu Ala
1               5                   10                  15

Val Leu Ala Leu Leu Pro Arg Leu Thr Ala Gln Thr Leu Leu Phe Ser
            20                  25                  30

Gly Pro Glu Gly Val Gly Arg Arg Thr Val Ala Arg Trp Tyr Ala Trp
        35                  40                  45
```

```
Gly Leu Asn Arg Gly Phe Pro Pro Ser Leu Gly Glu His Pro Asp
    50                  55                  60

Val Leu Glu Val Gly Pro Lys Ala Arg Asp Leu Arg Gly Arg Ala Glu
65                  70                  75                  80

Val Arg Leu Glu Glu Val Ala Pro Leu Leu Glu Trp Cys Ser Ser His
                85                  90                  95

Pro Arg Glu Arg Val Lys Val Ala Ile Leu Asp Ser Ala His Leu Leu
            100                 105                 110

Thr Glu Ala Ala Ala Asn Ala Leu Leu Lys Leu Leu Glu Glu Pro Pro
            115                 120                 125

Ser Tyr Ala Arg Ile Val Leu Ile Ala Pro Ser Arg Ala Thr Leu Leu
    130                 135                 140

Pro Thr Leu Ala Ser Arg Ala Thr Glu Val Ala Phe Ala Pro Val Pro
145                 150                 155                 160

Glu Glu Ala Leu Arg Ala Leu Thr Gln Asp Pro Gly Leu Leu Arg Tyr
                165                 170                 175

Ala Ala Gly Ala Pro Gly Arg Leu Leu Arg Ala Leu Gln Asp Pro Glu
            180                 185                 190

Gly Tyr Arg Ala Arg Met Ala Arg Ala Gln Arg Val Leu Lys Ala Pro
    195                 200                 205

Pro Leu Glu Arg Leu Ala Leu Leu Arg Glu Leu Leu Ala Glu Glu Glu
    210                 215                 220

Gly Val His Ala Leu His Ala Val Leu Lys Arg Pro Glu His Leu Leu
225                 230                 235                 240

Ala Leu Glu Arg Ala Arg Glu Ala Leu Glu Gly Tyr Val Ser Pro Glu
                245                 250                 255

Leu Val Leu Ala Arg Leu Ala Leu Asp Leu Glu Thr
            260                 265

<210> SEQ ID NO 95
<211> LENGTH: 350
<212> TYPE: PRT
<213> ORGANISM: Aquifex

<400> SEQUENCE: 95

Met Glu Thr Thr Ile Phe Gln Phe Gln Lys Thr Phe Thr Lys Pro
1               5                   10                  15

Pro Lys Glu Arg Val Phe Val Leu His Gly Glu Glu Gln Tyr Leu Ile
                20                  25                  30

Arg Thr Phe Leu Ser Lys Leu Lys Glu Lys Tyr Gly Glu Asn Tyr Thr
            35                  40                  45

Val Leu Trp Gly Asp Glu Ile Ser Glu Glu Phe Tyr Thr Ala Leu
    50                  55                  60

Ser Glu Thr Ser Ile Phe Gly Gly Ser Lys Glu Lys Ala Val Val Ile
65                  70                  75                  80

Tyr Asn Phe Gly Asp Phe Leu Lys Lys Leu Gly Arg Lys Lys Lys Glu
                85                  90                  95

Lys Glu Arg Leu Ile Lys Val Leu Arg Asn Val Lys Ser Asn Tyr Val
            100                 105                 110

Phe Ile Val Tyr Asp Ala Lys Leu Gln Lys Gln Glu Leu Ser Ser Glu
            115                 120                 125

Pro Leu Lys Ser Val Ala Ser Phe Gly Gly Ile Val Val Ala Asn Arg
    130                 135                 140

Leu Ser Lys Glu Arg Ile Lys Gln Leu Val Leu Lys Lys Phe Lys Glu
145                 150                 155                 160
```

-continued

```
Lys Gly Ile Asn Val Glu Asn Asp Ala Leu Glu Tyr Leu Leu Gln Leu
                165                 170                 175
Thr Gly Tyr Asn Leu Met Glu Leu Lys Leu Glu Val Glu Lys Leu Ile
            180                 185                 190
Asp Tyr Ala Ser Glu Lys Lys Ile Leu Thr Leu Asp Glu Val Lys Arg
        195                 200                 205
Val Ala Phe Ser Val Ser Glu Asn Val Asn Val Phe Glu Phe Val Asp
    210                 215                 220
Leu Leu Leu Leu Lys Asp Tyr Glu Lys Ala Leu Lys Val Leu Asp Ser
225                 230                 235                 240
Leu Ile Ser Phe Gly Ile His Pro Leu Gln Ile Met Lys Ile Leu Ser
            245                 250                 255
Ser Tyr Ala Leu Lys Leu Tyr Thr Leu Lys Arg Leu Glu Glu Lys Gly
        260                 265                 270
Glu Asp Leu Asn Lys Ala Met Glu Ser Val Gly Ile Lys Asn Asn Phe
    275                 280                 285
Leu Lys Met Lys Phe Lys Ser Tyr Leu Lys Ala Asn Ser Lys Glu Asp
290                 295                 300
Leu Lys Asn Leu Ile Leu Ser Leu Gln Arg Ile Asp Ala Phe Ser Lys
305                 310                 315                 320
Leu Tyr Phe Gln Asp Thr Val Gln Leu Leu Arg Asp Phe Leu Thr Ser
            325                 330                 335
Arg Leu Glu Arg Glu Val Val Lys Asn Thr Ser His Gly Gly
        340                 345                 350

<210> SEQ ID NO 96
<211> LENGTH: 347
<212> TYPE: PRT
<213> ORGANISM: Bacillus subtilis

<400> SEQUENCE: 96

Met Val Phe Asp Val Trp Lys Ser Leu Lys Lys Gly Glu Val His Pro
1               5                   10                  15
Val Tyr Cys Leu Tyr Gly Lys Glu Thr Tyr Leu Leu Gln Glu Thr Val
            20                  25                  30
Ser Arg Ile Arg Gln Thr Val Val Asp Gln Glu Thr Lys Asp Phe Asn
        35                  40                  45
Leu Ser Val Phe Asp Leu Glu Glu Asp Pro Leu Asp Gln Ala Ile Ala
    50                  55                  60
Asp Ala Glu Thr Phe Pro Phe Met Gly Glu Arg Arg Leu Val Ile Val
65                  70                  75                  80
Lys Asn Pro Tyr Phe Leu Thr Gly Glu Lys Lys Glu Lys Ile Glu
            85                  90                  95
His Asn Val Ser Ala Leu Glu Ser Tyr Ile Gln Ser Pro Ala Pro Tyr
        100                 105                 110
Thr Val Phe Val Leu Leu Ala Pro Tyr Glu Lys Leu Asp Glu Arg Lys
    115                 120                 125
Lys Leu Thr Lys Ala Leu Lys Lys His Ala Phe Met Met Glu Ala Lys
130                 135                 140
Glu Leu Asn Ala Lys Glu Thr Thr Asp Phe Thr Val Asn Leu Ala Lys
145                 150                 155                 160
Thr Glu Gln Lys Thr Ile Gly Thr Glu Ala Ala Glu His Leu Val Leu
            165                 170                 175
Leu Val Asn Gly His Leu Ser Ser Ile Phe Gln Glu Ile Gln Lys Leu
```

```
            180                 185                 190
Cys Thr Phe Ile Gly Asp Arg Glu Glu Ile Thr Leu Asp Asp Val Lys
            195                 200                 205

Met Leu Val Ala Arg Ser Leu Glu Gln Asn Ile Phe Glu Leu Ile Asn
            210                 215                 220

Lys Ile Val Asn Arg Lys Arg Thr Glu Ser Leu Gln Ile Phe Tyr Asp
225                 230                 235                 240

Leu Leu Lys Gln Asn Glu Glu Pro Ile Lys Ile Met Ala Leu Ile Ser
            245                 250                 255

Asn Gln Phe Arg Leu Ile Leu Gln Thr Lys Tyr Phe Ala Glu Gln Gly
            260                 265                 270

Tyr Gly Gln Lys Gln Ile Ala Ser Asn Leu Lys Val His Pro Phe Arg
            275                 280                 285

Val Lys Leu Ala Met Asp Gln Ala Arg Leu Phe Ser Glu Glu Glu Leu
            290                 295                 300

Arg Leu Ile Ile Glu Gln Leu Ala Val Met Asp Tyr Glu Met Lys Thr
305                 310                 315                 320

Gly Lys Lys Asp Lys Gln Leu Leu Leu Glu Leu Phe Leu Leu Gln Leu
            325                 330                 335

Leu Lys Arg Asn Glu Lys Asn Asp Pro His Tyr
            340                 345

<210> SEQ ID NO 97
<211> LENGTH: 342
<212> TYPE: PRT
<213> ORGANISM: Escherichia coli

<400> SEQUENCE: 97

Met Ile Arg Leu Tyr Pro Glu Gln Leu Arg Ala Gln Leu Asn Glu Gly
1               5                   10                  15

Leu Arg Ala Ala Tyr Leu Leu Leu Gly Asn Asp Pro Leu Leu Leu Gln
            20                  25                  30

Glu Ser Gln Asp Ala Val Arg Gln Val Ala Ala Ala Gln Gly Phe Glu
        35                  40                  45

Glu His His Thr Phe Ser Ile Asp Pro Asn Thr Asp Trp Asn Ala Ile
    50                  55                  60

Phe Ser Leu Cys Gln Ala Met Ser Leu Phe Ala Ser Arg Gln Thr Leu
65                  70                  75                  80

Leu Leu Leu Leu Pro Glu Asn Gly Pro Asn Ala Ala Ile Asn Glu Gln
            85                  90                  95

Leu Leu Thr Leu Thr Gly Leu Leu His Asp Asp Leu Leu Leu Ile Val
            100                 105                 110

Arg Gly Asn Lys Leu Ser Lys Ala Gln Glu Asn Ala Ala Trp Phe Thr
            115                 120                 125

Ala Leu Ala Asn Arg Ser Val Gln Val Thr Cys Gln Thr Pro Glu Gln
        130                 135                 140

Ala Gln Leu Pro Arg Trp Val Ala Arg Ala Lys Gln Leu Asn Leu Glu
145                 150                 155                 160

Leu Asp Asp Ala Ala Asn Gln Val Leu Cys Tyr Cys Tyr Glu Gly Asn
            165                 170                 175

Leu Leu Ala Leu Ala Gln Ala Leu Glu Arg Leu Ser Leu Leu Trp Pro
            180                 185                 190

Asp Gly Lys Leu Thr Leu Pro Arg Val Glu Gln Ala Val Asn Asp Ala
        195                 200                 205
```

```
Ala Ala His Phe Thr Pro Phe His Trp Val Asp Ala Leu Leu Met Gly
    210                 215                 220

Lys Ser Lys Arg Ala Leu His Ile Leu Gln Gln Leu Arg Leu Glu Gly
225                 230                 235                 240

Ser Glu Pro Val Ile Leu Leu Arg Thr Leu Gln Arg Glu Leu Leu Leu
                245                 250                 255

Leu Val Asn Leu Lys Arg Gln Ser Ala His Thr Pro Leu Arg Ala Leu
            260                 265                 270

Phe Asp Lys His Arg Val Trp Gln Asn Arg Arg Gly Met Met Gly Glu
        275                 280                 285

Ala Leu Asn Arg Leu Ser Gln Thr Gln Leu Arg Gln Ala Val Gln Leu
    290                 295                 300

Leu Thr Arg Thr Glu Leu Thr Leu Lys Gln Asp Tyr Gly Gln Ser Val
305                 310                 315                 320

Trp Ala Glu Leu Glu Leu Ser Leu Leu Leu Cys His Lys Pro Leu Ala
                325                 330                 335

Asp Val Phe Ile Asp Gly
            340

<210> SEQ ID NO 98
<211> LENGTH: 344
<212> TYPE: PRT
<213> ORGANISM: Haemophilus influenzae

<400> SEQUENCE: 98

Met Asn Arg Ile Phe Pro Glu Gln Leu Asn His His Leu Ala Gln Gly
1               5                   10                  15

Leu Ala Arg Val Tyr Leu Leu Gln Gly Gln Asp Pro Leu Leu Leu Ser
            20                  25                  30

Glu Thr Glu Asp Thr Ile Cys Gln Val Ala Asn Leu Gln Gly Phe Asp
        35                  40                  45

Glu Lys Asn Thr Ile Gln Val Asp Ser Gln Thr Asp Trp Ala Gln Leu
    50                  55                  60

Ile Glu Ser Cys Gln Ser Ile Gly Leu Phe Phe Ser Lys Gln Ile Leu
65                  70                  75                  80

Ser Leu Asn Leu Pro Glu Asn Phe Thr Ala Leu Leu Gln Lys Asn Leu
                85                  90                  95

Gln Glu Leu Ile Ser Val Leu His Lys Asp Val Leu Leu Ile Leu Gln
            100                 105                 110

Val Ala Lys Leu Ala Lys Gly Ile Glu Lys Gln Thr Trp Phe Ile Thr
        115                 120                 125

Leu Asn Gln Tyr Glu Pro Asn Thr Ile Leu Ile Asn Cys Gln Thr Pro
    130                 135                 140

Thr Val Glu Asn Leu Pro Arg Trp Val Lys Asn Arg Thr Lys Ala Met
145                 150                 155                 160

Gly Leu Asp Ala Asp Asn Glu Ala Ile Gln Gln Leu Cys Tyr Ser Tyr
                165                 170                 175

Glu Asn Asn Leu Leu Ala Leu Lys Gln Ala Leu Gln Leu Leu Asp Leu
            180                 185                 190

Leu Tyr Pro Asp His Lys Leu Asn Tyr Asn Arg Val Ile Ser Val Val
        195                 200                 205

Glu Gln Ser Ser Ile Phe Thr Pro Phe Gln Trp Ile Asp Ala Leu Leu
    210                 215                 220

Val Gly Lys Ala Asn Arg Ala Lys Arg Ile Leu Lys Gly Leu Gln Ala
225                 230                 235                 240
```

-continued

```
Glu Asp Val Gln Pro Val Ile Leu Leu Arg Thr Leu Gln Arg Glu Leu
                245                 250                 255

Phe Thr Leu Leu Glu Leu Thr Lys Pro Gln Gln Arg Ile Val Thr Thr
                260                 265                 270

Glu Lys Leu Pro Ile Gln Gln Ile Lys Thr Glu Phe Asp Arg Leu Lys
                275                 280                 285

Ile Trp Gln Asn Arg Arg Pro Leu Phe Leu Ser Ala Ile Gln Arg Leu
    290                 295                 300

Thr Tyr Gln Thr Leu Tyr Glu Ile Ile Gln Glu Leu Ala Asn Ile Glu
305                 310                 315                 320

Arg Leu Ala Lys Gln Glu Phe Ser Asp Glu Val Trp Ile Lys Leu Ala
                325                 330                 335

Asp Leu Ser Val Lys Ile Cys Leu
                340
```

THERMOPHILIC POLYMERASE III HOLOENZYME

CROSS-REFERENCE TO RELATED APPLICATIONS

The present application claims benefit to the filing date of U.S. Provisional Application No. 60/192,736, filed Mar. 28, 2000, herein incorporated by reference.

STATEMENT REGARDING FEDERALLY-SPONSORED RESEARCH AND DEVELOPMENT

Statement under MPEP 310. The U.S. Government has a paid-up license in this invention and the right in limited circumstances to require the patent owner to license others on reasonable terms as provided for by the terms of R44 GM 54482 awarded by The National Institutes of Health (NIH).

Part of the work performed during development of this invention utilized U.S. Government funds. The U.S. Government has certain rights in this invention.

BACKGROUND OF THE INVENTION

1. Field of the Invention

The present invention relates to gene and amino acid sequences encoding DNA polymerase III holoenzyme subunits and structural genes from thermophilic organisms. In particular, the present invention provides DNA polymerase III holoenzyme subunits and accessory proteins of *T. thermophilus*. The present invention also provides antibodies and other reagents useful to identify DNA Polymerase III molecules.

2. Background Art

Bacterial cells contain three types of DNA polymerases termed polymerase I, II and III. DNA polymerase III (pol III) is responsible for the replication of the majority of the chromosome. Pol III is referred to as a replicative polymerase; replicative polymerases are rapid and highly processive enzymes. Pol I and II are referred to as non-replicative polymerases although both enzymes appear to have roles in replication. DNA polymerase I is the most abundant polymerase and is responsible for some types of DNA repair, including a repair-like reaction that permits the joining of Okazaki fragments during DNA replication. Pol I is essential for the repair of DNA damage induced by UV irradiation and radiomimetic drugs. Pol II is thought to play a role in repairing DNA damage which induces the SOS response and in mutants which lack both pol I and III, pol II repairs UV-induced lesions. Pol I and II are monomeric polymerases while pol III comprises a multisubunit complex.

In *E. coli*, pol III comprises the catalytic core of the *E. coli* replicase. In *E. coli*, there are approximately 400 copies of DNA polymerase I per cell, but only 10–20 copies of pol III (Kornberg and Baker, *DNA Replication*, 2d ed., W. H. Freeman & Company, [1992], pp. 167; and Wu et al. J. Biol. Chem., 259:12117–12122 [1984]). The low abundance of pol III and its relatively feeble activity on gapped DNA templates typically used as a general replication assays delayed its discovery until the availability of mutants defective in DNA polymerase I (Kornberg and Gefter, J. Biol. Chem., 47:5369–5375 [1972]).

The catalytic subunit of pol III is distinguished as a component of *E. coli* major replicative complex, apparently not by its intrinsic catalytic activity, but by its ability to interact with other replication proteins at the fork. These interactions confer upon the enzyme enormous processivity. Once the DNA polymerase III holoenzyme associates with primed DNA, it does not dissociate for over 40 minutes—the time required for the synthesis of the entire 4 Mb *E. coli* chromosome (McHenry, Ann. Rev. Biochem., 57:519–550 [1988]). Studies in coupled rolling circle models of the replication fork suggest the enzyme can synthesize DNA 150 kb or longer without dissociation in vitro (Mok and Marians, J. Biol. Chem., 262:16644–16654 [1987]; Wu et al., J. Biol. Chem., 267:4030–4044 [1992]). The essential interaction required for this high processivity is an interaction between the α catalytic subunit and a dimer of β, a sliding clamp processivity factor that encircles the DNA template like a bracelet, permitting it to rapidly slide along with the associated polymerase, but preventing it from falling off (LaDuca et al., J. Biol. Chem., 261:7550–7557 [1986]; Kong et al., Cell 69:425–437 [1992]). The β-α association apparently retains the polymerase on the template during transient thermal fluctuations when it might otherwise dissociate.

The $\beta_2$ bracelet cannot spontaneously associate with high molecular weight DNA, it requires a multiprotein DnaX-complex to open and close it around DNA using the energy of ATP hydrolysis (Wickner, Proc. Natl. Acad. Sci. USA 73:35411–3515 [1976]; Naktinis et al., J. Biol. Chem., 270:13358–13365 [1985]; and Dallmann et al., J. Biol. Chem., 270:29555–29562 [1995]). In *E. coli*, the dnaX gene encodes two proteins, τ and γ. γ is generated by a programmed ribosomal frameshifting mechanism five-sevenths of the way through dnaX mRNA, placing the ribosome in a −1 reading frame where it immediately encounters a stop codon (Flower and McHenry Proc. Natl. Acad. Sci. USA 87:3713–3717 [1990]; Blinkowa and Walker, Nucl. Acids Res., 18:1725–1729 [1990]; and Tsuchihashi and Kornberg, Proc. Nati. Acad. Sci. USA 87:2516–2520 [1990]). In *E. coli*, the DnaX-complex has the stoichiometry $\gamma_2 \tau_2 \delta_1 \delta'_1 \chi_1 \psi_1$ (Dallmann and McHenry, J. Biol. Chem., 270:29563–29569 [1995]). The τ protein contains an additional carboxyl-terminal domain that interacts tightly with the polymerase, holding two polymerases together in one complex that can coordinately replicate the leading and lagging strand of the replication fork simultaneously (McHenry, J. Biol. Chem., 257:2657–2663 [1982]; Studwell and O'Donnell, Biol. Chem., 266:19833–19841 [1991]; McHenry, Ann. Rev. Biochem. 57:519–550 [1988]).

Conservation of a frameshifting mechanism to generate related ATPases is significant in that, by analogy to *E. coli*, can both assemble a processivity factor onto primed DNA. In *E. coli*, ribosomes frameshift at the sequence A AAA AAG into a −1 frame where the lysine UUU anticodon tRNA can base pair with 6As before elongating (Flower and McHenry, Proc. Natl. Acad. Sci. USA 87:3713–3717 [1990]; Blinkowa and Walker, Nucl. Acids Res., 18:1725–1729 [1990]; and Tsuchihashi and Kornberg, Proc. Natl. Acad. Sci. USA 87:2516–2520 [1990]).

Pol IIIs are apparently conserved throughout mesophilic eubacteria. In addition to *E. coli* and related proteobacteria, the enzyme has been purified from the firmicute *Bacillus subtilis* (Low et al., J. Biol. Chem., 251:1311–1325 [1976]; Hammond and Brown [1992]). With the proliferation of bacterial genomes sequenced, by inference from DNA sequence, pol III exists in organisms as widely divergent as Caulobacter, Mycobacteria, Mycoplasma, *B. subtilis* and Synechocystis. The existence of dnaX and dnaN (structural gene for β) is also apparent in these organisms. These general replication mechanisms are conserved even more broadly in biology. Although eukaryotes do not contain polymerases homologous to pol III, eukaryotes contain special polymerases devoted to chromosomal replication and β-like processivity factors (PCNA) and DnaX-like ATPases (RFC, Activator I) that assemble these processivity factors on DNA (Yoder and Burgers, J. Biol. Chem., 266:22689–22697 [1991]; Brush and Stillman, Meth. Enzymol., 262:522–548 [1995]; Uhlmann et al., Proc. Nati. Acad. Sci. USA 93:6521–6526 [1996]).

Helicases serve a variety of functions in DNA metabolism. Cellular (*E. coli* dnaB, priA, and rep proteins), phage (T4 gene 41 and dda proteins; T7 gene 4 protein), and viral (SV40 T antigen; HSV-1 UL5/UL52 complex and UL9 protein) helicases are involved in the initiation of replication, by unwinding DNA so that other proteins of the replication complex can assemble on the ssDNA. These proteins also participate in the elongation phase of replication, by unwinding the duplex DNA ahead of this complex to provide the required template. Other helicases (e.g., the *E. coli* recBCD and recQ proteins) are implicated in recombination by genetic criteria. Another class of helicases includes the *E. coli* uvrAB and uvrD. These helicases act in nucleotide excision repair or methyl-directed mismatch repair during both pre-incision (recognition of DNA damage or alteration) and post-incision (displacement of damaged fragment) steps. See, for example, U.S. Pat. No. 5,747,247.

DNA mispairing can occur in vivo and is recognized and corrected by repair proteins. Mismatch repair has been studied most intensively in *E. coli, Salmonella typhimurium,* and *S. pneumoniae.* The MutS, MutH and MutL proteins of *E. coli* are involved in the repair of DNA mismatches, as is the product of the uvrD gene in *E. coli,* helicase II. See, for example, U.S. Pat. No. 5,750,335.

The best defined mismatch repair pathway is the *E.coli* MutHLS pathway that promotes a long-patch (approximately 3 Kb) excision repair reaction which is dependent on the mutH, mutL, mutS and mutU (uvrD) gene products. The MutHLS pathway appears to be the most active mismatch repair pathway in *E.coli* and is known to both increase the fidelity of DNA replication and to act on recombination intermediates containing mispaired bases. The system has been reconstituted in vitro, and requires the mutH, mutL, mutS and uvrD (helicase II) proteins along with DNA polymerase III holoenzyme, DNA ligase, single-stranded DNA binding protein (SSB) and one of the single-stranded DNA exonucleases, Exo I, Exo VII or RecJ. A similar pathway in yeast includes the yeast MSH2 gene and two mutL-like genes referred to as PMS1 and MLH1. See, for example, U.S. Pat. No. 6,191,268.

The *E. coli* bacterial Uvr proteins are capable of excising damaged DNA sites caused by a broad spectrum of chemical agents that distort the backbone geometry of the DNA double helix. As a result, if the DNA were damaged by chemicals in the environmental sample, the Uvr proteins will cleave and excise the damaged region. Subsequent resynthesis by DNA polymerase I will incorporate labeled or unlabeled nucleotides into the DNA. See, for example, U.S. Pat. No. 6,060,288.

Replication of the lagging strand of DNA is mediated by a multiprotein complex composed of proteins priA, dnaT, dnaB, dnaC, and dnaG. This complex is referred to as a primosome. Purified priA has ATPase, helicase, translocase, and primosome assembly activities. This gene may be essential in recombination and DNA repair since it binds to D-loops, interacts with recG and has helicase activity. The 3'-5' DNA helicase activity of priA inhibits recombination. See, for example, U.S. Pat. No. 6,146,846.

BRIEF SUMMARY OF THE INVENTION

The invention is directed to an isolated polypeptide wherein said polypeptide comprises an amino acid sequence having at least 95% sequence identity to the amino acid sequence of SEQ ID NO: (uvrD helicase) 68.

The invention is directed to an isolated polypeptide wherein said polypeptide comprises an amino acid sequence having at least 95% sequence identity to the amino acid sequence of SEQ ID NO: (DNA-G Primase) 72.

The invention is directed to an isolated polypeptide wherein said polypeptide comprises an amino acid sequence having at least 95% sequence identity to the amino acid sequence of SEQ ID NO: (priA helicase) 76.

The invention is directed to an isolated polypeptide wherein said polypeptide comprises an amino acid sequence having at least 95% sequence identity to the amino acid sequence of SEQ ID NO: (delta subunit) 10.

The invention is directed to an isolated polypeptide wherein said polypeptide comprises an amino acid sequence having at least 95% sequence identity to the amino acid sequence of SEQ ID NO: (delta prime subunit) 17.

The invention is directed to an isolated polypeptide wherein said polypeptide comprises an amino acid sequence having at least 95% sequence identity to the amino acid sequence of SEQ ID NO: (beta subunit) 23.

The invention is directed to an isolated polypeptide wherein said polypeptide comprises an amino acid sequence having at least 95% sequence identity to the amino acid sequence of SEQ ID NO: (ssb protein) 32.

The invention is directed to an isolated polypeptide wherein said polypeptide comprises an amino acid sequence having at least 95% sequence identity to the amino acid sequence of SEQ ID NO: (epsilon-1, dnaQ-1) 37.

The invention is directed to an isolated polypeptide wherein said polypeptide comprises an amino acid sequence having at least 95% sequence identity to the amino acid sequence of SEQ ID NO: (epsilon-2, dnaQ-2) 82.

The invention is directed to a method of producing a polypeptide encoded by a nucleotide sequence, wherein said polypeptide comprises an amino acid sequence having at least 95% sequence identity to the amino acid sequence of one of SEQ ID NOS: 68, 72, 76, 10, 17, 23, 32, 37, and 82, comprising culturing a host cell comprising said nucleotide sequence under conditions such that said polypeptide is expressed, and recovering said polypeptide.

The invention is directed to a method of synthesizing DNA which comprises utilizing one or more polypeptides, said one or more polypeptides comprising an amino acid sequence having at least 95% sequence identity to an amino acid sequence selected from the group consisting of SEQ ID NOS: 68, 72, 76, 10, 17, 23, 32, 37 and 82.

Further objects and advantages of the present invention will be clear from the description that follows.

BRIEF DESCRIPTION OF THE FIGURES

In all of the following Figures that show alignments (DNA or amino acids), the "+" indicates similar, but not identical residues. In the DNA sequences with underlined regions, unless otherwise indicated, the underlining indicates bases generated by the degenerate primers used to generate the DNA of interest. Also unless otherwise indicated, the sequences between the sequences generated by the primers were used in the searches to generate deduced amino acid sequences (i.e., the primer-generated sequences were excluded from the searches).

FIGS. 9A and B. SDS-PAGE analysis of the fraction from the Ni++-NTA column purification of N-terminal tagged *T. thermophilus* DnaX.

FIGS. 10A and B. SDS-PAGE analysis of the fraction from the avidin column purification of N-terminal tagged *T. thermophilus* DnaX.

FIG. 13 The DNA sequence (SEQ ID NO:9) of the *T. thermophilus* holA gene (δ subunit).

FIG. 14. The amino acid sequence (SEQ ID NO: 10) of *T. thermophilus* δ-subunit (holA gene).

FIG. 15. Alignment of the amino acid sequence of δ from *T. thermophilus* (SEQ ID NO: 10) and *E. coli* (SEQ ID NO: 97); (consensus sequence is shown by SEQ ID NO:108).

FIG. 16 Alignment of the amino acid sequence of δ-subunit from *A. aerolicus* (SEQ ID NO: 95), *T. thermophilus* (SEQ ID NO: 10), *B. subtilis* (SEQ ID NO: 96), *E. coli* (SEQ ID NO: 97), and *H. influenzae* (SEQ ID NO: 98); (consensus sequence is shown by SEO ID NO:109).

FIGS. 19A and B. SDS-PAGE analysis of fractions from the Ni++-NTA column purification of *T. thermophilus* δ.

FIG. 22. The DNA sequence (SEQ ID NO: 16) of the *T. thermophilus* holB gene encoding the δ'-subunit of the *T. thermophilus* Pol III holoenzyme.

FIG. 23. The amino acid sequence (SEQ ID NO: 17) of the *T. thermophilus* δ'-subunit derived from the DNA sequence of the *T. thermophilus* holB gene.

FIG. 24. Alignment of the amino acid sequence comparing *E. coli* (SEQ ID NO: 91) and *T. thermophilus* δ' (SEQ ID NO: 94); (consensus sequence is shown by SEQ ID NO:110).

FIG. 25. Alignment of the amino acid sequence of δ'-subunit from *A. aerolicus* (SEQ ID NO: 89), *T. thermophilus* (SEQ ID NO: 94), *B. subtilis* (SEQ ID NO: 90), *E. coli* (SEQ ID NO: 91) and *H. influenzae* (SEQ ID NO: 92) and Rickettsia (SEQ ID NO: 93); (consensus sequence is shown by SEQ ID NO:111).

FIGS. 27A and B. SDS-PAGE Analysis Ni++-NTA column purification of N-terminal tagged *T. thermophilus* δ'.

FIGS. 35A and B. SDS-PAGE analysis of fractions eluting from a Sephacryl S-300 gel filtration column purification of *T. thermophilus* β.

FIG. 47. The DNA sequence (SEQ ID NO: 31) of the gene encoding T. thermophilus SSB.

FIG. 48. The amino acid sequence of (SEQ ID NO:32) the T. thermophilus SSB protein.

FIG. 49. Sequence alignment of T. thermophilus SSB (SEQ ID NO: 88) compared with SSB amino acid sequences from Aquifex (SEQ ID NO: 26), B. subtilis (SEQ ID NO: 27), E. coli (SEQ ID NO: 86) and H. influenzae (SEQ ID NO: 87); (consensus sequence is shown by SEQ ID NO:112).

FIG. 50. Sequence alignment of the N-terminal region of T. thermophilus SSB (residues 1–126 of SEQ ID NO:88) with the C-terminal region of T. thermophilus SSB (residues 127–263 of SEQ ID NO: 88); (consensus sequence is shown by SEQ ID NO:113).

FIG. 52. The DNA sequence of the gene encoding T. thermophilus epsilon-1 ($\epsilon$1, dnaQ-1)(SEQ ID NO:36).

FIG. 53. The amino acid sequence (SEQ ID NO:37) of a T. thermophilus epsilon-1 subunit ($\epsilon$-1).

FIG. 54. The DNA sequence (SEQ ID NO:67) of the gene encoding T. thermophilus uvrD.

FIG. 55. The amino acid sequence (SEQ ID NO:68) of a T. thermophilus uvrD protein.

FIG. 56. The DNA sequence (SEQ ID NO:71) of a T. thermophilus dnaG gene.

FIG. 57. The amino acid sequence (SEQ ID NO:72) of a T. thermophilus dnaG protein.

FIG. 58. The DNA sequence (SEQ ID NO:75) of a T. thermophilus priA gene.

FIG. 59. The amino acid sequence (SEQ ID NO:76) of a T. thermophilus priA protein.

FIG. 60. The DNA sequence (SEQ ID NO: 81) of a T. thermophilus dnaQ-2 gene ($\epsilon$2 subunit).

FIG. 61. The amino acid sequence (SEQ ID NO: 82) of a T. thermophilus $\epsilon$2 subunit.

FIG. 62. The DNA sequence (SEQ ID NO: 22) of a T. thermophilus dnaN gene ($\beta$ subunit).

FIG. 63. The amino acid sequence (SEQ ID NO: 23) of a T. thermophilus $\beta$ subunit.

DETAILED DESCRIPTION OF THE INVENTION

A. Definitions

Figure 1:
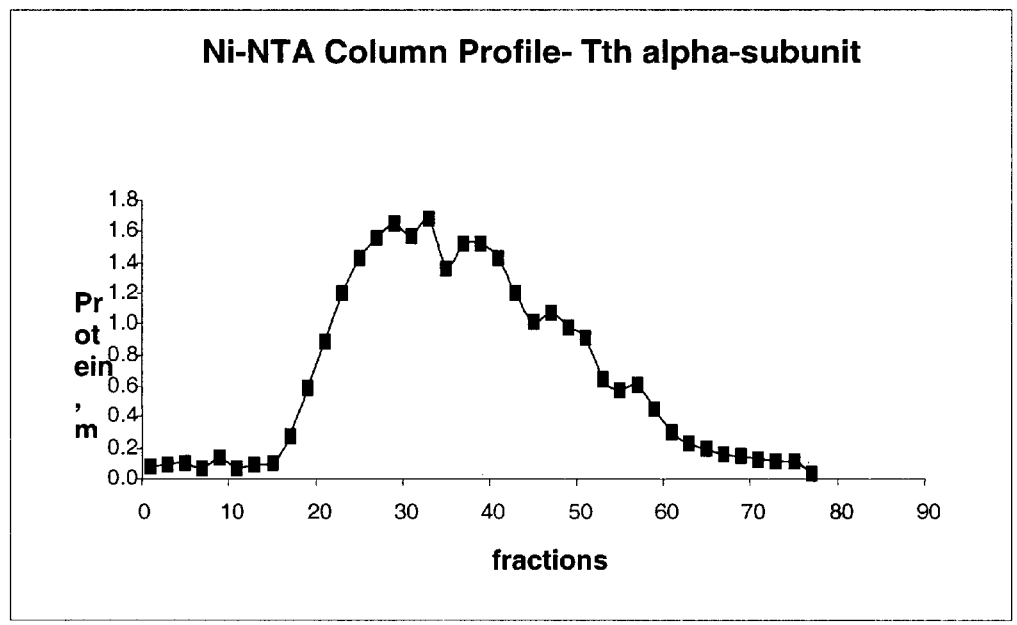
FIG. 1. Protein concentration profile of Ni++-NTA column purification of N-terminal tagged *T. thermophilus* α.

In order to provide a clear and consistent understanding of the specification and claims, including the scope to be given such terms, the following definitions are provided. It is also to be noted that the term "a" or "an" entity, refers to one or more of that entity, for example, "a polynucleotide," is understood to represent one or more polynucleotides.

As used herein, the term "DNA polymerase III holoenzyme" refers to the entire DNA polymerase III entity (i.e., all of the polymerase subunits, as well as the other associated accessory proteins, such as ssb, dnaG, uvrD and priA, required for processive replication of a chromosome or genome), while "DNA polymerase III" is just the core ($\alpha$, $\epsilon$, $\theta$). "DNA polymerase III holoenzyme subunit" is used in reference to any of the subunit entities that comprise the DNA polymerase III holoenzyme. Thus, the term "DNA polymerase III" encompasses "DNA polymerase III holoenzyme subunits" and "DNA polymerase III subunits."

The term "5' exonuclease activity" refers to the presence of an activity in a protein which is capable of removing nucleotides from the 5' end of an oligonucleotide. 5' exonuclease activity may be measured using any of the assays provided herein.

The term "3' exonuclease activity" refers to the presence of an activity in a protein which is capable of removing nucleotides from the 3' end of an oligonucleotide. 3' exonuclease activity may be measured using any of the assays provided herein.

The terms "DNA polymerase activity," "synthetic activity" and "polymerase activity" are used interchangeably and refer to the ability of an enzyme to synthesize new DNA strands by the incorporation of deoxynucleoside triphosphates. The examples below provide assays for the measurement of DNA polymerase activity. A protein which can direct the synthesis of new DNA strands (DNA synthesis) by the incorporation of deoxynucleoside triphosphates in a template-dependent manner is said to be "capable of DNA synthetic activity."

A DNA synthesis terminating agent which terminates DNA synthesis at a specific nucleotide base refers to compounds, including but not limited to, dideoxynucleosides having a 2',3' dideoxy structure (e.g., ddATP, ddCTP, ddGTP and ddTTP). Any compound capable of specifically terminating a DNA sequencing reaction at a specific base may be employed as a DNA synthesis terminating agent.

The term "gene" refers to a nucleic acid (e.g., DNA) sequence that comprises coding sequences necessary for the production of a polypeptide or precursor (e.g., DNA polymerase III holoenzyme, holoenzyme subunit, or accessory protein as appropriate). The polypeptide can be encoded by a full length coding sequence or by any portion of the coding sequence so long as the desired activity or functional properties (e.g., enzymatic activity, ligand binding, signal transduction, etc.) of the full-length polypeptide or fragment are retained. The term also encompasses the coding region of a structural gene and includes sequences located adjacent to the coding region on both the 5' and 3' ends for a distance of about 1 kb on either end such that the gene corresponds to the length of the full-length mRNA.

The term "gene" encompasses both cDNA and genomic forms of a gene. A genomic form or clone of a gene contains the coding region interrupted with non-coding sequences termed "intervening regions" or "intervening sequences." The mRNA functions during translation to specify the sequence or order of amino acids in a nascent polypeptide.

In particular, the terms "DNA polymerase III holoenzyme" and "holoenzyme subunit gene" refer to the full-length DNA polymerase III holoenzyme, and holoenzyme subunit nucleotide sequence(s), respectively. However, it is also intended that the term encompass fragments of the DNA polymerase III holoenzyme and holoenzyme subunit sequences, such as those that encode particular domains of interest, including subunit proteins, as well as other domains within the full-length DNA polymerase III holoenzyme or holoenzyme subunit nucleotide sequence. Furthermore, the terms "DNA polymerase III holoenzyme," "holoenzyme subunit nucleotide sequence," "DNA polymerase III holoenzyme," and "holoenzyme subunit polynucleotide sequence" encompasses DNA, cDNA, and RNA (e.g., mRNA) sequences.

As used herein, the term "accessory protein(s)" refers to a protein or polypeptide required for, or involved in, processive replication of a chromosome or genome. The term further encompasses the full length polypeptide or protein. Where fragments of accessory proteins are intended, the fragment of the polypeptide or protein will be clearly indicated.

"Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited proteins. Further, "polypeptide" and "protein" are used interchangeably unless clearly indicated otherwise. Where a distinction between "polypeptide" and "protein" is intended, such will be made clear.

Genomic forms of a gene may also include sequences located on both the 5' and 3' end of the sequences which are present on the RNA transcript. These sequences are referred to as "flanking" sequences or regions (these flanking sequences are located 5' or 3' to the translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The terms "nucleotide sequence encoding," "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "oligonucleotide" is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, PCR, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "coding region" when used in reference to a structural gene refers to the nucleotide sequences which encode the amino acids found in the nascent polypeptide as a result of translation of a mRNA molecule. The coding region is bounded on the 5' side by the nucleotide triplet "ATG" which encodes the initiator methionine and on the 3' side by one of the three triplets which specify stop codons (i.e., TAA, TAG, TGA). Occasionally, the ATG is replaced by GTG.

The term "polynucleotide molecule comprising a nucleotide sequence encoding a gene," means a nucleic acid sequence comprising the coding region of a gene or in other words the nucleic acid sequence which encodes a gene product. The coding region may be present in either a cDNA, genomic DNA or RNA form. When present in a DNA form, the polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc., or a combination of both endogenous and exogenous control elements.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see, Voss et al., Trends Biochem. Sci., 11:287 [1986]; and Maniatis et al., supra). For example, the SV40 early gene enhancer is very active in a wide variety of cell types from many mammalian species and has been widely used for the expression of proteins in mammalian cells (Dijkema et al., EMBO J. 4:761 [1985]). Two other examples of promoter/enhancer elements active in a broad range of mammalian cell types are those from the human elongation factor 1α gene (Uetsuki et al., J. Biol. Chem., 264:5791 [1989]; Kim et al., Gene 91:217 [1990]; and Mizushima and Nagata, Nucl. Acids. Res., 18:5322 [1990])

and the long terminal repeats of the Rous sarcoma virus (Gorman et al., Proc. Natl. Acad. Sci. USA 79:6777 [1982]) and the human cytomegalovirus (Boshart et al., Cell 41:521 [1985]).

The term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter. Many promoter/enhancer sequences can be used to express the proteins of the invention.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook, supra, at 16.6–16.7).

As used herein, the term "vector" is used in reference to nucleic acid molecules that transfer DNA segment(s) from one cell to another. The term "vehicle" is sometimes used interchangeably with "vector." "Vector" is also used interchangeably with "plasmid." Where a difference is intended, the difference will be made clear.

The term "expression vector" refers to a recombinant DNA molecule containing a desired coding sequence and appropriate nucleic acid sequences necessary for the expression of the operably linked coding sequence" in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transformation" as used herein refers to the introduction of foreign DNA into eukaryotic cells. Transformation may be accomplished by a variety of means known to the art including calcium phosphate-DNA co-precipitation, DEAE-dextran-mediated transfection, polybrene-mediated transfection, transfection, electroporation, microinjection, liposome fusion, lipofection, protoplast fusion, retroviral infection, and biolistics.

The term "selectable marker" refers to the use of a gene which encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene which is used in conjunction with tk⁻ cell lines, the CAD gene which is used in conjunction with CAD-deficient cells and the mammalian hypoxanthine-guanine phosphoribosyl transferase (hprt) gene which is used in conjunction with hprt⁻ cell lines. A review of the use of selectable markers in mammalian cell lines is provided in Sambrook et al., *Molecular Cloning: A Laboratory Manual,* 2nd ed., Cold Spring Harbor Laboratory Press, New York (1989) pp.16.9–16.15.

Eukaryotic expression vectors may also contain "viral replicons" or "viral origins of replication." Viral replicons are viral DNA sequences which allow for the extrachromosomal replication of a vector in a host cell expressing the appropriate replication factors. Vectors which contain either the SV40 or polyoma virus origin of replication replicate to high copy number. Vectors which contain the replicons from bovine papillomavirus or Epstein-Barr virus replicate extrachromosomally at low copy number (~100 copies/cell).

The thermophilic DNA polymerase III holoenzyme or holoenzyme subunits or accessory proteins (for example, dnaG, priA, uvrD) may be expressed in either prokaryotic or eukaryotic host cells. Nucleic acid encoding the thermophilic DNA polymerase III holoenzyme or holoenzyme subunit or accessory proteins (for example, dnaG, priA, uvrD) may be introduced into bacterial host cells by a number of means including transformation of bacterial cells made competent for transformation by treatment with calcium chloride or by electroporation. If the thermophilic DNA polymerase III holoenzyme or holoenzyme subunit or accessory proteins (for example, dnaG, priA, uvrD) are to be expressed in eukaryotic host cells, nucleic acid encoding the thermophilic DNA polymerase III holoenzyme or holoenzyme subunit or accessory proteins (for example, dnaG, priA, uvrD) may be introduced into eukaryotic host cells by a number of means including calcium phosphate co-precipitation, spheroplast fusion, electroporation and the like. When the eukaryotic host cell is a yeast cell, transformation may be affected by treatment of the host cells with lithium acetate or by electroporation or any other method known in the art. It is contemplated that any host cell will be useful in producing the peptides or proteins or fragments thereof of the invention.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, (See e.g., Marmur and Lane, Proc. Natl. Acad. Sci. USA 46:453 [1960]); and Doty et al., Proc. Natl. Acad. Sci. USA 46:461 [1960]) have been followed by the refinement of this process into an essential tool of modern biology. Nonetheless, a number of problems have prevented the wide scale use of hybridization as a tool in diagnostics. Among the more formidable problems are: 1) the inefficiency of hybridization; 2) the low concentration of specific target sequences in a mixture of genomic DNA; and 3) the hybridization of only partially complementary probes and targets.

With regard to efficiency, it is experimentally observed that only a fraction of the possible number of probe-target complexes are formed in a hybridization reaction. This is particularly true with short oligonucleotide probes (less than 100 bases in length). There are three fundamental causes: a) hybridization cannot occur because of secondary and tertiary structure interactions; b) strands of DNA containing the target sequence have rehybridized (reannealed) to their complementary strand; and c) some target molecules are prevented from hybridization when they are used in hybridization formats that immobilize the target nucleic acids to a solid surface.

Even where the sequence of a probe is completely complementary to the sequence of the target (i.e., the target's primary structure), the target sequence must be made accessible to the probe via rearrangements of higher-order structure. These higher-order structural rearrangements may concern either the secondary structure or tertiary structure of the molecule. Secondary structure is determined by intramolecular bonding. In the case of DNA or RNA targets this consists of hybridization within a single, continuous strand of bases (as opposed to hybridization between two different strands). Depending on the extent and position of intramolecular bonding, the probe can be displaced from the target sequence preventing hybridization.

Solution hybridization of oligonucleotide probes to denatured double-stranded DNA is further complicated by the fact that the longer complementary target strands can renature or reanneal. Again, hybridized probe is displaced by this process. This results in a low yield of hybridization (low "coverage") relative to the starting concentrations of probe and target.

With regard to low target sequence concentration, the DNA fragment containing the target sequence is usually in relatively low abundance in genomic DNA. This presents great technical difficulties; most conventional methods that use oligonucleotide probes lack the sensitivity necessary to detect hybridization at such low levels.

One attempt at a solution to the target sequence concentration problem is the amplification of the detection signal. Most often this entails placing one or more labels on an oligonucleotide probe. In the case of non-radioactive labels, even the highest affinity reagents have been found to be unsuitable for the detection of single copy genes in genomic DNA with oligonucleotide probes. (See, Wallace et al., Biochimie 67:755 [1985]). In the case of radioactive oligonucleotide probes, only extremely high specific activities are found to show satisfactory results. (See, Studencki and Wallace, DNA 3:1 [1984]; and Studencki et al., Human Genetics 37:42 [1985]).

With regard to complementarity, it is important for some diagnostic applications to determine whether the hybridization represents complete or partial complementarity. For example, where it is desired to detect simply the presence or absence of pathogen DNA (such as from a virus, bacterium, fungi, mycoplasma, protozoan) it is only important that the hybridization method ensures hybridization when the relevant sequence is present; conditions can be selected where both partially complementary probes and completely complementary probes will hybridize. Other diagnostic applications, however, may require that the hybridization method distinguish between partial and complete complementarity. It may be of interest to detect genetic polymorphisms. For example, human hemoglobin is composed, in part, of four polypeptide chains. Two of these chains are identical chains of 141 amino acids (alpha chains) and two of these chains are identical chains of 146 amino acids (beta chains). The gene encoding the beta chain is known to exhibit polymorphism. The normal allele encodes a beta chain having glutamic acid at the sixth position. The mutant allele encodes a beta chain having valine at the sixth position. This difference in amino acids has a profound (most profound when the individual is homozygous for the mutant allele) physiological impact known clinically as sickle cell anemia. It is well known that the genetic basis of the amino acid change involves a single base difference between the normal allele DNA sequence and the mutant allele DNA sequence.

Unless combined with other techniques (such as restriction enzyme analysis), methods that allow for the same level of hybridization in the case of both partial as well as complete complementarity are typically unsuited for such applications; the probe will hybridize to both the normal and variant target sequence. Hybridization, regardless of the method used, requires some degree of complementarity between the sequence being assayed (the target sequence) and the fragment of DNA used to perform the test (the probe). Of course, those of skill in the art know that one can obtain binding without any complementarity but this binding is nonspecific and to be avoided.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

Numerous equivalent conditions are known in the art that may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above.

The following terms are used to describe the sequence relationships between two or more polynucleotides: "reference sequence", "comparison window", "sequence identity", "percentage of sequence identity", and "substantial identity". The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparision (i.e., the window size), and multiplying the result by 100 to yield the percentage of sequence identity.

A "reference sequence" is a defined sequence used as a basis for a sequence comparision; a reference sequence may be a subset of a larger sequence, for example, as a segment of a full-length cDNA or gene sequence given in a sequence listing, such as any of the polynucleotide sequences provided herein, or may comprise a complete cDNA or gene sequence. Generally, but not always, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "substantial identity" denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length polynucleotide sequence or the full-length cDNA sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. see A gene may produce multiple RNA species which are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe which can hybridize (i.e., it is the complement of) the single-stranded nucleic acid sequence under conditions of low stringency as described. As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

The term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% G+C)$, when a nucleic acid is in aqueous solution at 1 M NaCl (See e.g., Anderson and Young, Quantitative Filter Hybridization, in *Nucleic Acid Hybridization* [1985]). Other references include more sophisticated computations which take structural as well as sequence characteristics into account for the calculation of $T_m$.

The term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 [1972]). Other nucleic acids will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (Erlich (ed.), *PCR Technology*, Stockton Press [1989]).

The term "amplifiable nucleic acid" is used in reference to nucleic acids which may be amplified by any amplification method. It is contemplated that "amplifiable nucleic acid" will usually comprise "sample template."

The term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The term "nested primers" refers to primers that anneal to the target sequence in an area that is inside the annealing boundaries used to start PCR. (See, Mullis et al., *Cold Spring Harbor Symposia*, Vol. LI, pp. 263–273 [1986]). Because the nested primers anneal to the target inside the annealing boundaries of the starting primers, the predominant PCR-amplified product of the starting primers is necessarily a longer sequence, than that defined by the annealing boundaries of the nested primers. The PCR-amplified product of the nested primers is an amplified segment of the target sequence that cannot, therefore, anneal with the starting primers.

The term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

The term "substantially single-stranded" when used in reference to a nucleic acid target means that the target molecule exists primarily as a single strand of nucleic acid in contrast to a double-stranded target which exists as two strands of nucleic acid which are held together by interstrand base pairing interactions.

Nucleic acids form secondary structures which depend on base-pairing for stability. When single strands of nucleic acids (single-stranded DNA, denatured double-stranded DNA or RNA) with different sequences, even closely related ones, are allowed to fold on themselves, they assume characteristic secondary structures. An alteration in the sequence of the target may cause the destruction of a duplex region(s), or an increase in stability of a thereby altering the accessibility of some regions to hybridization of the probes oligonucleotides. While not being limited to any particular theory, it is thought that individual molecules in the target population may each assume only one or a few of the structures (i.e., duplexed regions), but when the sample is analyzed as a whole, a composite pattern from the hybridization of the probes can be created. Many of the structures that can alter the binding of the probes are likely to be only a few base-pairs long and would appear to be unstable. Some of these structures may be displaced by the hybridization of a probe in that region; others may by stabilized by the hybridization of a probe nearby, such that the probe/substrate duplex can stack coaxially with the target intrastrand duplex, thereby increasing the stability of both. The formation or disruption of these structures in response to small sequence changes results in changes in the patterns of probe/target complex formation. As used herein, the term "polymerase chain reaction" ("PCR") refers to the method of Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used in reference to amplification methods such as PCR, the term "polymerase" refers to any polymerase suitable for use in the amplification of nucleic acids of interest. It is intended that the term encompass such DNA polymerases as the polymerase III of the present invention, as well as Taq DNA polymerase (i.e., the type I polymerase obtained from *Thermus aquaticus*), although other polymerases, both thermostable and thermolabile are also encompassed by this definition.

The term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods). The proteins and polypeptides of the invention can be used in any method of synthesizing or replicating DNA.

The terms "restriction endonucleases" and "restriction enzymes" refer to bacterial enzymes, each of which cut double-stranded DNA at or near a specific nucleotide sequence.

The term "recombinant DNA molecule" as used herein refers to a DNA molecule which is comprised of segments of DNA joined together by means of molecular biological techniques.

The terms "in operable combination," "in operable order," and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, the term "purified" or "to purify" refers to the removal of contaminants from a sample. For example, anti-DNA polymerase III holoenzyme and holoenzyme subunit and accessory protein antibodies are purified by removal of contaminating non-immunoglobulin proteins; they are also purified by the removal of immunoglobulin that does not bind DNA polymerase III holoenzyme or holoenzyme subunit or accessory proteins. The removal of non-immunoglobulin proteins and/or the removal of immunoglobulins that do not bind DNA polymerase III holoenzyme or holoenzyme subunit or accessory proteins results in an increase in the percent of DNA polymerase III holoenzyme or holoenzyme subunit or accessory protein-reactive immunoglobulins in the sample. In another example, recombinant DNA polymerase III holoenzyme or holoenzyme subunit or accessory protein polypeptides are expressed in bacterial host cells and the polypeptides are purified by the removal of host cell proteins; the percent of recombinant DNA polymerase III holoenzyme or holoenzyme subunit or accessory protein polypeptides is thereby increased in the sample.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein, the term "fusion protein" refers to a chimeric protein containing the protein of interest (i.e., DNA polymerase III holoenzyme or holoenzyme subunit or accessory proteins and fragments of the holoenzyme, subunit or accessory protein) joined to a fusion partner, which is an exogenous protein or peptide fragment. The fusion partner consists of a non-DNA polymerase III holoenzyme or holoenzyme subunit protein or accessory protein. The fusion partner may enhance solubility of the DNA polymerase III holoenzyme or holoenzyme subunit protein or accessory protein as expressed in a host cell, may provide an affinity tag to allow purification of the recombinant fusion protein from the host cell or culture supernatant, or both. If desired, the fusion protein may be removed from the protein of interest (i.e., DNA polymerase III holoenzyme, holoenzyme subunit protein, or accessory proteins or fragments of any of the foregoing) by a variety of enzymatic or chemical means known to the art.

In the present invention, the subunits and accessory proteins of the invention are fused to an N-terminal peptide that contains a hexahistidine site, a biotinylation site and a thrombin cleavage site. In other embodiments, the subunits and accessory proteins are expressed as translationally coupled proteins. In yet another embodiment, the amino terminal tag comprises a hexahistine site and a biotinylation site. In yet another embodiment, the subunits and accessory proteins of the invention are fused to a C-terminal peptide comprising a hexahistidine site and a biotinylation site. Other marker sequences are known in the art and can be linked to the subunits and accessory proteins of the invention.

A "variant" of DNA polymerase III holoenzyme or holoenzyme subunit or accessory protein refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of a glycine with a tryptophan). Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The term "sequence variation" refers to differences in nucleic acid sequence between two nucleic acid templates. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene. It is noted, however, that the invention does not require that a comparison be made between one or more forms of a gene to detect sequence variations. Because the method of the invention generates a characteristic and reproducible pattern of complex formation for a given nucleic acid target, a characteristic "fingerprint" may be obtained from any nucleic target without reference to a wild-type or other control. The invention contemplates the use of the method for both "fingerprinting" nucleic acids without reference to a control and identification of mutant forms of a target nucleic acid by comparison of the mutant form of the target with a wild-type or known mutant control.

The term "target nucleic acid" refers to the region of nucleic acid bounded by the primers used for polymerase chain reaction. Thus, the "target"is sought to be sorted out from other nucleic acid sequences. A "segment" is defined as a region of nucleic acid within the target sequence.

The term "nucleotide analog" refers to modified or non-naturally occurring nucleotides such as 7-deaza purines (i.e., 7-deaza-dATP and 7-deaza-dGTP). Nucleotide analogs include base analogs and comprise modified forms of deoxyribonucleotides as well as ribonucleotides. The term "nucleotide analog" when used in reference to targets present in a PCR mixture refers to the use of nucleotides other than dATP, dGTP, dCTP and dTTP; thus, the use of dUTP (a naturally occurring dNTP) in a PCR would comprise the use of a nucleotide analog in the PCR. A PCR product generated using dUTP, 7-deaza-dATP, 7-deaza-dGTP or any other nucleotide analog in the reaction mixture is said to contain nucleotide analogs.

Oligonucleotide primers matching or complementary to a gene sequence refers to oligonucleotide primers capable of facilitating the template-dependent synthesis of single or double-stranded nucleic acids. Oligonucleotide primers matching or complementary to a gene sequence may be used in PCRs, RT-PCRs and the like.

A "consensus gene sequence" refers to a gene sequence which is derived by comparison of two or more gene sequences and which describes the nucleotides most often present in a given segment of the genes; the consensus sequence is the canonical sequence. "Consensus protein," "consensus amino acid," consensus peptide," and consensus polypeptide sequences refer to sequences that are shared between multiple organisms or proteins.

The term "biologically active," refers to a protein or other biologically active molecules (e.g., catalytic RNA) having structural, regulatory, or biochemical functions of a naturally occurring molecule. Likewise, "immunologically active" refers to the capability of the natural, recombinant, or synthetic DNA polymerase III holoenzyme or holoenzyme subunit, or accessory proteins, or any oligopeptide or polynucleotide thereof, to induce a specific immune response in appropriate animals or cells and to bind with specific antibodies.

The term "agonist" refers to a molecule which, when bound to DNA polymerase III holoenzyme or holoenzyme subunit or accessory protein, causes a change in DNA polymerase III holoenzyme or holoenzyme subunit or accessory protein, which modulates the activity of DNA polymerase III holoenzyme or holoenzyme subunit or accessory protein. Agonists may include proteins, nucleic acids, carbohydrates, or any other molecules which bind or interact with DNA polymerase III holoenzyme or holoenzyme subunit or accessory protein.

The terms "antagonist" or "inhibitor" refer to a molecule which, when bound to DNA polymerase III holoenzyme or holoenzyme subunit, blocks or modulates the biological or immunological activity of DNA polymerase III holoenzyme or holoenzyme subunit or accessory protein. Antagonists and inhibitors may include proteins, nucleic acids, carbohydrates, or any other molecules which bind or interact with DNA polymerase III holoenzyme or holoenzyme subunit or accessory protein.

The term "modulate" refers to a change or an alteration in the biological activity of DNA polymerase III holoenzyme or holoenzyme subunit or accessory protein. Modulation may be an increase or a decrease in protein activity, a change in binding characteristics, or any other change in the biological, functional, or immunological properties of DNA polymerase III holoenzyme or holoenzyme subunit or accessory protein.

The term "derivative" refers to the chemical modification of a nucleic acid encoding DNA polymerase III holoenzyme or holoenzyme subunit or accessory protein, or the encoded DNA polymerase III holoenzyme or holoenzyme subunit or accessory protein. Illustrative of such modifications would be replacement of hydrogen by an alkyl, acyl, or amino group. A nucleic acid derivative would encode a polypeptide which retains essential biological characteristics of the natural molecule.

The term "Southern blot (analysis)" refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook et al., *Molecular Cloning: A Laboratory Manual,* Cold Spring Harbor Press, NY, pp 9.31–9.58 [1989]).

The term "Northern blot (analysis)" refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook et al., supra, pp 7.39–7.52 [1989]).

The term "Western blot" or "Western analysis" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein is generally less than the number of antigenic epitopes. See, for instance, Geysen, et al., Proc. Natl. Acad. Sci. USA 81:3998–4002 (1983). See, for example, U.S. Pat. No. 6,011,012.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody. See, for example, U.S. Pat. No. 6,011,012.

The terms "specific binding" or specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labelled "A" and the antibody will reduce the amount of labelled A bound to the antibody.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

The terms "test DNA polymerase III holoenzyme" and "test holoenzyme subunit" or "test protein" refers to a sample suspected of containing DNA polymerase III holoenzyme or holoenzyme subunit or accessory protein, respectively. The concentration of DNA polymerase III holoenzyme or holoenzyme subunit or accessory protein in the test sample is determined by various means, and may be compared with a "quantitated amount of DNA polymerase III holoenzyme or holoenzyme subunit or accessory protein" (i.e., a positive control sample containing a known amount of DNA polymerase III holoenzyme or holoenzyme subunit or accessory protein), in order to determine whether the concentration of test DNA polymerase III holoenzyme or holoenzyme subunit or accessory protein in the sample is within the range usually found within samples from wild-type organisms.

The term "microorganism" or "organism" as used herein means an organism too small to be observed with the unaided eye and includes, but is not limited to bacteria, virus, protozoans, fungi, and ciliates.

The term "microbial gene sequences" refers to gene sequences derived from a microorganism.

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery).

B. Methodologies

Unless otherwise indicated, all nucleotide sequences determined by sequencing a DNA molecule herein were determined using an automated DNA sequencer. A variety of sequencers are known in the art, such as the Model 373 from Applied Biosystems, Inc., for example. Amino acid sequences of polypeptides encoded by DNA molecules determined herein were predicted by translation of a DNA sequence determined as above. Alternatively the sequence can be determined by directly sequencing the polypeptide. As is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence cause a frame shift in translation of the nucleotide sequence such that the predicted amino acid sequence compared to the actual sequence will encoded by a determined nucleotide sequence will be completely different from the amino acid sequence actually encoded by the sequenced DNA molecule, beginning at the point of such an insertion or deletion. See for example, U.S. Pat. Nos. 6,171,816 and 6,040,157.

"Identity" per se has an art-recognized meaning and can be calculated using published techniques. (See, e.g.: (COMPUTATIONAL MOLECULAR BIOLOGY, Lesk, A. M., ed., Oxford University Press, New York, (1988); BIO-COMPUTING: INFORMATICS AND GENOME PROJECTS, Smith, D. W., ed., Academic Press, New York, (1993); COMPUTER ANALYSIS OF SEQUENCE DATA, PART I, Griffin, A. M., and Griffin, H. G., eds., Humana Press, New Jersey, (1994); SEQUENCE ANALYSIS IN MOLECULAR BIOLOGY, von Heinje, G., Academic Press, (1987); and SEQUENCE ANALYSIS PRIMER, Gribskov, M. and Devereux, J., eds., M Stockton Press, New York, (1991).) While there exists a number of methods to measure identity between two polynucleotide or polypeptide sequences, the term "identity" is well known to skilled artisans. (Carillo, H., and Lipton, D., SIAM J Applied Math 48:1073 (1988)). Methods commonly employed to determine identity or similarity between two sequences include, but are not limited to, those disclosed in Guide to Huge Computers, Martin J. Bishop, ed., Academic Press, San Diego, (1994), and Carillo, H., and Lipton, D., SIAM J Applied Math 48:1073 (1988). Methods for aligning polynucleotides or polypeptides are codified in computer programs, including the GCG program package (Devereux, J., et al., Nucleic Acids Research (1984) 12(1):387 (1984)), BLASTP, BLASTN, FASTA (Atschul, S. F. et al., J. Molec. Biol. 215:403 (1990), Bestfit program (Wisconsin Sequence Analysis Package, Version 8 for Unix, Genetics Computer Group, University Research Park, 575 Science Drive, Madison, Wis. 53711 (using the local homology algorithm of Smith and Waterman, Advances in Applied Mathematics 2:482–489 (1981)). See U.S. Pat. No. 6,040,157.

In certain embodiments, polynucleotides of the invention comprise a nucleic acid, the sequence of which is at least 90%, 91%, 92%, 93%, 94%, 95%, 96%, 97%, 98% or 99% identical to a sequence selected from the group consisting of SEQ ID NOS: 9, 16, 22, 31, 36, 67, 71, 75 and 81, or a complementary sequence thereof.

By a polynucleotide comprising a nucleic acid, the sequence of which is at least, for example, 95% "identical" to a reference nucleotide sequence is intended that the nucleic acid sequence is identical to the reference sequence except that the nucleic acid sequence may include up to five point mutations per each 100 nucleotides of the reference nucleic acid sequence. In other words, to obtain a nucleic acid, the sequence of which is at least 95% identical to a reference nucleic acid sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be any one of the entire nucleotide sequences shown in SEQ ID NOS: 9, 16, 22, 31, 36, 67, 71, 75 and 81, or any fragment of any of these sequences, as described infra. See U.S. Pat. Nos. 6,040,157 and 6,171,816, for example.

As a practical matter, whether any particular nucleic acid molecule is at least 95%, 96%, 97%, 98% or 99% identical to, for instance, the nucleotide sequence shown in SEQ ID NOS: 9, 16, 22, 31, 36, 67, 71, 75 and 81, can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed. Other sequence analysis programs, known in the art, can be used to determine percent identity. See U.S. Pat. Nos. 6,040,157 and 6,171,816.

Of course, due to the degeneracy of the genetic code, one of ordinary skill in the art will immediately recognize that a large number of the nucleic acid molecules having a sequence at least 95%, 96%, 97%, 98%, or 99% identical to the nucleic acid sequences shown in SEQ ID NOS: 9, 16, 22, 31, 36, 67, 71, 75 and 81 will encode a polypeptide or protein having biological activity. In fact, since degenerate variants of these nucleotide sequences all encode the same polypeptide, this will be clear to the skilled artisan even without performing the comparison assays. It will be further recognized in the art that, for such nucleic acid molecules that are not degenerate variants, a reasonable number will also encode a polypeptide have biological activity. This is because the skilled artisan is fully aware of amino acid substitutions that are either less likely or not likely to significantly effect protein function (e.g., replacing one aliphatic amino acid with a second aliphatic amino acid). See, U.S. Pat. Nos. 6,011,012; 6,171,186; 6,040,157.

One embodiment of the present invention is directed to polynucleotides comprising a nucleic acid, the sequence of which is at least 90%, 91%, 92%, 93%, 94%, 95%, 96%, 97%, 98% or 99% identical to a nucleic acid sequence of SEQ ID NOS: 9, 16, 22, 31, 36, 67, 71, 75 and 81, or a complementary sequence thereof, irrespective of whether they have functional activity. This is because even where a particular polynucleotide does not have functional activity, one of skill in the art would still know how to use the nucleic acid molecule, for instance, as a hybridization probe, an S1 nuclease mapping probe, or a polymerase chain reaction (PCR) primer.

Preferred, however, are polynucleotides comprising a nucleic acid, the sequence of which is at least 90%, 91%, 92%, 93%, 94%, 95%, 96%, 97%, 98% or 99% identical to a nucleic acid sequence of SEQ ID NOS: 9, 16, 22, 31, 36, 67, 71, 75 and 81, or a complementary sequence thereof, which do, in fact, encode proteins which have functional activity.

The present invention further relates to variants of the nucleic acid molecules of the present invention, which encode portions, analogs or derivatives of the DNA III subunits and accessory proteins. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985).

Non-naturally occurring variants may be produced using art-known mutagenesis techniques. Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the DNA Pol III subunits and accessory proteins or fragments or portions thereof. Also especially preferred in this regard are conservative substitutions. Most highly preferred are nucleic acid molecules encoding the mature proteins having the amino acid sequence shown in SEQ ID NOS: 10, 17, 23, 32, 37, 68, 72, 76 and 82.

By a polypeptide having an amino acid sequence at least, for example, 95% "identical" to a reference amino acid sequence of a polypeptide is intended that the amino acid sequence of the claimed polypeptide is identical to the reference sequence except that the claimed polypeptide sequence may include up to five amino acid alterations per each 100 amino acids of the reference amino acid of the polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 92%, 95%, 96%, 97%, 98% or 99% identical to, for instance, the amino acid sequence shown in SEQ ID NOS: 10, 17, 23, 32, 37, 68, 72, 76 and 82 or to the amino acid sequence encoded by a nucleic acid sequence can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed. See for example, U.S. Pat. Nos. 6,040,157 and 6,171,816.

For example, the identity between a reference sequence (query sequence, a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. See for example, U.S. Pat. No. 6,040,157.

Guidance concerning how to make phenotypically silent amino acid substitutions is provided in Bowie, J. U. et al., "Deciphering the Message in Protein Sequences: Tolerance to Amino Acid Substitutions," Science 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein. See for example, U.S. Pat. Nos. 6,040,157 and 6,171,816.

The DNA Pol III subunit polypeptides and accessory proteins of the invention may be expressed in a modified form, such as a fragment or a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Alternatively, a region of amino acids may be added to the C-terminus of the polypeptide. Methods for adding N-terminal linked peptides and C-terminal linked peptides are known in the art. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. Many such peptide moieties are known in the art and contemplated for use in the practice of the invention herei.

The present invention also provides methods for producing anti-DNA polymerase III holoenzyme and anti-DNA polymerase III holoenzyme subunit and anti accessory protein antibodies comprising, exposing an animal having immunocompetent cells to an immunogen comprising at least an antigenic portion (determinant) of DNA polymerase III holoenzyme (or holoenzyme subunit or accessory) protein, under conditions such that immunocompetent cells produce antibodies directed against the portion of DNA polymerase III protein holoenzyme or holoenzyme subunit or accessory protein. In one embodiment, the method further comprises the step of harvesting the antibodies. In an alternative embodiment, the method comprises the step of fusing the immunocompetent cells with an immortal cell line under conditions such that a hybridoma is produced.

The antibodies used in the methods invention may be prepared using various immunogens. In one embodiment, the immunogen is DNA polymerase III holoenzyme or holoenzyme subunit peptide, to generate antibodies that recognize DNA polymerase III holoenzyme or holoenzyme subunit(s). Antibodies binding to accessory proteins are prepared using identical or similar methods. Such antibodies include, but are not limited to polyclonal, monoclonal, chimeric, single chain, Fab fragments, and an Fab expression library.

Various procedures known in the art may be used for the production of polyclonal antibodies to DNA polymerase III holoenzyme or holoenzyme subunit or accessory proteins. For the production of antibody, various host animals can be immunized by injection with the peptide corresponding to the DNA polymerase III holoenzyme or holoenzyme subunit or accessory protein epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin [KLH]). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, and dinitrophenol.

For preparation of monoclonal antibodies directed toward DNA polymerase III holoenzyme or holoenzyme subunit or accessory protein, any technique that provides for the production of antibody molecules by continuous cell lines in culture may be used (See, e.g., Harlow and Lane, *Antibodies: A Laboratory Manual,* Cold Spring Harbor Laboratory Press, Cold Spring Harbor, N.Y.). These include but are not limited to the hybridoma technique originally developed by Kohler and Milstein (Köhler and Milstein, Nature 256:495–497 [1975]), as well as other techniques known in the art.

According to the invention, techniques described for the production of single chain antibodies (U.S. Pat. No. 4,946, 778; herein incorporated by reference) can be adapted to produce DNA polymerase III holoenzyme or holoenzyme subunit or accessory protein-specific single chain antibodies. An additional embodiment of the invention utilizes the techniques described for the construction of Fab expression libraries (Huse et al., Science 246:1275–1281 [1989]) to allow rapid and easy identification of monoclonal Fab fragments with the desired specificity for DNA polymerase III holoenzyme or holoenzyme subunit or accessory proteins.

Antibody fragments which contain the idiotype (antigen binding region) of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

In the production of antibodies, screening for the desired antibody can be accomplished by techniques known in the art (e.g., radioimmunoassay, ELISA [enzyme-linked immunosorbent assay], "sandwich" immunoassays, immunoradiometric assays, gel diffusion precipitin reactions, immunodiffusion assays, in situ immunoassays [using colloidal gold, enzyme or radioisotope labels, for example], Western Blots, precipitation reactions, agglutination assays (e.g., gel agglutination assays, hemagglutination assays, etc.), complement fixation assays, immunofluorescence assays, protein A assays, and immunoelectrophoresis assays, etc.

In one method, antibody binding is detected by detecting a label on the primary antibody. In another method, the primary antibody is detected by detecting binding of a secondary antibody or reagent to the primary antibody. In a further method, the secondary antibody is labeled. Many means are known in the art for detecting binding in an immunoassay and are within the scope of the present invention. (As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of DNA polymerase III holoenzyme or holoenzyme subunit or accessory protein (e.g., for Western blotting), measuring levels thereof in appropriate biological samples, etc. The biological samples can be tested directly for the presence of DNA polymerase III holoenzyme or holoenzyme subunit or accessory protein using an appropriate strategy (e.g., ELISA or radioimmunoassay) and format (e.g., microwells, dipstick [e.g., as described in International Patent Publication WO 93/03367], etc.). Alternatively, proteins in the sample can be size separated (e.g., by polyacrylamide gel electrophoresis (PAGE), in the presence or not of sodium dodecyl sulfate (SDS), and the presence of DNA polymerase III holoenzyme or holoenzyme subunit detected by immunoblotting (Western blotting). Immunoblotting techniques are generally more effective with antibodies generated against a peptide corresponding to an epitope or antigenic determinant of a protein, and hence, are particularly suited to the present invention.

The present invention provides isolatd DNA polymerase III holoenzyme subunits and accessory proteins from a thermophilic organism.

In preferred embodiments, the thermophilic organism is a thermophilic organism. The thermophilic organism can be selected from a member of the genera Thermus, Thermotoga, and Aquifex.

The present invention also provides full-length polypeptides or proteins. The invention also provides methods for providing, as well, fragments of any size of the protein (i.e, the entire amino acid sequence of the protein, as well as short peptides). Primers and gene amplification techniques are used to amplify the nucleotide sequence encoding the nucleotide region of interest, which upon ligation into a vector and transfection into a host cell, results in expression of the protein or peptide of interest.

The invention is directed to an isolated polypeptide wherein said polypeptide comprises an amino acid sequence having at least 95% sequence identity to the amino acid sequence of SEQ If) NO: (uvrD helicase) 68. In one embodiment, the polypeptide has the amino acid sequence of SEQ ID NO: 68. In another embodiment, the invention is directed to an isolated polynucleotide molecule comprising a nucleotide sequence encoding a polypeptide comprising an amino acid sequence having at least 95% sequence identity to the amino acid sequence of SEQ ID NO: (uvrD helicase) 68. In a different embodiment, the isolated polynucleotide molecule comprises a nucleotide sequence having the sequence of SEQ ID NO: 67. The invention also provides a vector comprising a polynucleotide encoding the polypeptide comprising an amino acid having at least 95% sequence identity to the amino acid sequence of SEQ ID NO: (uvrD helicase) 68. The invention also provides a host cell comprising a vector comprising a nucleotide sequence encoding a polypeptide comprising an amino acid sequence having at least 95% sequence identity to the amino acid sequence of SEQ ID NO: (uvrD helicase) 68. In one embodiment, the polypeptide is a uvrD helicase from a thermophilic organism. In a different embodiment, the thermophilic organism is *Thermus thermophilus*.

The invention is also directed to an isolated polypeptide wherein said polypeptide comprises an amino acid sequence having at least 95% sequence identity to the amino acid sequence of SEQ ID NO: (DNA-G Primase) 72. In one embodiment, the polypeptide has the amino acid sequence of SEQ ID NO: 72. The invention also provides an isolated polynucleotide molecule comprising a nucleotide sequence encoding a polypeptide comprising an amino acid sequence having at least 95% sequence identity to the amino acid sequence of SEQ ID NO: (DNA-G Primase) 72. In one embodiment, the isolated polynucleotide molecule comprises a nucleotide sequence having the sequence of SEQ ID NO: 71. The invention also provides a vector comprising a nucleotide sequence encoding a polypeptide comprising an amino acid sequence having at least 95% sequence identity to the amino acid sequence of SEQ ID NO: (DNA-G Primase) 72. The invention also provides a host cell comprising the vector. In one embodiment, the isolated polypeptide is a DNA G primase from a thermophilic organism. In another embodiment, the thermophilic organism is *Thermus thermophilus*.

The invention also provides an isolated polypeptide wherein said polypeptide comprises an amino acid sequence having at least 95% sequence identity to the amino acid sequence of SEQ ID NO: (priA helicase) 76. In one embodiment, the polypeptide has the amino acid sequence of SEQ ID NO: 76. The invention also provides an isolated polynucleotide molecule comprising a nucleotide sequence encoding a polypeptide comprising an amino acid sequence having at least 95% sequence identity to the amino acid sequence of SEQ ID NO: (priA helicase) 76. In one embodiment, the isolated polynucleotide molecule comprises a nucleotide sequence having the sequence of SEQ ID NO: 75. The invention further provides a vector comprising a nucleotide sequence encoding a polypeptide comprising an amino acid sequence having at least 95% sequence identity to the amino acid sequence of SEQ ID NO: (priA helicase) 76. The invention provides a host cell comprising the vector. In one embodiment, the isolated polypeptide is a priA helicase from a thermophilic organism. In another embodiment, the thermophilic organism is *Thermus thermophilus*.

The invention provides an isolated polypeptide wherein said polypeptide comprises an amino acid sequence having at least 95% sequence identity to the amino acid sequence of SEQ ID NO: (delta subunit) 10. In one embodiment, the polypeptide has the amino acid sequence of SEQ ID NO: 10. The invention also provides an isolated polynucleotide molecule comprising a nucleotide sequence encoding a polypeptide having at least 95% sequence identity to the amino acid sequence of SEQ ID NO: (delta subunit) 10. In one embodiment, the isolated polynucleotide molecule has the sequence of SEQ ID NO: 9. The invention provides a vector comprising a nucleotide sequence encoding a polypeptide comprising an amino acid sequence having at least 95% sequence identity to the amino acid sequence of SEQ ID NO: (delta subunit) 10. The invention provides a host cell comprising said vector. In one embodiment, the isolated polypeptide is a delta subunit from a thermophilic organism. In one embodiment, the thermophilic organism is *Thermus thermophilus*. The invention further provides an isolated antibody molecule, wherein said antibody specifically binds to at least one antigenic determinant on a polypeptide which comprises an amino acid sequence having at least 95% sequence identity to the amino acid sequence of SEQ ID NO: (delta subunit) 10.

The invention provides an isolated polypeptide wherein said polypeptide comprises an amino acid sequence having at least 95% sequence identity to the amino acid sequence of SEQ ID NO: (delta prime subunit) 17. In one embodiment, the polypeptide has the amino acid sequence of SEQ ID NO: 17. The invention is further directed to an isolated polynucleotide molecule comprising a nucleotide sequence encoding a polypeptide comprising an amino acid sequence having at least 95% sequence identity to the amino acid sequence of SEQ ID NO: (delta prime subunit) 17. In one embodiment, the isolated polynucleotide molecule has the sequence of SEQ ID NO: 16. The invention also provides a vector comprising a nucleotide sequence encoding a polypeptide comprising an amino acid sequence having at least 95% sequence identity to the amino acid sequence of SEQ ID NO: (delta prime subunit) 17. The invention further provides a host cell comprising the vector. In one embodiment, the isolated polypeptide is a δ' subunit from a thermophilic organism. In another embodiment, the thermophilic organism is *Thermus thermophilus*. The invention further provides an isolated antibody molecule, where in said antibody specifically binds to at least one antigenic determinant on the polypeptide which comprises an amino acid sequence having at least 95% sequence identity to the amino acid sequence of SEQ ID NO: (delta prime subunit) 17.

The invention is directed to an isolated polypeptide wherein said polypeptide comprises an amino acid sequence having at least 95% sequence identity to the amino acid sequence of SEQ ID NO: (beta subunit) 23. In one embodiment, the polypeptide has the amino acid sequence of SEQ ID NO: 23. The invention is also directed to an isolated polynucleotide molecule comprising a nucleotide sequence encoding a polypeptide comprising an amino acid sequence having at least 95% sequence identity to the amino acid sequence of SEQ ID NO: (beta subunit) 23. In one embodiment, the isolated polynucleotide molecule has the sequence of SEQ ID NO: 22. The invention further provides a vector comprising a nucleotide sequence encoding a polypeptide comprising an amino acid sequence having at least 95% sequence identity to the amino acid sequence of SEQ ID NO: (beta subunit) 23. The invention also provides a host cell comprising the vector. In one embodiment, the isolated polypeptide of is a δ' subunit from a thermophilic organism. In another embodiment, the thermophilic organism is *Thermus thermophilus*. The invention further provides an isolated antibody molecule, wherein said antibody specifically binds to at least one antigenic determinant on a polypeptide comprising an amino acid sequence having at least 95% sequence identity to the amino acid sequence of SEQ ID NO: (beta subunit) 23.

The invention is directed to an isolated polypeptide wherein said polypeptide comprises an amino acid sequence having at least 95% sequence identity to the amino acid sequence of SEQ ID NO: (ssb protein) 32. In one embodiment, the polypeptide has the amino acid sequence of SEQ ID NO: 32. The invention is also directed to an isolated polynucleotide molecule comprising a nucleotide sequence encoding a polypeptide comprising an amino acid sequence having at least 95% sequence identity to the amino acid sequence of SEQ ID NO: (ssb protein) 32. In one embodiment, the isolated polynucleotide molecule has the sequence of SEQ ID NO: 31. The invention further provides a vector comprising a nucleotide sequence encoding a polypeptide comprising an amino acid sequence having at least 95% sequence identity to the amino acid sequence of SEQ ID NO: (ssb protein) 32. The invention provides a host cell comprising the vector. In one embodiment, the isolated polypeptide is an SSB protein from a thermophilic organism. In another embodiment, the thermophilic organism is *Thermus thermophilus*. The invention further provides an isolated antibody molecule, wherein said antibody specifically binds to at least one antigenic determinant on the polypeptide which comprises an amino acid sequence having at least 95% sequence identity to the amino acid sequence of SEQ ID NO: (ssb protein).

The invention is directed to an isolated polypeptide wherein said polypeptide comprises an amino acid sequence having at least 95% sequence identity to the amino acid sequence of SEQ ID NO: (epsilon-1, dnaQ-1) 37. In one embodiment, the polypeptide has the amino acid sequence of SEQ ID NO: 37. The invention is further directed to an isolated polynucleotide molecule comprising a nucleotide sequence encoding a polypeptide comprising an amino acid sequence having at least 95% sequence identity to the amino acid sequence of SEQ ID NO: (epsilon, dnaQ-1) 37. In one embodiment, the isolated polynucleotide molecule has the sequence of SEQ ID NO: 36. The invention also provides a vector comprising a nucleotide sequence encoding a polypeptide comprising an amino acid sequence having at least 95% sequence identity to the amino acid sequence of SEQ ID NO: (epsilon, dnaQ-1) 37. The invention further provides a host cell comprising the vector. In one embodiment, the isolated polypeptide is an epsilon-1 subunit from a thermophilic organism. In another embodiment, the thermophilic organism is *Thermus thermophilus*. The invention further provides an isolated antibody molecule, where in said antibody specifically binds to at least one antigenic determinant on a polypeptide which comprises an amino acid sequence having at least 95% sequence identity to the amino acid sequence of SEQ ID NO: (epsilon, dnaQ-1) 37.

The invention is directed to an isolated polypeptide wherein said polypeptide comprises an amino acid sequence having at least 95% sequence identity to the amino acid sequence of SEQ ID NO: (dnaQ-2) 82. In one embodiment, the polypeptide has the amino acid sequence of SEQ ID NO: 82. The invention is further directed to an isolated polynucleotide molecule comprising a nucleotide sequence encoding a polypeptide comprising an amino acid sequence having at least 95% sequence identity to the amino acid sequence of SEQ ID NO: (dnaQ-2) 82. In one embodiment, the isolated polynucleotide molecule has the sequence of SEQ ID NO: 81. The invention is further directed to a vector comprising a nucleotide sequence encoding a polypeptide comprising an amino acid sequence having at least 95% sequence identity to the amino acid sequence of SEQ ID NO: (dnaQ-2) 82. The invention is also directed to a host cell comprising the vector. In one embodiment, the isolated polypeptide is an epsilon-2 subunit from a thermophilic organism. In another embodiment, the thermophilic organism is *Thermus thermophilus*. The invention further provides an isolated antibody molecule, where in said antibody specifically binds to at least one antigenic determinant on a polypeptide which comprises an amino acid sequence having at least 95% sequence identity to the amino acid sequence of SEQ ID NO: (epsilon-2, dnaQ-2) 82.

The invention is directed to a method of producing a polypeptide encoded by a nucleotide sequence, wherein said polypeptide comprises an amino acid sequence having at least 95% sequence identity to the amino acid sequence of one of SEQ ID NOS: 68, 72, 76, 10, 17, 23, 32, 37, and 82, comprising culturing a host cell comprising said nucleotide sequence under conditions such that said polypeptide is expressed, and recovering said polypeptide.

The invention is also directed to a method of synthesizing DNA which comprises utilizing one or more polypeptides, said one or more polypeptides comprising an amino acid sequence having at least 95% sequence identity to an amino acid sequence selected from the group consisting of SEQ ID NOS: 68, 72, 76, 10, 17, 23, 32, 37 and 82. In one embodiment, the method further comprises providing in any order: a reaction mixture comprising components comprising template, and nucleotides, and incubating said reaction mixture for a length of time and at a temperature sufficient to obtain DNA synthesis. In another embodiment of the method, the method further comprises an N-terminal linked peptide or a C-terminal linked peptide.

It is contemplated that purified DnaQ-1 protein (epsilon subunit 1) and DnaQ-2 (epsilon subunit 2) find use in PCR and other applications in which high fidelity DNA synthesis is required or desirable. Although an understanding of the mechanism is not necessary in order to use the present invention, DnaQ-1 protein or DnaQ-2 protein bind to the α subunit of DNA polymerase III, and works with it to efficiently remove errors made by the DNA polymerase III.

It is also contemplated that DnaQ-1 or DnaQ-2 will find use in place of an adjunct proofreading polymerase in PCR and other amplification amplifications. For example, when combined in an amplification reaction with a DNA polymerase that lacks a proofreading exonuclease, the DnaQ-1 or DnaQ-2 will facilitate elongation of PCR product as it is capable of removing mismatches within the PCR product. Thus, it is contemplated that the present invention (DnaQ-1 or DnaQ-2) will find use in such applications as long-range PCR (e.g., PCR involving 5–50 kb targets).

It is contemplated that the DnaN protein will find use in purification of the β subunit (i.e., the critical subunit that permits pol III to catalyze a processive (i.e., long-distance without dissociating) amplification reaction. DnaN is useful with pol III alone (e.g., α or α plus ε) on linear templates in the absence of additional subunits, or it can be used with the DnaX complex, as well as with additional proteins (e.g., single-stranded binding proteins, helicases, and/or other accessory factors), to permit very long PCR reactions.

It is contemplated that the α subunit, β subunit, δ subunit, δ' subunit, ε-1 subunit, ε-2 subunit, γ subunit, τ subunit, ssb protein, uvrD protein, dnaG protein, and priA protein will find use separately or together in PCR and other applications in which high fidelity DNA synthesis is required or desirable, such as, for example, very long PCR reactions (5–50 kb targets). It is further contemplated that the foregoing N-terminal or C-terminal linked subunits and proteins will find use separately or together in PCR and other applications in which high fidelity DNA synthesis is required or desireable, such as for example, very long PCR reactions (5–50 kb).

Existing PCR technology is limited by relatively non-processive repair-like DNA polymerases. The present invention provides a thermophilic replicase capable of rapid replication and highly processive properties at elevated temperatures. It is contemplated that the compositions of the present invention will find use in many molecular biology applications, including megabase PCR by removing the current length restrictions, long range DNA sequencing and sequencing through DNA with high secondary structure, as well as enabling new technological advances in molecular biology.

All patents and publications referred to herein are expressly incorporated by reference in their entirety.

EXAMPLES

The following examples serve to illustrate certain preferred embodiments and aspects of the present invention and are not to be construed as limiting the scope thereof.

In the experimental disclosure which follows, the following abbreviations apply: g (gram); L (liter); μg (microgram); ml (milliliter); bp (base pair); °C. (degrees Centigrade); kb or Kb (kilobases); kDa or kd (kilodaltons); EDTA (ethylenediaminetetraacetic acid); DTT (dithiothreitol); LB (Luria Broth); -mer (oligomer); DMV (DMV International, Frazier, N.Y.); PAGE (polyacrylamide gel electrophoresis); SDS (sodium dodecyl sulfate); SDS-PAGE (sodium dodecyl sulfate polyacrylamide gel electrophoresis); SSPE (2×SSPE contains 0.36 mM NaCl, 20 mM NaH$_2$PO$_4$, pH 7.4, and 20 mM EDTA, pH 7.4; the concentration of SSPE used may vary), SOP media (20 g/l tryptone (Difco), 10 g/l yeast extract (Difco), 5 g/l NaCl, 2.5 g/l potassium phosphate, dibasic (Fisher), 1 g/l MgSO$_4$ 7H$_2$O (Fisher), pH 7.2); TE buffer (10 mM Tris, 1 mM EDTA); 50×TAE (242 g Tris base, 57.1 ml glacial acetic acid, 100 ml 0.5 M EDTA pH 8.0); Blotto (10% skim milk dissolved in dH$_2$O and 0.2% sodium azide); Gel Loading Dye (0.25% Bromophenol blue, 0.25% xylene cyanol, 25% Ficoll (Type 400) in dH$_2$O);

Pre-hybridization mix (50% Formamide, 5×SSPE, 1% SDS, 0.5% CARNATION™ non-fat dried milk, 10% skim milk, 0.2% Na Azide); FBS (fetal bovine serum); ABS, Inc. (ABS, Inc., Wilmington, Del.); GeneCodes (GeneCodes, Ann Arbor, Mich.); Boehringer Mannheim (Boehringer Mannheim, Indianapolis, Ind.); Champion Industries (Champion Industries, Clifton, N.J.); Organon (Organon Teknika Corp., Durham N.C.); Difco (Difco, Detroit, Mich.); Enzyco (Enzyco Inc., Denver, Colo.); Fisher Scientific (Fisher Scientific, Fair Lawn, N.J.); FMC (FMC, Rockland, Me.); Gibco BRL (Gibco BRL Gaithersburg, Md.); Hyclone (Hyclone, Logan Utah); Intermountain or ISC (ISC BioExpress, Bountiful, Utah); Invitrogen (Invitrogen, Carlsbad, Calif.); Millipore (Millipore, Marlborough, Mass.); MJ Research (MJ Research, Watertown, Mass.); Molecular Probes (Molecular Probes, Eugene, Oreg.); National Diagnostics (National Diagnostics, Manville, N.J.); Pharmacia Biotech (Pharmacia Biotech., Piscataway, N.J.); Promega (Promega Corp., Madison, Wis.); Qiagen (Qiagen, Chatsworth, Calif.); Sigma PE/ABI (Perkin Elmer Applied Biosystems Division, Foster City, Calif.); (Sigma, St. Louis, Mo.); Stratagene (Stratagene, LaJolla Calif.); Tecan (Tecan, Research Triangle Park, N.C.); Whatman (Whatman, Maidstone, England); Lofstrand Labs (Lofstrand Labs, Ltd., Gaithersburg, Md.) and LSPI (LSPI Filtration Products, Life Science Products, Denver, Colo.); Irvine (Irvine Scientific, Irvine Calif.); and Jackson Labs (Jackson Labs, Bar Harbor, Me.).

In Examples in which a molecular weight based on SDS-PAGE gels is reported for a protein, the molecular weight values reported are approximate values.

Example 1

Construction of Starting Vectors
Construction of pA1-CB-Cla-2

Plasmid pA1-CB-Cla-1 was described in U.S. patent application Ser. No. 09/151,888, incorporated herein by reference. For the pA1-CB-Cla-1 plasmid to be useful for expression of several of the *T. thermophilus* genes, modifications were needed. To remove a KpnI restriction site downstream of the C-terminal biotin tag, pA1-CB-Cla-1 plasmid DNA was prepared. All plasmid DNA preparations listed here and below were purified using Promega's Wizard® and Wizard® Plus DNA Purification Systems according to instruction from manufacturer. The pA1-CB-Cla-1 DNA plasmids were digested with KpnI. The resulting 3' and 5' overhanging ends were removed by filling in with Klenow fragment and resealed with T4 DNA ligase in the presence of 1 mM ATP. Plasmids were transformed into DH5α, and plasmid-containing colonies were selected for ampicillin-resistance. Growth of starting vector are in 2×YT culture media (16 g/L bacto-tryptone, 10 g/L bacto-yeast extract, 5 g/L NaCl (pH 7.0) here and in following sections. Destruction of the KpnI site in these plasmids was confirmed by DNA sequencing (ATG seq.#630–631; primers P64-A215 and P38-S5576). One of the colonies that contained isolates that could not be cleaved by KpnI was selected, grown, and used for preparation of the intermediate plasmid pA1-CB-Cla1(Kpn⁻) (ATG glycerol stock #424). Subunits of *T. thermophilus* DNA polymerase III holoenzyme were expressed in *E. coli* host cells. Nucleic acid (plasmids) may be introduced into bacterial host cells by a number of means including transformation of bacterial cells made competent for transformation by treatment with calcium chloride or by electroporation. A review of the use of transformation techniques is provided in Sambrook et al., Molecular Cloning: A Laboratory Manual, 2nd ed., Cold Spring Harbor Laboratory Press, New York (1989) pp.1.74–1.84. The strategy used to introduce plasmids into DH5α bacteria here is also used in all following similar transformation reactions.

The plasmid pA1-CB-Cla1l(Kpn⁻) was digested with the restriction endonucleases ClaI and SpeI to remove the polylinker containing the restrictions sites: EagI, BamHI, XhoI, XbalI and DraIII. Two oligonucleotides (ATG linker/adaptor #P67-S1 and P67-A1) were annealed to form the adaptor/linker (shown below).

| 5'-CGATA AAAAAAAAGG CCGGCCGCTA GCGGTACCA-3' | (SEQ ID NO:1) |
|---|---|
| 3'-TAT TTTTTTTTCC GGCCGGCGAT CGCCATGGTG ATC-5' | (SEQ ID NO:99) |

This adaptor/linker contained ClaI and SpeI sticky ends to allow insertion into these restriction sites present on the plasmid pA1-CB-Cla1 (Kpn⁻). The introduction of this adaptor/linker into ClaI ISpeI digested pA1-CB-Cla1(Kpn⁻) formed a new polylinker containing the restriction sites ClaI-spacer-FseI-NheI KpnI-SpeI and resulted in a new plasmid pA1-CB-Cla-2. This plasmid was transformed into DH5α and plasmid containing colonies were selected by ampicillin-resistance. Plasmids were isolated from one positive clone and the sequence of the inserted DNA was confirmed by DNA sequencing (ATG seq.#649, primer P38-S5576). The isolate containing the confirmed pA1-CB-Cla-2 plasmid was grown and stored as a stock culture (ATG glycerol stock #440).

Construction of pA1-CB-Nco-1

To construct pA1-CB-Nco-1 pDRK-C was first modified (See, Kim, D. R. and McHenry, C. S. (1996) *J Biol Chem* 271, 20690–20698). Plasmid pDRKC DNA was prepared and digested with KpnI. The resulting recessed and overhanging 3' ends were blunted with Klenow fragment and the plasmid was resealed. Plasmids were transformed into DH5α and plasmid-containing colonies were selected by ampicillin-resistance. The plasmids were prepared and screened for loss of the KpnI site. One positive clone containing a plasmid that could not be cleaved by KpnI was selected and the DNA sequence was confirmed by DNA sequencing (ATG SEQ #627 and 632; primers P38-S5576 and P64-A215). This plasmid was named pDRK-C (Kpn−) and the isolate was stored as a glycerol stock culture (ATG glycerol stock #414).

The plasmid pDRK-C (Kpn⁻) was digested with restriction endonucleases XbaI and SpeI to remove the polylinker containing the restriction sites NcoI, EagI, and DraIII. Two oligonucleotides (ATG linker/adaptor #P63-S1 and P63-A1) were annealed to form the adaptor/linker (shown below).

| 5'-CTAGAGGAGGTTAATTAACCATG-GAAAAAAAAAGGTACCAAAAAAAAA GGCCGGCCA-3' | (SEQ ID NO:2) |
|---|---|
| 3'-TCCTCCAATTAATTGGTAC-CTTTTTTTTTCCATGGTTTTTTTTCC GGCCGGTGATC-5' | (SEQ ID NO:100) |

This adaptor/linker contained XbaI and SpeI sticky ends to allow insertion into the corresponding restriction sites present on the pDRK-C (Kpn−) plasmid. The plasmid containing the inserted region was resealed and transformed into DH5α. The introduction of this adaptor/linker into pDRK-C (Kpn−) formed a new polylinker containing the restriction sites XbaI-PacI-NcoI-spacer-KpnI-spacer-FseI-SpeI. The resulting ampicillin-resistant clones were screened for introduction of a KpnI restriction site. The plasmid from one positive clone was sequenced and was found to have the correct sequence in the region of the inserted linker/adaptor (ATG SEQ #646 and 647; primers p38-S5576 and P65-A106). This plasmid was named pA1-CB-Nco-1. This isolate was grown and stored as a stock culture (ATG glycerol stock #438).

Construction of pA1-CB-Nsi1

To prepare the pA1-CB-Nsi1 plasmid, pA1-CB-Nco-1 was digested with restriction endonucleases PacI and KpnI to remove the polylinker containing the restriction sites PacI-NcoI-spacer-KpnI. Two oligonucleotides (ATG linker/adaptor #P68-S1 and P68-A1) were annealed to form the adaptor/linker (shown below).

5'-TTAAATGCATAAAAAAAAAGGTAC-3'   (SEQ ID NO:3)

3'-TAATTTACGTATTTTTTTTTC-5'   (SEQ ID NO:101)

This adaptor/linker contained PacI and KpnI sticky ends to allow insertion into the corresponding PacI/KpnI digested pA1-CB-Nco-1 plasmid. The plasmid was resealed and transformed into DH5α. Introduction of this adaptor/linker into pA1-CB-Nco-1 formed a new polylinker containing the restriction sites XbaI-PacI-NsiI-spacer-KpnI-spacer-FseI-SpeI. The only change was replacement of the NcoI restriction site with an NsiI restriction site. The resulting clones were selected for ampicillin-resistance and isolated plasmids were screened for introduction of an NsiI restriction site. The plasmid from one positive isolate was sequenced and was found to have the correct sequence in the region of the inserted linker/adaptor (ATG SEQ #663, primer P65-A106). This plasmid was named pA1-CB-Nsi-1 and the isolate was grown and stored as a stock culture (ATG glycerol stock #445).

Construction of pA1-CB-NdeI

To construct plasmid pA1-CB-NdeI, pA1-CB-NcoI was digested with NdeI. The overhanging ends were blunted with Klenow fragment to destroy the NdeI restriction site outside of the polylinker region. The linear plasmid was resealed forming pA1-CB-NcoI(NdeI-). This plasmid was transformed into DH5α and plasmids were isolated from one resulting ampicillin-resistant colony. The plasmids were screened for loss of a NdeI site. The region filled in by Klenow fragment was sequenced to confirm the loss of the NdeI site (ATG SEQ 661, primer P65-S2529). pA1-CB-NcoI(NdeI-) was digested with PacI and SpeI restriction enzymes. This removed the polylinker containing PacI-NcoI-spacer-KpnI-spacer-FseI-SpeI restriction sites. An annealed DNA duplex or adaptor/linker (shown below) containing PacI and SpeI sticky ends (ATG linker/adaptor P65-S1 and P65-A1) was inserted into the digested pA1-CB-NcoI(NdeI-) plasmid.

5'-TAACATATGAAAAAAAAAACCAGGT-
    TGCTAGCGGTACCA-3'   (SEQ ID NO:4)

3'-TAATTGTATACTTTTTTTTTTGGTC-
    CAACGATCGCCATGGTGATC-5'   (SEQ ID NO:102)

The introduction of this adaptor/linker into pA1-CB-NcoI (NdeI⁻) formed a new polylinker containing the restriction sites PacI-NdeI-spacer-NheI-KpnI-FseI-SpeI. This plasmid was transformed into DH5α and the plasmids were isolated from one resulting ampicillin-resistant colony. These plasmids were screened for the introduction of a NdeI site. The region containing the inserted sequence was subjected to DNA sequencing to confirm insertion of the correct sequence (ATG SEQ #718, primer P38-S5576). This plasmid was named pA1-CB-NdeI and the positive isolate was grown and stored as a stock culture (ATG glycerol stock #464).

Construction of pA1-NB-Avr-2

To construct pA1-NB-Avr-2, DRK-N(M), a plasmid designed for expression of proteins with an amino-terminal tag was used as the starting plasmid. The amino-terminal tag is composed of a 30 amino acid peptide that is biotinylated in vivo, a hexahistidine site, and thrombin cleavage site (See, Kim and McHenry, J. Biol. Chem., 271:20690–20698 [1996]). Also, there is a pBR322 origin of replication, a gene expressing the laqI$^Q$ repressor protein, and a semisynthetic *E. coli* promoter (pA1) that is repressed by the lacI$^Q$ repressor.

The following two oligonucleotides were separately synthesized, annealed to form a duplex with sticky ends (AvrII and SalI), and inserted into the AvrII/SalI digested pDRK-N(M). The synthetic linker/adaptor consisted of two annealed oligonucleotides (ATG linker/adaptor P64-S1 and P64-A1) (shown below).

5'-CTAGGAAAAAAAAAAGGTAC-
    CAAAAAAAAAGGCCGGCCACTAGTG-3'   (SEQ ID NO:5)

3'-CTTTTTTTTTCCATGGTTTTTTTTTCCG-
    GCCGGTGATCACAGCT-5'   (SEQ ID NO:103)

The insertion of these annealed DNA fragments into pDRK-N(M) converted the polylinker following the fusion peptide from AvrII-DraIII-SalI to AvrII--spacer--KpnI--spacer--FseI--SpeI--SalI. These plasmids were transformed into DH5α and the resulting ampicillin-resistant colonies were screened for plasmids that contained a SpeI site carried by the linker/adaptor. One positive clone was selected and the sequence of the inserted region was confirmed by DNA sequencing across the linker/adaptor region (ATG SEQ #648, primer P64-A215). This plasmid was named pA1-NB-Avr-2 and the isolate was grown and stored as a glycerol stock culture (ATG glycerol stock #439).

Construction of pA1-NB-Kpn1

The pA1-NB-Avr-2 plasmid was modified to construct pA1-NB-Kpn1 by replacing the polylinker containing the AvrII--spacer--KpnI--spacer--FseI--SpeI--SalI with a polylinker containing the restriction sites PstI-KpnI-Spacer-NsiI-SacI-NheI-HindIII-spacer-SpeI. This was accomplished by digestion of pA1-NB-Avr-2 with PstI and SpeI restriction enzymes and insertion of the annealed DNA duplex shown below (ATG adaptor/linker #P64--S1 and P64-A1). The ends of the annealed duplex DNA formed sticky ends corresponding to PstI/SpeI restriction sites (shown below).

5'-GGTACCAAAAATGCATGAGCTCGCTAG-
    CAAGCTTAAAAAAAAAA-3'   (SEQ ID NO:6)

3'-ACGTCCATGGTTTTTACGTACTCGAGC-
    GATCGTTCGAATTTTTTTTTGATC-5'   (SEQ ID NO:104)

The first spacer allows PstI/NsiI double digests and the last spacer allows HindIII/SpeI double digests. The plasmids were transformed into DH5α bacteria and ampicillin-resistant colonies were screened for plasmids that contained HindIII restriction site carried by the linker/adaptor. The DNA sequence of the linker/adaptor region was confirmed by DNA sequencing (ATG SEQ #662, primer P64-A215). This plasmid was named pA1-NB-Kpn-1 and the isolate was grown and stored as a glycerol stock culture (ATG glycerol stock #446).

Construction of pA1-NB-AgeI

The pA1-NB-Avr-2 plasmid was modified to construct pA1-NB-AgeI. This was done by replacing the polylinker in pA1-NB-Avr-2 which contained the restriction sites PstI-AvrII-KpnI-FseI-SpeI with a polylinker containing the restriction sites PstI-spacer-AgeI-BamHI-SacII-spacer-NcoI-SpeI. First, a BamHI site upstream of the polylinker was destroyed. This was accomplished by digesting pA1-NB-Avr-2 with BamHI and filling in the sticky ends created by the digestion with Klenow fragment. The blunted ends of the DNA were resealed. The plasmid was transformed into DH5α and positive isolates were selected by ampicillin-resistance. Plasmids were isolated from one positive isolate and were screened for by the loss of the Bamfi restriction site. The loss of the BamHI restriction site was confirmed by DNA sequencing (ATG SEQ #1171, primer P64-A215). This plasmid was named pA1-NB-Avr2(BamHI⁻) and the positive isolate was stored as a stock culture (ATG glycerol stock #688).

pA1-NB-Avr2(BamHI-) was digested with PstI/SpeI restriction enzymes. This removed the polylinker containing the restriction sites PstLArvI-KpnI-FseI-SpeI. An annealed duplex (ATG adaptor/linker #P116-S1 and P116-A1) (shown below) was inserted into digested pA1-NB-Avr2 (BamHI-).

| 5'-GAAAAAAAAAAACCGGTGGATCCGCG-<br>GAAAAAAAACCATGGA-3' | (SEQ ID NO:7) |
| --- | --- |
| 3'-ACGTCTTTTTTTTTGGCCACCTAG-<br>GCGCCTTTTTTTTGGTACCTGATC-5' | (SEQ ID NO:105) |

The ends of the annealed duplex DNA forms sticky ends corresponding to PstI and SpeI restriction sites. This plasmid was transformed into DH5α and plasmids isolated from the growth of one clone were screened for by the ability to be digested with AgeI, BamI, SacH and NcoI restriction enzymes. The sequence of the inserted region in this plasmid was confirmed by DNA sequencing (ATG SEQ #1176, primer #P64-A215). This plasmid was named pA1-NB-AgeI and the positive isolate was stored as a stock culture (ATG glycerol stock #698).

Construction of pTAC-CC-ClaI

In an attempt to express native proteins from *T. thermophilus* in *E. coli* that have not expressed well, a vector system was constructed that can be used to express proteins as translationally coupled proteins. Plasmid (pTACCCA (pTC9) contains a gene encoding *E. coli* ATP(CTP):tRNA nucleotidyl transferase (referred to as CCA adding enzyme) under control of a tac promoter. This gene is expressed at very high levels. All of this gene was removed except the 5' 12 codons so that the *T. thermophilus* dnaE gene could be coupled to this remaining 5' end as a translationally coupled protein (pTAC-CCA-TE) (discussed below). Beginning with the plasmid pTACCCA-TE, a plasmid was designed containing a polylinker that will allow insertion of other target proteins that can be expressed as translationally coupled proteins. First, pTAC-CCA-TE was digested with NsiI and SpeI. The NsiI restriction site is approximately 35 nucleotide downstream of the CCA adding enzyme start ATG and the SpeI is downstream of the *T. thermophilus* dnaE stop TAG. This removed the entire *T. thermophilus* dnaE (TE) gene and the region linking the CCA adding enzyme gene 5' end to the TE gene. Next, the annealed DNA duplex (below) (ATG adaptor/linker#P152-SL and P152-AL), containing NsiI and SpeI sticky ends was inserted into the digested pTAC-CCA-TE plasmid.

| 5'-TTGAGGAGG*TATCGA*taaAAAAACCGGTCCTAGGCTA<br>GCTCGAGA-3' | (SEQ ID NO:8) |
| --- | --- |
| 3'-ACGTAACTCCTCCATAGCTATTTTTTTG-<br>GCCAGGATCCGATCGAGCTCTGATC-5' | (SEQ ID NO:106) |

This DNA duplex contains "AGGAGG" (italics), the ribosome binding site (RBS), downstream of the NsiI sticky end, followed by a ClaI restriction site (underlined) for insertion of the 5' end of target genes. The ClaI restriction site contains the "t" of the "taa" stop (lower case) for terminating translation of the CCA adding enzyme gene 5' end including the linker region. The added sequence provided by the adaptor/linker (including the ribosome binding site and ClaI restriction site) is such that codon maintenance is in frame with the CCA adding enzyme gene 5' end up to the "taa" stop codon. Here and in the remainder of the text, when a region of DNA is addressed as being "in frame" with another DNA region, this indicates that the codon maintenance for the two regions is such that continued protein expression (translation) is possible without encountering a "stop" codon and therefore terminating the synthesis of the protein. The second "a" of the stop will be used to form the first nucleotide of the "ATG" start codon of the target translationally coupled gene, which is out of frame with the CCA adding enzyme. The remainder of the adaptor/linker contains a polylinker containing the restriction sites ClaI-taa-spacer-AgeI-AvrII-NheI-XhoI-SpeI to accommodate internal restriction sites or sites downstream of stop codons for insertion of target genes. This plasmid was transformed into DH5α and plasmid containing colonies were selected for by ampicillin-resistance. One positive colony was selected and the isolated plasmids were screened for by digesting with NsiI, ClaI and SpeI giving single cuts resulting in linear fragments (5.5 kb). The sequence of the inserted region in this plasmid was confirmed by DNA sequencing (ATG SEQ #1617, primer #P144-S23). This plasmid was named pTAC-CCA-ClaI and the positive isolate was grown and stored as a stock culture (ATG glycerol stock #980).

Target genes will be amplified using PCR in which the forward/sense primer contains ATCGATA<u>atg</u>........ The underlined sequence will be complementary to the 5' end of the target gene, while the upper case is non-complementary and contains the ClaI site needed for insertion into pTAC-CCA-ClaI. Adjacent to the ClaI site is the 5' TA of the stop codon. The "a" (italics) corresponds to the final "a" of the stop "TAa" and also to the "a" of the start "atg" which are overlapping. The reverse/antisense primer must include one of the restriction sites in the polylinker region to allow insertion of the 3' end of the target gene into pTAC-CCA-ClaI. The mechanism of translationally coupling is that the messenger RNA (mRNA) of a highly expressed protein (CCA adding enzyme) is partially translated and then the ribosome encounters the premature stop codon. The inserted RBS inhibits disengagement of the ribosome from the mRNA until the ribosome recognizes the new start codon and proceeds to translate the target protein. Our assumption is that the ribosome RNA helicase activity disrupts secondary structure in the GC-rich *T. thermophilus* sequences, permitting more efficient translational initiation.

Example 2

Verification of Expression of *T. thermophilus* α-subunit Fused to an N-Terminal Peptide that Contains Hexahistidine and a Biotinylation Site by pA1-NB-TE/MGC1030

In U.S. patent application Ser. No. 09/151,888, the cloning of Tth dnaE gene into the pA1-NB-Avr-2 and transformation into MGC1030 was described. Insertion of the dnaE gene into this vector allows the α-subunit to be expressed as an N-terminal tagged protein. The verification of expression was as described below.

PA1-NB-TE was transformed into MGC1030 *E. coli* bacteria (mcrA, mcrB, lamBDA(-), (RRND-RRNE)1, lexA3) (ATG glycerol stock #938) and AP1.L1 *E. coli* (ATG glycerol stock #939). The parent to the AP1.L1 bacterial strain was Novagen BLR bacterial strain [F–, ompT hsdSB (rB– mB–) gal dcm.(srl-recA)306::Tn10. A T1 phage-resistant version of this BLR strain was designated AP1.L1. Single colonies (3 colonies from each transformation) of transformed cells selected for by ampicillin-resistance were inoculated into 2 ml of 2×YT culture media containing 100 μg/ml ampicillin and grown overnight at 37° C. in a shaking incubator. In the morning, 0.5 ml of the turbid culture from the overnight growth was inoculated into 1.5 ml of fresh 2×YT culture media. The cultures were grown for 1 hour at 37° C. with shaking and expression was induced by addition of isopropyl-β-D-thiogalactopyranoside (IPTG) to a final concentration of 1 mM. The cells were harvested by centrifugation 3 hours post-induction. The cell pellets were immediately resuspended in 1/10 culture volume of 2×Laemelli sample buffer (2×solution: 125 mM Tris-HCl (pH 6.8), 20% glycerol, 4% sodium dodecyl sulfate (SDS), 5% β-mercaptoethanol, and 0.005% bromophenol blue w/v), and sonicated to complete lysis of cells and to shear the DNA. The samples were heated for 10 minutes at 90–100° C., and centrifuged to remove insoluble debris. A small aliquot of each supernatant (3 μl) containing total cellular protein was electrophoresised onto a 4–20% SDS-polyacrylamide mini-gel (Novex, EC60255; 1 mm thick, with 15 wells/gel) in 25 mM in Tris base, 192 mM glycine, and 0.1% SDS. The mini-gels were stained with Coomassie Blue. A protein migrating just above the 120 kDa molecular weight standard of the Gibco 10 kDa protein ladder could be detected as a distinct protein band, but was not observed in the uninduced control. This protein band corresponds to the expected molecular weight of the *T. thermophilus* α-subunit fused to the N-terminal fusion protein (141 kDa).

Next, the total protein in each lysate was transferred (blotted) from polyacrylamide gel to nitrocellulose. The total protein in each lysate was transferred (blotted) from polyacrylamide gel to nitrocellulose membrane using a Novex transfer apparatus at 30 V constant voltage in 12 mM Tris base, 96 mM glycine, 0.01% SDS (w/v), and 20% methanol (v/v) for 60 minutes at room temperature. The membrane was blocked in 0.2% Tween 20 (v/v)-TBS (TBST) (tris-buffered saline; 8 g/L NaCl, 0.2 g/L KCl, 3 g/L Tris-HCl (pH 7.4)) containing 5% non-fat dry milk (w/v) for 1 hour at room temperature. The blotted nitrocellulose was next rinsed TBST, and then incubated in 2 μg/ml alkaline phosphatase-conjugated streptavidin (Pierce Chemical Co. #21324) in TBST for 1 hour at room temperature. Following extensive washing TBST, the blot was developed with BCIP/NBT (KPL #50-81-07; one component system). The endogenous *E. coli* biotin-carboxyl carrier protein (biotin-CCP), ~20 kDa was detectable in both induced and non-induced samples. A very intense protein band corresponding to α migrated above the 140 kDa molecular weight standards of the Gibco 10 kDa protein ladder. This protein was observed as a distinct band in the induced cultures, but was not observed in the uninduced control.

The proceedures described here to verify protein expression, which includes lysing cells, obtaining total cellular protein and analysing the protein in SDS-polyacrylamide gel electrophoresis and biotin blot analysis will be used in all following procedures to verify expression of native and tagged proteins. All protein concentrations here and below are determined using the Coomassie Protein Assay Reagent from Pierce and bovine serum albumin (BSA) as a standard.

Large Scale Growth of pA1-NB-TE/MGC1030

Strain pA1-NB-TE/MGC1030 was grown in a 250 L fermentor to produce cells for purification of *T. thermophilus* α as described in the section entitled "Large Scale Growth of Native *T. thermophius* dnaE (α-subunit) by pTAC-CCA-TE". Cell harvest was initiated 3 hours after induction, at $OD_{600}$ of 7.2, and the cells were chilled to 10° C. during harvest. The harvest volume was 175 L, and the final harvest weight was approximately 2.47 kg of cell paste. An equal amount (w/w) of 50 mM Tris (pH 7.5) and 10% sucrose solution was added to the cell paste. Quality control results showed 10 out of 10 positive colonies on ampicillin-containing medium in the inoculum and 10/10 positive colonies at harvest. Cells were frozen by pouring the cells suspension into liquid nitrogen, and stored at –20° C., until processed.

Purification of *T. thermophilus* α Fused to an N-terminal Peptide Containing a Hexahistidine and a Biotinylation Site Lysis was accomplished by creation of spheroplasts of the cells carrying the expressed *T. thermophilus* α-subunits. First, from 600 g of a 1:1 suspension of frozen cells (300 g cells) in Tris-sucrose which had been stored at –20° C., Fri was prepared (875 ml, 21.6 mg/ml). The preparation was as described in the section entitled "Determination of Optimal Ammonium Sulfate Precipitation Conditions of *T. thermophilus* α-subunit Expressed as a Translationally Coupled Protein." To Fr I, ammonium sulfate (0.258 g to each initial ml Fraction I-45% saturation) was added over a 15 min interval. The mixture stirred for an additional 30 min at 4° C. and the precipitate was collected by centrifugation (23, 000×g, 45 min, 0° C.). The resulting pellets were quick frozen by immersion in liquid nitrogen and stored at –80° C.

The pellets from Fr I were resuspended in 90 ml of $Ni^{++}$-NTA suspension buffer and homogenized using a Dounce homogenizer. The sample was clarified by centrifugation (16,000×g) and the supernatant constituted Fr II (98 ml, 25 mg/ml). Fr II was added to 50 ml of a 50% slurry of Ni-NTA resin and rocked for 1.5 hours at 4° C. This slurry was then loaded onto a BioRad Econo-column (2.5×5 cm). The column was washed with 250 ml of $Ni^{++}$-NTA wash buffer at a flow rate of 0.5 ml/min. *T. thermophilus* α was eluted in 150 ml of $Ni^{++}$-NTA elution buffer containing a 10–200 mM imidazole gradient. The eluate was collected in 80×2 ml fractions (FIG. 1). Fractions 30–50 were pooled (see FIG. 1) and constitute FrIII (63 ml, 2 mg/ml).

Construction of Plasmids (pTAC-CCA-TE) that Overexpress *T. thermophilus* α-Subunit as a Translationally Coupled Protein In the preceeding patent application (U.S. application Ser. No. 09/151,888) the *T. thermophilus* dnaE gene (TE) expressing the α-subunit was cloned into pA1-CB-NcoI resulting in the plasmid pA1-TE. This plasmid was designed to express the native form of the α-subunit, but yields of the α-subunit were at very low levels (as previously discussed). In an attempt to increase the level of expression of the native α-subunit a vector was designed to express the α-subunit as a translationally coupled protein. Translational coupling with an upstream highly expressed protein will be used to disrupt strong secondary structures present in the GC-rich *T. thermophilus* dnaE mRNA, permitting more efficient translational initiation and higher levels of *T. thermophilus* expression. The starting plasmid was pTACCCA (pTC9) and contained the CCA adding enzyme under control of a pTAC promoter. This plasmid expresses the CCA adding enzyme at high levels. The strategy was to remove most of the CCA adding enzyme leaving only the 5'-12 codons by digesting pTACCCA plasmid with NsiI and KpnI. The NsiI restriction site is approximately 12 codons downstream of the ATG start site of the CCA adding enzyme and the KpnI restriction site is downstream of the stop codon.

The TE gene was inserted behind the CCA adding enzyme and translationally coupled in two steps. First, the 5' end of the TE gene was amplified using pA1-TE as a template by polymerase chain reaction (PCR). The forward primer (ATG primer #P69-S541) is shown below.

```
5'-GGATATGCATTGAGGAGGATCGATTA
   atgggccgcaaactccgc-3'
```
(SEQ ID NO:20)

The non-complementary portion of the primer is shown as upper case and the portion of the primer complementary to the 5' end of the gene is shown as lower case. The NsiI site (ATGCAT) and the ClaI site (ATCGAT) are shown as underlined italic. The RBS (AGGAGG) is shown as underlined. Both the RBS and the ClaI restriction site maintain codons that are inframe with the structural gene for the CCA adding enzyme. The last two nucleotides of the non-complementary portion of the primer "TA" and the first nucleotides of the complementary portion of the primer "a" form a premature stop codon, in frame with the 5' end of the CCA adding enzyme. The "a" also is the first nucleotide of the "atg" start codon of the TE gene. This places the gene for the CCA adding enzyme and the TE gene out of frame with respect to each other. The sequence of the reverse primer (5'-CGGCTCGCCAGGCGCACCAGG-3') (SEQ ID NO:21) (ATG primer #P69-A971) is complementary to a region just down stream of a unique Kpn I site located approximately 316 bp downstream of the start "ATG" codon.

The PCR product resulting from the forward and reverse primers described in the preceding paragraph (430 base pairs in length) was cut with NsiI and KpnI yielding a 350 bp fragment and inserted into the NsiI/KpnI digested PTAC-CCA plasmid. By cutting the pTACCCA plasmid with these two enzymes the C-terminal (3') ca. 95% of the CCA adding enzyme gene along with approximately 600 bp of sequence downstream of the stop codon was removed. The resulting plasmid was transformed into DH5α and positive isolates were selected by ampicillin-resistance. Plasmid isolated from one positive isolate was verified by digestion with NsiI and KpnI (yielding the expected 0.35 and 5.3 kb fragments). The sequence of the insert was confirmed by DNA sequencing (ATG SEQ #1512 and 1513, primers #P144-S23 and P144-A1965, respectively). This plasmid was named pTAC-CCA-TEmp and the isolate was stored as a glycerol stock culture (ATG glycerol stock #898).

To reconstruct the remainder of the T. thermophilus dnaE gene, the pA1-TE plasmid was digested using the restriction enzymes KpnI and SalI. The SalI restriction site is approximately 254 bp downstream of the end of the TE gene. It is also located downstream of a C-terminal biotin-hexahistidine fusion peptide. The resulting 3601 base pair KpnI-SalI fragment encompassing the C-terminal (3') 95% of the T. thermophilus dnaE gene, was inserted into the KpnI/SalI digested pTAC-CCA-TEmp plasmid. The plasmid was ligated, transformed into DH5α and positive isolates were selected for ampicillin-resistance. Plasmid isolated from one positive isolate was verified by digestion with KpnI and SalI restriction enzymes (yielding the expected 3.6 and 5.6 kb fragments). The sequence of the insert was confirmed by DNA sequencing (ATG SEQ #1550 and 1551, primers #P144-S23 and P144-A1965, respectively). This plasmid was named pTAC-CCA-TE and the isolate pTAC-CCA-TE/DH5α was stored as a glycerol stock culture (ATG glycerol stock #933).

Verification of Expression of Native T. thermophilus dnaE Gene (α-subunit) as a Translationally Coupled Protein by pTAC-CCA-TE pTAC-CCA-TE plasmids were transformed into MGC1030 (ATG glycerol stock #938) and AP1.L1 E. coli (ATG glycerol stock #939). Three isolates from each transformation were grown and total protein isolated as described above. An aliquot (3 µl) of each supernatant was subjected to electrophoresis in a 4–20% SDS-polyacrylamide mini-gel (Novex, EC60255; 1 mm thick, with 15 wells/gel) in 25 mM in Tris base, 192 mM glycine, and 0.1% SDS. The resulting gels were stained with Coomassie Brilliant Blue. Distinct protein bands from both MGC1030 and AP1.L1 bacterial preparations, migrating slightly above the 120 kDa molecular weight standard, of the Gibco 10 kDa protein ladder, were observed as distinct bands in the induced cultures, but were not observed in the uninduced controls. These proteins were determined to be consistent with the expected molecular weight expected for native T. thermophilus α (137.5 kDa). The detected proteins represented approximately 5% of the total E. coli protein, based on the intensity of Coomassie Blue staining of the protein bands on the gel.

Optimization of T. thermophilus Protein Expression

In an attempt to optimize the yield of expressed recombinant T. thermophilus proteins, induction times were analyzed for each new protein. F-media (Bacto Yeast Extract, 14 g/L, Bacto Tryptone, 8 g/L, potassium phosphate-dibasic, 12 g/L, potassium phosphate-monobasic, 1.2 g/L, (pH 7.2), 1% glucose) is used as a growth medium. A small amount of F-media (10–20 ml) containing a ampicillin is innoculated with the target bacteria and grown overnight at 37° C. while shaking. This overnight growth is used to inoculate fresh F-media containing ampicillin pre-warmed to 37° C. The fresh media is inoculated at a 20:1 ratio using the culture grown overnight. This allows enough time for cell density to double 3–4 times before induction. The freshly innoculated culture is grown to an $OD_{600}$=0.6–0.8 (The optical density $(OD)_{600}$ is a unit used to measure light scattered by cells in solution at 600 nanometers in calculating the density of cells in the solution) and expression induced by addition of IPTG to 1 mM. At the time of induction d-biotin is added to proteins containing hexahistidine and a biotinylation site to a final concentration of 10 µM. The control culture received d-biotin only—they were not induced with IPTG.

Equal sample volumes (5 ml) of culture are collected at the time of induction and every hour after induction up to 5 hours post induction for analysis to determine optimum growth times. The $OD_{600}$ is each sample is determined. The samples collected are centrifuged in a Fisher Centrific Model 228 (1380×g) for 10 min. The supernatant is discarded and the cell pellets were retained for analysis. To maintain equal concentration of total protein in each sample, 50 ul of Laemmli lysis buffer (125 mM Tris-HCl, (pH 6.8), 20% glycerol, 5% SDS) was added per $OD_{600}$ of each sample multiplied by the sample volumes (5 ml). The cell pellets are resuspended and heated to 90–100° C. for 10 min. The samples are centrifuged at maximum rpm (16,000×g) for 10 min using a table top microfuge, and the supernatant is retained. Small aliquots containing total cellular protein, of each supernatant (5 µl) are loaded onto a 10% SDS-polyacrylamide gel electrophoresis gel (16×18×0.75 cm) in 25 mM in Tris base, 192 mM glycine, and 0.1% SDS. The gels are electrophoresised for 2 h at 250 volts. The gels are stained with Coomassie Blue or (for proteins containing hexahistidine and a biotinylation site) transferred to nitrocellulose and analyzed by biotin blot analysis. Biotin blot analysis is used to refer to proteins that have been transferred from SDS-polyacrylamide gels to nitrocellulose membrane and proteins detected by virtue of biotin bound to an N- or C-terminal peptide that contains a biotinylation site. In normally growing cells a certain percentage of proteins containing a biotinylation site is bound by biotin. The detection of these proteins is by virtue of avidin binding to the biotin bound to the fusion peptide. Alkaline phosphatase-conjugated streptavidin (Pierce Chemical Co. #21324) is used and can be detected using chemicals that allow the alkaline phosphatase and therefore the protein of interest to be visualized.

Figure 2:
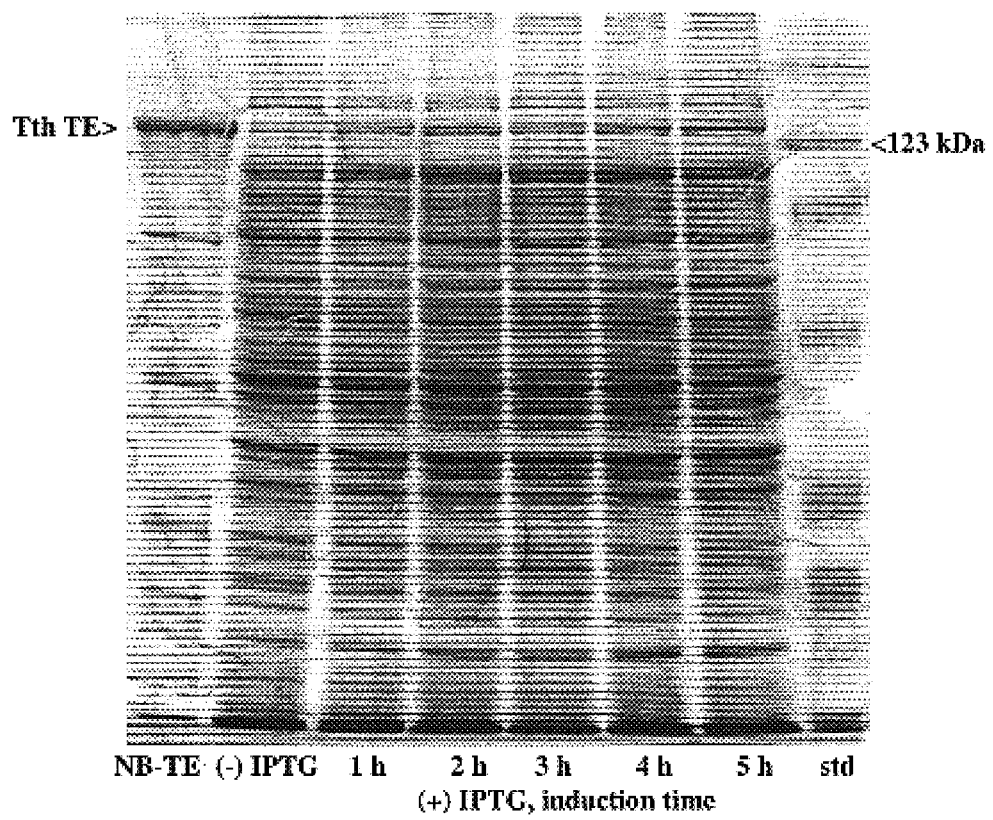
FIG. 2. SDS-PAGE analysis of expression optimization of pTAC-CCA-TE.

Optimization of Expression of T. thermophilus dnaE Gene (α-subunit) by pTAC-CCA-TE In preliminary experiments, T. thermophilus α appeared to be synthesized at higher levels in the AP1.L1 strain. Therefore, the optimum induction times for expression of T. thermophilus from pTAC-CCA-TE carried in AP1.L1 were analyzed. The yield of T. thermophilus α was analyzed at 1, 2, 3, 4, and 5 h induction times as described above in section "Optimization of T. thermophilus Protein Expression. The optimum yield of T. thermophilus α was attained by 3 h post induction; this induction time was used in subsequent experiments (FIG. 2).

Gap-Filling Assay for Determination of T. thermophilus α-subunit Activity

The catalytic subunit of a replicative complex has a very low processivity in the absence of other holoenzyme subunits on a primed-template. However, the catalytic subunit can fill the gaps of nuclease-activated (gapped) DNA very effectively by fast association and dissociation reactions in low salt conditions (shown below) (See, McHenry and Crow (1979), *J. Biol. Chem.*, 254, 1748–1753). To be able to assay for activity in different purification steps of T. thermophilus α-subunit the gap-filling assay was used.

Assay mixtures (25 $\mu$l) contained 32 mM Hepes (pH 7.5), 13% glycerol, 0.01% Nonidet P40, 0.13 mg/ml BSA, 10 mM $MgCl_2$, 0.2 mg/ml activated calf-thymus DNA, 57 uM each of dGTP, dATP, and dCTP, and 21 $\mu$M [$^3$H] TTP (approximately 100 cpm/pmol). The mixture was assembleded on ice, and reactions were started by the addition of a dilution of samples of DNA polymerase and placing in a 60° C. water bath for 5 minutes. The reactions were stopped by placing the tubes on ice and the DNA precipitated by adding 2 drops of 0.2M sodium pyrophosphate (PPi) and 0.5 ml of 10% TCA. Trapping of precipitated DNA and removal of unincorporated nucleotide triphosphates was accomplished by filtering the mixture through GFC filters (Whatman) and washing the filters with 12 ml 0.2M sodium PPi/1M HCL and then 4 ml of ethanol. The filters were then allowed to dry and [$^3$H]TTP incorporated was quantified by immersing the filters in 5 ml of liquid scintillation fluid (Ecoscint-O, National Diagnostics) and counting on a Beckman LS 3801 scintillation counter. One unit of enzyme activity is defined as one picomole of total nucleotides incorporated per min at 60° C. Positive controls, containing *E. coli* DNA pol III (assayed at 30° C.), and negative controls, containing no polymerase, were included in each set of assays.

Large Scale Growth of Native T. thermophilus α by pTAC-CCA-TE/AP1.L1

Strain pTAC-CCA-TE/AP1.L1 was grown in a 250 L fermentor to produce cells for purification of T. thermophilus dnaE product (α). F-medium (1.4% yeast extract, 0.8% tryptone, 1.2% $K_2HPO_4$, and 0.12% $KH_2PO_4$, pH to 7.2 with NaOH) was sterilized, glucose was added to 1% from a 40% sterile solution and ampicillin (100 mg/L) was added. A large-scale inoculum (28 L), was initiated from a 1 ml glycerol stock culture (i.e., culture stored in 15% glycerol at −80° C.) and grown overnight at 37° C. with 40 L/min aeration. The inoculum was transferred (approximately 4.2 L) to the 250 L fermentor containing 180 L of F-medium with 1% glucose, and 100 mg/L ampicillin (starting $OD_{600}$ of 0.06). To calculate the amount of overnight culture to add to the fermentor, in this fermentation there was 180 L initial F-media, enough should be added to bring the media present in the fermentor to an $OD_{600}$=0.06. This allows enough time for the cell density to double 3–4 times before induction. The culture was incubated at 37° C., with 40 LPM aeration, and stirred at 20 rpm. Expression of T. thermophilus α was induced by addition of IPTG to 1 mM when the culture reached an $OD_{600}$ of 0.79 (expression of foreign proteins in *E. coli* is induced when the cell density reaches approximately an $OD_{600}$=0.6–0.8). Additional ampicillin (100 mg/L) was added at same time as induction. The temperature was maintained at approximately 37° C. throughout the growth. The pH was maintained at 7.2 throughout the growth by addition of $NH_4OH$. Cell harvest was initiated 3 hours after induction at $OD_{600}$=4.88, and the cells were chilled to 10° C. during harvest. The harvest volume was 180 L, and the final harvest weight was approximately 1.9 kg of cell paste. An equal amount (w/w) of 50 mM Tris (pH 7.5) and 10% sucrose solution was added to the cell paste. Cells were frozen by pouring the cells suspension into liquid nitrogen, and stored at −20° C., until processed. Quality control results showed 10 out of 10 positive colonies on ampicillin-containing medium in the inoculum and 10 out of 10 positive colonies on ampicillin-containing medium at harvest. Positive colonies are colonies grown from samples streaked on LB plates that also grow when the colony is transferred to LB plates containing a selective antibiotic. Luria-Bertani (LB) growth medium (bacto-tryptone, 10 g/L, bacto-yeast extract, 5 g/L, NaCl, 10 g/L) is used in selection of positive colonies here and in following sections.

Figure 3:
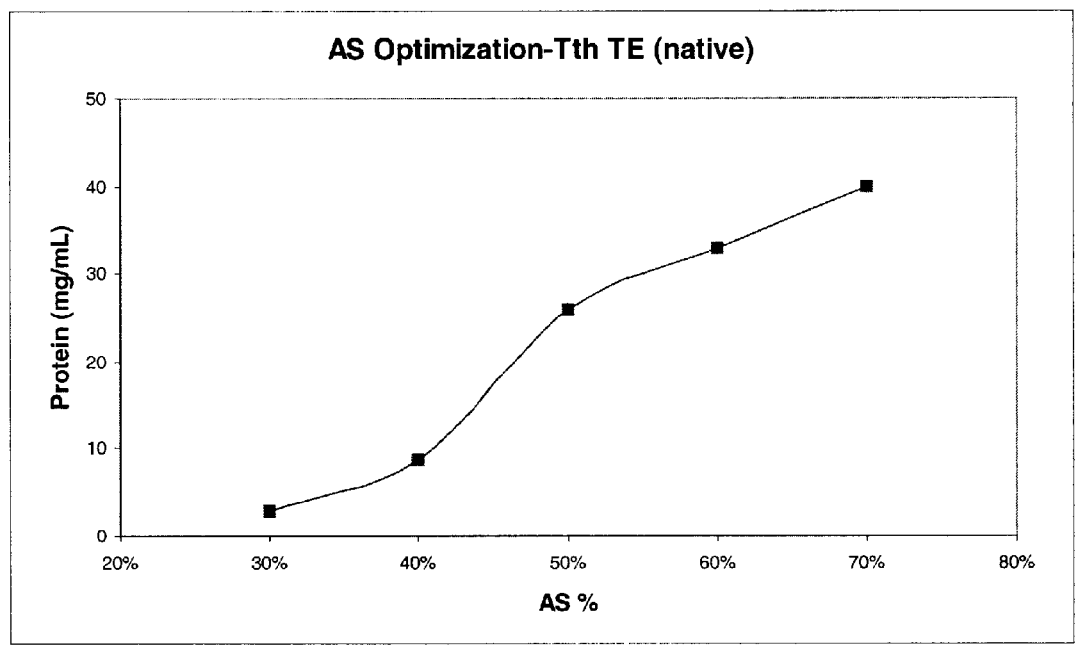
FIG. 3. Protein concentration profile of ammonium sulfate precipitation optimization of native *T. thermophilus* α.

Determination of Optimal Ammonium Sulfate Precipitation Conditions of T. thermophilus α Expressed as a Translationally Coupled Protein Lysis was accomplished by creation of spheroplasts of the cells carrying the expressed T. thermophilus α-subunits. First, 50 g of a 1:1 suspension of frozen cells (25 g cells) in Tris-sucrose which had been stored at −20° C. were added to 69 ml tris-sucrose that had been pre-warmed to 55° C. (2.75 ml/g of cells). To the stirred mixture, 1.25 ml of 0.5 M 1,4-dithiothreitol (DTT) (0.05 ml/g of cells) and 6.25 ml of lysis buffer (2M NaCl, 0.3M spermidine in Tris-sucrose adjusted to pH 7.5) (0.25 ml/g of cells) was added. The presence of 18 mM spermidine kept the nucleoid condensed within partially disrupted cells and displaced DNA binding proteins. The pH of the slurry was adjusted to pH 8.0 by the addition of 0.5 ml of 2 M Tris base (pH is adjusted to 8.0 with 2 M Tris base), and 125 mg lysozyme was added resuspended in 4.5 ml of Tris-sucrose buffer (5 mg lysozyme/g of cells). The slurry was distributed into 250 ml centrifuge bottles after stirring 5 min and incubated at 4° C. for 1 hour. The 250 ml centrifuge bottles were then placed in a 37° C. swirling water bath and gently inverted every 30 seconds for 4 minutes. The supernatant was separated form insoluble cellular debris by centrifugation (23,000×g, 60 min, 4° C.). The recovered supernatant (0.1 l) constituted Fraction I (Fr I) (13 mg protein/ml). All protein concentrations here and below are determined using the Coomassie Protein Assay Reagent from Pierce and bovine serum albumin (BSA) as a standard. FrI was divided into 5 equal volumes and 0.164, 0.226, 0.291, 0.361 and 0.436 g of ammonium sulfate (30%, 40%, 50%, 60% and 70% saturation) was added for each ml of FrI in the separate sample, respectively, over a 15 min interval at 4° C. The mixture was stirred for an additional 30 min at 4° C. The precipitate was collected by centrifugation (23,000×g, 45 min, 0° C.). The resulting pellets were resuspended in 2 ml Ni-NTA suspension buffer (50 mM Tris-HCl (pH 7.5), 40 mM KCl, 7 mM MgCl₂ and 10% glycerol. The protein concentration of each sample was determined using the Coomassie Protein Assay Reagent (Pierce) and bovine serum albumin (BSA) as a standard. The 30%, 40%, 50%, 60% and 70% ammonium sulfate precipitated samples contained protein concentrations of 2.4, 8.0, 18.0, 35.0 and 38.0 mg/ml, respectively (FIG. 3).

Figure 4:
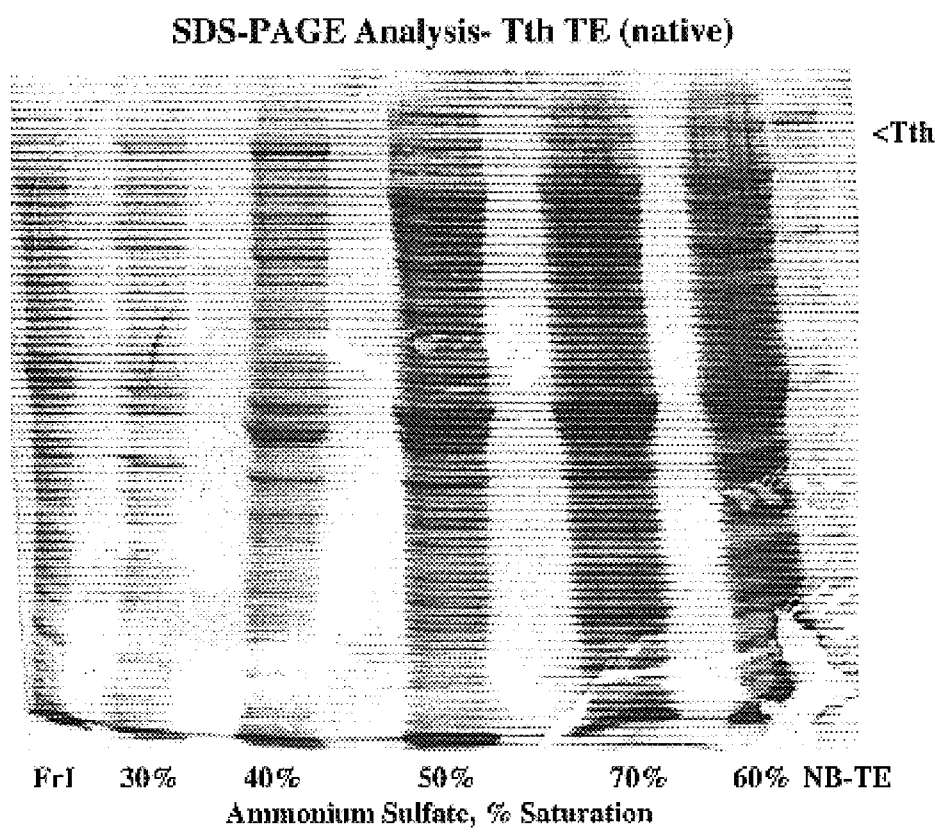
FIG. 4 SDS-PAGE analysis of ammonium sulfate precipitation optimization of *T. thermophilus* α.

The samples were analyzed by SDS-polyacrylamide gel electrophoresis (FIG. 4). The 40% ammonium sulfate precipitated samples contained over 90% of the α-subunit.

Figure 5:
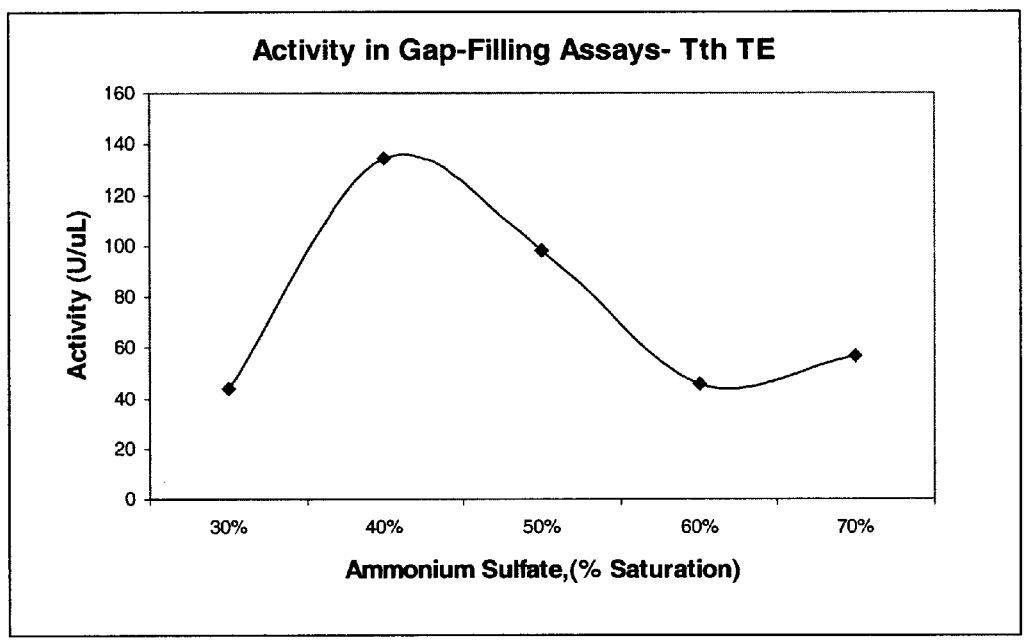
FIG. 5. Activity assay analysis of ammonium sulfate precipitation optimization of *T. thermophilus* α using the gap-filling assay.

Each ammonium sulfate cut was also assayed for activity in gap-filling assays describe above in the section entitled "Gap Filling Assay for Determination of *T. thermophilus* α-subunit Activity". The activity appears to be highest at 40% ammonium sulfate saturation and drops as percent ammonium sulfate saturation increased (FIG. 5). This is due to either higher salt being retained in the resuspended pellet and effecting the gap filling reaction, or an inhibiting contaminant precipitating at the higher ammonium sulfate concentrations and effecting activity of the *T. thermophilus* α-subunit. Since SDS-polyacrylamide gel electrophoresis and activity assays indicate that most of the α-subunit is being recovered in 40% ammonium sulfate cuts, this concentration of ammonium sulfate was used in subsequent preparations.

Purification of *T. thermophilus* dnaE Product (α-subunit) from pTAC-CCA-TE

Lysis was accomplished by creation of spheroplasts of cells carrying the expressed *T. thermophilus* α (large-scale preparation of 7–10–2000). First, 500 g of a 1:1 suspension of frozen cells (250 g cells) in Tris-sucrose stored at −20° C. were used to prepare FrI (770 ml, 27.4 mg/ml). The preparation was as described in the section entitled "Determination of Optimal Ammonium Sulfate Precipitation Conditions of *T. thermophilus* α-subunit Expressed as a Translationally Coupled Protein". To Fr I, ammonium sulfate (0.258 g to each initial ml Fraction I-45% saturation) was added over a 15 min interval. The mixture was stirred for an additional 30 min at 4° C. and the precipitate was collected by centrifugation (23,000×g, 45 min, 0° C.). The resulting pellets were quick frozen by immersion in liquid nitrogen and stored at −80° C.

The pellets from Fr I were resuspended in 160 ml of 50 mM Tris-HCl, (pH 7.5), 25% glycerol, 1 mM EDTA, 1 mM DTT and homogenized using a Dounce homogenizer. The sample was clarified by centrifugation (16,000×g) and the supernatant constituted Fr II (164 ml, 11.4 mg/ml). Fr II was further purifed using a Butyl Sepharose Fast Flow (Pharmacia Biotech) column. The butyl resin (360 ml) was equilibrated in butyl equilibration buffer (50 mM Tris-HCl, (pH 7.5), 25% glycerol, 1 mM EDTA, 1 mM DTT, 0.5 M ammonium sulfate). The column was poured using 250 ml of Butyl resin. The remaining 110 ml of Butyl resin was mixed with Fr II giving 274 ml. To this mixture, 0.5 volume of saturated amonium sulfate was added slowly while stirring over a period of 1 hour. This mixture was added to the column at 1.3 ml/min. The column was then washed with 1 L of equilibration buffer. The protein was eluted in 10 column volumes of a gradient begining with butyl equilibration buffer and ending in a buffer containing 50 mM Tris-HCl, (pH 7.5), 25% glycerol, 1 mM EDTA, 1 mM DTT, 50 mM KCl. Remaining protein was removed from the column by eluting with an additional 10 column volumes "bump" of the end buffer. The α-subunit eluted in the first half of the "bump", and was pooled (242 ml, 0.15 mg/ml). The gap-filling assay was used to assay fractions for activity.

Figure 6:
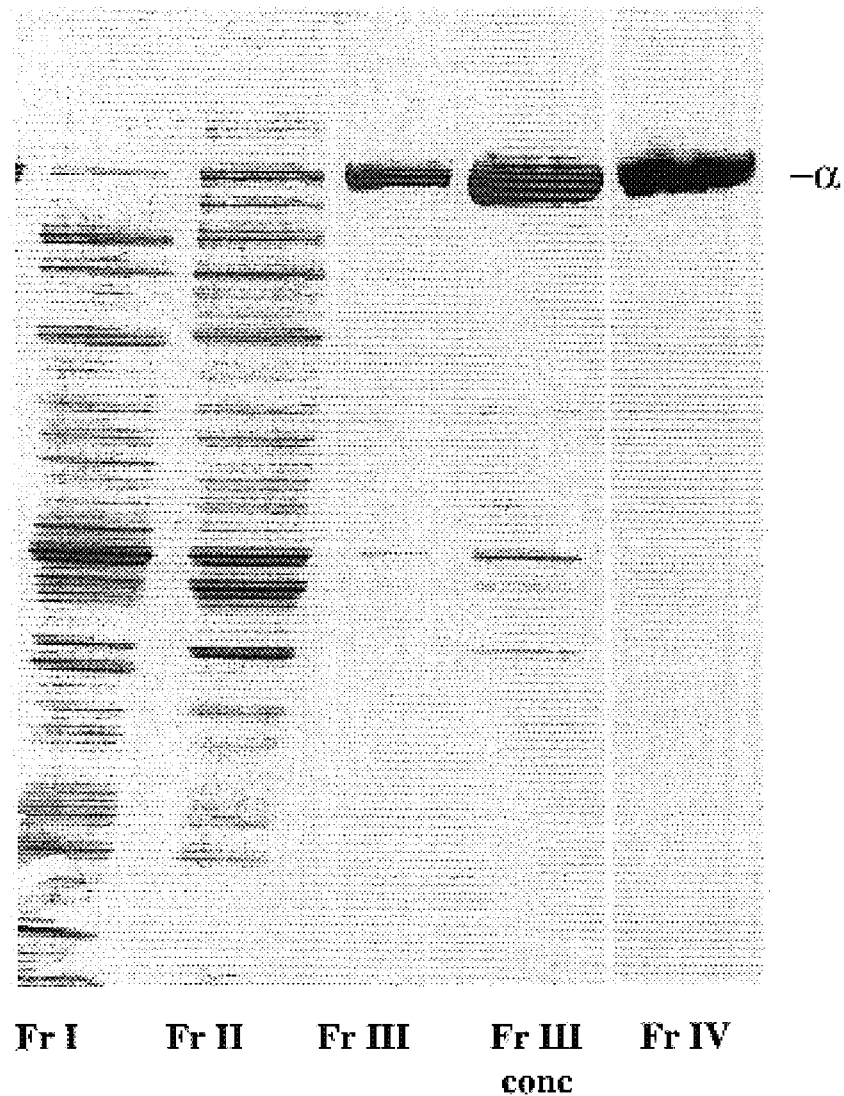
FIG. 6. SDS-polyacrylamide summary gel of the different purification steps of native *T. thermophilus* expressed as a translationally coupled protein.

The pool was concentrated to 27 ml (1.5 mg/ml) using polyethylene glycol (PEG) 8000 in powder form (Fisher). *T. thermophilus* α was further purified using a Sephacryl S300 HR (Pharmacia Biotech) gel filtration column (510 ml, 3 cm×120 cm) equilibrated in 50 mM Tris-HCl, (pH 7.5), 20% glycerol, 100 mM NaCl, 1 mM EDTA, 5 mM DTT. The column was loaded and the protein eluted at a flow rate of 0.7 ml/min. The α-subunit was isolated as a highly purified protein (35 ml, 0.23 mg/ml). A 10% SDS-polyacrylamide gel summarized the stages of purification of native *T. thermophilus* α (FIG. 6).

Example 3

Construction of pA1-NB-TX that Expresses *T. thermophilus* dnaX (τ and γ-subunits) Fused to an N-Terminal Peptide that Contains Hexahistidine and a Biotinylation Site The *T. thermophilus* dnaX gene was previously inserted into pA1-CB-ClaI to be expressed as both native (pA1-TX) and C-terminal tagged proteins (pA1-CB-TX) (U.S. application Ser. No. 09/151,888). Both τ and γ subunits were expressed at low levels from both constructs. The *T. thermophilus* dnaX gene was also previously inserted into pET-CB-ClaI plasmids to be expressed as both native (pET-TE) and C-terminal tagged proteins (pET-CB-TX) (U.S. application Ser. No. 09/151,888). As when under control of the pA1 promoter, when expressed under control of the T7 promoter, both τ and γ-subunits were express at low levels. In an attempt to increase expression levels of τ and γ subunits, plasmids were designed to fuse the dnaX gene to DNA encoding an N-terminal peptide that contains hexahistidine and a biotinylation site (ATG project S). First, a PCR reaction was designed to amplify a fragment of the N-terminus (5') of the dnaX gene from the plasmid pA1-TX. The forward (ATG primer #P38-S1586, 5'-AACTGCAG <u>AGCGCCCTCTACCG</u>-3') (SEQ ID NO:47) adds a PstI site to the 5' end of the dnaX gene so that the actual PCR product excludes the ATG start codon and begins at codon 2. The PstI restriction site adjacent to codon 2 brings the 5' portion of the dnaX gene in frame with the N-terminal fusion peptide coding sequences. The reverse primer (ATG primer #P38-A2050, 5'-<u>CGGTGGTGGCGAAGACGAAGAG</u>-3') (SEQ ID NO:48) was designed so that it is downstream of the BamH1 restriction site within *T. thermophilus* dnaX (the BamH1 restriction site is approximately 318 bases downstream of the start codon). This PCR product was cut with PstI and BamH1 and ligated into pA1-NB-AgeI that had been cut with the same two restriction enzymes. This plasmid was transformed into DH5α and positive isolates were selected by ampicillin-resistance. Plasmids from one positive clone were verified by BamHI/PstI restriction digest (yielding the expected 5.5 kb and 0.32 kb fragments) and NcoI digest (yielding the expected 5.6 and 0.16 kb fragments). The sequence of the inserted region was confirmed by DNA sequencing (ATG SEQ #1185 and 1186, primers P64-S10 and P64-A215) and compared to the sequence of pA1-TX. This precursor plasmid was named pA1-NB-TX5' and the isolate (pA1-NB-TX5'/DH5α) was stored as a stock culture (ATG glycerol stock #702).

Next, the 3' region (C-terminus) of the dnaX gene (1.6 kb) was cut out of the pA1-TX plasmid using the restrictions enzymes BamH1 and SpeI. This fragment was ligated into the precursor plasmid pA1-NB TX5' that has been cut with the same two restriction enzymes. This plasmid was transformed into DH5α and plasmid containing colonies were selected by ampicillin-resistance. Positive isolates were verified by BamHI/SpeI digest yielding the expected 5.9 and 1.6 kb fragments. This plasmid containing the entire gene for TX linked to the N-terminal fusion peptide was named pA1-NB-TX and the isolate (pA1-NB-TX/DH5α) was stored as a stock culture (ATG glycerol stock #740).

Verification of Expression of *T. thermophilus* dnaX Gene (τ and γ-subunits) Fused to an N-Terminal Peptide that Contains Hexahistidine and a Biotinylation Site by pA1-NB-TX/AP1.L1

The pA1-NB-TX plasmid was prepared and transformed into both MGC1030 (ATG glycerol stock #740) and AP1.L1 bacteria (ATG glycerol stock #741). The bacterial growth and isolation of total protein was as described in Example 2. An aliquot of supernatant (3 μl) containing total protein was loaded onto a 4–20% SDS-polyacrylamide mini-gel (Novex, EC60255; 1 mm thick, with 15 wells/gel) in 25 mM in Tris base, 192 mM glycine, and 0.1% SDS. The mini-gel was stained with Coomassie Blue, and one protein (doublet band) was observed to be migrating below 60 kDa and the other protein band slightly above the 60 kDa molecular weight standards, of the Gibco 10 kDa protein ladder. These protein bands were observed as distinct bands in the induced cultures from both bacterial strains, but was not observed in the uninduced controls. These proteins were determined to be consistent with the expected molecular weights of 53.6 and 61.9 kDa. The detected proteins bands representing *T. thermophilus* DnaX represented less than 2% of the total *E. coli* protein, based on the intensity of Coomassie Blue staining of the protein bands on the gel.

In *T. thermophilus*, the putative frameshift site, allowing expression of both (τ and γ-subunits, has the sequence A AAA AAA A, which would enable either a +1 or −1 frameshift. The +1 frameshift product would extend only one residue beyond the lys-lys encoding sequence, similar to the *E. coli* −1 frameshift product. However, the −1 frameshift would encode a protein with a 12-amino acid extension. This would allow the expression of two γ-subunits differing in size by 11 amino acids. Alternatively, recent work has indicated that the *T. thermophilus* γ-unit may be expressed as the result of transcriptional slippage producing a sub-population of different length mRNAs encoding two different length gamma subunits (Larsen, B., Wills, et al., *Proc. Natl. Acad. Sci.* 97:1683–1688 (2000)). We observe γ-unit as a doublet protein band, confirming that one of these processes is occurring.

Next, the expressed proteins were subjected to biotin blot analysis as described in Example 2. The endogenous *E. coli* biotin-CCP protein, ~20 kDa was detectable in both induced and non-induced samples. Two bands of equal intensity were visualized, one just below 60 kDa and the other slightly above 60 kDa molecular weight standards, of the Gibco 10 kDa protein ladder in the induced cultures from both bacterial strains, but was not observed in the uninduced control.

Optimization of Expression of *T. thermophilus* DnaX by pA1-NB-TX

Figure 7:
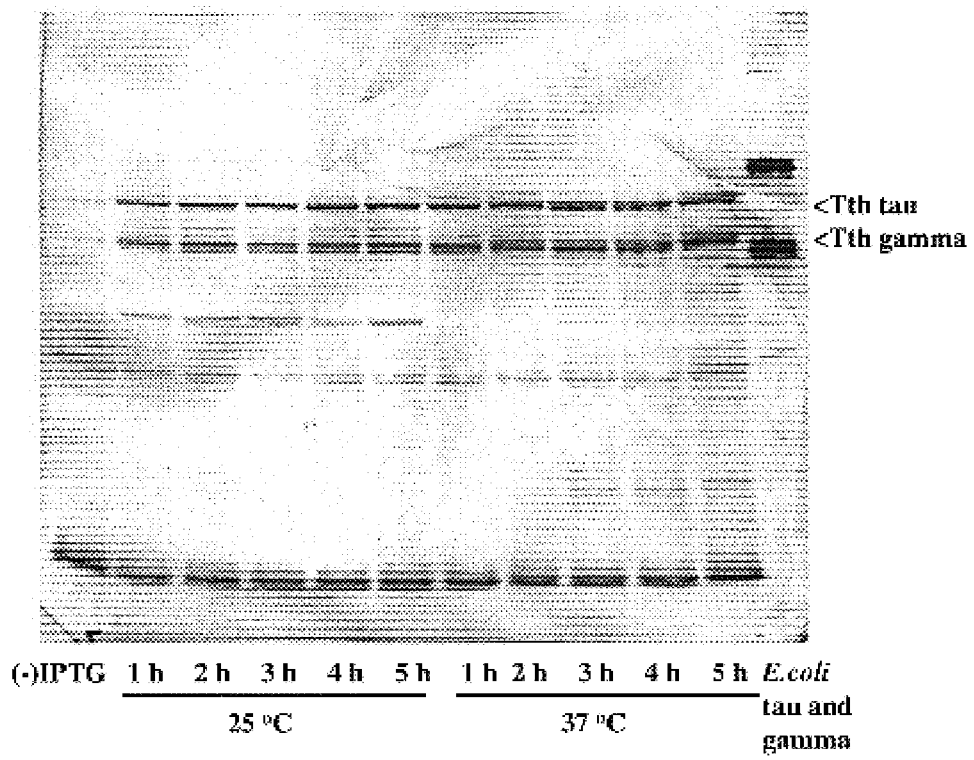
FIG. 7. Biotin blot analysis of the growth optimization for expression of N-terminal tagged *T. thermophilus* DnaX subunits from pA1-NB-TX/AP1.L1.

Since expression of *T. thermophilus* dnaX gene yielded low or no detectable proteins when expressed as both a native or coupled to an C-terminal fusion peptide, extra care was taken with dnaX linked to an N-terminal fusion peptide to achieve optimum expression. Expression was analyzed using both *E. coli* strains MGC1030 and AP1.L1 carrying pA1-NB-TX at different induction times and also at different growth temperatures (25 and 37° C.). Growth of bacterial cultures and analysis were carried out as described in Example 2. Biotin blot analysis indicated that expression levels were higher at 37° C. and also slightly better when expressed in the AP1.L1 bacterial strain (FIG. 7). The optimum yield of *T. thermophilus* DnaX was attained by 4 h post induction and at 37° C.; this induction time will be used in subsequent experiments.

Large Scale Growth of pA1-NB-TX/AP1.L1

Strain pA1-NB-TX/AP1.L1 was grown in a 250 L fermentor (fermentation run #99-17), to produce cells for purification of *T. thermophilus* dnaX (τ and γ-subunits) fused to an N-terminal peptide that contains hexahistidine and biotinylation site as described Example 2. Cell harvest was initiated 4 hours after induction at $OD_{600}$=7.0, and the cells were chilled to 10° C. during harvest. The harvest volume was 172 L, and the final harvest weight was approximately 2.2 kg of cell paste. An equal amount (w/w) of 50 mM Tris-HCl (pH 7.5) and 10% sucrose solution was used to resuspend the cell paste. Cells were frozen by pouring the cell suspension into liquid nitrogen, and stored at −20° C. until processed. Quality control results showed 10 out of 10 positive colonies on ampicillin-containing medium in the inoculum and 10 out of 10 positive colonies at harvest.

Purification of *T. thermophilus* dnaX Product ((τ and γ-subunits) Fused to an N-Terminal Peptide that Contains Hexahistidine and a Biotinylation Site Lysis of 800 g of a 1:1 suspension of frozen cells (400 g of cells) containing pA1-NB-TX stored in Tris-sucrose at −20° C., was preformed as described in Example 2. The recovered supernatant (1.75 l) constituted Fraction I (Fr I) (13.5 mg/ml). To Fr I, ammonium sulfate (0.226 g to each initial ml Fraction I-40% saturation) was added over a 15 min interval. The mixture was stirred for an additional 30 min at 4° C. and the precipitate was collected by centrifugation (23,000×g, 45 min, 0° C.). The resulting pellets were quick frozen by immersion in liquid nitrogen and stored at −80° C.

Figure 8:
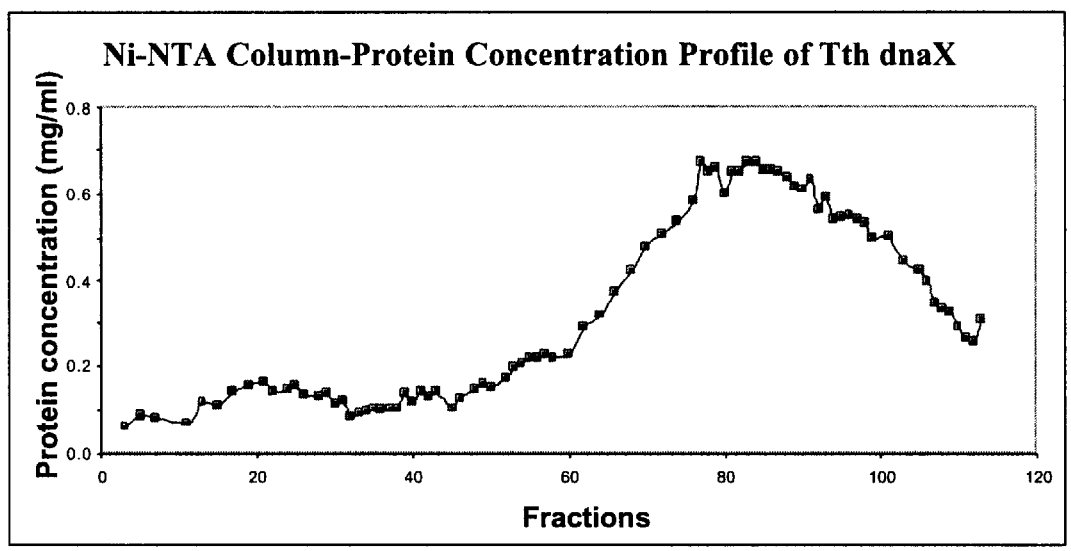
FIG. 8. Protein concentration profile of the fractions from the Ni++-NTA column purification of N-terminal tagged *T. thermophilus* DnaX.

The pellets from Fr I were resuspended in 125 ml of $Ni^{++}$-NTA suspension buffer (50 mM Tris-HCl (pH 7.5), 40 mM KCl, 7 mM $MgCl_2$, 10% glycerol, 7 mM βME, 0.1 mM PMSF) and homogenized using a Dounce homogenizer. The sample was clarified by centrifugation (16,000×g) and the supernatant constituted Fr II (13.3 mg/ml). Fr II was added to 60 ml of a 50% slurry of Ni-NTA resin in $Ni^{++}$-NTA suspension buffer and rocked for 1.5 hours at 4° C. This slurry was then loaded onto a BioRad Econo-column (2.5×5 cm). The column was washed with 300 ml of $Ni^{++}$-NTA wash buffer (50 mM Tris-HCl (pH 7.5), 1 M KCl, 7 mM $MgCl_2$, 10% glycerol, 10 mM Imidazole, 7 mM βME) at a flow rate of 0.5 ml/min. The NB-TX protein was eluted in 300 ml of $Ni^{++}$-NTA elution buffer (50 mM Tris-HCl (pH 7.5), 40 mM KCl, 7 mM $MgCl_2$, 10% glycerol, 7 mM βME) containing a 10–200 mM imidazole-HCl (pH 7.5) gradient. The eluate was collected in 150×2 ml fractions. The protein concentration of each fraction was determined (FIG. 8).

Fractions were analyzed by SDS-polyacrylamide gel electrophoresis, (FIGS. 9A and 9B) and observed to contain only one major higher molecular weight contaminant. This contaminant migrated just above the τ-subunit and disappeared by fraction 96. Fractions 66–95 and 96–113 were pooled and the proteins were precipitated by addition of ammonium sulfate (0.226 g to each initial ml Fraction I-40% saturation). The precipitate was collected by centrifugation (23,000×g, 45 min, 0° C.) and stored at −80° C. A portion of N-terminal tagged *T. thermophilus* DnaX purified using $Ni^{++}$-NTA column chromatography was stored as laboratory stocks.

In an additional purification step for antibody production, pellets containing ammonium sulfate precipitated N-terminal tagged *T. thermophilus* DnaX were resuspended in 30 ml of phosphate buffered saline (PBS) (137 mM NaCl, 2.7 mM KCl, 4.3 mM $Na_2HPO_4:7H_2O$, 1.4 mM $KH_2PO_4$ (pH 7.3)) plus 10% glycerol and homogenized using a Dounce 75 homogenizer. The resulting solution was clarified by centrifugation (16,000×g) and the supernatant constituted Fr III (2.9 mg/ml).

Fr III was loaded onto a 2 ml UltraLink™ Immobilized Monomeric Avidin column (1.1 cm×2.5 cm) (Pierce) equilibrated in PBS plus 10% glycerol as per manufacturer instructions. The sample was loaded at a flow rate of 0.09 ml/min. The flow through was passed back through the column three times to allow all biotinylated protein to bind the avidin. The column was next washed with 10 ml PBS plus 10% glycerol at a flow rate of 0.08 ml/min. The protein was eluted from the column in 20 ml of elution buffer (2 mM D-biotin, 10% glycerol in PBS) at a flow rate of 0.09 ml/min (FIGS. 10A and 10B).

This purification step removed the upper molecular weight contaminant observed in the $Ni^{++}$-NTA column purification. Fractions 1–24 (19 ml) were pooled (0.43 mg/ml) and the protein was precipitated by addition of ammonium sulfate (0.258 g to each ml of pooled fractions) and centrifuged as described above and stored at −80° C. This sample was used in production of polyclonal antibodies described below.

Production of Polyclonal Antibodies Against *T. thermophilus* DnaX (τ and γ-subunits)

For production of polyclonal antibodies, the pellets containing N-tagged *T. thermophilus* DnaX from the avidin purification were dissolved in 2 ml of PBS and dialyzed against 500 ml of PBS two times (2.5 mg/ml, 2 ml). The sample was diluted to 50 μg/ml in PBS and 2 ml was injected directly into a vial containing adjuvant (RIBI Adjuvant System (RAS)). This solution was mixed and allowed to come to room temperature. One ml of the adjuvant/NB-TX mixture was used to inoculate a rabbit (#598); 0.05 ml in each of six sites intradermal injections, 0.3 ml intramuscular injections in each hind leg, and 0.1 ml subcutaneous injection in the neck region. Before the initial injection a 5 ml preinjection bleed was collected. The rabbit received a booster using one-half the initial injection volume 28 days post initial inoculation. A test bleed (10 ml) was collected on day 37. The rabbit received a second booster using the same formulation as original inoculation at day 58. Total blood was collected on day 72.

Figure 11:
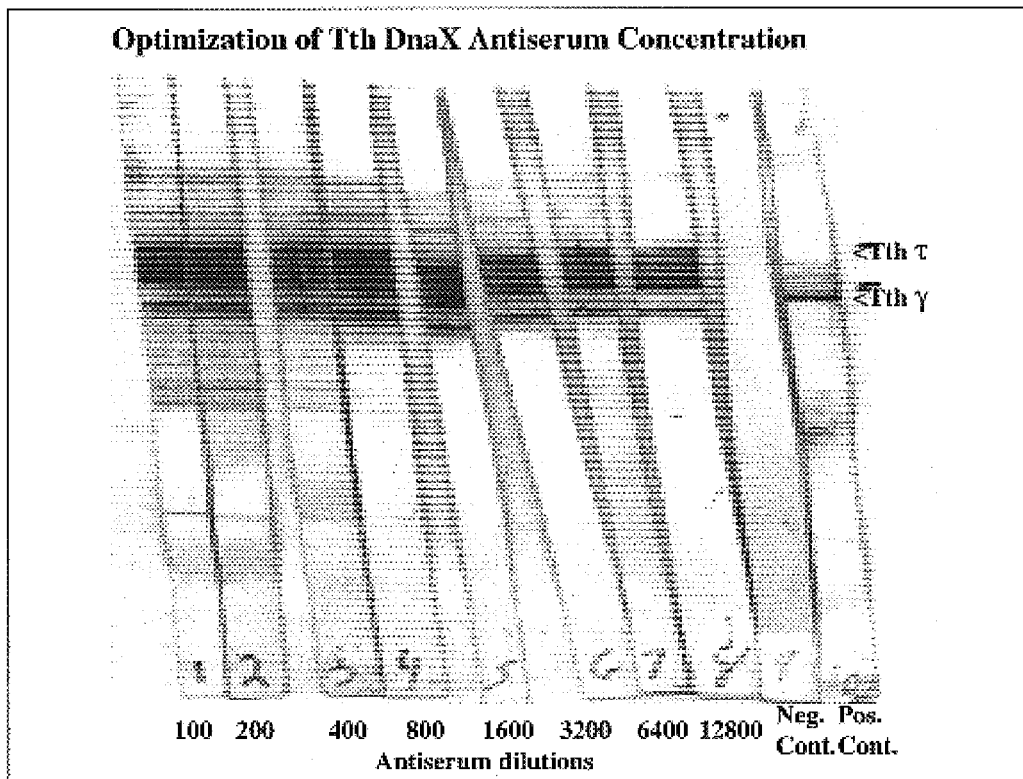
FIG. 11. Western analysis of various antiserum dilutions for determination of dilutions to use in *T. thermophilus* DnaX detection.

The optimum dilutions of anti-serum for binding NB-TX was determined after the test bleed and after the final bleed. This was carried out using SDS-polyacrylamide gel electrophoresis in which a small aliquot of *T. thermophilus* N-terminal tagged DnaX (1.0 μg/well) was electrophoresed onto a 10% SDS-polyacrylamide mini-gel (10×10 cm), and then the protein was transferred onto nitrocellulose membrane. The membrane was cut into strips with each strip containing an identical band of *T. thermophilus* N-terminal tagged DnaX. The membrane was blocked in 0.2% Tween 20 (v/v)-TBS (TBST) containing 5% non-fat dry milk (w/v) for 1 hour at room temperature, rinsed with TBST. The strips were placed in antiserum/TBST (dilutions of; 1:100,1:200, 1:400, 1:800, 1:1600, 1:3200, 1:6400, and 1:12800) for 1 hour and then washed 4 times for 5 min in TBST. Next, the strips were placed in secondary antibody-conjugated to alkaline phosphatase (goat anti-rabbit IgG (H+L), 1:3000 dilution in TBST) (BioRad) for 1 hour. The strips were then washed 4 times for 5 min with TBST. Following this extensive washing, the blots were developed with BCIP/NBT (KPL #50-81-07; one component system). Proteins corresponding to the τ and γ-subunits were visualized as distinct bands even at the highest dilution of antiserum. These bands became more intense as the dilution of antiserum was decreased. The negative control contained antiserum taken from the rabbit prior to inoculating with antigen. The positive control is a biotin blot analysis of the antigen at the same concentration (1.0 μg) as used in antiserum detection (FIG. 11).

Figure 12:
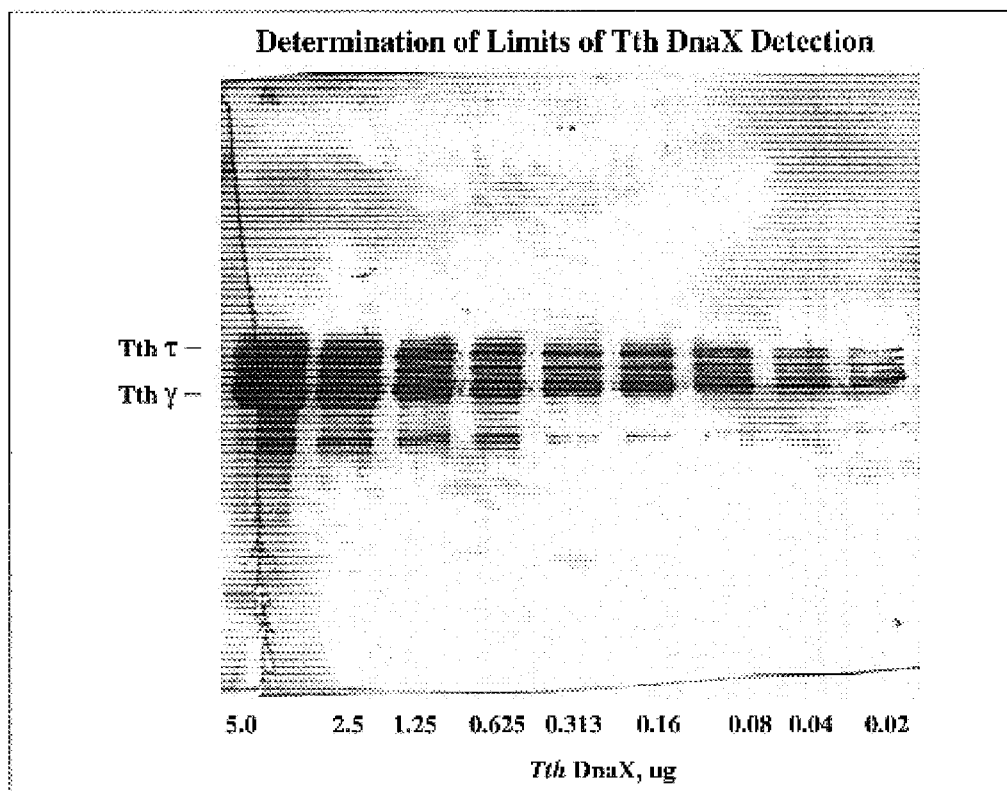
FIG. 12. Western analysis of various *T. thermophilus* DnaX dilutions for determination of the limit of DnaX detection at antiserum dilution of 1:6400.

Next, the minimum amount of *T. thermophilus* N-terminal tagged DnaX needed for recognition by antibody serum was determined. This was carried out using SDS-polyacrylamide gel electrophoresis in which small aliquots of *T. thermophilus* N-terminal tagged DnaX (0.02, 0.04, 0.08, 0.16, 0.32, 0.625, 1.25, 2.50, and 5.0 μg/well) were electrophoresed onto a 10% SDS-polyacrylamide mini-gel (10×10 cm). The protein was transferred onto nitrocellulose membrane. The blotted nitrocellulose was blocked in TBST containing 5% non-fat dry milk (w/v) for 1 hour at room temperature, rinsed with TBST. The blot were placed in antiserum/TBST (dilution of 1:6400) for 1 hour and then washed 4 times for 5 min in TBST. Next, the blot was placed in secondary antibody-conjugated to alkaline phosphatase (goat anti-rabbit IgG (H+L), 1:3000 dilution in TBST) (BioRad) for 1 hour. The blot was then washed 4 times for 5 min with TBST. Following this extensive washing, the blot was developed with BCIP/NBT (KPL #50-81-07; one component system) (FIG. 12).

Proteins corresponding to τ and γ were visualized as distinct bands at 0.02 μg of DnaX. These bands became more intense as the concentration of DnaX was increased (FIG. 12).

Production of Monoclonal Antibodies Against *T. thermophilus* dnaX (τ and γ-subunits)

Two ml of the sample of *T. thermophilus* DnaX was diluted to 50 μg/ml in PBS (described above) was injected directly into a vial containing adjuvant (RIBI Adjuvant System (RAS)). On day 0, three mice were inoculated with the DnaX-adjuvant sample (0.2 ml/mouse). At day 21, each mouse received a booster of 0.2 ml of the DnaX-adjuvant sample. On day 41, a test bleed was collected from tail clippings. The three mice were boosted a second time on day 44, and a second bleed from tail clippings was collected on day 58. Antiserum from this bleed was used for Western analysis as described in the section entitled "Production of polyclonal antibodies against *T. thermophilus* dnaX (τ and γ-subunits)". The antiserum was used at a 1:400 dilution to detect 1 μg/lane of *T. thermophilus* DnaX. The antiserum was also used in ELISA screening (Tissue Culture/Monoclonal Antibody Facility, UCHSC). Mouse #2 and #3 gave equal response to *T. thermophilus* DnaX in both Western analysis and ELISA screening, while mouse #1 gave a lower response. Mouse #2 was selected and given to the Tissue Culture/Monoclonal Antibody Facility (UCHSC) for production of mono-clonal antibodies against N-terminal tagged *T. thermophilus* DnaX.

Cloning *T. thermophilus* dnaX Gene (τ/γ) into a translationally coupled vector pTAC-CCA-ClaI To efficiently express τ/γ as a native protein a vector was designed to express τ/γ as a translationally coupled proteins. The goal here is again to use translational coupling as described Example #2. The dnaX gene was inserted behind the CCA adding enzyme and translationally coupled as described for native *T. thermophilus* α. First, the dnaX gene was amplified by using pA1-TX as a template by PCR. The forward/sense primer (ATG primer #P38-Slc1a2, 5'-ACTTATCGATA<u>ATGAGCGCCCTCTACCGCC</u>-3') (SEQ ID NO:49) has a ClaI restriction site in the non-complementary region. The non-complementary region also contains the "TA" of the stop (TAA) for the upstream CCA-adding protein fragment. The region of the primer complementary to the 5' end of the *T. thermophilus* holA gene begins with "A" which is the first nucleotide of the "ATG" start codon and the final "A" of the "TAA" stop codon. The reverse/antisence primer (ATG primer #P38-A1603STOPspe, 5'-GAGGACTAGTTA TTATATACCAGTACCCCCTATC-3') (SEQ ID NO:50) contains a SpeI restriction site in the non-complementary portion of the primer and also an additional stop codon adjacent to the native stop codon, giving two stop codons in tandem. There was also a clamp region for efficient cutting with SpeI. Next, the PCR product was digested with ClaI/SpeI restriction enzymes and inserted into the pTAC-CCA-ClaI plasmid digested with the same enzymes. The plasmid was transformed into DH5α bacteria and plasmids from ampicillin-resistant positive isolates were screened for by digestion with ClaI/SpeI restriction enzymes yielding 1.6 and 5.5 kb fragments. The sequence of both strands of the insert were verified by DNA sequencing (ATG SEQ #1666–1674, 1617, 1719; primers, P144-S23, P144-A1965, P38-S394, P38-S809, P38-S1169, P38-A1272, P38-A946, P38-A541, P38-A282, P38-A106). Sequence analysis confirmed the correct sequence was contained within the inserted region. This plasmid was named pTAC-CCA-TX and the isolate was stored as a stock culture (ATG glycerol stock #1030).

Verification of Expression of Native *T. thermophilus* DnaX Proteins by PTAC-CCA-TX/MGC1030 and pTAC-CCA-TX/AP1.L1

The pTAC-CCA-TX plasmid was prepared and transformed into MGC1030 bacteria (ATG glycerol stock #1067, 1068, 1069) and AP1.L1 (ATG glycerol stock #1075, 1076, 1077). The bacterial growths and isolation of total cellular protein were as described in Example 2. A small aliquot of each supernatant (3 μl) containing total cellular protein was electrophoresed onto a 4–20% SDS-polyacrylamide mini-gel (Novex, EC60255; 1 mm thick, with 15 wells/gel) in 25 mM in Tris base, 192 mM glycine, and 0.1% SDS. The mini-gels were stained with Coomassie Blue. The region of the gels expected to contain τ (58.3 kDa) or γ (51.0 kDa) contained many native *E. coli* proteins and τ or γ could not be visualized in any of the isolates.

Example 4

Identification of *T. thermophilus* holA Gene (δ-subunit)

The sequences of δ-subunits from *E. coli* and *Haemophilus influenzae* and putative δ-subunit sequences from *Bacillus subtilis, Aquiflex aeolicus* were used to search the *T. thermophilus* genome database at Goettingen Genomics Laboratory. A partial crude sequence of a region of the *T. thermophilus* genome containing a putative *T. thermophilus* holA gene was identified (using BLAST) and obtained (from Dr. Carsten Jacobi, Goettingen Genomics Laboratory, Institute of Microbiology and Genetics, Grisebachstrasse 8, Goettingen, Germany). There appeared to be several possible start sites that were all ATG and also a number of possible stop codons. Unsure of the accuracy of the crude sequence, the region of the *T. thermophilus* genome suspected of containing the *T. thermophilus* holA gene and flanking regions were amplified by PCR. PCR primers were designed using sequences derived from the crude sequence. The forward/sense primer (ATG primer P134-S415, 5'-CGGGAGGGTGAAGCGCAAGATGTC-3') (SEQ ID NO:51) and reverse/antisense primer (ATG primer P134-A2099, 5'-GCCGCACCCCCGCCCCGTAGT-3') (SEQ ID NO:52) using *T. thermophilus* genomic DNA as a template yielded a PCR product 1685 bp in length which contained the region of DNA encoding holA. This PCR fragment was inserted into pGEM-T Easy™ (Promega) vector per directions furnished by the manufacturer. The pGEM-T Easy™ Vector Systems takes advantage of the template independent addition of a single deoxyadenosine onto the 3'-end of PCR products by some thermostable DNA polymerases. The PCR fragments were ligated to linearized vector DNA that had been cleaved at the EcoRV site and had a single 3'-terminal thymidine added to both ends. By using these vectors, PCR products can be directly cloned without further enzymatic manipulation while taking advantage of the high efficiency of a cohesive-end ligation. This plasmid was transformed into DH5α bacteria and positive isolates were selected by ampicillin-resistance. Plasmids from one positive clone were isolated and screened by digestion with EcoRi restriction digest yielding 1.7 and 3.1 kb fragments. The sequence of the inserted DNA region was confirmed by DNA sequencing (ATG SEQ #1336–1345; primers, SP6, T7, P134-S621, P134-S1016, P134-S1279, P134-S1633, P134-A1849, P134-A1464, P134-A1091 and P134-A655). Numerous base changes were observed in the PCR clone compared to the crude sequence obtained from Goettingen Genomics Laboratory. An 876 bp open reading frame (ORF) was identified in the region containing the putative *T. thermophilus* holA gene. This isolate was stored as a stock culture (ATG glycerol stock #787).

The ORF identified in the PCR product above was amplified by PCR with *T. thermophilus* genomic DNA as a template. The forward/sense primer (ATG primer #P134-S585de).

5'-GGATCCAAGCTTCAT ATGGTCATCGCCTTCAC-3') (SEQ ID NO:53) contained a region complementary to the 5' end of the ORF. An NdeI site overlapped the ATG start codon, and there was also an upstream HindIII and BamHI site. The reverse/antisense primer (ATG primer #P134-A1493kpn, 5'-AGATCTGGTACCTCA TCAACGGGCGAGGCGGAG-3') (SEQ ID NO:54) contained an additional stop codon adjacent to the native stop codon in the non-complementary region, giving two stop codons in tandem. There was a KpnI site upstream of the stop codons and a BgkIII restriction site upstream of the KpnI restriction site. This PCR fragment was inserted into pGEM-T Easy™ plasmids (Promega) as per manufacturer directions. The plasmid was then transformed into DH5α bacteria and plasmids from ampicillin-resistant positive isolates were screened by NdeIIKpnI restriction digest yielding 0.9 and 3.0 kb fragments. The sequence of both DNA strands of the inserted region was confirmed by DNA sequencing (ATG SEQ #1392–1397, 1408; primers, SP6, T7, P134-S1279, P134-S1633, P134-A1464, P134-A790 and P134-A1849). This plasmid was named pT-TD(Kpn) and the isolate was stored as a stock culture (ATG glycerol stock #817).

The DNA coding sequence of the *T. thermophilus* holA gene (SEQ ID NO:9) is shown in FIG. 13. The start codon (atg) and the stop codon (tga) are in bold print. Also shown, in FIG. 14, is the protein (amino acid) sequence (SEQ ID NO: 10) derived from the DNA coding sequence.

The amino acid sequence of *T. thermophilus* δ-subunit was compared with the *E. coli* δ-subunit (FIG. 15). Alignments were also made with all of the δ-subunit sequences used in the *T. thermophilus* database search, *E. coli* and *Haemophilus influenzae* and putative δ-subunit sequences from *Bacillus subtilis* and *Aquiflex aeolicus* (FIG. 16). The T. thermophilus δ-subunit was 34%, 29%, 31% and 27% identical over a 193, 182, 110 and 169 amino acid overlap with E. coli, H. influenzae, A. aeolicus and B. subtilis δ-subunits, respectively.

Construction of a Plasmid (pA1-NB-TD) that Overexpress T. thermophilus holA (δ-subunit) Fused to an N-Terminal Peptide that Contains Hexahistidine and a Biotinylation Site Since the δ-subunit coupled to a C-terminal fusion peptide expressed poorly (described below), it was decided to attempt enhancement of expression by coupling the holA gene to an N-terminal fusion peptide. The T. thermophilus holA gene was inserted into the pA1-NB-Avr2 plasmid to be expressed fused to an N-terminal peptide containing hexahistidine and a biotinylation site. The holA gene was amplified by PCR using the pA1-TD plasmid as a template. The forward/sense primer adds a Pst1 site to the 5end of the gene so that the actual PCR product excludes the ATG start codon and begins at codon 2, with the Pst1 site adjacent to codon 2 (ATG primer P134-S592pst, 5'-GAATTCTGCAG GTCATCGCCT TCACCG-3') (SEQ ID NO:11). The PstI site will bring the holA gene into frame with the N-terminal fusion peptide and will add two amino acids (Leu and Gln) between the N-terminal fusion peptide and the second codon of the holA gene. The reverse primer was the same primer used in making pA1-TD (P134-A1493kpn). This primer was designed so two things could be accomplished. First, an additional TGA (stop codon) was added to the end of the gene giving two stop codons in tandem (the natural stop codon and another one added in the non-complementary part of the primer). Second, a KpnI restriction site was added in the non-complementary region of the primer for insertion into the vector. There was also a clamp region for efficient digestion with KpnI. The PCR product was digested with PstI and KpnI restriction enzymes and inserted into the pA1-NB-Avr2 plasmid digested with the same enzymes. The plasmid was transformed into DH5α bacteria and plasmids from ampicillin-resistant positive isolates were screened for by digestion with PstI and KpnI restriction enzymes yielding 0.9 and 5.62 kb fragments. This plasmid was selected and the sequence of both strands of the insert was verified by DNA sequencing (ATG SEQ #1530–1536; primers, P64-S10, P64-A215, P134-S1279, P134-S1633, P134-A1849, P134-A1464, P134-A790). This plasmid was named pA1-NB-TD and the isolate was stored as a stock culture (ATG glycerol stock #915).

Verification of Expression of T. thermophilus δ-subunit Fused to an N-Terminal Peptide that Contains Hexahistidine and a Biotinylation Site by pA1-NB-TD/MGC1030

The pA1-NB-TD plasmid was prepared and transformed into MGC1030 bacteria (ATG glycerol stock #931). The bacterial growths and isolation of total cellular protein were as described in Example 2. A small aliquot of each supernatant (3 µl) containing total cellular protein was electrophoresised onto a 4–20% SDS-polyacrylamide mini-gel (Novex, EC60255; 1 mm thick, with 15 wells/gel) in 25 mM in Tris base, 192 mM glycine, and 0.1% SDS. The mini-gels were stained with Coomassie Blue. A protein migrating just below the 40 kDa molecular weight standard of the Gibco 10 kDa protein ladder could be detected as a distinct protein band, but was not observed in the uninduced control. This protein band corresponds to the expected molecular weight of the T. thermophilus δ-subunit fused to the N-terminal fusion protein (36.2 kDa).

Next, the total protein in each lysate was transferred (blotted) from polyacrylamide gel to nitrocellulose as described in Example 2. Each lane contained 1.5 ul of the supernatant. The endogenous E. coli biotin-carboxyl carrier protein (biotin-CCP), ~20 kDa, was detectable in both induced and non-induced samples. A very intense protein band corresponding to the δ-subunit migrated just below the 40 kDa molecular weight standards of the Gibco 10 kDa protein ladder. This protein was observed as a distinct band in the induced cultures, but was not observed in the uninduced control.

Figure 17:
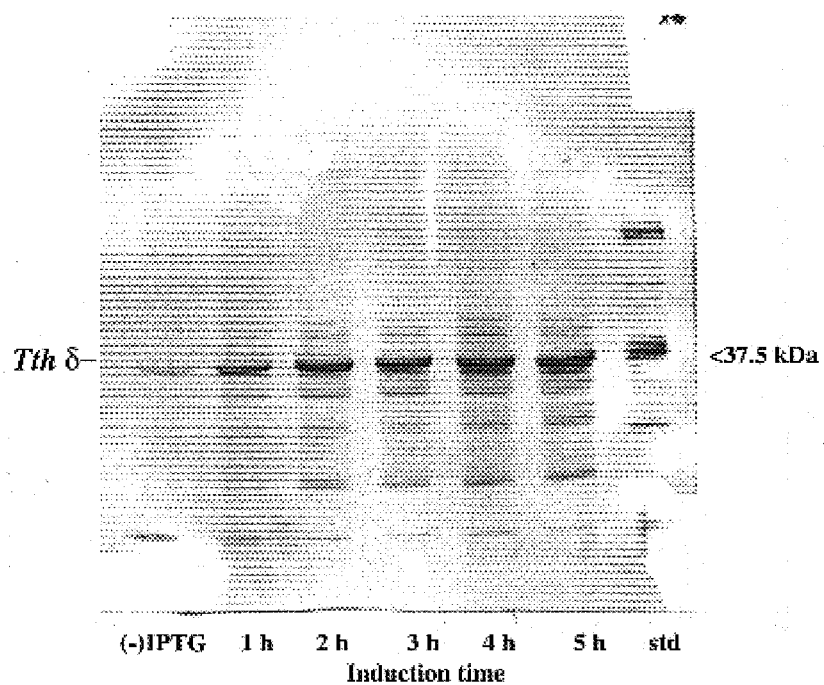
FIG. 17 Biotin blot analysis of growth/induction time optimization of expression of *T. thermophilus* δ by pA1-NB-TD/AP1.L1.

Optimization of Expression of T. thermophilus holA Gene (δ-subunit) by pA1-NB-TD Expression was analyzed using the bacterial strains AP1.L1 carrying the pA1-NB-TD plasmid at different induction times. Bacterial growths and analysis were carried out as described Example 2. The growths and analysis were at 37° C. The total protein was analyzed using both SDS-polyacrylamide gel electrophoresis and biotin blot analysis (FIG. 17). Distinct protein bands corresponding to the δ-subunit was observed by both forms of analysis. Biotin blot analysis indicates that most of the δ-subunit is being expressed in 4 hours and at 37° C., these growth condition were used in subsequent preparations.

Large Scale Growth of T. thermophilus holA Gene Product (δ-subunit) Fused to an N-Terminal Peptide that Contains Hexahistidine and Biotinylation Site by pA1-NB-TD/MGC1030

Strain pA1-NB-TD/MGC1030 was grown in a 250 L fermentor to produce cells for purification of T. thermophilus δ-subunit as described in Example 2. Cell harvest was initiated 3 hours after induction, at $OD_{600}$ of 7.2, and the cells were chilled to 10° C. during harvest. The harvest volume was 175 L, and the final harvest weight was approximately 2.47 kg of cell paste. An equal amount (w/w) of 50 mM Tris (pH 7.5) and 10% sucrose solution was added to the cell paste. Quality control results showed 10 out of 10 positive colonies on ampicillin-containing medium in the inoculum and 10/10 positive colonies at harvest. Cells were frozen by pouring the cell suspension into liquid nitrogen, and stored at −20° C., until processed.

Determination of Optimal Ammonium Sulfate Precipitation Conditions of δ Fused to an N-Terminal Peptide that Contains Hexahistidine and Biotinylation Site by pA1-NB-TD/MGC1030

Lysis was accomplished by creation of spheroplasts of the cells carrying the expressed T. thermophilus δ-subunits. First, from 100 g of a 1:1 suspension of frozen cells (50 g cells) in Tris-sucrose which had been stored at −20° C., FrI was prepared (160 ml, 23 mg/ml). The preparation was as described in Example 2. FrI was added to 2.4 ml of a 50% slurry of Ni-NTA resin equilibrated in Ni-NTA suspension buffer (50 mM Tris-HCl, (pH 7.5), 40 mM KCl, 7 mM $MgCl_2$, 10% glycerol, 7 mM βME). The resin and sample were rocked for 1.5 hours at 4° C. The sample was then passed through a 5 ml fritted polypropylene column (Qiagen) to filter out the Ni-NTA resin and bound δ. The resin was washed by passing 50 ml of Ni-NTA wash buffer through the column and eluted in 9 ml of Ni-NTA elution buffer (2.6 mg/ml).

Figure 18:
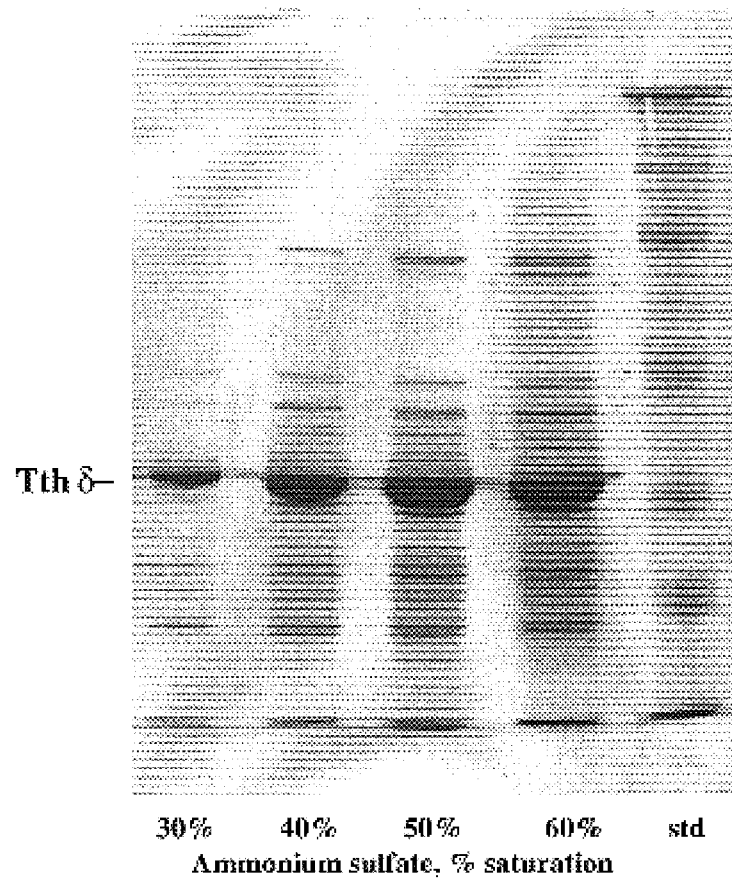
FIG. 18. Optimization of precipitation of *T. thermophilus* δ by ammonium sulfate.

The eluted sample was brought to 40 ml by added Ni-NTA suspension buffer. The sample was then divided into 4 equal volumes (10 ml) and 1.64, 2.26, 2.91 and 3.61 g of ammonium sulfate (30%, 40%, 50% and 60% saturation) was added to each separate sample, respectively, over a 15 min interval at 4° C. The mixture was stirred for an additional 30 min at 4° C. and the precipitate was collected by centrifugation (23,000×g, 45 min, 0° C.). The resulting pellets were resuspended in 1 ml Ni-NTA suspension buffer. The protein concentration of each sample was determined using the Coomassie Protein Assay Reagent (Pierce) and bovine serum albumin (BSA) as a standard. The 30%, 40%, 50% and 60% ammonium sulfate precipitated samples contained protein concentrations of 0.4, 2.6, 3.2 and 3.5 mg/ml, respectively. The samples were analyzed by SDS-polyacrylamide gel electrophoresis (FIG. 18).

The 50% and 60% ammonium sulfate precipitated samples contained equal amounts of the δ-subunit. The 40% ammonium sulfate precipitated samples contained approximately 90% of that of the 50% and 60% ammonium sulfate precipitated samples, while the 30% ammonium sulfate precipitated sample contained very small amounts of the δ-subunit. All future preparations of the δ-subunit will be ammonium sulfate precipitated at 40% saturation.

Purification of T. thermophilus holA Product (δ-subunit) Fused to an N-Terminal Peptide that Contains Hexahistidine and a Biotinylation Site by pA1-NB-TD/MGC1030

Lysis was accomplished by creation of spheroplasts of the cells carrying expressed T. thermophilus δ. First, from 800 g of a 1:1 suspension of frozen cells (400 g cells) in Tris-sucrose which had been stored at −20° C., FrI was prepared (1280 ml, 30.8 mg/ml). The preparation was as described Example 2. To Fr I, ammonium sulfate (0.226 g to each initial ml Fraction I-40% saturation) was added over a 15 min interval. The mixture stirred for an additional 30 min at 4° C. and the precipitate was collected by centrifugation (23,000×g, 45 min, 0° C.). The resulting pellets were quick frozen by immersion in liquid nitrogen and stored at −80° C.

The pellets from Fr I were resuspended in 160 ml of $Ni^{++}$-NTA suspension buffer and homogenized using a Dounce homogenizer. The sample was clarified by centrifugation (16,000×g) and the supernatant constituted Fr II (27.6 mg/ml). Fr II was added to 50 ml of a 50% slurry of Ni-NTA resin and rocked for 1.5 hours at 4° C. This slurry was then loaded onto a BioRad Econo-column (2.5×5 cm). The column was washed with 250 ml of $Ni^{++}$-NTA wash buffer at a flow rate of 0.5 ml/min. The protein was eluted in 230 ml of $Ni^{++}$-NTA elution buffer containing a 10–200 mM imidazole gradient. The eluate was collected in 92×2.5 ml fractions. Fractions were analyzed by SDS-polyacrylamide gel electrophoresis, and fractions 25–92 were found to contain δ that was over 95% pure (FIGS. 19A and 19B). Fractions 25–92 were pooled (160 ml, 2.3 mg/ml) and dialyzed against 3.5 L of HG.04 buffer (20 mM Hepes, (pH 7.6), 40 mM KCl, 1 mM $MgCl_2$, 0.1 mM EDTA, 6 mM βME, 10% glycerol). The dialyzed sample constituted Fr III (160 ml, 2.1 mg/ml). The sample was aliquoted, fast frozen in liquid nitrogen and stored at −80° C.

Production of Polyclonal Antibodies against T. thermophilus holA (δ-subunits)

Figure 20:
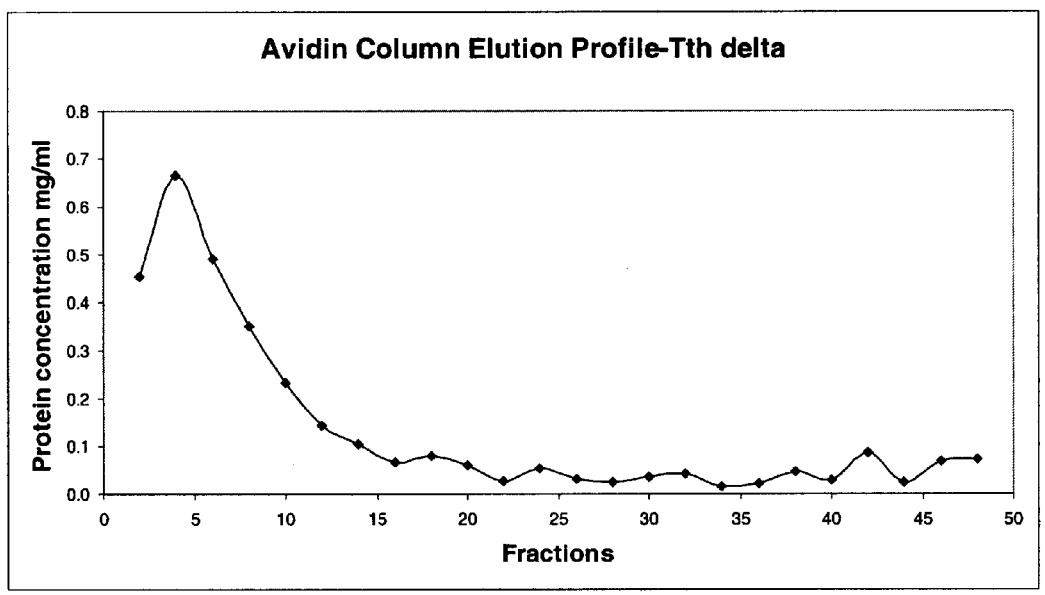
FIG. 20. Protein concentration profile of fractions from the avidin column purification of *T. thermophilus* δ.
Figure 21:
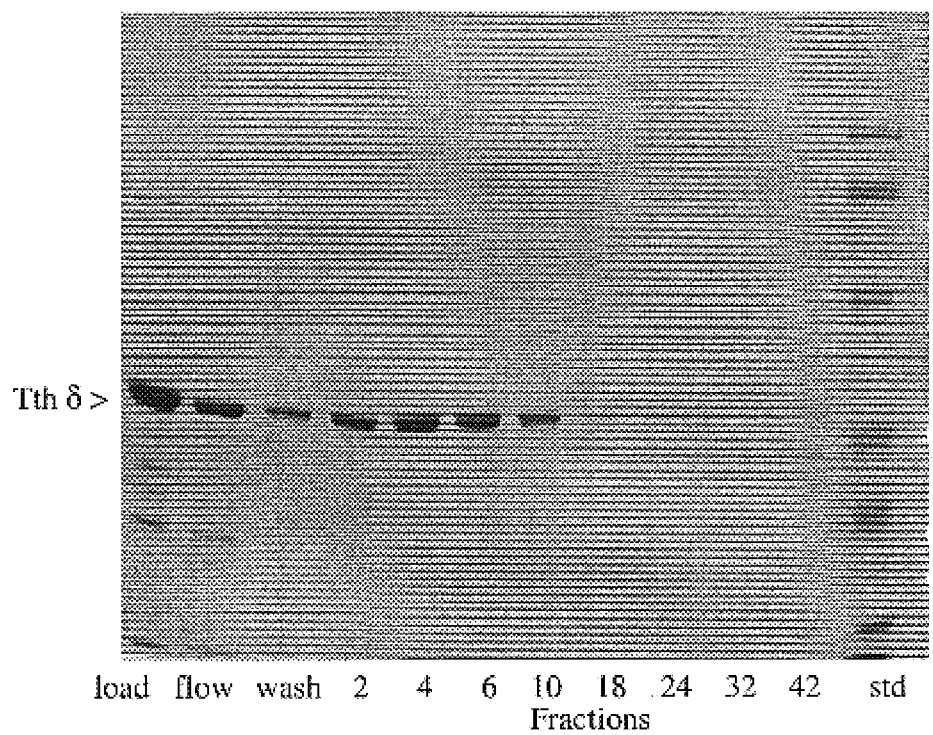
FIG. 21 SDS-PAGE analysis of fractions from the avidin column purification of *T. thermophilus* δ.

To recover ultra-pure protein for antibody production thirty ml of δ-subunit Fr III from above (2.1 mg/ml) was precipitated using ammonium sulfate (7.75 g per initial ml of FrIII, 45% saturation). The precipitated pellets were resuspended in 20 ml PBS and purified using UltraLink™ Immobilized Monomeric Avidin column as described in Example 3. The protein elution profile of the avidin column is shown in FIG. 20. Fractions 2–6 (5 ml) were pooled (0.35 mg/ml). FIG. 21 shows the SDS-PAGE analysis of the Aviden column profile for T. thermophilus δ.

The pooled samples were used to produce polyclonal antibodies against T. thermophilus holA gene product (δ-subunit) as described in Example 3.

Construction of Plasmid (pA1-TD) that Overexpresses T. thermophilus holA Gene (δ-Subunit) as a Native Protein Prior to construction of vector pA1-NB-TD to express δ as an N-terminal tagged protein, several attempts were made to first express δ as a native and a C-terminal tagged protein. These attempts were unsuccessful in producing adequate yields of δ to justify purification attempts. These attempts are described in this section.

The T. thermophilus holA gene contained within the plasmid pT-TD(Kpn) was extracted by digestion of the plasmid with NdeI/KpnI restriction enzymes. This 0.9 kb fragment was inserted into pA1-CB-NdeI which had been digested with the same restriction enzymes. The "ATG" of the NdeI site served as the start codon for the holA gene. This placed the start codon the correct distance (11 nucleotides) from the RBS for optimum translation. This plasmid was then transformed into DH5α bacteria, and plasmids from ampicillin-resistant positive isolates were screened for by digestion with NdeI and KpnI restriction enzymes yielding 0.9 and 5.65 kb fragments. One plasmid was selected and the sequence of the insert verified by DNA sequencing (ATG SEQ #1428 and 1429, primers P38-S5576 and P134-S1633). This plasmid was named pA1-TD and the isolate was stored as a stock culture (ATG glycerol stock #841).

Verification of Expression of Plasmid (pA1-TD) that Overexpresses T. thermophilus holA Gene (δ-Subunit) as a Native Protein from pA1-TD/MGC1030

Plasmid pA1-TD was prepared from DH5α bacteria and transformed into MGC1030 bacteria (ATG glycerol stock #856, 857, 858). The bacterial growths of three isolates and isolation of total cellular protein were as described Example 2. A small aliquot (3 μl) of supernatant containing total cellular protein from each of the three isolates was electrophoresed onto a 4–20% SDS-polyacrylamide mini-gel (Novex, EC60255; 1 mm thick, with 15 wells/gel) in 25 mM in Tris base, 192 mM glycine, and 0.1% SDS. The mini-gel was stained with Coomassie Blue. There were no visible protein bands from any of the isolates corresponding to the predicted molecular weight of δ.

Construction of a Plasmid (pA1-CB-TD) that Overexpresses T. thermophilus holA Gene (δ-subunit) Fused to a C-Terminal Peptide that Contains Hexahistidine and a Biotinylation Site Again, since attempts to express the native δ-subunit failed, we next tried to express this protein coupled to a C-terminal fusion peptide. The holA gene was amplified by PCR with T. thermophilus genomic DNA as a template. The forward/sense primer (ATG primer #P134-S585'de) was the same primer used in construction of named pT-TD(Kpn) and contained a region complementary to the 5' end of the gene. Also, a NdeI site overlapped the ATG start codon, and there was also an upstream HindIII and BamHI site. The reverse/antisense primer was complementary to the 3' end of the ORF excluding the stop codon (ATG primer #P134-A1486spe, 5'-GAGGACTAGT ACGGGCGAGGCGGAGGACC-3') (SEQ ID NO:43). This primer contained a SpeI restriction site adjacent to the complementary region of the primer. The SpeI site allowed for the expressed protein to contain two additional amino acids (Thr and Ser) between the C-terminal amino acid of the δ-subunit and the C-terminal fusion peptide. This 901 bp PCR product was inserted into pGEM-T Easy™ as previously described in the section entitled "Identification of T. thermophilus holA gene (δ-subunit)". This plasmid was transformed into DH5α bacteria and plasmids from ampicillin-resistant positive isolates were screened for by digestion with NdeI and KpnI restriction enzymes yielding 0.9 and 3.0 kb fragments. Both strands of the insert were verified by DNA sequencing (ATG SEQ #1398–1403 and 1409–1411; primers, SP6, T7, P134-S1279, P134-S1633, P134-A1464, P134-A790, P134-S1279, P134-A1849). This plasmid was named pT-TD(Spe) and the isolate was stored as a stock culture (ATG glycerol stock #818).

Plasmid pT-TD(spe) was prepared and the holA gene was extracted by digestion with NdeI and KpnI restriction enzymes. This 0.9 kb fragment was inserted into the pA1-CB-NdeI plasmid digested with the same restriction enzymes. This plasmid was transformed into DH5α bacteria and plasmids from ampicillin-resistant positive isolates were screened for by digestion with NdeI and KpnI restriction enzymes yielding 0.9 and 5.65 kb fragments. The sequence of the inserted DNA fragment was confirmed by DNA sequencing (ATG SEQ #1430,1431; primers, P38-S5576 and P134-S1633). This plasmid was named pA1-CB-TD and the positive isolate was stored as a stock culture (ATG glycerol stock #842).

Verification of Expression of T. thermophilus δ-subunit Fused to a C-Terminal Peptide that Contains Hexahistidine and a Biotinylation Site by pA1-CB-TD/MGC1030

The pA1-CB-TD plasmid was prepared and transformed into MGC1030 bacteria (ATG glycerol stock #859). The bacterial growths of three isolates and isolation of total cellular protein were as described Example 2. A small aliquot of each supernatant (3 μl) containing total cellular protein from each isolate was electrophoresised onto a 4–20% SDS-polyacrylamide mini-gel (Novex, EC60255; 1 mm thick, with 15 wells/gel) in 25 mM in Tris base, 192 mM glycine, and 0.1% SDS. The mini-gels were stained with Coomassie Blue. The region of the gel in which CB-TD was expected contained other intense protein bands and δ could not be visualized.

Next, the total protein in each lysate was transferred (blotted) from polyacrylamide gel to nitrocellulose as described in Example 2. Each lane contained 1.5 ul of the supernatant. The endogenous E. coli biotin-CCP, ~20 kDa was detectable in both induced and non-induced samples. A very faint protein band corresponding to δ migrated just below the 40 kDa molecular weight standard of the Gibco 10 kDa protein ladder. The predicted molecular weight of δ is 36.2 kDa. This protein was observed as a faint band in the induced cultures, but was not observed in the uninduced control in lysates. The intensity of the protein bands indicated δ was being expressed at very low levels.

Cloning T. thermophilus holA Gene (δ) into a Translationally Coupled Vector pTAC-CCA-ClaI To efficiently express δ as a native protein we designed a vector to express δ as a translationally coupled protein. As with expression of DnaX as a translationally coupled protein, our goal here is also to use translational coupling as described in the Example 2. The holA gene was inserted behind the CCA adding enzyme and translationally coupled in two steps. First, the holA gene was amplified using pA1-TD as a template by PCR. The forward/sense primer (ATG primer #P134-S588cla2, 5'-ACTGATCGATA ATGGTCATCGCCTTCAC-3') (SEQ ID NO:55) has a ClaI restriction site in the non-complementary region. As in the cloning strategy developed for pTAC-CCA-TX, the non-complementary region also contains the "TA" of the stop (TAA) for the upstream CCA-adding protein fragment. The region of the primer complementary to the 5' end of the T. thermophilus holA gene begins with "A" which is the first nucleotide of the "ATG" start codon and the final "A" of the "TAA" stop codon. The reverse/antisence primer (ATG primer #P134-A1491stopspe, 5'-GAGGTACTAGTCA TCAACGGGCGAGGCGGAGGA-3') (SEQ ID NO:56) contains a SpeI restriction site in the non-complementary portion of the primer and also an additional stop codon adjacent to the native stop codon, giving two stop codons in tandem. There was also a clamp region for efficient cutting with SpeI. Next, the PCR product was digested with ClaI/SpeI restriction enzymes and inserted into the pTAC-CCA-ClaI plasmid digested with the same enzymes. The plasmid was transformed into DH5α bacteria and plasmids from ampicillin-resistant positive isolates were screened for by digestion with ClaI/SpeI restriction enzymes yielding 0.9 and 5.5 kb fragments. The sequence of both strands of the insert were verified by DNA sequencing (ATG SEQ #1675–1681; primers, P144-S23, P144-A1965, P65-A106, P134-S1279, P134-S1633, P134-A1849, P134-A1464, P134-A790). Sequence analysis confirmed that the correct sequence was contained within the inserted region. This plasmid was named pTAC-CCA-TD and the isolate was stored as a stock culture (ATG glycerol stock #1031).

Verification of Expression of Native T. thermophilus δ-subunit by PTAC-CCA-TD/MGC1030 and pTAC-CCA-TD/AP1.L1

The pTAC-CCA-TD plasmid was prepared and transformed into MGC1030 bacteria (ATG glycerol stock #1070) and AP1.L1 (ATG glycerol stock #1078). The bacterial growths and isolation of total cellular protein were as described in Example #2. A small aliquot of each supernatant (3 μl) containing total cellular protein was electrophoresised onto a 4–20% SDS-polyacrylamide mini-gel (Novex, EC60255; 1 mm thick, with 15 wells/gel) in 25 mM in Tris base, 192 mM glycine, and 0.1% SDS. The mini-gels were stained with Coomassie Blue. A protein band corresponding to the predicted molecular mass of T. thermophilus δ (32.5 kDa) was visualized migrating mid-way between the 30 and 40 kDa molecular weight standard of the Gibco 10 kDa protein ladder.

Large Scale Growth of pA1-CCA-TD/AP1.L1

Strain pA1-CCA-TD/AP1.L1 was grown in a 250 L fermentor to produce cells for purification of native T. thermophilus δ as described in Example #2. Optimum induction times were determined as described in Example #2. Cell harvest was initiated 3 hours after induction, at $OD_{600}$ of 3.38, and the cells were chilled to 10° C. during harvest. The harvest volume was 180 L, and the final harvest weight was approximately 1.56 kg of cell paste. An equal amount (w/w) of 50 mM Tris (pH 7.5) and 10% sucrose solution was added to the cell paste. Quality control results showed 10 out of 10 positive colonies on ampicillin-containing medium in the inoculum and 10/10 positive colonies at induction and 10/10 positive colonies at harvest. Cells were frozen by pouring the cells suspension into liquid nitrogen, and stored at −20° C., until processed.

Purification of Native T. thermophilus δ from pA1-CCA-TD

Lysis was accomplished by creation of spheroplasts of the cells carrying the expressed T. thermophilus δ-subunits. First, from 300 g of a 1:1 suspension of frozen cells (150 g cells) in Tris-sucrose which had been stored at −20° C., FrI was prepared (930 ml, 16.4 mg/ml). The preparation was as described in Example #2. To Fr I, ammonium sulfate (0.258 g to each initial ml Fraction I-45% saturation) was added over a 15 min interval. The mixture stirred for an additional 30 min at 4° C. and the precipitate was collected by centrifugation (23,000×g, 45 min, 0° C.). The resulting pellets were quick frozen by immersion in liquid nitrogen and stored at −80° C.

In the following purification steps, fractions from purification columns were assayed using the reconstitution assay (described in Example 7) to determine fractions that contained activity and therefore the δ-subunit. The first purification step was conducted by Q Sepharose High Performance (Amersham Pharmacia) column chromatography (200 ml, 5.5×13 cm). The Q Sepharose resin was equilibrated in Q-sepharose equilibration buffer (25 mM Tris-HCl, (pH 7.5), 10% glycerol, 1 mM EDTA, 1 mM DTT, 10 mM KCl). The pellets from Fr I was resuspended in Q-sepharose resuspension buffer (25 mM Tris-HCl, (pH 7.5), 10% glycerol, 1 mM EDTA, 1 mM DTT) and homogenized using a Dounce homogenizer and clarified by centrifugation (16, 000×g). The sample was diluted in Q-sepharose resuspension buffer until the conductivity reached that of the equilibrated column and constituted Fr II (2250 ml, 0.8 mg/ml). Fraction II contained $3.5 \times 10^9$ units of activity at $1.84 \times 10^6$ units/mg protein. The sample was loaded onto the column and washed with 5 column volumes of Q-sepharose equilibration buffer. The wash was collected in 17 ml fractions (50 fractions). Analysis of the flow through from the column load and the fractionated wash indicated that δ was present in the flow through from the column load and the first fractions from the column wash. The flow through from the column load and fractions 1–13 of the column wash were pooled and constituted Fr III (2470 ml, 0.05 mg/ml). SDS-polyacrylamide gel analysis of the pool indicated that *T. thermophilus* δ had been purified over 16 fold by this purification step and contained $3.5 \times 10^9$ units of activity at $3.2 \times 10^7$ units/mg protein.

Fr III was further purifed using Macro Prep Methyl HIC Support (BioRad) column chromatography. The methyl resin (60 ml) was equilibrated in methyl equilibration buffer (50 mM Tris-HCl, (pH 7.5), 10% glycerol, 1 mM EDTA, 1 mM DTT, 1 M ammonium sulfate). The column was poured using 40 ml of methyl resin. The remaining 20 ml of methyl resin was mixed with Fr III giving 2490 ml. To this mixture, saturated ammonium sulfate (0.5 sample volume) was added slowly while stirring over a 1 hour period. This mixture was added to the column and allowed to flow through the column by gravity. The column was then washed with 5 column volumes (300 ml) of methyl equilibration buffer. The protein was eluted in 10 column volumes of 50 mM Tris-HCl, (pH 7.5), 10% glycerol, 1 mM EDTA, 1 mM DTT buffer containing a 0.9 to 0.1 M gradient of ammonium sulfate and collected in 7 ml fractions (80 fractions). Fractions 29–42 contained *T. thermophilus* δ that was over 90% pure. These fractions were pooled and analyzed using reconstitution assays (see Example 7) and SDS-polyacrylamide gels. The pooled fractions (100 ml, 0.14 mg/ml) constituted Fr IV and contained $1.7 \times 10^9$ units of activity at $1.23 \times 10^8$ units/mg protein.

*T. thermophilus* δ was further purified using a Sephacryl S300 HR (Pharmacia Biotech) gel filtration column (510 ml, 3 cm×120 cm) equilibrated in 50 mM Tris-HCl, (pH 7.5), 20% glycerol, 100 mM NaCl, 1 mM EDTA, 5 mM DTT. The volume of Fr IV was reduced using PEG 8000 to 35 ml (0.22 mg/ml, $8.2 \times 10^8$ Units). The sample was loaded onto the Sephacryl S-300 column and the protein eluted at a flow rate of 0.7 ml/min. The δ-subunit was isolated as a highly purified protein (24 ml, 0.2 mg/ml). The pooled fractions constituted Fr V and contained $5.8 \times 10^8$ units of activity at $1.23 \times 10^8$ units/mg protein.

Example 5

Identification of *T. thermophilus* holB Gene (δ'-subunit)

The amino acid sequence of δ' from *E. coli* was used to search the *T. thermophilus* genome database at Goettingen Genomics Laboratory. A partial crude sequence of a region of the *T. thermophilus* genome containing a putative *T. thermophilus* holB gene was identified (using BLAST) and obtained (from Dr. Carsten Jacobi, Goettingen Genomics Laboratory, Institute of Microbiology and Genetics, Grisebachstrasse 8, Goettingen, Germany). Unsure of the accuracy of the crude sequence, the region of the *T. thermophilus* genome suspected of containing the *T. thermophilus* holB gene and flanking regions were amplified by PCR. Two sets of PCR primers were designed using sequences derived from the crude sequence to insure that the proper sequence was identified. The first PCR reaction (ATG primers P139-S181, 5'-GGGGGACCGGATCGCCTTCTA-3' (SEQ ID NO:12) and P139-A1082, 5'-GTACGCCCACGGTCATGTCTCTAAGTCT AAG-3' (SEQ ID NO:13)) used *T. thermophilus* genomic DNA as a template and yielded a PCR product of 901 bp fragment. This PCR fragment was inserted into pGEM-T Easy™ (Promega) vector per manufacturers directions. This plasmid was transformed into DH5α bacteria and ampicillin-resistant positive isolates were screened for by plasmid digestion with EcoRI restriction digest yielding 0.9 and 3.0 kb fragments. The correct sequence of both strands of the DNA in the inserted region were identified by DNA sequencing across the inserted region (ATG SEQ #1363, 1365–1367, 1379–1380; primers, SP6, T7, P139-S651, P139-S321, P139-A681, P139-A287). Three base changes (deletions of a "C" at positions 845 and 849, and G>C change at position 681) were observed in the PCR clone compared to the crude sequence obtained from Goettingen Genomics Laboratory. The deletions caused a frameshift leading to a larger open reading frame (ORF) (804 bp) than was seen in the crude sequence. This plasmid was named pT-TD'-1 and the isolate was stored as a stock culture (ATG glycerol stock #811).

The second PCR reaction utilized primers placed farther out from the putative holB gene (ATG primers #P139-S91, 5'-CTCCCCCCCTCGGTGCGGGCCCTGGTGAA-3' (SEQ ID NO:14) and #P139-A1407, 5'-CTCGGCGCTGTAGTGGATGACG-3' (SEQ ID NO:15)) and also used the *T. thermophilus* genomic DNA as a template and yielded a PCR product of 1361 bp fragment. This PCR fragment was also inserted into pGEM-T Easy™ (Promega) vector per manufacturer directions. This plasmid was also transformed into DH5α bacteria and ampicillin-resistant positive isolates were screened for by plasmid digestion with EcoRI restriction digest yielding 1.3 and 3.0 kb fragments. The correct sequence of both strands of the DNA in the inserted region were identified by DNA sequencing (ATG SEQ #1368–1372, 1381–1383; primers, SP6, T7, P139-S651, P139-S321, P139–1042, P139-A681, P139-A287, P139-A1082). Other base changes were observed in the 3' non-translated region when compared to the crude sequence obtained from Goettingen Genomics Laboratory. This plasmid was named pT-TD'-2 and the isolate was stored as a stock culture (ATG glycerol stock #812).

The DNA coding sequence of the *T. thermophilus* holB gene (SEQ ID NO:16) is in FIG. 22. The start codon (atg) and the stop codon (tga) are in bold print. Also shown, in FIG. 23, is the protein (amino acid) sequence (SEQ ID NO:17) derived from.the DNA coding sequence.

The amino acid sequence of *T. thermophilus* δ was compared with that of the *E. coli* δ'-subunit (FIG. 24). Other sequence alignments were carried out with δ' sequences from *Bacillus subtilis, E. coli,* and *Haemophilus influenzae,* Rickettsia and putative δ' sequences from *Aquiflex aeolicus* (FIG. 25). The *T. thermophilus* δ'-subunit was 30%, 29%, 31%, 39% and 31% identical over a 163, 149, 229, 104 and 104 amino acid overlap with *Bacillus subtilis, E. coli,* and

*Haemophilus influenzae*, Rickettsia and a putative δ'-subunit sequences from Aquiflex aeolicus, respectively.

Construction of a Plasmid (pA1-NB-TD') that Overexpress *T. thermophilus* holB (δ') Fused to an N-Terminal Peptide that Contains Hexahistidine and a Biotinylation Site To enhance expression of the *T. thermophilus* δ'-subunit, the holB gene was cloned into the pA1-NB-AgeI plasmid to be expressed fused to an N-terminal peptide containing hexahistidine and a biotinylation site. The holB gene was amplified by PCR using the pA1-TD' plasmid (described below) as a template. The forward/sense primer adds a Pst1 site to the 5' end of the gene so that the actual PCR product excludes the ATG start codon and begins at codon 2, with the PstI site adjacent to codon 2 (ATG primer P139-S254pst, 5'-GAATTCTGCAGGCTCTAC ACCCGGCTCACCC-3' (SEQ ID NO:18)). The PstI site will bring the holB gene into frame with the N-terminal fusion peptide and will add two amino acids (Leu and Gln) between the N-terminal fusion peptide and the second codon of the holB gene. The reverse primer (ATG primer P139-A1081stopspe, 5'-GGACACTAGTTCATCATGTCTCTAAGTCTAA-3' (SEQ ID NO:19) was complementary to the 3' end of the holB gene including the additional TGA (stop codon). Also, a SpeI restriction site was added in the non-complementary region of the primer for insertion into the vector. There was also a clamp region for efficient cutting with SpeI. The PCR product was digested with PstI/SpeI restriction enzymes and inserted into the pA1-NB-AgeI plasmid digested with the same enzymes. The plasmid was transformed into DH5α bacteria and plasmids from ampicillin-resistant positive isolates were screened for by digestion with PstI/SpeI restriction enzymes yielding 0.8 and 5.6 kb fragments. The sequence of both strands of the insert were verified by DNA sequencing (ATG SEQ #1537–1541, 1543; primers, P64-S10, P64-A215, P139-S321, P139-S651, P139-A681, P64-A215). Sequence analysis confirmed that the correct sequence was contained within the inserted region. This plasmid was named pA1-NB-TD' and the isolate was stored as a stock culture (ATG glycerol stock #913).

Verification of Expression of *T. thermophilus* δ'-subunit Fused to an N-Terminal Peptide that Contains Hexahistidine and a Biotinylation Site by pA1-NB-TD'/MGC1030

The pA1-NB-TD' plasmid was prepared and transformed into MGC1030 bacteria (ATG glycerol stock #930). The bacterial growths and isolation of total cellular protein were as Example 2. A small aliquot of each supernatant (3 μl) containing total cellular protein was electrophoresised onto a 4–20% SDS-polyacrylamide mini-gel (Novex, EC60255; 1 mm thick, with 15 wells/gel) in 25 mM in Tris base, 192 mM glycine, and 0.1% SDS. The mini-gels were stained with Coomassie Blue. A protein migrating just below the 40 kDa molecular weight standard of the Gibco 10 kDa protein ladder could not be detected in the lysates.

Next, the total protein in each lysate was transferred (blotted) from polyacrylamide gel to nitrocellulose as described Example 2. The endogenous *E. coli* biotin-CCP, ~20 kDa, was detectable in both induced and non-induced samples. An intense protein band corresponding to *T. thermophilus* δ' migrated midway between the 30 and 40 kDa molecular weight standards of the Gibco 10 kDa protein ladder. The predicted molecular weight of *T. thermophilus* δ' is 33 kDa. This protein was observed as a distinct band in the induced cultures, but was not observed in the uninduced control in lysates.

Optimization of Expression of *T. thermophilus* holB Gene (δ'-subunit) by pA1-NB-TD'

Figure 26:
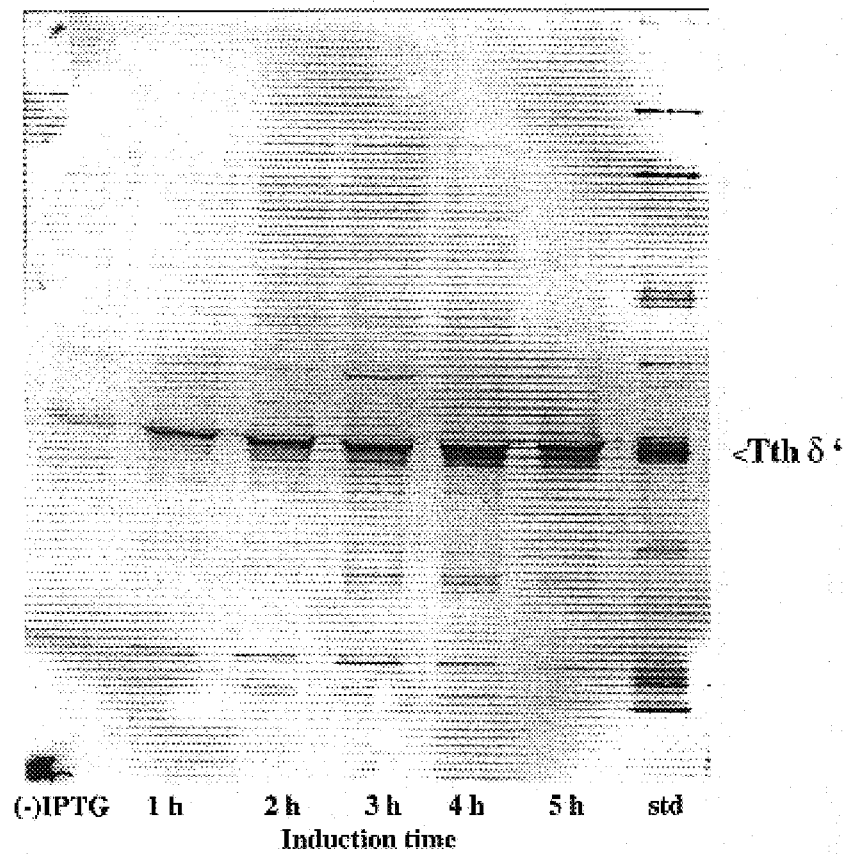
FIG. 26. Biotin blot analysis of growth/induction time optimization of expression of *T. thermophilus* δ' by pA1-NB-TD'/AP1.L1.

Expression was analyzed using the bacterial strains AP1.L1 carrying the pA1-NB-TD' plasmid at different induction times. Bacterial growths and analysis were carried out as described Example 2. The growths and analysis were at 37° C. The total protein was analyzed using both SDS-polyacrylamide gel electrophoresis and biotin blot analysis (FIG. 26). Distinct protein bands corresponding to δ' were observed by both forms of analysis. Biotin blot analysis indicated that most of the δ'-subunit is being expressed in 4 hours and at 37° C., these growth condition were used in subsequent preparations.

Determination of Optimal Ammonium Sulfate Precipitation Conditions of the δ'-subunit Fused to an N-Terminal Peptide that Contains Hexahistidine and Biotinylation Site by pA1-NB-TD'/MGC1030

Lysis was accomplished by creation of spheroplasts of the cells carrying the expressed *T. thermophilus* δ'-subunits. First, from 76.4 g of a 1:1 suspension of frozen cells (38.2 g cells) in Tris-sucrose which had been stored at −20° C., FrII was prepared and purified using a $Ni^{++}$-NTA column as described in Example 2. The eluted sample was brought to 40 ml by added Ni-NTA suspension buffer. The sample was then divided into 4 equal volumes (10 ml) and 1.64, 2.26, 2.91 and 3.61 g of ammonium sulfate (30%, 40%, 50% and 60% saturation) was added to each separate sample, respectively, over a 15 min interval at 4° C. The mixture rested for an additional 30 min at 4° C. and was then centrifuged at 23,000×g for 45 min at 0° C. The resulting pellets were resuspended in 1 ml Ni-NTA suspension buffer. The 30%, 40%, 50% and 60% ammonium sulfate precipitated samples contained protein concentrations of 0.47, 0.55, 1.3 and 1.2 mg/ml, respectively. The samples were analyzed by SDS-polyacrylamide gel electrophoresis. All four ammonium sulfate precipitated samples contained equal amounts of the δ'-subunit. All future preparations of the δ'-subunit will be ammonium sulfate precipitated at 35% saturation.

Large Scale Growth of *T. thermophilus* holB Gene Product (δ'-subunit) Fused to an N-Terminal Peptide that Contains Hexahistidine and Biotinylation Site by pA1-NB-TD'/MGC1030

Strain pA1-NB-TD'/MGC1030 was grown in a 250 L fermentor, to produce cells for purification of *T. thermophilus* δ'-subunit as described in Example 2. Cell harvest was initiated 3 hours after induction, at $OD_{600}$ of 5.8, and the cells were chilled to 10° C. during harvest. The harvest volume was 186 L, and the final harvest weight was approximately 2.1 kg of cell paste. An equal amount (w/w) of 50 mM Tris (pH 7.5) and 10% sucrose solution was added to the cell paste. Cells were frozen by pouring the cells suspension into liquid nitrogen, and stored at −20° C., until processed. Quality control results showed 10 out of 10 positive colonies on ampicillin-containing medium in the inoculum, 10/10 positive colonies at induction and 7/10 positive colonies at harvest.

Purification of *T. thermophilus* holB Product (d'-subunit) Fused to an NTerminal Peptide that Contains Hexahistidine and a Biotinylation Site by pA1-NB-TD'/MGC1030

Lysis was accomplished by creation of spheroplasts of the cells carrying the expressed *T. thermophilus* δ'-subunits as described in Example 2. First, from 800 g of a 1:1 suspension of frozen cells (400 g cells) in Tris-sucrose which had been stored at −20° C., FrI was prepared (1200 ml, 17 mg/ml). To Fr I, ammonium sulfate (0.194 g to each initial ml Fraction I-35% saturation) was added over a 15 min interval. The mixture stirred for an additional 30 min at 4° C. and the precipitate was collected by centrifugation (23,000×g, 45 min, 0° C.). The resulting pellets were quick frozen by immersion in liquid nitrogen and stored at −80° C.

The pellets from Fr I were resuspended in 150 ml of $Ni^{++}$-NTA suspension buffer and homogenized using a Dounce homogenizer. The sample was clarified by centrifugation (16,000×g) and the supernatant constituted Fr II (4 mg/ml). Fr II was added to 50 ml of a 50% slurry of Ni-NTA resin and rocked for 1.5 hours at 4° C. This slurry was then loaded onto a BioRad Econo-column (2.5×5 cm). The column was washed with 400 ml of $Ni^{++}$-NTA wash buffer at a flow rate of 1.5 ml/min. The NB-TD' protein was eluted in 200 ml of $Ni^{++}$-NTA elution buffer containing a 10–200 mM imidazole gradient. The eluate was collected in 92×2 ml fractions. Fractions were analyzed by SDS-polyacrylamide gel electrophoresis, and fractions 40–75 were found to contain δ' that was over 95% pure (FIGS. 27A and 27B).

Fractions 40–75 were pooled (70 ml, 0.7 mg/ml) and dialyzed against 2.5 L of HG.04 buffer (20 mM Hepes, (pH 7.6), 40 mM KCl, 1 mM $MgCl_2$, 0.1 mM EDTA, 6 mM βME, 10% glycerol). The dialyzed sample constituted Fr III (70 ml, 0.5 mg/ml). From the pool, 75% of the sample was aliquoted, fast frozen in liquid nitrogen and stored at −80° C. The remaining 25% was further purified for antibody production.

Production of Polyclonal Antibodies Against *T. thermophilus* δ'

Figure 28:
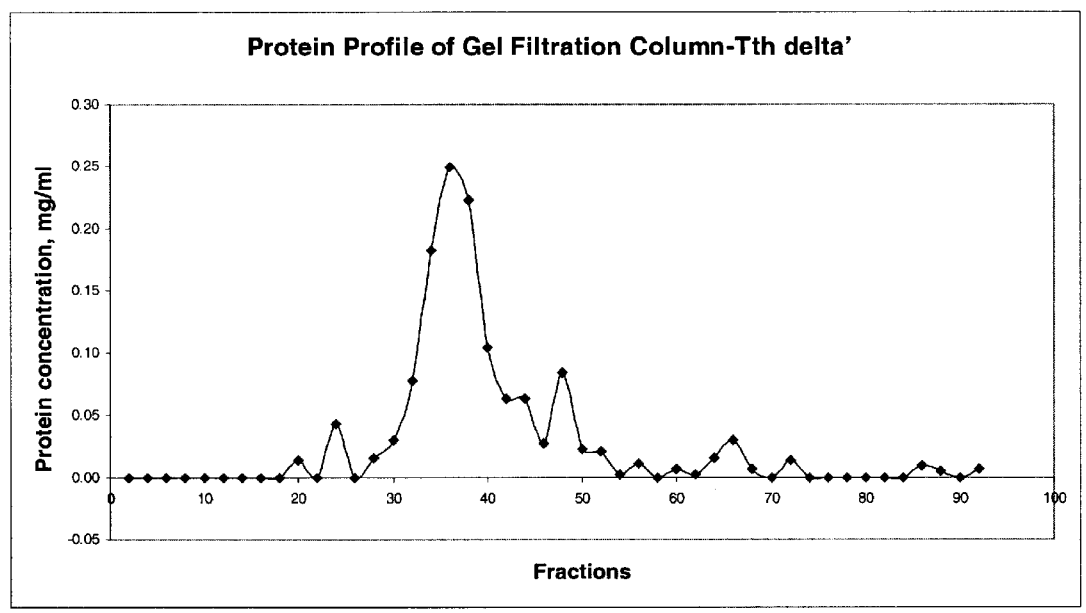
FIG. 28. Protein concentration profile of fractions eluting from the Sephacryl S-300 gel filtration column purification of *T. thermophilus* δ'.
Figure 29:
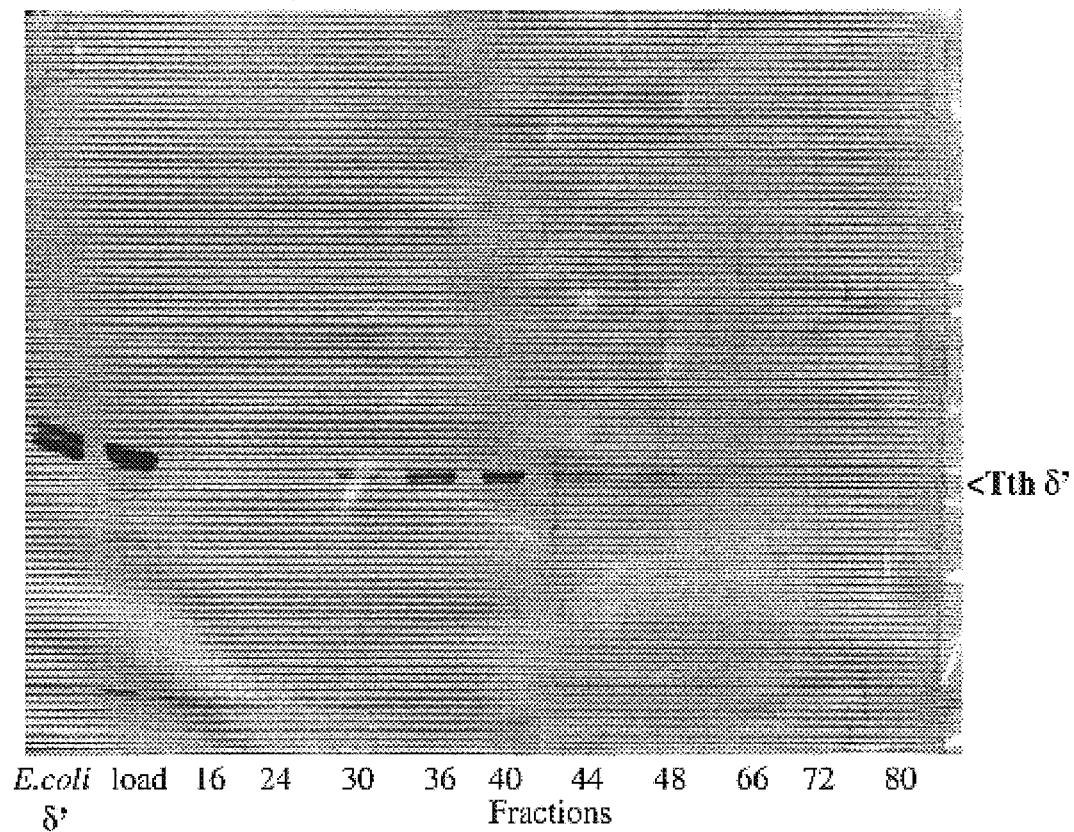
FIG. 29. SDS-PAGE analysis of fractions from the Sephycryl S-300 column purification of *T. thermophilus* δ'.

The 25% of *T. thermophilus* δ' FrII discussed above was precipitate by adding ammonium sulfate to 40% saturation (0.226 g of ammonium sulfate per initial ml). The protein pellet was resuspended in 2 ml of 20 mM potassium phosphate, pH 6.5, 100 mM KCl, 25% glycerol and 5 mM DTT buffer. The sample was loaded onto a Sephacryl S-300 column (88 ml, 40:1 height:width ratio) equilibrated in the same buffer. This was accomplished by running the column head down to the resin bed, adding the sample (2 ml), running the sample into the resin and rebuilding the column head. The sample was then eluted in the same buffer at a flow rate of 0.2 ml/min and collected in 1.5 ml fractions. Protein concentrations of each fraction was determined using the Coomassie Protein Assay Reagent (FIG. 28). Fractions were analyzed by SDS-polyacrylamide gel electrophoresis and the fractions were observed to contain homologous δ" (FIG. 29).

Fractions 30 to 40 were pooled and the protein was precipitate by adding ammonium sulfate to 40% saturation as previously described. The protein was then resuspended in 3 ml of PBS and dialyzed against 500 ml PBS two times. This constituted Fr IV and was used for antibody production (0.133 mg/ml). The dialyzed samples were used to produce polyclonal antibodies against *T. thermophilus* holB gene product (δ'-subunit) as described in Example 3.

Construction of Plasmid (pA1-TD') that Overexpresses *T. thermophilus* holB Gene (δ'-Subunit) as a Native Protein Prior to construction of vector pA1-NB-TD' to express δ'-subunit as an N-terminal tagged protein, several attempts were made to first express δ' as a native and a C-terminal tagged protein. These attempts were unsuccessful in producing adequate yields of δ' to justify purification attempts. These attempts are described in this section.

The holB gene was amplified by PCR using pT-TD'-2 as a template and expressed as a native protein. The forward/sense primer (ATG primer #P139-S253, 5'-CTTTCCCCC ATGGCTCTACACCCG-3') (SEQ ID NO:44) contained a region complementary to the 5' end of the gene. An NcoI site overlapped the ATG start codon. The reverse/antisense primer (ATG primer #P139-A1085, 5'-GGATCCGGCCGGCCTCAT CATGTCTCTAAGTCTAAGGC-3') (SEQ ID NO:45) contained and additional stop codon adjacent to the native stop codon, giving two stop codons in tandem. There is a FseI site adjacent to the second stop codon and a BamlI restriction site adjacent to the FseI restriction site. This PCR fragment was digested with NcoI and FseI restriction enzymes and inserted into the plasmid pA1-CB-NcoI digested with the same two enzymes. The plasmid was resealed and transformed into DH5α bacteria. Plasmids from ampicillin-resistant positive isolates were screened by NcoI and FseI restriction digest yielding 0.8 and 5.6 kb fragments. The sequence of the inserted region was confirmed by DNA sequencing (ATG SEQ #1447–1450; primers, P38-S5576, P65-A106, P139-S651 and P139-A681). The sequence of the clone showed unexpected extra bases downstream of the FseI restriction site, although the remainder of the insert had the correct sequence. Therefore, the NcoI/FseI fragment contained the correct sequence. This plasmid was named pA1-TD'(a) and the isolate was stored as a stock culture (ATG glycerol stock #844). To insure that the downstream region contained the correct sequence, pA1-TD'(a) was digested with NcoI/FseI restriction enzymes and inserted into another pA1-CB-NcoI plasmid digested with the same restriction enzymes. This plasmid was resealed and also transformed into DH5α bacteria. Plasmids from ampicillin-resistant colonies were again screened by NcoI and FseI restriction digest yielding 0.8 and 5.6 kb fragments. The sequence of the inserted region was again confirmed by DNA sequencing (ATG SEQ #1473–1476, 1485; primers, P38-S5576, P65-A106, P139-S651, P139-A681 and P139-S321). Sequence analysis confirmed the correct sequence throughout the region sequenced. This plasmid was named pA1-TD' and the isolate was stored as a stock culture (ATG glycerol stock #878).

Verification of Expression of Plasmid (pA1-TD') that Overexpresses *T. thermophilus* holB Gene (δ'-Subunit) as a Native Protein from pA1-TD'/MGC1030

Plasmid pA1-TD' was prepared from DH5α bacteria. The plasmid was transformed into MGC1030 bacteria (ATG glycerol stock #893, 894, 895). The bacterial growths of three isolates and isolation of total cellular protein were as described in Example 2. A small aliquot (3 μl) of supernatant containing total cellular protein from each of the three isolates was electrophoresised onto a 4–20% SDS-polyacrylamide mini-gel (Novex, EC60255; 1 mm thick, with 15 wells/gel) in 25 mM in Tris base, 192 mM glycine, and 0.1% SDS. The mini-gel was stained with Coomassie Blue. There were no visible protein bands from any of the isolates corresponding to the predicted molecular weight of *T. thermophilus* δ.

Construction of a Plasmid (pA1-CB-TD') that Overexpresses *T. thermophilus* holB (δ'-subunit) Fused to a C-Terminal Peptide that Contains Hexahistidine and a Biotinylation Site Again, since attempts to express native δ' failed, expression of this protein was attempted by coupling the protein to a C-terminal fusion peptide. The gene encoding *T. thermophilus* holB above was amplified by PCR using pT-TD'-2 plasmid as a template. The forward/sense primer (ATG primer #P139-S253) was the same primer used in construction of pA1-TD' and contained a region complementary to the 5' end of the *T. thermophilus* holB gene. As before, an NcoI site overlapped the ATG start codon. The reverse/antisense primer was complementary to the 3' end of the *T. thermophilus* holB gene excluding the stop codon (ATG primer #P139-A1075, 5'-GAGGACTAGT TGTCTCTAAGTCTAA GGC-3') (SEQ ID NO:46). This primer contained a SpeI restriction site adjacent to the complementary region of the primer. The SpeI site allowed for the expressed protein to contain two additional amino acids (Thr and Ser) between the C-terminal amino acid of the δ'-subunit and the C-terminal fusion peptide. This 822 bp PCR product was digested with NcoI and SpeI and inserted into the plasmid pA1-CB-NcoI digested with the same restriction enzymes. This plasmid was transformed into DH5α bacteria and plasmids from ampicillin-resistant positive isolates were screened for by digestion with NcoI and SpeI restriction enzymes yielding 0.8 and 5.6 kb fragments. The sequence of the insert was verified by DNA sequencing (ATG SEQ #1500–1503; primers, P38-S5576, P65-A106, P139-S651, P139-S321). This plasmid was named pA1-CB-TD☐ and the isolate was stored as a stock culture (ATG glycerol stock #896).

Verification of Expression of *T. thermophilus* δ'-subunit Fused to a C-Terminal Peptide that Contains Hexahistidine and a Biotinylation Site by pA1-CB-TD'/MGC1030

The pA1-CB-TD' plasmid was prepared and transformed into MGC1030 bacteria (ATG glycerol stock #920). The bacterial growths of three isolates and isolation of total cellular protein were as described in Example 2. A small aliquot of each supernatant (3 μl) containing total cellular protein was electrophoresised onto a 4–20% SDS-polyacrylamide mini-gel (Novex, EC60255; 1 mm thick, with 15 wells/gel) in 25 mM in Tris base, 192 mM glycine, and 0.1% SDS. The mini-gels were stained with Coomassie Blue. The region of the gel in which δ was expected contained other intense protein bands and δ could not be visualized.

Next, the total protein in each lysate was transferred (blotted) from polyacrylamide gel to nitrocellulose as described in Example 2. Each lane contained 1.5 ul of the supernatant. Proteins on the blotted nitrocellulose were visualized by interactions with phosphatase-conjugated streptavidin as described above. The endogenous *E. coli* biotin-CCP, ~20 kDa, was detectable in both induced and non-induced samples. A very faint protein band corresponding to δ' migrated midway between the 30 and 40 kDa molecular weight standard of the Gibco 10 kDa protein ladder. The predicted molecular weight of δ' is 33 kDa. This protein was observed as a faint band in the induced cultures, but was not observed in the uninduced control in lysates. *T. thermophilus* δ' was not expressed in great enough quantities to justify growth and purification.

Cloning *T. thermophilus* holB Gene (δ') Into a Translationally Coupled Vector pTAC-CCA-ClaI To efficiently express δ' as a native protein we designed a vector to express δ' as a translationally coupled protein. The goal is to use translational coupling as described in Example #2. The holB gene was inserted behind the CCA adding enzyme and translationally coupled in two steps. First, the holB gene was amplified by using pA1-TD' as a template by PCR. The forward/sense primer (ATG primer #P139-S250cla2, 5'-ACTGATCGATA ATGGCTCTACACCCGGCTCACCC-3') (SEQ ID NO:57) has a ClaI restriction site in the non-complementary region. The non-complementary region also contains the "TA" of the stop (TAA) for the upstream CCA-adding protein fragment. The region of the primer complementary to the 5' end of the *T. thermophilus* holB gene begins with "A" which is the first nucleotide of the "ATG" start codon and the final "A" of the "TAA" stop codon. The reverse/antisense primer (ATG primer #P139-A1081 stopspe, 5'-GGACACTAGTTCATCATGTCTCTAAGTCTAA-3') (SEQ ID NO:58) contains a SpeI restriction site in the non-complementary portion of the primer and also an additional stop codon adjacent to the native stop codon, giving two stop codons in tandem. There was also a clamp region for efficient cutting with SpeI. In the second step the PCR product was digested with ClaI/SpeI restriction enzymes and inserted into the pTAC-CCA-ClaI plasmid digested with the same enzymes. The plasmid was transformed into DH5α bacteria and plasmids from ampicillin-resistant positive isolates were screened for by digestion with ClaI/SpeI restriction enzymes yielding 0.8 and 5.5 kb fragments. The sequence of both strands of the insert were verified by DNA sequencing (ATG SEQ #1737–1742; primers, P144-S23, P65-A106, P139-S321, P139-S651, P139-A681, P139-A1081stopspe). Sequence analysis confirmed that the correct sequence was contained within the inserted region. This plasmid was named pTAC-CCA-TD' and the isolate was stored as a stock culture (ATG glycerol stock #1055).

Verification of Expression of Native *T. thermophilus* δ'-subunit Expressed from pTAC-CCA-TD'/MGC1030 and pTAC-CCA-TD'/AP1.L1

The pTAC-CCA-TD' plasmid was prepared and transformed into MGC1030 bacteria (ATG glycerol stock #1083) and AP1.L1 (ATG glycerol stock #1080, 1081, 1082). The bacterial growths and isolation of total cellular protein were as described in Example #2. A small aliquot of each supernatant (3 μl) containing total cellular protein was electrophoresised onto a 4–20% SDS-polyacrylamide mini-gel (Novex, EC60255; 1 mm thick, with 15 wells/gel) in 25 mM in Tris base, 192 mM glycine, and 0.1% SDS. The mini-gels were stained with Coomassie Blue. The expected location of the *T. thermophilus* δ' protein band was in an area containing many bands of native *E. coli* proteins and *T. thermophilus* δ' could not be resolved from these other protein bands.

Large Scale Growth of pA1-CCA-TD'/AP1.L1

Strain pA1-CCA-TD'/AP1.L1 was grown in a 250 L fermentor to produce cells for purification of *T. thermophilus* δ' as described in Example #2. Optimum induction times were determined as described in Example #2. Cell harvest was initiated 3 hours after induction, at $OD_{600}$ of 3.12, and the cells were chilled to 10° C. during harvest. The harvest volume was 175 L, and the final harvest weight was approximately 1.37 kg of cell paste. An equal amount (w/w) of 50 mM Tris (pH 7.5) and 10% sucrose solution was added to the cell paste. Quality control results showed 10 out of 10 positive colonies on ampicillin-containing medium in the inoculum and 10/10 positive colonies at induction and 10/10 positive colonies at harvest. Cells were frozen by pouring the cells suspension into liquid nitrogen, and stored at −20° C., until processed.

Purification of Native *T. thermophilus* δ from pA1-CCA-TD'

Lysis was accomplished by creation of spheroplasts of the cells carrying the expressed *T. thermophilus* δ'. First, from 400 g of a 1:1 suspension of frozen cells (200 g cells) in Tris-sucrose which had been stored at −20° C., Fr I was prepared (700 ml, 13.7 mg/ml). The preparation was as described in Example #2. To Fr I, ammonium sulfate (0.258 g to each initial ml Fraction I-45% saturation) was added over a 15 min interval. The mixture stirred for an additional 30 min at 4° C. and the precipitate was collected by centrifugation (23,000×g, 45 min, 0° C.). The resulting pellets were quick frozen by immersion in liquid nitrogen and stored at −80° C.

In the following purification steps, fractions from purification columns were assayed using the reconstitution assay (described in Example 7) to determine fractions that contained activity and therefore the δ'-subunit. One-half of the pellets from Fr I was resuspended in 270 ml of 50 mM Tris-HCl, (pH 7.5), 25% glycerol, 1 mM EDTA, 1 mM DTT and homogenized using a Dounce homogenizer. The sample was clarified by centrifugation (16,000×g) and the supernatant constituted Fr II (270 ml, 7.7 mg/ml). Fr II was further purifed using a Butyl Sepharose Fast Flow (Pharmacia Biotech) column. The butyl resin (400 ml) was equilibrated in butyl equilibration buffer (50 mM Tris-HCl, (pH 7.5), 25% glycerol, 1 mM EDTA, 1 mM DTT, 0.5 M ammonium sulfate). The column was poured using 260 ml of butyl resin. The remaining 140 ml of butyl resin was mixed with Fr II giving 410 ml. To this mixture, saturated ammonium sulfate (0.5 sample volume) was added slowly while stirring over a 1 hour period. This mixture was added to the column at 1.3 ml/min. The column was then washed with 4 L of butyl equilibration buffer. The protein was eluted in 10 column volumes of a gradient beginning with butyl equilibration buffer and ending in a buffer containing 50 mM Tris-HCl, (pH 7.5), 25% glycerol, 1 mM EDTA, 1 mM DTT, 50 mM KCl. Remaining protein was removed from the column by eluting with a additional 7.5 column volumes "bump" of the end buffer. The δ'-subunit eluted in the first half of the "bump", and was pooled (485 ml, 0.1 mg/ml). The other one-half of the pellets from Fr I was purified exactly the same as describe. The two preparations were combined to give 972 ml (0.1 mg/ml) of Fr III.

Fr III was further purifed using an Octyl Sepharose Fast Flow (Pharmacia Biotech) column. The octyl resin (20 ml) was equilibrated in octyl equilibration buffer (50 mM Tris-HCl, (pH 7.5), 10% glycerol, 1 mM DTT, 1 mM EDTA, 0.5 M ammonium sulfate). The column was poured using 13 ml of octyl resin. The remaining 7 ml of octyl resin was mixed with Fr III giving 979 ml. To this mixture saturated ammonium sulfate (0.5 sample volume) was added slowly while stirring over a 1 hour period. This mixture was added to the column at 1.3 ml/min. The column was then washed with 600 ml of octyl wash buffer (50 mM Tris-HCl, (pH 7.5), 10% glycerol, 1 mM DTT, 1 mM EDTA, 200 mM ammonium sulfate). The wash was collected in fractions (10 ml). The protein was eluted in 10 column volumes (200 ml) of a gradient beginning with octyl wash buffer and ending in a buffer containing 50 mM Tris-HCl, (pH 7.5), 25% glycerol, 1 mM EDTA, 1 mM DTT, 50 mM KCl. The δ'-subunit was recovered in fractions making up the wash. These fractions were pooled (210 ml, 0.07 mg/ml) and concentrated using PEG 8000 and constitute Fr IV (38 ml, 0.26 mg/ml).

Figure 30:
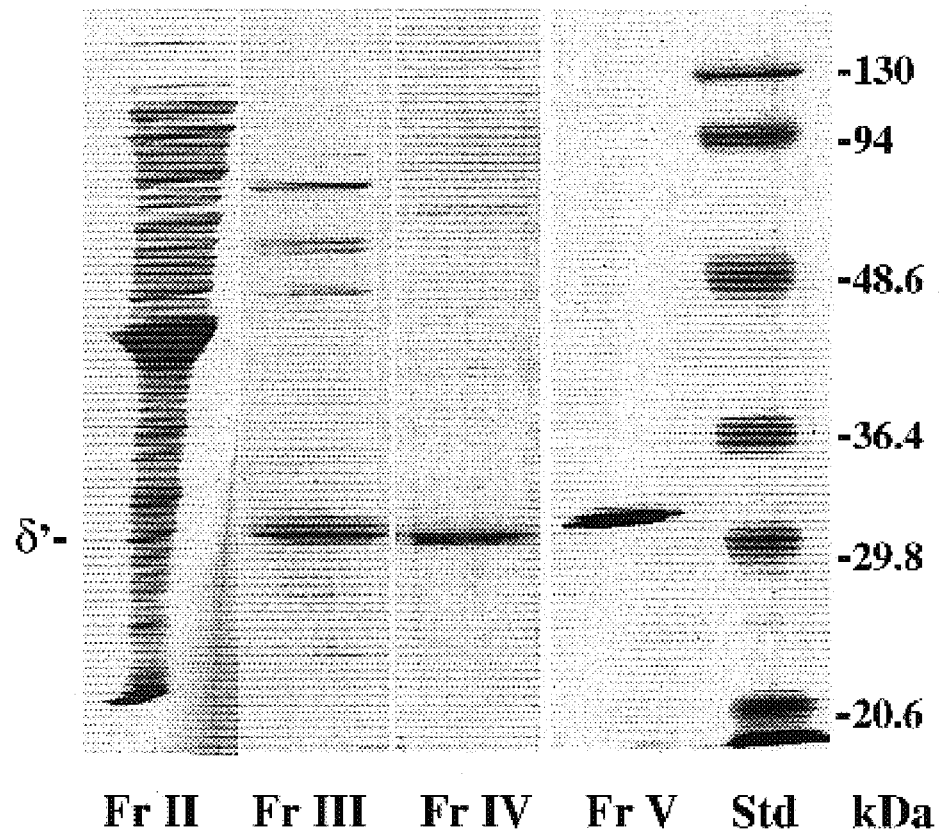
FIG. 30. SDS-PAGE summary of the purification of *T. thermophilus* δ' as a translationally coupled protein.

*T. thermophilus* δ' was further purified using a Sephacryl S300 HR (Pharmacia Biotech) gel filtration column (510 ml, 3 cm×120 cm) equilibrated in 50 mM Tris-HCl, (pH 7.5), 20% glycerol, 100 mM NaCl, 1 mM EDTA, 5 mM DTT. The column was loaded and the protein eluted at a flow rate of 0.7 ml/min. The δ'-subunit was isolated as a highly purified protein (54 ml, 0.08 mg/ml). The products of the different purification steps for δ' expressed as a translationally coupled protein were analyzed by a SDS-polyacrylamide gel (FIG. 30).

Example 6

Construction of a Plasmid (pA1-NB-TN) that Overexpresses *T. thermophilus* dnaN (β-subunit) Fused to an N-Terminal Peptide that Contains Hexahistidine and a Biotinylation Site In *E. coli* the β-subunit is functional as a homodimer (see Johanson, K. O. and Charles S. "Purification and Characterization of the β-subunit of the DNA Polymerase III Holoenzyme of *Escherichia coli*", *J. Biol. Chem.*, 255:10984–10990 (1980)). This dimer confers the ability of high processive synthesis to the core polymerase. In the previous patent application (U.S. application Ser. No. 09/151,888), the identification of the *T. thermophilus* gene (dnaN) encoding the β-subunit was described. From the lambda vector preparation described in Example 9 of the previous application (U.S. application Ser. No. 09/151,888), the 2.2 kb DraI/EcoRI fragment was cloned into a pBluescript II SK+ vector (Stratagene). This sub-clone was then transformed into XL I Blue cells. A total of ten ligation reactions were attempted before achieving a successful clone. This clone (UCO9) was grown and plasmid DNA was isolated. Both strands of the DNA from the inserted region was sequenced (Lark Technologies Inc., DNA SEQ#UC0: 9.2.T7X, 9.23.AP124, 9.AP110, 9.2.AP114, 9.23.AP125, 9.2.AP112, 9.2.AP113, 9.23.AP128, 9.6.AP119, 9.25.AP35, 9.6.AP118, 9.25.AP36, 9.23.AP126, 9.25.AP34B, 9.23.AP32B, 9.6.AP121, 9.25.AP40, 9.23.AP121, 9.2.–48R, 9.6.AP116, 9.23.AP131, 9.6.AP122, 9.23.AP122). Each nucleotide in the inserted region was confirmed using at least three individual primers. This sub-clone was designated UCO9.

In the DNA coding sequence of the *T. thermophilus* dnaN gene (SEQ ID NO:22) (FIG. 62) the start codon (atg) and the stop codon (tag) are in bold print. The 5' and 3' UTRs are also shown (lower case). Also shown is the protein (amino acid) sequence (SEQ ID NO:23) (FIG. 63) derived from the DNA coding sequence.

To simplify purification, the β-subunit coupled to an N-terminal fusion peptide that contains hexahistidine and a biotinylation site was expressed first. Plasmids were designed to fuse the dnaN gene to DNA encoding an N-terminal peptide that contains hexahistidine and a biotinylation. First, a PCR fragment containing the 5'-portion of the Tth dnaN gene was amplified from plasmid UCO9 using a forward primer (ATG #P118-S85, 5'-AACTGCAG <u>AACATAACGGTTCCCAAGAAACTCC</u>-3') (SEQ ID NO:24) that adds a Pst1 site to the 5'-end of the gene so that the actual PCR product excluded the ATG start codon and begins at codon 2. The underlined region of forward primers indicates nucleotides that are complementary to the 5' end of the gene, here and in all other primers used. The Pst1 site is adjacent to codon 2, so that when this fragment was inserted into the pA1-NB Age-1 plasmid the dnaN gene was in frame with the DNA encoding the N-terminal fusion peptide. The reverse primer (ATG #P118-A731, 5'-<u>GACCCGCACCATCTCGTCCACG</u>-3') (SEQ ID NO:25) is downstream of the SacII restriction site (which is near position 496 downstream of the ATG start codon). The resulting PCR product was digested with Pst1 and SacII and ligated into the Pst1/SacII cut pA1-NB Age-1 and transformed into DH5α. Plasmids from ampicillin-selected positive isolates were verified by digestion with Pst1/SacII restriction digestion yielding the expected 0.5 and 5.5 kb fragments. This plasmid (pA1-NB-TN5') was sequenced across the PCR inserted regions to confirm the correct sequence (ATG SEQ #1187–1190, primers P64-S10, P64-A215, P118-S290 and P118-A411). This sequence was also compared to that from the UCO9 insert. This precursor plasmid was named pA1-NB-TN5' and the positive isolate (pA1-NB-TN5'/DH5α) was stored as a stock culture (ATG glycerol stock #708).

The 3' region (C-terminus) of the *T. thermophilus* dnaN gene was cut out of the UCO9 plasmid in a partial digest using the two restriction enzymes SacII and NcoI. The NcoI digested site is approximately 150 bases downstream of the stop codon. This gave a fragment size of approximately 800 bases. There is also a second SacII restriction site further downstream of the NcoI restriction site approximately 400 bases. This second site gave an additional fragment of approximately 400 bases in length. The proper fragment was easily identified, as it was twice as large as the fragment given by the secondary SacII restriction site. The fragments were separated by electrophoresis, and the 800 bp fragment was eluted in water. This fragment containing the 3' portion of the TN gene was inserted into the pA1-NB-TN5' plasmid that had been digested with both SacII and NcoI restriction enzymes. This plasmid (pA1-NB-TN) contained the entire *T. thermophilus* dnaN fused to the DNA encoding an N-terminal fusion peptide. This plasmid was transformed into DH5α. Plasmids from ampicillin-resistant colonies were verified by cleavage with SacII/NcoI yielding the expected 6.1 kb and 0.8 kb fragments. The positive isolate (pA1-NB-TN/DH5α) was stored as a stock culture (ATG glycerol stock #722).

Verification of Expression of *T. thermophilus* β-subunit Fused to an N-Terminal Peptide that Contains Hexahistidine and a Biotinylation Site pA1-NB-TN was prepared and transformed into MGC1030 (ATG glycerol stock #765) and AP1.L1 bacteria (ATG glycerol stock #743). The bacterial growths of three isolates and isolation of total cellular protein were as described in Example 2. An aliquot (4 μl) of each supernatant containing total cellular protein was loaded onto a 4–20% SDS-polyacrylamide mini-gel (Novex, EC60255; 1 mm thick, with 15 wells/gel) in 25 mM in Tris base, 192 mM glycine, and 0.1% SDS. The mini-gels were stained with Coomassie Blue. The region of the gel in which N-tagged *T. thermophilus* β was expected contained many other very intensely stained protein bands and N-terminal tagged *T. thermophilus* β could not be visualized.

The total protein in each lysate was analyzed by biotin blot analysis as described in Example 2. The endogenous *E. coli* biotin-CCP, ~20 kDa was detectable in both induced and non-induced samples. A protein band corresponding to the β-subunit migrated approximately midway between the 40 and 50 molecular weight standards of the Gibco 10 kDa protein ladder. This protein was observed as a distinct band in the induced cultures, but was not observed in the uninduced control in lysates from the AP1.L1 strain. No expression could be detected in the MGC1030 strain.

Optimization of Expression of *T. thermophilus* dnaN Gene (β-subunit)

Figure 31:
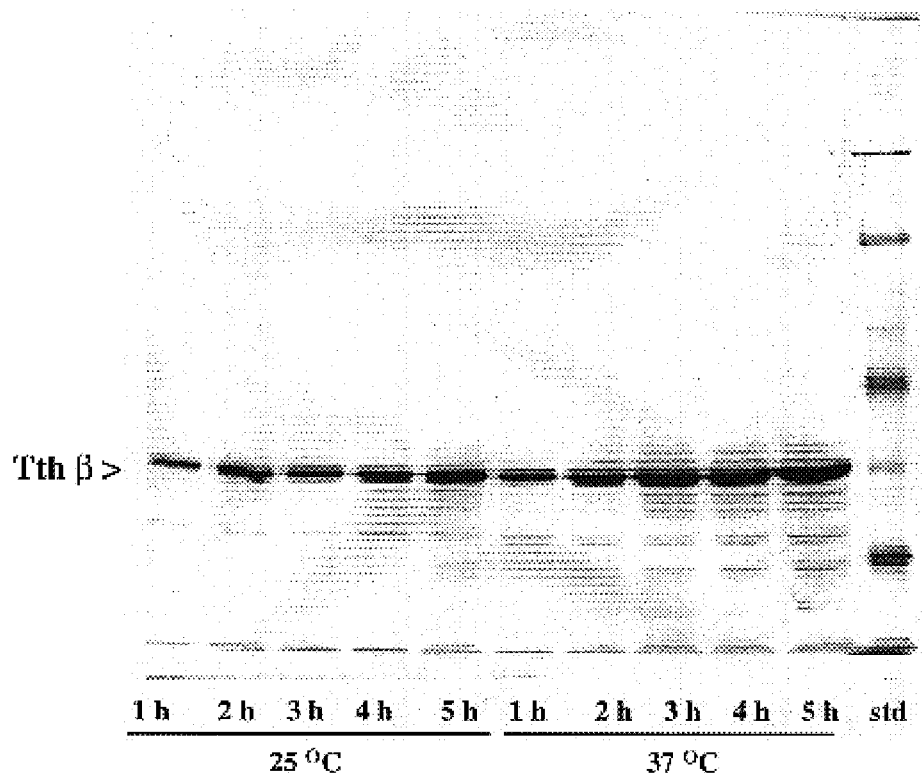
FIG. 31. Biotin blot analysis of growth/induction time optimization at different temperatures of expression of *T. thermophilus* β by pA1-NB-TN/AP1.L1.

Expression was analyzed using the bacterial strains AP1.L1 carrying the pA1-NB-TN plasmid at different induction times and also at different growth temperatures (25° C. and 37° C.). Growth of bacterial cultures and analysis were carried out as described in Example 2. Biotin blot analysis indicated that expression levels were highest at 37° C. (FIG. 31). Since SDS-polyacrylamide gel electrophoresis indicates that most of the β-subunit is being expressed in 4 hours and at 37° C., these growth condition were used in subsequent preparations.

Large Scale Growth of pA1-NB-TN/AP1.L1

Strain pA1-NB-TN/AP1.L1 was grown in a 250 L fermentor to produce cells for purification of *T. thermophilus* β-*subunit as described in Example* 2. Cell harvest was initiated 4 hours after induction, at OD$_{600}$ of 6.7, and the cells were chilled to 10° C. during harvest. The harvest volume was 180 L, and the final harvest weight was approximately 2.2 kg of cell paste. An equal amount (w/w) of 50 mM Tris (pH 7.5) and 10% sucrose solution was added to the cell paste. Cells were frozen by pouring the cells suspension into liquid nitrogen, and stored at −20° C., until processed. Quality control results showed 10 out of 10 positive colonies on ampicillin-containing medium in the inoculum and 10/10 positive colonies at harvest.

Determination of Optimal Ammonium Sulfate Precipitation Conditions for N-terminal Tagged *T. thermophilus* β

Lysis was accomplished by creation of spheroplasts of the cells carrying the expressed *T. thermophilus* β-subunits. First, from 100 g of a 1:1 suspension of frozen cells (50 g cells) in Tris-sucrose which had been stored at −20° C., FrI was prepared (390 ml, 9.8 mg/ml). The preparation was as described in Example 2. FrI was divided into 5 equal volumes and 0.164, 0.226, 0.291, 0.361 and 0.436 g of ammonium sulfate (30%, 40%, 50%, 60% and 70% saturation) was added to each separate sample, respectively, over a 15 min interval at 4° C. The mixture stirred for an additional 30 min at 4° C. and the precipitate was collected by centrifugation (23,000×g, 45 min, 0° C.). The resulting pellets were resuspended in 1 ml Ni-NTA suspension buffer (50 mM Tris-HCl (pH 7.5), 40 mM KCl, 7 mM MgCl$_2$ and 10% glycerol). The protein concentration of each sample was determined using the Coomassie Protein Assay Reagent (Pierce) and bovine serum albumin (BSA) as a standard. The 30%, 40%, 50%, 60% and 70% ammonium sulfate precipitated samples contained protein concentrations of 2.4, 8.0, 18.0, 35.0 and 38.0 mg/ml, respectively. The samples were analyzed by SDS-polyacrylamide gel electrophoresis. The 40% ammonium sulfate precipitated samples contained over 90% of the β-subunit, this concentration of ammonium sulfate was used in subsequent preparations.

Purification of *T. thermophilus* N-Terminal Tagged β

Lysis was accomplished by creation of spheroplasts of the cells carrying the expressed *T. thermophilus* β-*subunits.* First, from 600 g of a 1:1 suspension of frozen cells (300 g cells) in Tris-sucrose which had been stored at −20° C., FrI was prepared (1.05 L, 15.4 mg/ml). The prepatation was as described in Example 2. To Fr I, ammonium sulfate (0.266 g to each initial ml Fraction I-40% saturation) was added over a 15 min interval. The mixture was stirred for an additional 30 min at 4° C. and the precipitate was collected by centrifugation (23,000×g, 45 min, 0° C.). The resulting pellets were quick frozen by immersion in liquid nitrogen and stored at −80° C.

Figure 32:
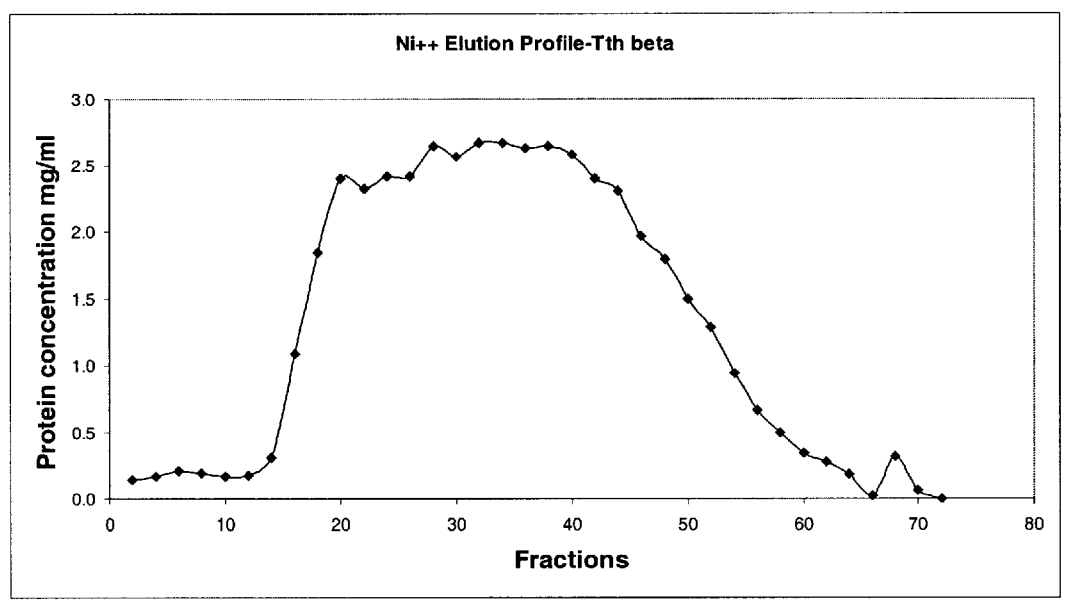
FIG. 32. Protein concentration profile of fractions eluting from the Ni++-NTA column purification of *T. thermophilus* β.

The pellets from FrI ammonium sulfate precipitation were resuspended in 100 ml of Ni$^{++}$-NTA suspension buffer and homogenized using a Dounce homogenizer. The sample was clarified by centrifugation (16,000×g) and the supernatant constituted Fr II (19.5 mg/ml, 100 ml). Fr II was added to 30 ml of a 50% slurry of Ni-NTA resin and rocked for 1.5 hours at 4° C. This slurry was then loaded onto a BioRad Econo-column (2.5×5 cm). The column was washed with 200 ml of Ni$^{++}$-NTA wash buffer at a flow rate of 0.5 ml/min. The N-terminal tagged β was eluted with a 150 ml 10–200 mM imidazole gradient in Ni$^{++}$-NTA elution buffer. The eluate was collected in 75×2 ml fractions. Fractions were analyzed by SDS-polyacrylamide gel electrophoresis, and fractions 26–60 were found to contain over 90% of total β-subunit protein (FIG. 32). These fractions also contained most of the ability to stimulate the β-subunit in primer extension assays (discussed below).

Fractions 26–60 were pooled (67 ml) and dialyzed two times against 1 L of buffer HG.04 (20 mM Hepes (pH 7.0), 40 mM KCl, 1 mM MgCl$_2$, 0.1 mM EDTA, 10% glycerol and 6 mM βME). The sample constituted FrIII (65 ml, 3.8 mg/ml), which was aliquoted and fast frozen in liquid nitrogen and stored at −80° C.

Development of a Simple Processivity Assay for *T. thermophilus* β on a Defined Linear Template Replicative polymerases ranging from *E. coli* to yeast are stimulated by their cognate "sliding clamp processivity factors", β and PCNA respectively, in the absence of other holoenzyme subunits if they are present at high non-physiological concentrations on linear templates (see Crute, J. J., et al., *J.Biol.Chem.* 258:11344–11349 (1983)). This is due to the ability to these factors to assemble on linear DNA in the absence of the clamp loader (DnaX or RFC) at high concentrations. To develop an assay for detection of *T. Thermophilus* β we have taken advantage of the low processitivity of DNA replicative polymerases in the absence of other members of the replicative complex. In the absence of β the DNA polymerase (α-subunit) will only extend a primer by approximately 10 nucleotides per each binding event (see Crute, J. J., et al., *J.Biol.Chem.* 258:11344–11349 (1983)). The substrate (shown below) (SEQ ID NO:28) allows detection of stimulation by β.

5'-TGCAAATCGCGTTAGCTTAG-3' (EO-8)  (SEQ ID NO:28)

3'-ACGTTTAGCGCAATCGAATCTGTCCTGT-GTGTTCCTGCTGTCTCCGTTTCAAAAAAAAAAAAAAAA AAAA-5'(EO-7)  (SEQ ID NO:107)

*T. thermophilus* β would be expected to bind the annealed primer/template and extend the primer for a relatively short distance per binding event in the absence of β. The template lacks "A"s for the first 30 nucleotides and then contains a string of "A"s. If replication is allowed to proceed in a large excess of template primer and limiting polymerase, a template, on average, will only encounter a polymerase once during the course of the assay. Thus, in the absence of β *T. thermophilus* α would not be expected to incorporate significant levels of radiolabeled dTTPs opposite the terminal sequence of "A"s. Therefore, it should be possible to use this system to detect stimulation of the processitivity of the DNA polymerase in the presence of β.

To allow annealing, the template (EO7) and primer (EO8) were diluted to 10 μM each in annealing buffer (10 mM Tris-HCl, pH 7.5, 0.1 mM EDTA), heated to 90° C. in a heating block and allowed to slowly cool to room temperature. Reactions (25 μl) were carried out at 30° C. for 5 min in enzyme dilution buffer (EDB) (50 mM Hepes (pH 7.5), 20% glycerol, 0.02% Nonidet P40, 0.2 mg/ml BSA, 10 mM DTT, 10 mM MgCl$_2$), dNTP mix (50 μM dATP, dCTP, dGTP and 18 μM [$^3$H]dTTP, 100 cpm/pmol) and varying amounts of DNA polymerase (1 μl), β and annealed DNA.

In reactions using *E. coli* DNA polymerase α, the concentration of primer/template was varied between 0.1–1.3 μM to determine the amount needed to maintain the level of incorporation of radioactivity to that of the background signal, due to single binding events. These reactions were carried out in the absence of β at 0.3, 0.6, and 1.2 nM α. There was no increase in the total dTTP incorporated between 0.6 and 1.3 μM of primer/template. Therefore, in reactions to optimize levels of *T. thermophilus* α, 1.3 μM primer/template was used.

To determine the optimum amount of *T. thermophilus* polymerase (1 mg/ml) to use, assays were set up using 100, 250, 500, 1000, 2000 and 4000:1 dilution ratios of *T. thermophilus* N-terminal tagged *T. thermophilus* α (1–4 μl polymerase/reaction). The samples containing 250:1 dilution of *T. thermophilus* α gave a signal equal to the background signal, therefore this concentration of N-terminal tagged *T. thermophilus* α was used in reactions to screen for β stimulation.

Figure 33:
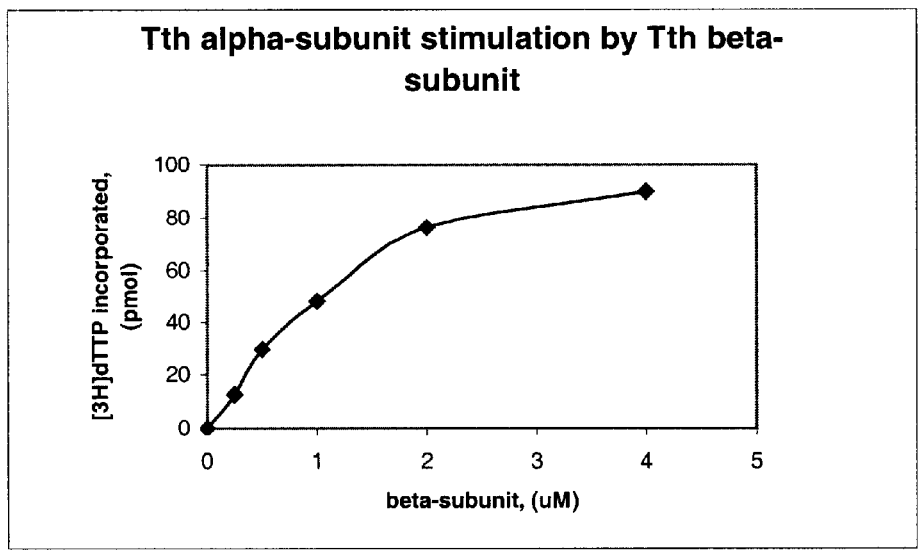
FIG. 33. Primer extension assay to determine stimulation of *T. thermophilus* α by *T. thermophilus* β.

To assay for the ability of various amounts of N-terminal tagged *T. thermophilus* β to stimulate the activity of the *T. thermophilus* α, the primer-extension assay was used. Using a 250:1 dilution of the α-subunit (1 mg/ml) and 1.3 μM of annealed primer/template, assays were carried out at 0, 0.25, 0.5, 1.0, 2.0 and 4.0 μM *T. thermophilus* β (FIG. 33). *T. thermophilus* α was stimulated by increasing concentrations of β (FIG. 33) consistent with a functional β, proving the capability of purified *T. thermophilus* α and β to cooperate in a processive replicative reaction at elevated temperatures.

Production of Polyclonal Antibodies Against *T. thermophilus* β

Figure 34:
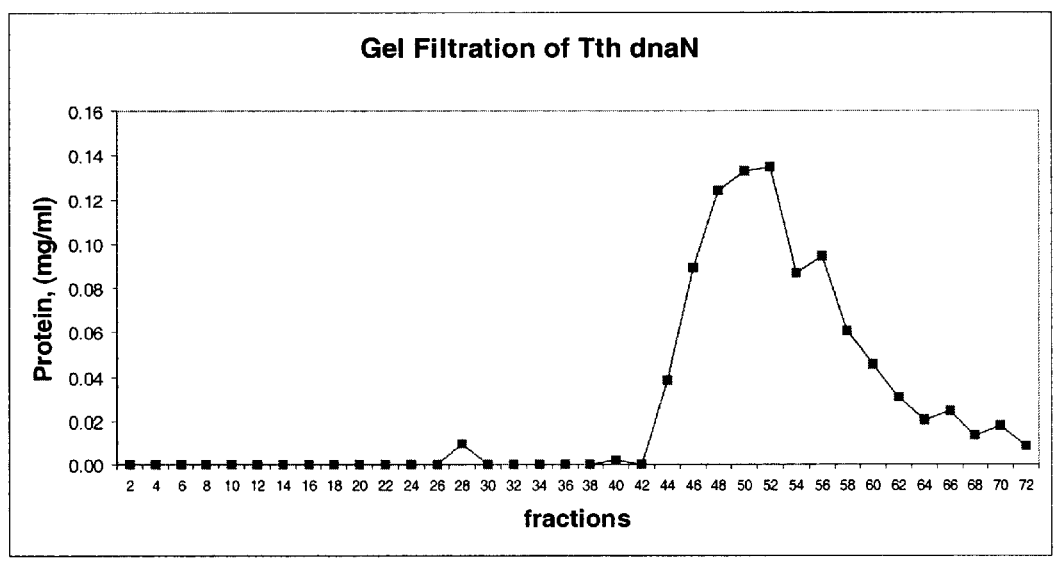
FIG. 34. Protein concentration profile of fractions eluting from a Sephacryl S-300 gel filtration column purification of *T. thermophilus* β.

From N-terminal tagged *T. thermophilus* β FrIII described in the section entitled "Purification of *T. thermophilus* dnaN Product (β-subunit) Fused to an N-Terminal Peptide That Contains Hexahistidine and a Biotinylation Site by pA1-NB-TN/AP1.L1", 2 ml (3.8 mg/ml) was loaded onto an Sephacryl S-300 column (88 ml, 40:1 height:width ratio) equilibrated in 20 mM potassium phosphate, pH 6.5, 100 mM KCl, 25% glycerol and 5 mM DTT. This was accomplished by running the buffer above the column bed down to the resin bed, adding the sample (2 ml), running the sample into the resin and rebuilding the buffer above column bed. The sample was then eluted in in the same buffer at a flow rate of 0.2 ml/min and collected in 1 ml fractions. Protein concentrations of each fraction was determined using the Coomassie Protein Assay Reagent (FIG. 34). The fractions were analyzed by SDS-polyacrylamide gel electrophoresis and fractions 43–66 were pooled (20 ml, 0.15 mg/ml) (FIG. 35).

Figure 36:
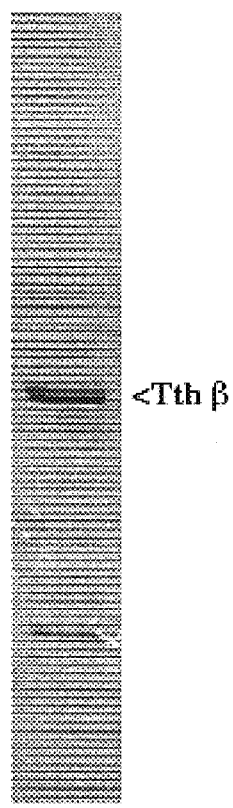
FIG. 36. The pooled fractions of *T. thermophilus* β from the Sephacryl S-300 gel filtration column that was used in production of antibodies directed against β.

Protein in the pooled fractions were precipitated by addition of ammonium sulfate (0.436 g to each ml of pooled fractions-70% saturation) and the precipitate was collected by centrifugation (23,000×g, 45 min, 0° C.). The ammonium sulfate precipitated pellets were dissolved in 2 ml of PBS (0.24 mg/ml) and dialyzed against 500 ml of PBS two times. This dialyzed sample was analyzed by SDS-polyacrylamide gel electrophoresis (FIG. 36).

Figure 37:
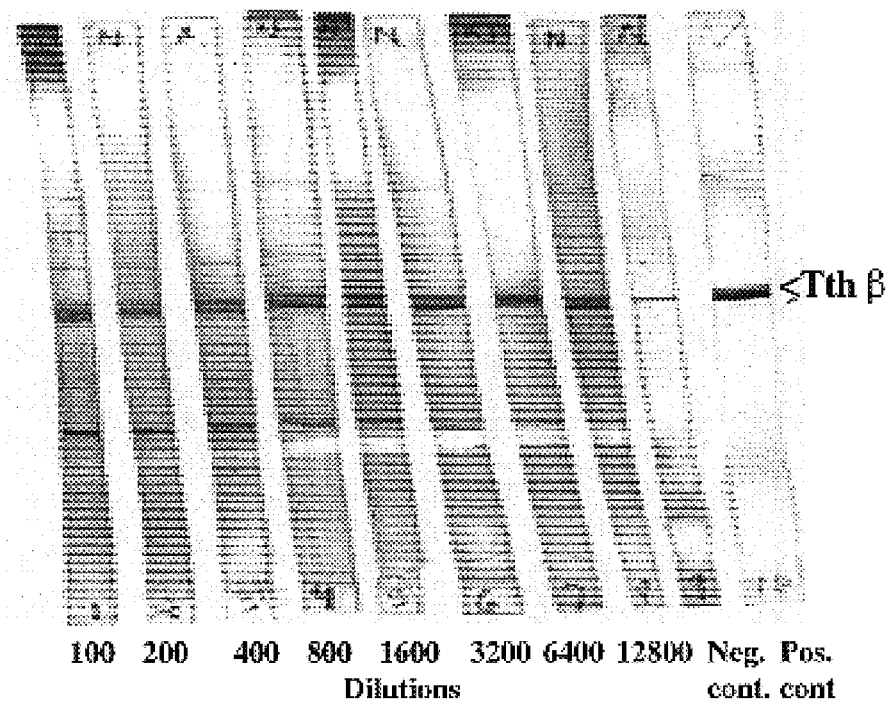
FIG. 37. Western analysis of various antiserum dilutions for determination of dilutions to use in *T. thermophilus* β detection.

Polyclonal antibodies against *T. thermophilus* β were produced by inoculation of a rabbit with N-terminal tagged *T. thermophilus* β and harvested from the rabbit as described in Example 3. The optimum dilution of anti-serum for binding N-tagged *T. thermophilus* β was determined after the test bleed and after the final bleed. This was carried out by SDS-polyacrylamide gel electrophoresis, in which a small aliquot of N-terminal tagged *T. thermophilus* β (0.5 μg/well) was electrophoresed onto a 10% SDS-polyacrylamide mini-gel (10×10 cm). The protein was transferred onto nitrocellulose membrane as described above in Example 3. The membrane was cut into strips with each strip containing an identical band of N-terminal tagged *T. thermophilus* β. The membrane was blocked in 0.2% Tween 20 (v/v)-TBS (TBST) containing 5% non-fat dry milk (w/v) for 1 hour at room temperature, rinsed with TBST. The strips were placed in antiserum/TBST (dilutions: 1:100, 1:200, 1:400, 1:800, 1:1600, 1:3200, 1:6400, and 1:12800) for 1 hour and then washed 4 times for 5 min in TBST. Next, the strips were placed in secondary antibody-conjugated to alkaline phosphatase (goat anti-rabbit IgG (H+L), 1:3000 dilution in TBST) (BioRad) for 1 hour. The strips were then washed 4 times for 5 min with TBST. Following this extensive washing, the blots were developed with BCIP/NBT (KPL #50-81-07; one component system). Proteins corresponding to β were visualized as distinct bands even at the highest dilution of antiserum (FIG. 37). These bands became more intense as the dilution of antiserum was decreased. The negative control contained antiserum taken from the rabbit prior to inoculating with antigen. The positive control is a biotin blot analysis of the antigen at the same concentration (0.5 μg) as used in antiserum detection.

Next, the minimum amount of β needed for recognition by antibody serum was determined. This was carried out using SDS-polyacrylamide gel electrophoresis in which small aliquots of β (0.02, 0.04, 0.08, 0.16, 0.32, 0.64, 1.25, 2.50, and 5.0 μg/well) were electrophoresed onto a 10%

Figure 38:
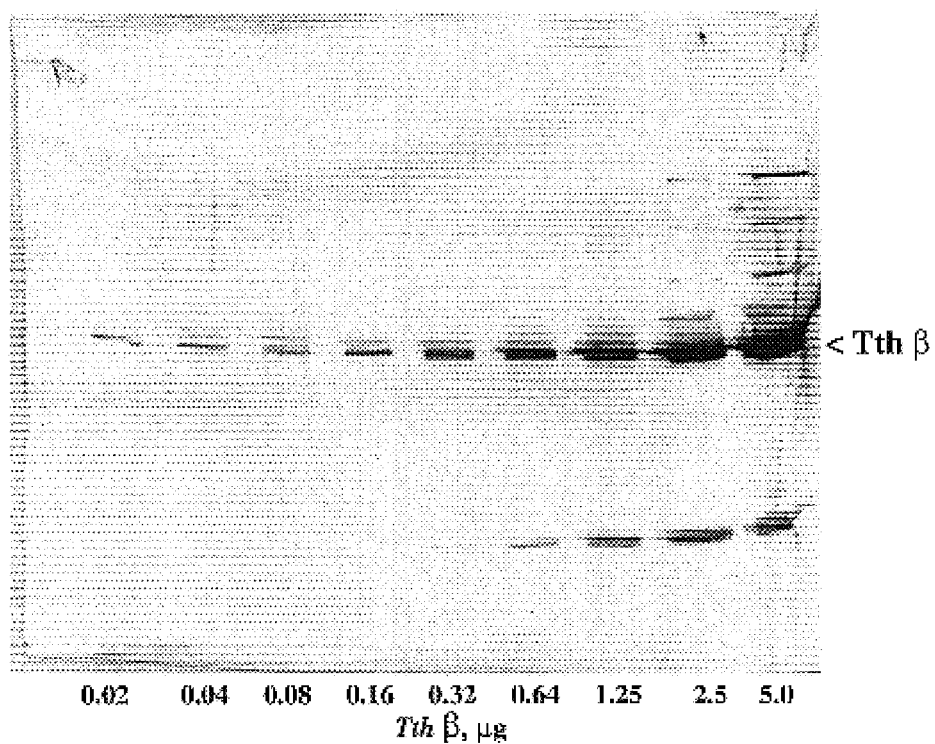
FIG. 38. Western analysis of various *T. thermiophilus* β dilutions for determination of the limit of β detection at antiserum dilution of 1:6400.

SDS-polyacrylamide mini-gel (10×10 cm). The protein was transferred onto nitrocellulose membrane. The blotted nitrocellulose was blocked in TBST containing 5% non-fat dry milk (w/v) for 1 hour at room temperature, rinsed with TBSt. The blot were placed in antiserum/TBST (dilution of 1:6400) for 1 hour and then washed 4 times for 5 min in TBSt. Next, the blot was placed in secondary antibody-conjugated to alkaline phosphatase (goat anti-rabbit IgG (H+L), 1:3000 dilution in TBST) (BioRad) for 1 hour. The blot was then washed 4 times for 5 min with TBST. Following this extensive washing, the blot was developed with BCIP/NBT (KPL #50-81-07; one component system) (FIG. 38). The lowest level (0.02 µg) of N-tagged T. thermophilus β could be detected.

Construction of a Plasmid (pA1-TN) that Overexpress Native T. thermophilus dnaN (β-subunit)

To express native (un-tagged) T. thermophilus β the dnaN gene was inserted into the vector pA1-CB-NdeI. The C-terminal biotin-hexahis tag carried by this plasmid will be downstream and out of frame with the inserted dnaN gene. The forward primer was designed so that CAT was added in the non-complementary region of the primer immediately proceeding the ATG start codon. This resulted in CATATG, an NdeI restriction site (ATG primer #P118-S74, 5'-GGATCCAAGCTTCAT ATGAACATAACGGTTCCCAAGAAA-3') (SEQ ID NO:41) The reverse primer was designed so that an additional stop codon was added in the non-complementary region producing two stop codons in tandem. The non-complementary region of the reverse primer contains an NheI restriction site and additional nucleotides for efficient digestion of the PCR product with the restriction enzyme (ATG primer #P118-1231, 5'-GAGCAGCTAGCCTA CTAGACCCTGAGGGGCACCAC-3') (SEQ ID NO:42). The PCR reaction resulted in a product which contained the entire T. thermophilus dnaN gene with an NdeI site overlapping the start codon and an additional stop codon in tandem with the natural stop codon (TAG) and an NheI site downstream of the tandem stop. Digestion of the PCR product and the pGEM-T Easy plasmid with NdeI and NheI allowed the T. thermophilus dnaN gene to be inserted into the pGEM-T Easy plasmid. The PCR product was ligated into the pGEM-T Easy plasmid as a preliminary plasmid for sequencing of the insert region. This plasmid was transformed into DH5α, and ampicillin-resistant positive isolates were selected. Plasmids from one positive isolate was isolated and screened by EcoRI digestion of plasmids yielding 1.15 and 3.0 kb fragments. The correct sequence of both DNA strands of the insert containing the dnaN gene were verified by DNA sequencing (ATG SEQ #1420–1427; primers, SP6 sequencing primer, T7 sequencing primer, P118-S290, P118-S639, P118-S1003, P118-A996, P118-A731 and P118-A411). This sequence was compared to the sequence obtained in the section entitled "Construction of a Plasmid (pA1-NB-TN) that Overexpresses T. thermophilus dnaN (β-subunit) Fused to an N-Terminal Peptide That Contains Hexahistidine and a Biotinylation Site". This plasmid was named pT-TN and the positive isolate (pT-TN/DH5α) was stored as a stock culture (ATG glycerol stock #839).

The T. thermophilus dnaN gene was recovered from the preliminary pT-TN plasmid and inserted into an expression vector. The pT-TN plasmid was digested with NdeI/NheI restriction enzymes and the entire TN gene was inserted into the pA1-CB-NdeI plasmid digested with the same restriction enzymes. This placed the dnaN gene into the pA1-CB-Nde1 plasmid out of frame with the downstream biotin-hexahis tag. This also placed the start codon 11 nucleotides downstream of the RBS. The plasmid was transformed into DH5α and positive isolates were selected by ampicillin-resistance. Plasmid from one positive clone was verified by NdeI/NheI and XbaI restriction digest yielding the expected 1.1 and 5.6 kDa and 0.1 and 6.7 kDa fragments, respectively. The sequence of the inserted region was confirmed by DNA sequencing (ATG SEQ #1443 and #1444, primers P118-S1003 and P38-S5576). This sequence was compared to the sequence obtained in the section entitled "Construction of a Plasmid (pA1-NB-TN) that Overexpresses T. thermophilus dnaN (β-subunit) Fused to an N-Terminal Peptide That Contains Hexahistidine and a Biotinylation Site". This plasmid was named pA1-TN and the isolate (pA1-TN/DH5α) was stored as a stock culture (ATG glycerol stock #845).

Verification of Expression of T. thermophilus β by pA1-TN/AP1.L1

The pA1-TN plasmid was prepared and transformed into AP1.L1 bacteria (ATG glycerol stock #860, 861, 871). The bacterial growths of three isolates and isolation of total cellular protein were as described Example 2. A small aliquot (3 µl) of supernatant from each of the three isolates was loaded onto a 4–20% SDS-polyacrylamide mini-gel (Novex, EC60255; 1 mm thick, with 15 wells/gel) in 25 mM in Tris base, 192 mM glycine, and 0.1% SDS. The mini-gel was stained with Coomassie Blue. There were no visible protein bands from any of the isolates corresponding to the predicted migration region of β. Perhaps secondary structure of the high GC T. thermophilus sequences was interfering with initiation. In an attempt to overcome this difficulty, we constructed vectors with a gene encoding the native T. thermophilus β translationally coupled to the highly expressed E. coli cca gene.

Cloning T. thermophilus dnaN Gene (β) into a Translationally Coupled Vector pTAC-CCA-ClaI To efficiently express β as a native protein we designed a vector to express β as a translationally coupled protein. As with expression of other T. thermophilus proteins in native form, our goal here is again to use translational coupling as described in Example #2. The dnaN gene was inserted behind the CCA adding enzyme and translationally coupled described for T. thermophilus β. First, the dnaN gene was amplified by using pA1-TN as a template by PCR. The forward/sense primer (ATG primer #P118-S78cla2, 5'-AGTCATCGATA ATGAACATAACGGTTCCCAAGAAA-3') (SEQ ID NO:59) has a ClaI restriction site in the non-complementary region. As in the cloning strategy developed for pTAC-CCA-TX, the non-complementary region also contains the "TA" of the stop (TAA) for the upstream CCA-adding protein fragment. The region of the primer complementary to the 5' end of the T. thermophilus holA gene begins with "A" which is the first nucleotide of the "ATG" start codon and the final "A" of the "TAA" stop codon. The reverse/antisence primer (ATG primer #P118-A1230spe, 5'-GAGGACTAGTCTA CTAGACCCTGAGGGGCACCAC-3') (SEQ ID NO:60) contains a SpeI restriction site in the non-complementary portion of the primer and also an additional stop codon adjacent to the native stop codon, giving two stop codons in tandem. There was also a clamp region for efficient cutting with SpeI. Next, the PCR product was digested with ClaI/SpeI restriction enzymes and inserted into the pTAC-CCA-ClaI plasmid digested with the same enzymes. The plasmid was transformed into DH5α bacteria and plasmids from ampicillin-resistant positive isolates were screened for by digestion with ClaI/SpeI restriction enzymes yielding 1.1 and 5.5 kb fragments. The sequence of both strands of the insert were verified by DNA sequencing (ATG SEQ #1749–1756; primers, P144-S23, P144-A1965, P118-S290, P118-S639, P118-S1003, P118-A996, P118-A731, P118-A411). Sequence analysis confirmed the correct sequence was contained within the inserted region. This plasmid was named pTAC-CCA-TN and the isolate was stored as a stock culture (ATG glycerol stock #1074).

Verification of Expression of Native T. thermophilus β-Subunit by PTAC-CCA-TN/MGC1030 and pTAC-CCA-TN/AP1.L1

The pTAC-CCA-TN plasmid was prepared and transformed into MGC1030 bacteria (ATG glycerol stock #1087, 1088, 1089) and AP1.L1 (ATG glycerol stock #1090, 1091). The bacterial growths and isolation of total cellular protein were as described in Example #2. A small aliquot of each supernatant (3 μl) containing total cellular protein was electrophoresised onto a 4–20% SDS-polyacrylamide minigel (Novex, EC60255; 1 mm thick, with 15 wells/gel) in 25 mM in Tris base, 192 mM glycine, and 0.1% SDS. The mini-gels were stained with Coomassie Blue. A faint protein band corresponding to the predicted molecular mass of T. thermophilus β (40.5 kDa) was visualized slightly above the 40 kDa molecular weight standard of the Gibco 10 kDa protein ladder from the MGC1030 isolates, but could not be discerned in the AP1.L1 isolates.

Large Scale Growth of pA1-CCA-TN/AP1.L1

Strain pA1-CCA-TN/AP1.L1 was grown in a 250 L fermentor (fermentor run #00-13), to produce cells for purification of T. thermophilus β as described in Example #2. Optimum induction times were determined as described in Example #2. Cell harvest was initiated 3 hours after induction, at OD600 of 3.04, and the cells were chilled to 10° C. during harvest. The harvest volume was 170 L, and the final harvest weight was approximately 0.9 kg of cell paste. An equal amount (w/w) of 50 mM Tris (pH 7.5) and 10% sucrose solution was added to the cell paste. Quality control results showed 10 out of 10 positive colonies on ampicillin-containing medium in the inoculum and 10/10 positive colonies at induction and 10/10 positive colonies at harvest. Cells were frozen by pouring the cells suspension into liquid nitrogen, and stored at −20° C., until processed.

Example 7

Reconstitution of T. thermophilus DNA polymerase III holoenzyme

A primary goal of our endeavor has been to obtain the minimal assembly of the essential subunits of a processive thermophilic replicase that should permit processive synthesis of long stretches of DNA rapidly at elevated temperatures. We hypothesized that, minimally, T. thermophilus α, β, DnaX, δ and δ' would be required. With the availability of these proteins in N-terminal tagged forms, these proteins were used in an initial successful attempt at reconstitution. A modified form of the standard assay for the E. coli DNA polymerase III holoenzyme was used. The method comprised synthesis on a long single-stranded circular template primed by an RNA primer. M13 Gori single-stranded DNA was primed by the action of the E. coli DnaG primase in a large volume reaction that was aliquoted and frozen away for use in all reported assays. RNA primed M13 Gori single-stranded DNA is prepared (9.5 ml) by adding: 0.5 ml MgOAc (250 mM), 1.125 ml M13 Gori (240 μM, nt), 0.2 ml purified E. coli SSB proteins (4.3 mg/ml), 1.5 ml dNTP mix (400 μM dATP, dCTP, dGTP and 150 μM [$^3$H]-dTTP (100 cpm/pmol), 0.5 ml rNTP mix (5 mM of each ATP, CTP, GTP and UTP), 0.025 ml purified E. coli primase (0.665 mg/ml) and 5.65 ml EDB (50 mM HEPES (pH 7.5), 20% glycerol, 0.02% NP40, 0.2 mg/ml BSA). The radioactive dNTP mix was not used in the priming reaction but was used by the replication polymerase when it is added in the actual replication reaction (M13 Gori reaction). The priming mix was incubated at 30° C. for 5 min and then placed on ice. The mixture was divided into 400 ul aliquots and stored at −80° C. until use. This mixture was used in all M13 Gori assays and is referred to as the primed-template mix.

Figure 39:
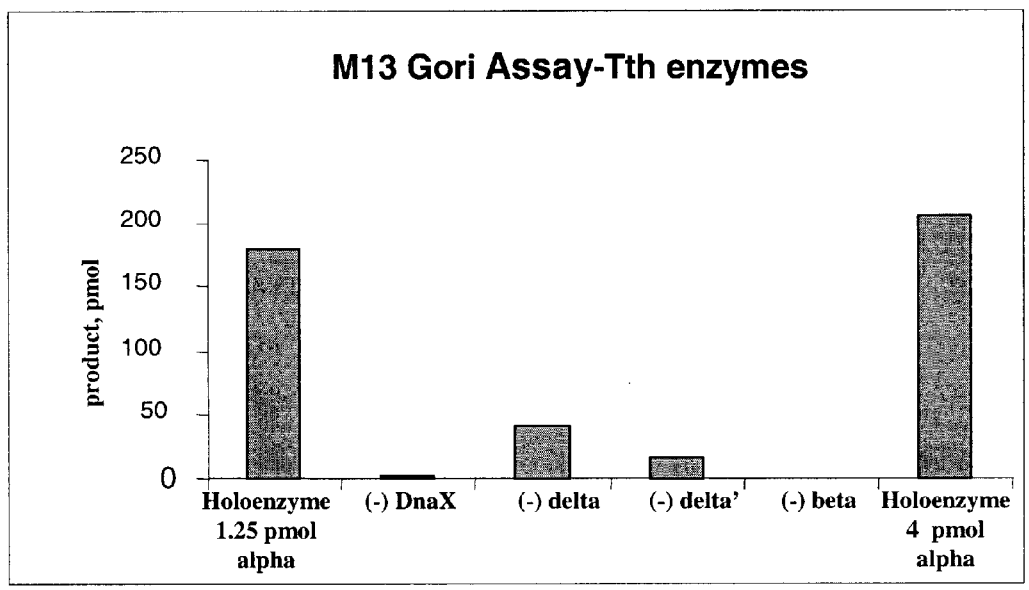
FIG. 39. M13gori reconstitution of *T. thermophilus* Pol III subunits.

Initially all of the purified T. thermophilus subunits (N-terminal tagged α, β, DnaX, δ and δ') were assayed together to determine if the complex could support processive polymerization of the M13 Gori primed template. The initial concentration of each T. thermophilus subunit used in this initial assay was arbitrarily set at 10 times the concentration of the E. coli Pol III subunits used in similar assays (Olson, et al., J. Biol. Chem. 270:29570–29577 (1995)). The subunits were diluted in EDB buffer so that when combined (6 ul total) and combined with 19 ul of the primed-template mix to yield a 25 μl reaction, the total levels of α, β, δ, δ' and DnaX were 1.25, 1.25, 1.0, 1.0 and 2.0 pmols, respectively (all subunit concentrations are as monomers). The reactions contained approximately 550 pmol of primed-template (total nucleotides). Reactions were initiated by combining the enzyme mix and the primed-template mix and incubating for 5 min at 50° C. The reactions were terminated by placing the reaction tubes on ice and adding 2 drops of 0.2 M NaPP$_i$ and 0.5 ml 10% TCA. The solution was filtered under vacuum through Whatman GF/C glass microfibre filters. The filters were then washed with 3 ml of 1M HCl/0.2 M NaPP$_1$ and 1 ml 95% EtOH and dried using a heat lamp. The pmol of nucleotides incorporated were quantified by scintillation counting. Other reactions were carried out, in which a different subunit was sequentially omitted from the reaction (FIG. 39). The final reaction (far right, FIG. 39) in which all subunits were present, but the concentration of α was increased to 4.0 pmols. From the graph of these reactions in FIG. 39, when any subunit is omitted from the reaction the synthesis of DNA is decreased to very low levels, however, in the presence of all reactants maximum synthesis is observed. The results of these assays indicated that each subunit was functional and required for processive polymerization.

Figure 40:
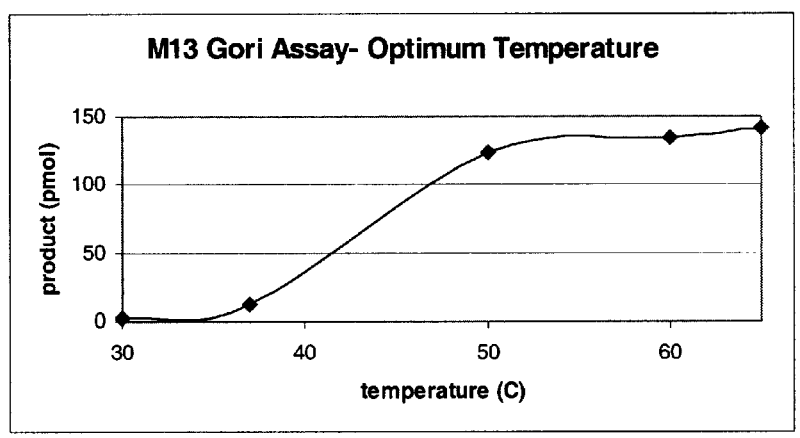
FIG. 40. Temperature dependence for a functional *T. thermophilus* holoenzyme in the reconstitution assay.

The optimum temperature for the M13 Gori assay using T. thermophilus Pol III subunits was determined. Reconstituted holoenzyme reactions were carried out as described above (using 4 pmol of α). The reactions were incubated for 5 min at the indicated temperatures. Results indicated that 50–65° C. provided optimal temperatures for assaying T. thermophilus replicative complex subunits (FIG. 40). Future assays will be carried out at 60° C.

Figure 41A:
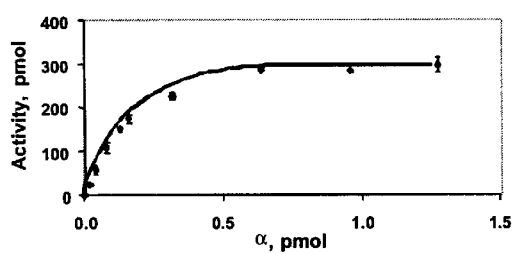
FIG. 41. The reconstitution assay in which *T. thermophilus* A. α, B. τ/γ, C. β, D. δ, and E. δ' is/are titrated while the other subunits are held constant.

The activity of each of the subunits used to reconstitute T. thermophilus holoenzyme was assessed individually in the presence of excess levels of the other four subunits. M13 Gori assays were initially designed so all of the subunits were present at the concentrations described in the experiment β, δ, δ' and DnaX were 1.25, 1.0, 1.0 and 2.0 pmols, respectively) except α. The α-subunit was added to different reactions in amounts varying from 0.125 to 4.2 pmol. Reactions were carried out at 60° C. for 5 min. The results indicate that all available M13 Gori template has been replicated in the presence of 1 pmol of α (FIG. 41A).

Figure 42:
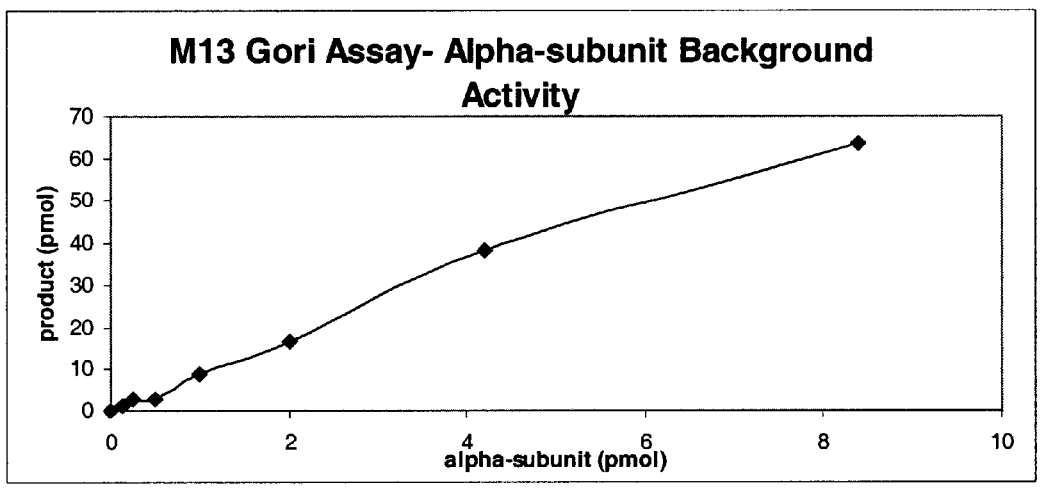
FIG. 42. Reconstitution assay in the absence of all subunits except α to determine the background activity present due to spurious binding of α alone to the template and extending the primer a short distance at each binding event.

In the absence of the other subunits, there is a background level of non-processive synthesis catalyzed by α. To define the background, α was assayed in the M13 Gori reactions in varying amounts (0.125 to 8.4 pmol) (FIG. 42).

In the assay in which α was titrated in M13 Gori holoenzyme assays, all the available template were replicated in the presence of 2 pmol of α. In assays used to determine the background activity of α at a concentration of 2 pmol, only 17 pmol nucleotide were incorporated. Therefore, all future assays will contain 2 pmol α.

Figure 43:
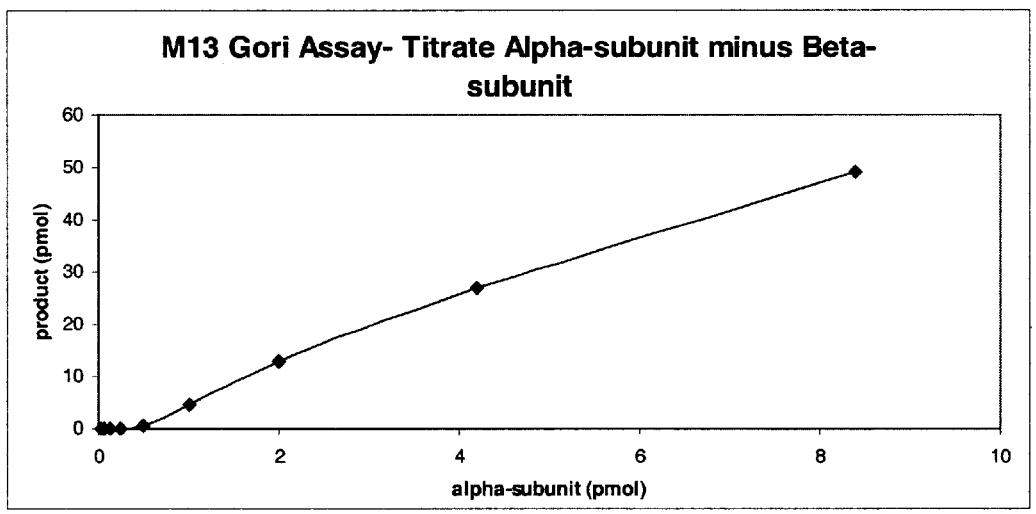
FIG. 43. Reconstitution assay in the absence of β, but in the presence of the other subunits, to determine the effect of the other subunits on background activity present due to spurious binding of α.
Figure 44A:
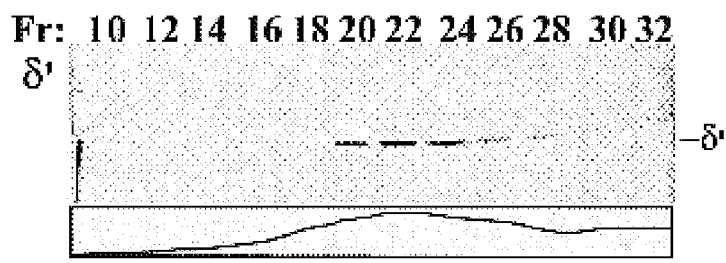
FIGS. 44A–E. Sephacryl S-200 gel filtration of subunits of the clamp loading complex showing protein-protein interactions.
Figure 44B:
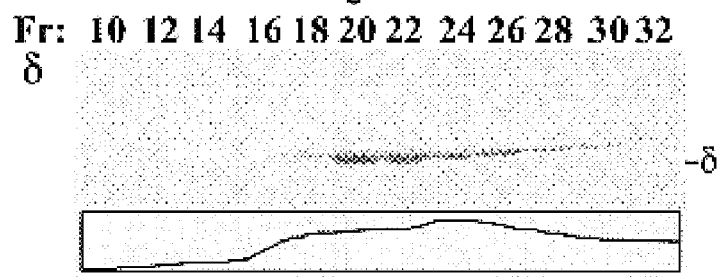
Figure 44C:
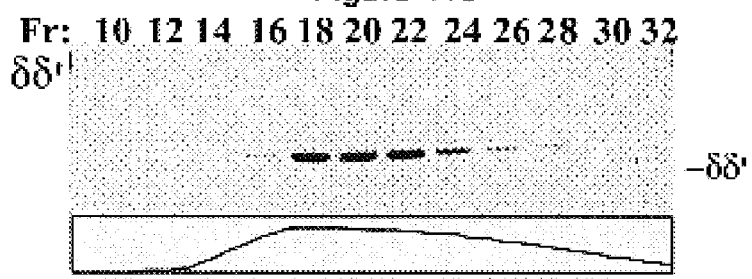
Figure 44D:
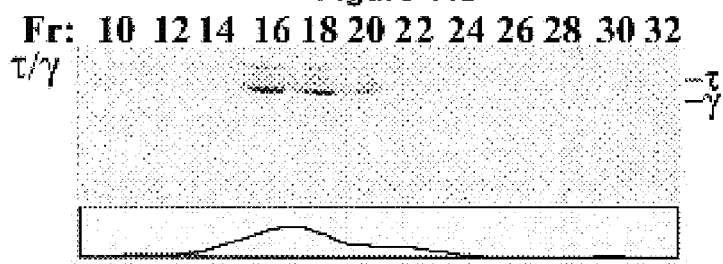
Figure 44E:
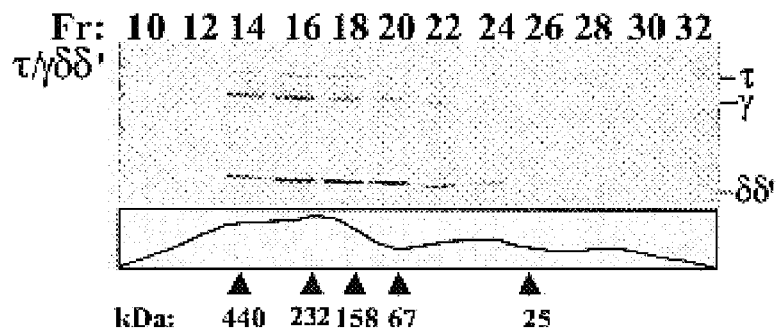

To determine the influence of β on the ability of the α to processively replicate the primed-template, α was assayed at varying amounts in the presence of all of the other subunits excluding β (FIG. 43). As can be seen when compared with the activity of α alone (FIG. 42), α was only slightly stimulated by the presence of the other holoenzyme subunits in the absence of the β-subunit.

Figure 41B:
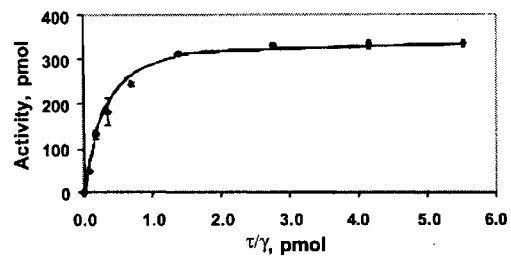

As discussed above, translation of the *T. thermophilus* dnaX gene results in the expression of both τ- and γ-units. The dnaX gene products in *E. coli* function as part of the clamp loading apparatus which catalyzes the assembly of the β-sliding clamp. The τ-subunit also functions to dimerize Pol III by direct contact with α (Dallmann, H. G., and McHenry, C. S., *J. Biol. Chem.* 270:29563–29569 (1995)). From the Coomassie Blue stained gel (FIG. 10) of τ- and γ it appears that approximately 60% expression is of the γ-subunit, while approximately 40% expression is of the τ-subunit. Therefore, to determine the optimum amounts of τ- and γ to use in the M13 Gori assays a wider range of concentrations were assayed (0.312 to 20 pmol). These assays are shown in FIG. 41B, and approximately 4 pmol of τ- and γ are required to achieve maximum reconstitution of the replicative complex. In future M13 Gori assays, 4 pmol of DnaX will be used.

Figure 41C:
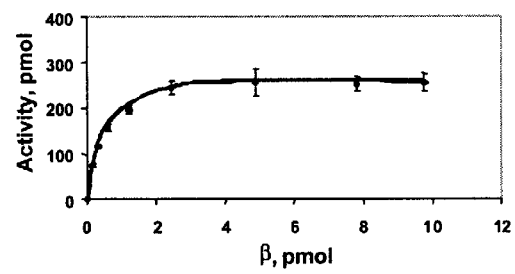

The β-subunit of replicative polymerases dramatically increased the processivity by linking the catalytic subunit to the DNA. To test the ability of β to reconstitute holoenzyme activity in the *T. thermophilus* system, β was titrated in the M13 Gori assay (0.08 to 10.0 pmol) (FIG. 41C). To insure maximum activity in following M13 Gori assays β will be present at 4 pmol.

Both δ and the δ' are constituents of the clamp loading complex in *E. coli* and likely serve a similar function in *T. thermophilus*. In *E. coli* they are both present in single copies and therefore smaller amounts may be needed to fully stimulate processive replications.

Figure 41D:
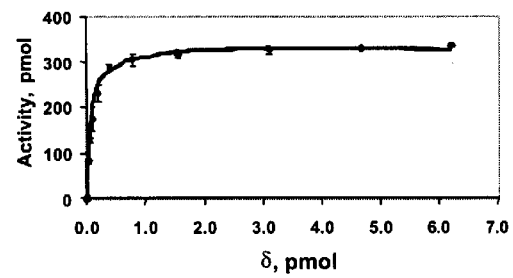
Figure 41E:
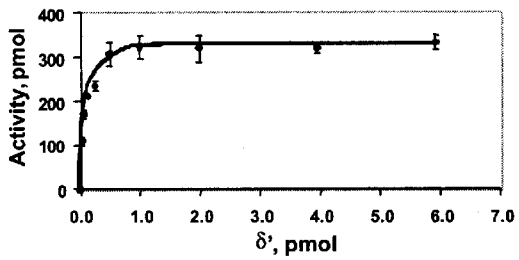

In future M13 Gori reactions, δ and the δ' will be at 2 pmol. These assays (FIGS. 41D and 41E) have allowed us to determine the concentration of all of the holoenzyme subunits required for optimal polymerization by the catalytic subunit (α). All of the subunits are required for processive polymerization. In the future, for purification of native subunits, assay conditions determined here will be used to follow each native protein through different purification steps. The assays will be designed so that the N-terminal tagged subunit corresponding to the native target subunit is omitted from the reaction mixes and aliquots from column elution fractions will be substituted. In this way fractions containing the target native protein will be detected.

Example 8

Protein-Protein Interactions Involving the Subunits of *T. thermophilus* Pol III In view of considerable homology between DNA polymerase III genes of *E. coli* and *T. thermophilus*, we tested whether some of the known interactions of subunits in *E. coli* also occur in *T. thermophilus*. Gel filtration analysis of the interaction of Pol III subunits was preformed using a Sephacryl® S-200 (Pharmacia Biotech) column (0.7×30 cm) equilibrated with HG.04 buffer. In all gel filtration experiments, the subunits (alone or in various combinations) were incubated at 60° C. for 5 minutes (300 μl) prior to loading onto a Sephacryl S-200 column. The first three fractions (1 ml each) contained the void volume and all subsequent fractions contained 300 μl. Fractions were analyzed in 10% SDS-polyacrylamide gels stained with Commassie Brilliant Blue. The fractions were also analyzed in reconstitution activity assays in which all of the subunits were present as described in Example 7, except the subunit (s) being analyzed. In these reactions, 2 μl of each fraction was added to the reconstitution assay. If there was activity observed it was indicative of the presence of the subunit being analyzed in that fraction. All of these assays were carried out with N-terminal tagged proteins.

Protein Interactions of Subunits Composing the Clamp-Loading Apparatus

In the *E. coli* clamp-loading complex, δ and δ' interact with each other and together with the DnaX subunits (τ and γ). Therefore, to determine if this interaction is exist between the subunits composing the *T. thermophilus* clamp-loading complex we first carried out gel filtration experiments using δ, δ', and τ/γ alone and in different combinations. Analysis of δ, δ' and τ/γ alone was performed using 200, 100 and 70 μg of protein, respectively. The elution profiles of the proteins assayed alone are shown in panel A, B and D of FIG. 44. δ eluted two fractions (fraction 18) before δ' (fraction 20). τ/γ likewise eluted two fractions (fraction 16) before δ. The activity observed for fractions in reconstitution assays are shown in the boxes beneath the SDS-polyacrylamide gels (FIG. 44) and correspond to the fractions containing protein bands. Next, δ (150 μg) and δ' (150 μg) were assayed together to determine if an interaction occurs. A shift in the elution position would indicate an interaction between the tested subunits to form a larger complex than either subunit alone. In this assay (FIG. 44, panel C), δ and δ' eluted two fraction earlier than δ alone indicating an interaction between these two proteins was occuring. There is also a shift if the activity profile corroborating the protein elution profiles and further support an interaction between the two subunits. Unfortunately, δ and δ' are similar in size and could not be resolved on either 10% or on gradient polyacrylamide gels (data not shown). When τ/γ (35 μg) was assayed with δ (70 μg) and δ' (85 μg), the elution profile was shifted to fractions earlier than any of the subunits alone (FIG. 44, panel E). The SDS-polyacrylamide gels indicate that all subunits are contained within the shifted fractions and the activity profile supports this observation.

To determine if the clamp-loading complex formed through interactions with either δ or δ' and τ/γ, gel filtration experiments were carried out in which τ/γ (60 μg) and δ (75 μg) or δ' (40 μg) were analyzed. When τ and γ/δ were assayed together, no interaction was seen in either SDS-polyacrylamide gels or activity assays. However, when τ/γ and δ' were assayed together both DnaX proteins and δ' were observed to be shifted together in both SDS-polyacrylamide gels and also in activity assays of the elution profile (data not shown). From these data, we theorize that the clamp-loader apparatus forms through interaction between δ' and both τ/γ and δ.

Figure 45A:
FIGS. 45A–C. Sephacryl S-200 gel filtration of *T. thermophilus* α with the subunits of the clamp loading complex showing protein-protein interactions.
Figure 45B:
Figure 45C:

Protein Interactions of the Catalytic Subunit α and Subunits Composing the Clamp-Loading Apparatus In the *E. coli* Pol III holoenzyme, two α catalytic subunits that replicate the leading and lagging DNA strands are held together by interactions with the DnaX protein τ. (See, McHenry, C. S., J. Biol. Chem., 257:2657–2663, [1982]). To determine if there are similar interactions occurring in the *T. thermophilus* holoenzyme the interaction of the α-subunit with the DnaX proteins and other members of the clamp-loading apparatus were assayed by gel filtration. When α (75 μg) was subjected to gel filtration in the absence of other subunits the peak fraction eluted in fraction 16 (FIG. 45, panel A). In the presence of τ/γ (170 μg), the elution is shifted to fraction 14 (FIG. 45, panel B). From the previous section τ/γ alone eluted in fraction 16 (FIG. 44, panel D). These observations indicate that α interacts with τ/γ and probably through interactions with τ since a larger relative amount of τ appears to be shifted than y when in the presence of α (comparing FIG. 44, panel D and FIG. 45 panel B).

Next, α (40 μg), τ/γ (115 μg), δ (50 μg) and δ' (50 μg) are assayed together to determine if δ and δ' are also shifted in the presence of α and τ/γ. In these assays, δ/δ' appear to be shifted to fraction 14 (FIG. 45, panel C) from fraction 18 when they are assayed together (FIG. 44, panel C).

Figure 46:
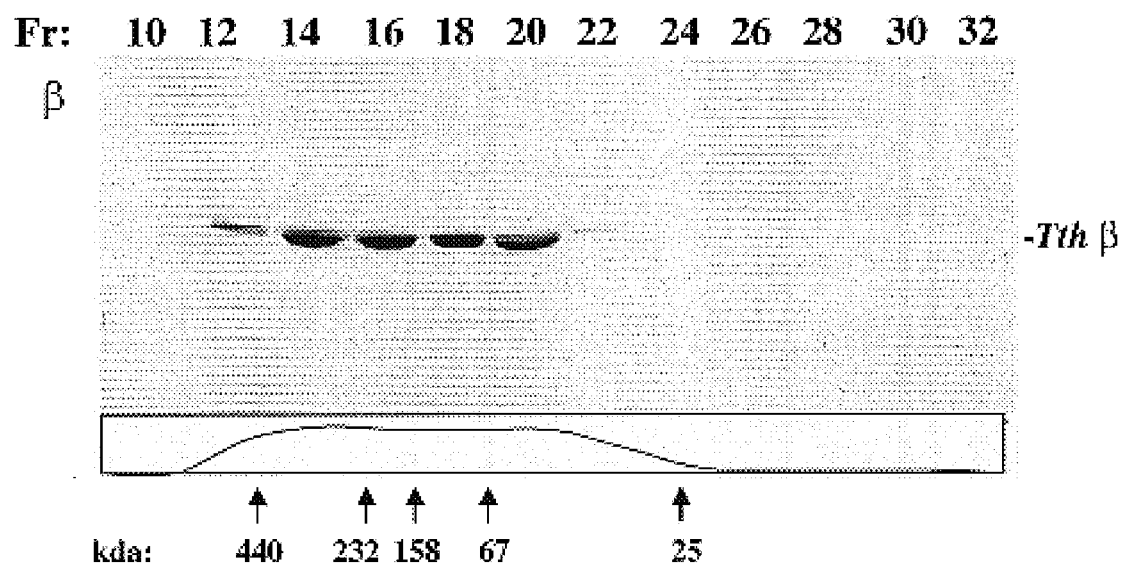
FIG. 46. Sephacryl S-200 gel filtration of *T. thermophilus* β.

A dimer of β forms a ring structure that is loaded onto DNA and acts to tether the replicative complex to DNA during replication thereby construing the processivity characteristic to the Pol III holoenzyme in *E. coli*. In an attempt to determine the interaction of *T. thermophilus* β with other members of the *T. thermophilus* holoenzyme, β was assayed in gel filtration experiments. Initially, β was assayed alone (250 μg, 20 μM) to determine the elution profile in the absence of other proteins. The β subunit eluted from the Sephacryl S-200 column in fractions 12–20, suggesting the formation of large molecular weight multimers (FIG. 46). To address the possibility that formation of multimers might be concentration dependent, β was re-assayed at a 10 fold lower concentration (25 μg, 20 μM). The results of these assays were identical to that seen at the higher concentration. Therefore, the interaction of β subunit with other components of the DNA polymerase III holoenzyme could not be examined by this method.

Example 9

Identification of *T. thermophilus* ssb Gene

The ssb gene sequences from *A. aeolicus, B. subtilis, E. coli,* and *H. influenzae* was used to search the *T. thermophilus* genome database at Goettingen Genomics Laboratory. A sequence of a region of the *T. thermophilus* genome containing a putative *T. thermophilus* ssb gene was identified (using BLAST) and obtained (from Dr. Carsten Jacobi, Goettingen Genomics Laboratory, Institute of Microbiology and Genetics, Grisebachstrasse 8, Goettingen, Germany). Using the crude sequence, two PCR primers were designed to amplify the ssb gene. In the PCR reaction, the forward/sense primer (ATG primers P138-S540, 5'-GATCC ATGGCTCGAGGCCTGAACCGC-3') (SEQ ID NO:29) was designed so that an NcoI site overlapped the start "ATG" codon. The reverse/antisense primer (P138-A1348, 5'-GACGGTACCTCATCAAAACGGCAAATCCTC-3') (SEQ ID NO:30) was designed to add an additional "TGA" stop codon adjacent to the native "TGA" stop codon and a KpnI restriction site in the non-complementary region. Both primers contained addition nucleotides to allow for efficient digestion with the NcoI and KpnI restriction enzymes. The PCR reaction used *T. thermophilus* genomic DNA as a template and yielded a PCR product of 808 bp in length. This PCR fragment was inserted into pGEM-T Easy™ (Promega) vector per manufacturer directions. This plasmid was transformed into DH5α bacteria and positive isolates were screened for by plasmid digestion with EcoRI restriction digest yielding 0.8 and 3.0 kb fragments. The plasmids from one positive isolate was selected and the correct sequence of both strands of the DNA were identified by DNA sequencing across the inserted region (ATG SEQ #1432–1436; primers, SP6, T7, P138-S913, P138-A1148, P138-A824). This plasmid was named pT-TSSB and the isolate was stored as a glycerol stock culture (ATG glycerol stock #838).

The DNA coding sequence of the *T. thermophilus* ssb gene (SEQ ID NO:31) in FIG. 47. The start codon (atg) and the stop codon (tga) are in bold print. Also shown below (FIG. 48) is the protein (amino acid) sequence (SEQ ID NO:32) derived from the DNA coding sequence.

The amino acid sequence of the *T. thermophilus* SSB protein was compared by sequence alignment with the sequence of several other SSB proteins (FIG. 49). The sequence of the *T. thermophilus* SSB protein was shown to contained an additional 50–70 amino acids in these comparisons. This is approximately 25% of the entire protein.

We know from previous studies that the SSB proteins from *E. coli* are functional in a homotetrameric form (Lowman and Ferrari, *Annu. Rev. Biochem.* 63:527–570 (1994)). The N-terminal 115 amino acids of the *E. coli* SSB contain the ssDNA-binding region. Other identified SSB proteins share similarities with *E. coli* SSB and contain the ssDNA binding region within the N-terminal region. These other SSB proteins are also thought to be active as tetramers. As shown (in FIG. 49) the *T. thermophilus* SSB contains an N-terminal region similar to the *E. coli* SSB and others, but is approximately 50% larger than the *E. coli* SSB. The sequence of the additional region (C-terminal region) of the *T. thermophilus* SSB was compared with its own N-terminal ssDNA binding regions (FIG. 50). Surprisingly, there was extensive sequence homology suggesting that this additional region may contain a second ssDNA binding region. If the *T. thermophilus* SSB contains two ssDNA binding regions it would be unique in SSB proteins yet studied and might explain the ability of *T. thermophilus* SSB to bind ssDNA at elevated temperatures.

Construction of Plasmid (pA1-TSSB) that Overexpresses *T. thermophilus* ssb gene (SSB) as a Native Protein The TSSB gene contained an internal KpnI restriction site, therefore a partial NcoI/KpnI restriction digest allowed the entire *T. thermophilus* ssb gene to be extracted from the pT-TSSB plasmid. The NcoI/KpnI restriction fragment containing the entire *T. thermophilus* ssb gene was inserted into the pA1-CB-NcoI plasmid digested with the same two restriction enzymes. The pA1-CB-NcoI plasmid contains a downstream hexahistidine and a biotinylation site, but it is downstream of the stop codon of the ssb gene and out of frame and will not be expressed. This plasmid was transformed into DH5α bacteria and positive isolates were screened for by plasmid digestion with NcoI/KpnI restriction enzymes yielding 161 bp, 642 bp and 3.0 kb fragments. The plasmids from one positive isolate was selected and the correct sequence of the inserted DNA were confirmed by DNA sequencing across the inserted region (ATG SEQ #1445 and 1446; primers, P138-S5576, P138-S913). This plasmid was named pA1-TSSB and the isolate was stored as a glycerol stock culture (ATG glycerol stock #846).

Verification of Expression of Plasmid (pA1-TSSB) that Overexpresses *T. thermophilus* ssb Gene as a Native Protein from pA1-TSSB/MGC1030

Plasmid pA1-TSSB was prepared from DH5α bacteria as previously described. The plasmid was transformed into MGC1030 bacteria (ATG glycerol stock #872, 873, 874). The bacterial growths and isolation of total cellular protein were as described in Example 2. A small aliquot of supernatant (3 µl) containing total cellular protein from each of the three isolates was loaded onto a 4–20% SDS-polyacrylamide mini-gel (Novex, EC60255; 1 mm thick, with 15 wells/gel) in 25 mM in Tris base, 192 mM glycine, and 0.1% SDS. The mini-gel was stained with Coomassie Blue. There were no visible protein bands from any of the isolates corresponding to the predicted molecular weight of the *T. thermophilus* SSB.

Construction of a Plasmid (pA1-CB-TSSB) that Overexpress *T. thermophilus* SSB Gene Fused to a C-Terminal Peptide that Contains Hexahistidine and a Biotinylation Site The gene encoding *T. thermophilus* SSB above was amplified by PCR using the pA1-TSSB plasmid as a template. The forward/sense primer (ATG primer #P138-S540) was the same primer used in construction of pA1-TSSB and contained a region complementary to the 5' end of the *T. thermophilus* SSB gene. As before, a NcoI site overlapped the ATG start codon. The reverse/antisense primer was complementary to the 3' end of the *T. thermophilus* SSB gene excluding the stop codon (ATG primer #P138-A1343spe, 5'-GACGACTAGT AAACGGCAAATCCTCCTCC-3') (SEQ ID NO:33). This primer contained a SpeI restriction site adjacent to the complementary region of the primer. The SpeI site allowed for the expressed protein to contain two additional amino acids (Thr and Ser) between the C-terminal amino acid of the SSB protein and the C-terminal fusion peptide. This 800 bp PCR product was digested with NcoI/SpeI and inserted into the plasmid pA1-CB-NcoI digested with the same restriction enzymes as previously described. This plasmid was transformed into DH5α bacteria and plasmids from positive isolates were screened for by digestion with NcoI/SpeI restriction enzymes yielding 0.8 and 5.6 kb fragments. One positive plasmid was selected and the sequence of the insert verified by DNA sequencing (ATG SEQ #1504–1507; primers, P38-S5576, P65-A106, P138-S913, P138-A1148). This plasmid was named pA1-CB-TSSB and the isolate was stored as a glycerol stock culture (ATG glycerol stock #897). Verification of Expression of *T. thermophilus* SSB Protein Fused to a C-Terminal Peptide that Contains Hexahistidine and a Biotinylation Site by pA1-CB-TSSB/MGC1030

The pA1-CB-TSSB plasmid was prepared and transformed into MGC1030 bacteria (ATG glycerol stock #919). The bacterial growths and isolation of total cellular protein were as described Example 2. A small aliquot of each supernatant (3 µl) containing total cellular protein was loaded onto a 4–20% SDS-polyacrylamide mini-gel (Novex, EC60255; 1 mm thick, with 15 wells/gel) in 25 mM in Tris base, 192 mM glycine, and 0.1% SDS. The mini-gels were stained with Coomassie Blue. The region of the gel in which CB-TSSB was expected contained other intense protein bands and the *T. thermophilus* SSB protein could not be visualized.

Next, the total protein in each lysate was transferred (blotted) from polyacrylamide gel to nitrocellulose as described in Example 2. Each lane contained 1.5 µl of the supernatant. Proteins on the blotted nitrocellulose were visualized by interactions with phosphatase-conjugated streptavidin as described above. The endogenous *E. coli* biotin binding protein, ~20 kDa was detectable in both induced and non-induced samples. A protein band corresponding to the *T. thermophilus* SSB protein migrated just below the 40 kDa molecular weight standard of the Gibco 10 kDa protein ladder. The predicted molecular weight of CB-TSSB is 33.5 kDa. This protein was observed as a faint band in the induced cultures, but was not observed in the uninduced control lysates.

Large Scale Growth of *T. thermophilus* ssb Gene Product Fused to a C-Terminal Peptide that Contains Hexahistidine and Biotinylation Site by pA1-CB-TSSB/MGC1030

Strain pA1-CB-TSSB/MGC1030 was grown in a 250 L fermentor to produce cells for purification of *T. thermophilus* SSB protein as described in Example 2. Cell harvest was initiated 3 hours after induction, at $OD_{600}$ of 8.4, and the cells were chilled to 10° C. during harvest. The harvest volume was 178 L, and the final harvest weight was approximately 2.4 kg of cell paste. An equal amount (w/w) of 50 mM Tris (pH 7.5) and 10% sucrose solution was added to the cell paste. Quality control results showed 10 out of 10 positive colonies on ampicillin-containing medium in the inoculum, 8/10 positive colonies at induction and 8/10 positive colonies at harvest. Cells were frozen by pouring the cells suspension into liquid nitrogen, and stored at −20° C., until processed.

Determination of Optimal Ammonium Sulfate Precipitation Conditions of SSB Fused to a C-Terminal Peptide that Contains Hexahistidine and Biotinylation Site by pA1-CB-TSSB/MGC1030

Lysis was accomplished by creation of spheroplasts of the cells carrying the expressed *T. thermophilus* SSB proteins. First, from 100 g of a 1:1 suspension of frozen cells (50 g cells) in Tris-sucrose which had been stored at −20° C., Fr I (170 ml, 14 mg/ml) was prepared. The preparation was as described in Example 2. The sample was then divided into 4 equal volumes (40 ml) and 6.56, 9.04, 11.64 and 14.44 g of ammonium sulfate (30%, 40%, 50% and 60% saturation) was added to each separate sample, respectively, over a 15 min interval at 4° C. The mixture rested for an additional 30 min at 4° C. and was then centrifuged at 23,000×g for 45 min at 0° C. The resulting pellets were resuspended in 2 ml Ni-NTA suspension buffer. The 30%, 40%, 50% and 60% ammonium sulfate precipitated samples contained protein concentrations of 0.04, 0.18, 1.6 and 2.9 mg/ml, respectively. The samples were analyzed by SDS-polyacrylamide gel electrophoresis. The 30% and 40% ammonium sulfate precipitated samples contained no detectable SSB protein. The 50% and 60% samples contained bands of equal intensity of a protein migrating in the region corresponding to the molecular weight of *T. thermophilus* SSB. This band was faint compared to other proteins cited above and yields from large-scale preparations of the protein were thought to be small. Analysis by SDS-polyacrylamide gel electrophoresis of samples purified using Ni-NTA resin, but not ammonium sulfate precipitated also failed to allow a distinctive *T. thermophilus* protein band to be visualized.

Purification of *T. thermophilus* SSB Protein Fused to an C-Terminal Peptide that Contains Hexahistidine and a Biotinylation Site by pA1-CB-TSSB/MGC1030

Even though the initial analysis of expression levels of *T. thermophilus* SSB indicated low yields, enough protein could be isolated from large-scale preparations for antibody production. Lysis was accomplished by creation of spheroplasts of the cells carrying the expressed *T. thermophilus* SSB. FrI (1270 ml, 10.6 mg/ml) was prepared from 800 g of a 1:1 suspension of frozen cells (400 g cells) stored in Tris-sucrose which had been stored at −20° C. as described in Example 2. To Fr I, ammonium sulfate (0.291 g to each initial ml Fraction I-50% saturation) was added over a 15 min interval. The mixture rested for an additional 30 min at 4° C. and was then centrifuged at 23,000×g for 45 min at 0° C. The resulting pellets were quick frozen by immersion in liquid nitrogen and stored at −80° C.

Figure 51:
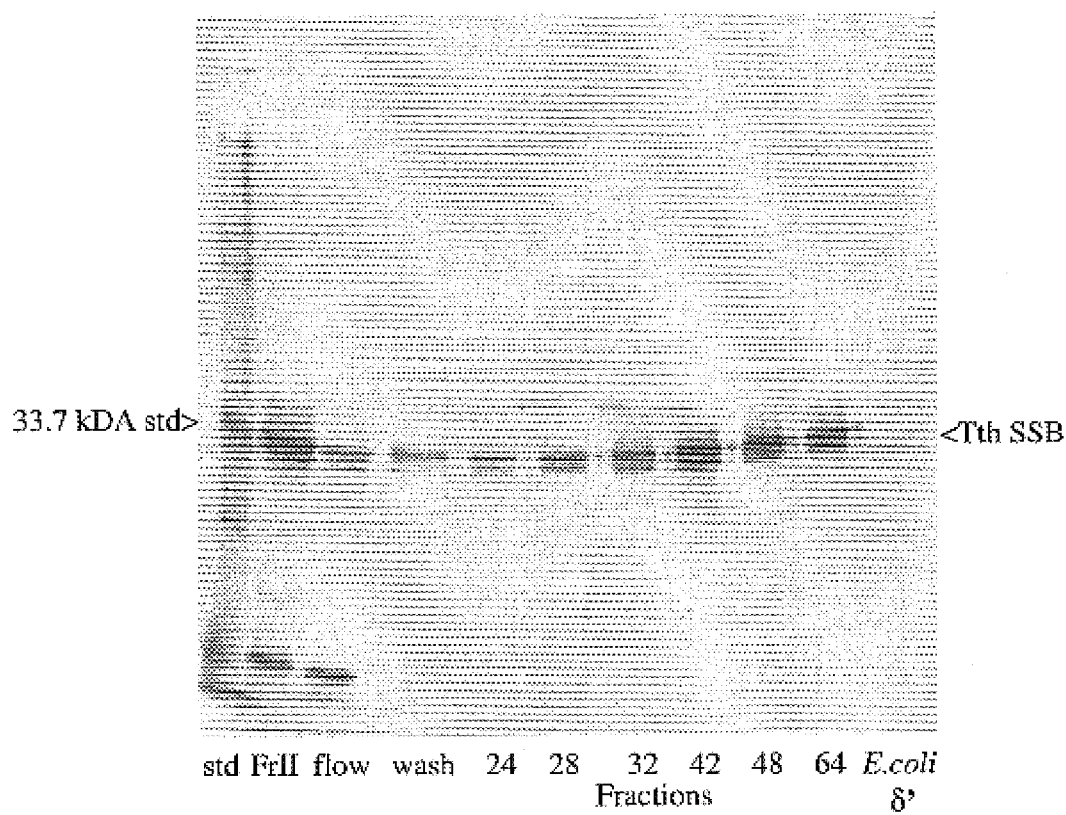
FIG. 51. Biotin blot analysis of relevant fractions from the $Ni^{++}$-NTA column purification of T. thermophilus SSB.

The protein pellets were resuspended in 150 ml of $Ni^{++}$-NTA suspension buffer and homogenized using a Dounce homogenizer. The sample was clarified by centrifugation (16,000×g) and the supernatant constituted Fr II (30 mg/ml). Fr II was added to 50 ml of a 50% slurry of Ni-NTA resin and rocked for 1.5 hours at 4° C. This slurry was then loaded onto a BioRad Econo-column (2.5×5 cm). The column was washed with 400 ml of $Ni^{++}$-NTA wash buffer at a flow rate of 1.5 ml/min. *T. thermophilus* SSB was eluted in 250 ml of $Ni^{++}$-NTA elution buffer containing a 10–200 mM imidazole gradient. The eluate was collected in 96×2.5 ml fractions. Fractions were subjected to SDS-polyacrylamide gel electrophoresis and biotin blot analysis, and fractions 28–70 were found to contain over 95% of total SSB protein (FIG. 51). *E. coli* δ was used as a control since the molecular weight is similar to *T. thermophilus* SSB. In the Coomassie Blue stained gel, no clear protein bands corresponding to *T. thermophilus* SSB could be defined, however, the biotin blot analysis allowed us to determine fractions containing *T. thermophilus* SSB protein. Fractions 28–70 were pooled (100 ml, 0.76 mg/ml) and precipitated by addition of ammonium sulfate to 50% saturation. This sample was centrifuged as previously described resulting in two protein pellets.

Production of Polyclonal Antibodies Against *T. thermophilus* SSB Protein

One of the two *T. thermophilus* SSB precipitated protein pellets from above was resuspended in 20 ml of PBS and represented Fr III (1.5 mg/ml). A 2 ml UltraLink™ Immobilized Monomeric Avidin column (1.1 cm×2.5 cm) (Pierce) was equilibrate in PBS plus 10% glycerol as per manufacturers instructions. The Fr III sample was loaded onto the avidin column, which was then washed (15 ml) and eluted (40 ml) in fractions as described in Example 3. The fractions were analyzed by SDS-polyacrylamide gel electrophoresis, and faint protein bands corresponding to *T. thermophilus* SSB could be detected in fractions 4–35. These fractions were pooled (27 ml, 0.01 mg/ml) and the protein was precipitated by adding ammonium sulfate to 50% saturation and the precipitate was collected by centrifugation (23,000× g, 45 min, 0° C.) and stored at −80° C. The pellet was then resuspended in 2 ml of PBS (0.01 mg/ml) and subjected to SDS-polyacrylamide gel electrophoresis and biotin blot analysis. This sample contained two faint upper molecular weight contaminating proteins, however because of the low yield of SSB protein, we decided to use this sample for antibody production.

The dialyzed samples were used to produce polyclonal antibodies against *T. thermophilus* ssb gene product (SSB protein) as described in Example 3.

Construction of a Plasmid (pA1-NB-TSSB) that Overexpress *T. thermophilus* ssb Gene Fused to an N-Terminal Peptide that Contains Hexahistidine and a Biotinylation Site To increase expression of *T. thermophilus* SSB a vector was designed to express SSB as an N-terminal tagged protein. The forward/sense primer (ATG primer P138-S539pst, 5'-AAACTGCAGGCTCGAGGCCTGAACCGCGTTTTCC-3') (SEQ ID NO:61) is designed so that the non-complementary portion contains a "AAA" clamp region and a PstI site. The complementary portion of the primer is complementary to the first 25 nt of the ssb gene beginning at codon 2, so that the first codon (the "ATG" start codon) is excluded. This will allow the PCR product to be inserted into the vector pA1-NB-AgeI at the PstI site therefore fusing the ssb gene inframe with the N-terminal tagged peptide. The reverse/antisense primer (ATG primer P138-A1348stopspe, 5'-GACAACTAGTCATCAAAACGGCAAATCCTCC-3') (SEQ ID NO:62) contains a "GACA" clamp region and a SpeI restriction site in the non-complementary region. The non-complementary region also contains an additional "TGA" (TC) stop codon that will be adjacent to the native "TGA" stop codon, giving two stop codons in tandem.

The PCR reaction used pA1-TSSB as a template and yielded a PCR product of 815 bp in length. This PCR fragment digested with PstI and SpeI was inserted into pA1-NB-AgeI digested with PstI and SpeI and resulted in the plasmid pA1-NB-TSSB which contained the entire gene encoding the *T. thermophilus* SSB. PAI-NB-TSSB was transformed into DH5α bacteria and positive isolates were screened for by plasmid digestion with PstI and SpeI restriction digest yielding 5.6 and 0.8 kb fragments. The plasmids from one positive isolate was selected and the correct sequence of both strands of the DNA were identified by DNA sequencing across the inserted region (ATG SEQ #1855–1859 and #1884–1885; primers: P138-S913, P138-A1148, P138-A824, NB-Sseq, p64-A215). This isolate was stored as a glycerol stock culture (ATG glycerol stock #1101).

Verification of Expression of *T. thermophilus* SSB Fused to an N-terminal Peptide that Contains Hexahistidine and a Biotinylation Site The pA1-NB-TSSB plasmid was prepared and transformed into MGC1030 (ATG glycerol stock #1128) and AP1.L1 bacteria (ATG glycerol stock #1129). Three isolates from each tranformation were selected for farther study. The bacterial growths and isolation of total cellular protein were as described in Example #2. A small aliquot of supernatant (3 μl) containing total cellular protein from each of the three isolates was loaded onto a 4–20% SDS-polyacrylamide mini-gel (Novex, EC60255; 1 mm thick, with 15 wells/gel) in 25 mM in Tris base, 192 mM glycine, and 0.1% SDS. The mini-gel was stained with Coomassie Blue. Distinct protein bands from all of the isolates corresponding to the predicted migration region of *T. thermophilus* SSB (approximately 33.5 kDa) were visualized.

Next, the total protein in each lysate was transferred (blotted) from polyacrylamide gel to nitrocellulose as described in Example #2. Each lane contained 1.5 ul of the supernatant containing total protein. Proteins on the blotted nitrocellulose were visualized by interactions with phosphatase-conjugated streptavidin as described above. The endogenous *E. coli* biotin binding protein, ~20 kDa was detectable in both induced and non-induced samples. A protein band corresponding to the *T. thermophilus* SSB protein migrated midway between the 30 and 40 kDa molecular weight standard of the Gibco 10 kDa protein ladder. This protein was observed as a very intense band in the induced cultures, but was not observed in the uninduced control lysates.

Optimization of Expression of *T. thermophilus* SSB by pA1-NB-TSSB

Since expression of *T. thermophilus* ssb gene yielded low or no detectable proteins when expressed as both a native or coupled to an C-terminal fusion peptide, extra care was taken with *T. thermophilus* SSB linked to an N-terminal fusion peptide to achieve optimum expression. Expression was analyzed using both *E. coli* strains MGC1030 and AP1.L1 carrying pA1-NB-TSSB at different induction times. Growth of bacterial cultures and analysis were carried out as described in Example #2. Biotin blot analysis indicated that expression levels were higher at 37° C. and also slightly better when expressed in the AP1.L1 bacterial strain. The optimum yield of *T. thermophilus* SSB was attained by 3 h post induction and at 37° C.; this induction time will be used in subsequent experiments.

Large Scale Growth of pA1-NB-TSSB/AP1.L1

Strain pA1-NB-TSSB/AP1.L1 was grown in a 250 L fermentor to produce cells for purification of *T. thermophilus* SSB fused to an N-terminal peptide that contains hexahistidine and biotinylation site as described in Example #2. Cell harvest was initiated 3 hours after induction at $OD_{600}$=5.0, and the cells were chilled to 10° C. during harvest. The harvest volume was 180 L, and the final harvest weight was approximately 2.07 kg of cell paste. An equal amount (w/w) of 50 mM Tris-HCl (pH 7.5) and 10% sucrose solution was used to resuspend the cell paste. Cells were frozen by pouring the cell suspension into liquid nitrogen, and stored at −20° C. until processed. Quality control results showed 10 out of 10 positive colonies on ampicillin-containing medium in the inoculum, 10 out of 10 positive colonies at induction and 10 out of 10 positive colonies at harvest.

Purification of *T. thermophilus* ssb Product Fused to an N-Terminal Peptide that Contains Hexahistidine and a Biotinylation Site Lysis of 800 g of a 1:1 suspension of frozen cells (400 g of cells) containing pA1-NB-TSSB stored in Tris-sucrose at −20° C. was preformed as described Example #2. The recovered supernatant (1.4 l) constituted Fr I (10.7 mg/ml). To Fr I, ammonium sulfate (0.291 g to each initial ml Fraction 1–50% saturation) was added over a 15 min interval. The mixture was stirred for an additional 30 min at 4° C. and the precipitate was collected by centrifugation (23,000×g, 45 min, 0° C.). The. resulting pellets were quick frozen by immersion in liquid nitrogen and stored at −80° C.

The pellets from Fr I were resuspended in 100 ml of $Ni^{++}$-NTA suspension buffer (50 mM Tris-HCl (pH 7.5), 40 mM KCl, 7 mM $MgCl_2$, 10% glycerol, 7 mM βME, 0.1 mM PMSF) and homogenized using a Dounce homogenizer. The sample was clarified by centrifugation (16,000×g) and the supernatant constituted Fr II. Fr II was added to 40 ml of a 50% slurry of $Ni^{++}$-NTA resin in $Ni^{++}$-NTA suspension buffer and rocked for 1.5 hours at 4° C. This slurry was then loaded onto a BioRad Econo-column (2.5×5 cm). The column was washed with 300 ml of $Ni^{++}$-NTA wash buffer (50 mM Tris-HCl (pH 7.5), 1 M KCl, 7 mM $MgCl_2$, 10% glycerol, 10 mM Imidazole, 7 mM βME) at a flow rate of 0.5 ml/min. The protein was eluted in 300 ml of $Ni^{++}$-NTA elution buffer (50 mM Tris-HCl (pH 7.5), 40 mM KCl, 7 mM $MgCl_2$, 10% glycerol, 7 mM βME) containing a 10–200 mM imidazole-HCl (pH 7.5) gradient. The *T. thermophilus* SSB eluted across the second half of the gradient and contained a number of contaminating proteins as determined by SDS-polyacrylamide gels. These fractions were pooled and the protein isolated by precipitation with ammonium sulfate (0.291 g to each initial ml of sample-50% saturation).

One-third of the precipitated protein was was resuspended in 20 ml of PBS containing 10% glycerol and further purified using a monomeric avidin column as describe in Example #3. The yield from this column was almost homologous *T. thermophilus* SSB (20 ml, 0.23 mg/ml).

The remaining two-thirds of the precipitated protein was resuspended in 20 ml of $Ni^{++}$-NTA suspension buffer, mixed with 10 ml of a 50% slurry of $Ni^{++}$NTA resin and rocked for 1.5 hours at 4° C. The resin was poured into a column and purified as before. The yield from this column was also almost homologous *T. thermophilus* SSB (68 ml, 0.5 mg/ml). Both protein purifications were frozen by imersion in liquid nitrogen and stored at −80° C. for future analysis.

Cloning *T. thermophilus* ssb Gene (SSB) into a Translationally Coupled Vector pTAC-CCA-ClaI To efficiently express SSB as a native protein we designed a vector to express SSB as a translationally coupled protein. We again use translational coupling as described in Example 2. The *T. thermophilus* ssb gene was inserted behind the CCA. adding enzyme and translationally coupled as described for the other *T. thermophilus* proteins expressed by translationally coupling. First, the ssb gene was amplified by using pA1-TSSB as a template by PCR. The forward/sense primer (ATG primer #P138-S533c1a2, 5'-ACTGATCGATA<u>ATGGCTCGAGGCCTGAACCGC</u>-3') (SEQ ID NO:63) has a ClaI restriction site in the non-complementary region. The non-complementary region also contains the "TA" of the stop (TAA) for the upstream CCA-adding protein fragment. The region of the primer complementary to the 5' end of the *T. thermophilus* holA gene begins with "A" which is the first nucleotide of the "ATG" start codon and the final "A" of the "TAA" stop codon. The reverse/antisence primer (ATG primer #P138-A1348stopspe, 5'-GACAACTAGTCA<u>TCAAAACGGCAAATCCTCC</u>-3') (SEQ ID NO:64) contains a SpeI restriction site in the non-complementary portion of the primer and also an additional stop codon adjacent to the native stop codon, giving two stop codons in tandem. There was also a clamp region for efficient cutting with SpeI. Next, the PCR product was digested with ClaI/SpeI restriction enzymes and inserted into the pTAC-CCA-ClaI plasmid digested with the same enzymes. The plasmid was transformed into DH5α bacteria and plasmids from ampicillin-resistant positive isolates were screened for by digestion with ClaI/SpeI restriction enzymes yielding 0.8 and 5.5 kb fragments. The sequence of both strands of the insert were verified by DNA sequencing (ATG SEQ #1688–1692, 1721; primers, P144-S23, P144-A1965, P65-A106, P138-S913, P138-A1148, P138-A828). Sequence analysis confirmed that the correct sequence was contained within the inserted region. This plasmid was named pTAC-CCA-TSSB and the isolate was stored as a stock culture (ATG glycerol stock #1033).

Verification of Expression of Native *T. thermophilus* SSB by PTAC-CCA-TSSB/MGC1030 and pTAC-CCA-TSSB/AP1.L1

The pTAC-CCA-TSSB plasmid was prepared and transformed into MGC1030 bacteria (ATG glycerol stock #1071, 1072, 1073) and AP1.L1 (ATG glycerol stock #1079). The bacterial growths and isolation of total cellular protein were as described in Example 2. A small aliquot of each supernatant (3 μl) containing total cellular protein was electrophoresised onto a 4–20% SDS-polyacrylamide mini-gel (Novex, EC60255; 1 mm thick, with 15 wells/gel) in 25 mM in Tris base, 192 mM glycine, and 0.1% SDS. The mini-gels were stained with Coomassie Blue. A faint protein band corresponding to the predicted molecular mass of *T. thermophilus* SSB (29.8 kDa) was visualized migrating just above the 30 kDa molecular weight standard of the Gibco 10 kDa protein ladder in the AP1.L1 isolates.

Example 10

Identification of Two *T. thermophilus* dnaQ Genes (ε-subunits)

From the previous Tth patent application (U.S. Application #09/151888), the probe 5'-CCT CGA ACA CCT CCT GCC GCA AGA CCC TTC GAC CCA-3' (SEQ ID NO:34) was used to screen a lambda library containing *T. thermophilus* genomic DNA. Using this probe, over 100 strong positive plaques were identified and verified by replating. Three were grown up and the DNA purified as described for dnaE. One (cl#5.1.1) was selected for further sequencing. The sequence of a major portion of the dnaQ gene was obtained by direct sequencing of the insert in the isolated lambda DNA using sequences selected from the PCR product to initiate sequencing. As previously described (U.S. application Ser. No. 09/151,888), upon preliminary examination of the sequence, it was found to encode one continuous open reading frame (ORF) that showed significant homology to other DNA polymerase III ε-subunits from other bacteria (based on a BLAST search). A strong secondary structure or other block prevented obtaining more 3' sequence of the *T. thermophilus* dnaQ gene.

The *T. thermophilus* genome database at Goettingen Genomics Laboratory was searched for using the sequence of the ORF identified above. It indicated two open reading frames that showed close similarity to our partial Tth dnaQ sequence. The closest match was designated dnaQ-1 and the poorer-scoring match dnaQ-2. DnaQ2 is described in Example 14. Only homology scores, not the actual sequence data was available from the web site. Dr. Carsten Jacobi (Goettingen Genomics Laboratory, Institute of Microbiology and Genetics, Grisebachstrasse 8, Goettingen, Germany) agreed to provide crude, unannotated incomplete sequence information in the regions of our BLAST hits on their website. Examination of the sequences indicated two clearly independent but homologous dnaQ-like genes. Initially, focusing on dnaQ-1, several restriction sites (NgoMIV, BamHI, NcoI and SacI) were identified upstream and downstream of the dnaQ-1 gene. To obtain the entire correct sequence of the *T. thermophilus* dnaQ-1 gene, the lambda clone #5.1.1 (described in U.S. application Ser. No. 09/151,888) was digested with NgoMIV, BamHI, NcoI and SacI restriction enzymes. Restriction digest was carried out on 5 μl (approx. 2.8 μg DNA) of the lambda clone #5.1.1. The digested DNA samples were electrophoresised on a 1% agarose gel and transferred by capillary transfer to MSI Magnagraph nylon membrane. The blot (10×15 cm) was treated with 20 ml of Ambion Ultrahyb™ hybridization solution at 42° C. for 2 h, then 20 ng of the biotinylated probe (probe 5'-CCT CGA ACA CCT CCT GCC GCA AGA CCC TTC GAC CCA-3' (SEQ ID NO:35) was added to the hybridization bag and the blot was incubated at 42° C. overnight. The blot was processed and detected using an NEB Phototope CDP-Star chemiluminescence detection kit per manufacturer's instructions (New England BioLabs). The probe hybridized with a 1 kb NgoMIV/SacI restriction fragment. This 1 kb NgoMIV/SacI restriction fragment was chosen for subcloning and sequencing.

A pUC21 cloning vector (Sigma) was chosen as the recipient DNA, and was subjected to NgoMIV/SacI digestion. The NgoMIV/SacI fragment of the lambda clone #5.1.1 was ligated into the digested pUC21. The resulting plasmid was transformed into DH5α and isolates were selected for by ampicillin-resistance. Plasmids were purified from one isolate and screened by NgoMIV/SacI and XhoI digestion of plasmids yielding the expected 1.0 and 2.7 kb and 480 bp and 3.3 kb fragments, respectively. Both DNA strands of the inserted region were sequenced (ATG SEQ #1437–1442; primers, M13 reverse primer, P140-S839, P140-S1209, P140-A1443, P140-A1089 and pUC21-A829). This plasmid was named pUC21-TQ and the isolate was stored as a stock culture (ATG glycerol stock #843).

The DNA coding sequence of the *T. thermophilus* dnaQ-1 gene (SEQ ID:NO:36) is shown in FIG. 52. The start codon (gtg) and the stop codon (tga) are in bold print. Also shown in FIG. 53 is the protein (amino acid) sequence (SEQ ID NO:37) derived from the DNA coding sequence.

Construction of Plasmid (pA1-TQ) that Expresses *T. thermophilus* dnaQ-1 Gene

Expression of *T. thermophilus* dnaQ-1 gene product (ε1-subunit) as a native protein was accomplished. The construction of pA1-TQ was performed by insertion of the native *T. thermophilus* dnaQ-1 gene into the pA1-CB-Cla-2 plasmid. The pUC21-TQ plasmid was prepared and the *T. thermophilus* dnaQ-1 gene was amplified out of the pUC21-TQ plasmid using PCR. The forward/sense primer (ATG primer #P140-S96cla; 5'-CCATCGATG CCTGCAGGTCTGGAGG-3') (SEQ ID NO:38) used in the PCR reaction was designed to have an upstream ClaI site that overlaps the AT of the ATG start codon used for the dnaQ-1 gene. The native start codon for the dnaQ-1 gene is GTG, this has been replace in the primer with an ATG start codon to allow for expression in *E. coli*. The reverse/antisense primer (ATG primer #P140-A713kpn; 5'-GACGGTACCTCA TCAGTACCTGAGCCGGGCCAA-3') (SEQ ID NO:39) was designed to have an additional stop codon placed in tandem with the native stop codon. This additional stop codon was adjacent to a KpnI restriction site in the non-complementary region of the primer. The PCR product was digested with ClaI and KpnI restriction enzymes. The digested PCR product was inserted into the ClaI/KpnI digested pA1-CB-Cla-2 plasmid. These plasmids were transformed into DH5α bacteria and positive isolates were selected by ampicillin-resistance. Plasmids were purified from one clone and screened by ClaI/KpnI digest of purified plasmids yielding 0.6 and 5.6 kb fragments. The inserted region in this plasmid was subjected to DNA sequencing to confirm the correct sequence (ATG SEQ #1508–1511; primers, P38-S5576, P65-A106, P140-S839 and P140-A1089). This plasmid was named pA1-TQ and the isolate was stored as a stock culture (ATG glycerol stock #900).

Verification of Expression of Plasmid (pA1-TQ) that Overexpresses *T. thermophilus* dnaQ-1 Gene (ε-Subunit) as a Native Protein from pA1-TQ/MGC1030

The pA1-TQ plasmid was prepared and transformed into MGC1030 bacteria. Three isolates were selected (ATG glycerol stock #921, 922, 923) for further study. The bacterial growths and isolation of total cellular protein were as described in Example 2. A small aliquot (3 μl) of supernatant containing total cellular protein from each of the three isolates, was loaded onto a 4–20% SDS-polyacrylamide mini-gel (Novex, EC60255; 1 mm thick, with 15 wells/gel) in 25 mM in Tris base, 192 mM glycine, and 0.1% SDS. The mini-gel was stained with Coomassie Blue. There were no visible protein bands from any of the isolates corresponding to the predicted migration region of the ε-subunit.

Construction of a Plasmid (pA1-CB-TQ) that Overexpress *T. thermophilus* dnaQ-1 (ε1-subunit) Fused to a C-Terminal Peptide that Contains Hexahistidine and a Biotinylation Site Since initial attempts to express the native ε-subunit failed, a vector was designed to couple the *T. thermophilus* dnaQ-1 gene to a fusion peptide containing a hexahistidine and a biotinylation site. The construction of pA1-CB-TQ was also performed by insertion of the *T. thermophilus* dnaQ-1 gene into the pA1-CB-Cla-2 plasmid. The reverse/antisense primer however was designed to add a SpeI site onto the 3' end of the gene allowing insertion into the pA1-CB-Cla-2 plasmid in frame with the DNA encoding the C-terminal peptide that contains hexahistidine and a biotinylation site. The pUC21-TQ plasmid was prepared for use as the PCR template. The *T. thermophilus* dnaQ-1 gene was amplified out of the pUC21-TQ plasmid using PCR. The forward/sense primer (ATG primer #P140-S96cla) was the same as used in producing pA1-TQ. The reverse/antisense primer (ATG primer #P140-A708Spe; 5'-CCTCACTAGT GTACCTGAGCCGGGCCAA-3') (SEQ ID NO:40) was designed so that a SpeI restriction site was adjacent to the penultimate codon (the stop codons were excluded). The SpeI site allowed for the expressed protein to contain two additional amino acids (Thr and Ser) between the C-terminal amino acid of the ε-subunit and the C-terminal fusion peptide. The PCR product was digested with ClaI and SpeI restriction enzymes and inserted into the ClaI/SpeI digested pA1-CB-Cla-2 plasmid. The plasmid was then transformed into DH5α bacteria and plasmids from positive isolates were selected by ampicillin-resistance. Plasmids were isolated from one positive isolate and screened by digestion with ClaI and SpeI restriction enzymes yielding 0.6 and 5.6 kb fragments. The correct sequence of the inserted region was confirmed by DNA sequencing (ATG SEQ #1526–1529; primers, P38-S5576, P65-A106, P140-S839 and P140-A1089). This plasmid was named pA1-CB-TQ and the isolate was stored as a stock culture (ATG glycerol stock #911).

Verification of Expression of Plasmid (pA1-CB-TQI) that Overexpresses *T. thermophilus* dnaQ-1 Gene (ε-Subunit) Fused to a C-Terminal Peptide that Contains Hexahistidine and a Biotinylation Site from pA1-CB-TQ/MGC1030

The pA1-CB-TQ1 plasmid was prepared and transformed into MGC1030 bacteria. Three isolate was selected (ATG glycerol stock #929) for further study. The bacterial growths and isolation of total cellular protein were as described in Example 2. A small aliquot (3 μl) of supernatant containing total cellular protein from each of the three isolates was electrophoresised onto a 4–20% SDS-polyacrylamide mini-gel (Novex, EC60255; 1 mm thick, with 15 wells/gel) in 25 mM in Tris base, 192 mM glycine, and 0.1% SDS. The mini-gel was stained with Coomassie Blue. There were no protein bands from any of the isolates corresponding to the predicted migration region of the ε-subunit.

Next, the total protein from the lysate was transferred (blotted) from polyacrylamide gel to nitrocellulose as described in Example 2. Proteins on the blotted nitrocellulose were visualized by interactions with phosphatase-conjugated streptavidin. The endogenous *E. coli* biotin-CCP protein, ~20 kDa was detectable in both induced and non-induced samples. A protein band corresponding to the ε1-subunit migrated approximately midway between the 20 and 30 molecular weight standards of the Gibco 10 kDa protein ladder. This is consistent with the expected molecular weight of 25.8 kDa. This protein was observed as a faint band in the induced cultures, but was not observed in the uninduced control in lysates from the AP1.L1 strain. The protein was expressed at levels too low to justify purification attempts.

Example 11

*T. thermophilus* UvrD Helicase
Identification and Cloning *T. thermophilus* uvrD Gene The UvrD protein sequence from *E. coli* was used to search the *T. thermophilus* genome database at Goettingen Genomics Laboratory. The region of the *T. thermophilus* genome (Feb. 4, 2000 contig working.0.15372, region 40201–46740) containing a putative *T. thermophilus* uvrD gene was identified (using BLAST) and obtained (from Dr. Carsten Jacobi, Goettingen Genomics Laboratory, Institute of Microbiology and Genetics, Grisebachstrasse 8, Goettingen, Germany). Using the crude sequence, two PCR primers were designed to amplify the uvrD gene. All of the vectors that we have for expressing N-terminal tagged proteins require a PstI site for insertion of the 5' end of the gene into the vectors. However, there is a PstI site within the uvrD gene. To overcome this problem a NsiI site was added to the non-complementary portion of the forward/sense primer (ATG primer P159-S1689, 5'-GACTATGCAT AGCGACGCCCTCCTAGCCCCCCTCAAC-3') (SEQ ID NO:65). The NsiI restriction cut site of the PCR product will leave a four nucleotide overhang (TGC) that can be utilized (annealed) by a PstI restriction cut site on the pA1-NB-AgeI plasmid. The PstI and the NsiI site will be destroyed by the ligation, but the uvrD gene will be inserted inframe with the DNA encoding the N-terminal fusion peptide. The PCR product will exclude the GTG start codon and begins at codon 2, with the Nsi1 site adjacent to codon 2. The reverse/antisense primer (ATG primer P159-A3786, 5'-GACTACTAGTCTA TCATGCCGGCTTAAGCTCCGCG-3') (SEQ ID NO:66) was designed to add an additional "TAG" stop codon adjacent to the native "TGA" stop codon and a SpeI restriction site in the non-complementary region. Both primers contained addition nucleotides to allow for efficient digestion with the NsiI and SpeI restriction enzymes. The PCR reaction used *T. thermophilus* genomic DNA as a template and yielded a PCR product of 2410 bp in length. This PCR fragment digested with NsiI and SpeI was inserted into pA1-NB-AgeI digested with PstI and SpeI and resulted in the plasmid pA1-NB-TuvrD which contained the entire gene encoding the *T. thermophilus* UvrD helicase.

PA1-NB-TuvrD was transformed into DH5α bacteria and positive isolates were screened for by plasmid digestion with NdiI and SpeI restriction digest yielding 5.5 and 2.5 kb fragments. The plasmids from one positive isolate was selected and the correct sequence of both strands of the DNA were identified by DNA sequencing across the inserted region (ATG SEQ #1993–2005; primers: P159-S1926, P159-S2326, P159-S2733, P159-S3134, P159-S3540, P159-A3592, P159-A3332, P159-A3154, P159-A2770, P159-A2471, P159-A2060, NB-Sseq, p64-A215). This isolate was stored as a glycerol stock culture (ATG glycerol stock #1161).

Upon comparing this DNA sequence with the crude sequence obtained from the *T. thermophilus* genome database at Goettingen Genomics Laboratory several discrepancies were observed. Therefore, to confirm the sequence of the DNA encoding the uvrD gene obtained by sequencing the inserted region of this isolate a second clone was sequenced in the critical areas (ATG SEQ #2007–2008, primers: P159-A3154 and P159-A2471). The changes observed by sequencing the gene from those reported for the crude DNA sequence were: C>G at position 337 (no amino acid change); C>T at position 466 (no amino acid change); G deletion at position 731 (frameshift); G insertion at position 776 (frameshift); T>C at postion 1474 (no amino acid change); T>C at position 1475 (Ser>Pro amino acid change); G>C at position 1481 (Pro>Ala amino acid change).

The DNA coding sequence of the *T. thermophilus* uvrD gene is shown (FIG. 54, SEQ ID NO:67). The start codon (gtg) and the stop codon (tga) are in bold print. Also shown is the protein (amino acid) sequence (FIG. 55, SEQ ID NO:68) derived from the DNA coding sequence.

Verification of Expression of *T. thermophilus* UvrD Fused to an N-terminal Peptide that Contains Hexahistidine and a Biotinylation Site The pA1-NB-TuvrD plasmid was prepared and transformed into MGC1030 and AP1.L1 bacteria. Three isolates from each tranformation were selected for farther study. The bacterial growths and isolation of total cellular protein were as described in Example 2. A small aliquot of supernatant (3

μl) containing total cellular protein from each of the three isolates was loaded onto a 4–20% SDS-polyacrylamide mini-gel (Novex, EC60255; 1 mm thick, with 15 wells/gel) in 25 mM in Tris base, 192 mM glycine, and 0.1% SDS. The mini-gel was stained with Coomassie Blue. There were no protein bands from any of the isolates corresponding to the predicted migration region of uvrD (approximately 80 kDa).

Next, the total protein in each lysate was transferred (blotted) from polyacrylamide gel to nitrocellulose as described in Example 2. Each lane contained 1.5 ul of the supernatant. Protein bands on the blotted nitrocellulose were visualized by interactions with phosphatase-conjugated streptavidin as described above. The endogenous *E. coli* biotin-CCP protein, ~20 kDa was detectable in both induced and non-induced samples. A protein band corresponding to the *T. thermophilus* UvrD protein migrated just below the 80 kDa molecular weight standard of the Gibco 10 kDa protein ladder. This protein was observed as a faint band in the induced cultures, but was not observed in the uninduced control lysates. The glycerol stocks of pA1-NB-TuvrD in MGC1030 and AP1.L1 (ATG glycerol stock #1177 and 1178, respectively) were stored at −80° C.

Example 12

*T. thermophilus* DnaG—Primase
Identification and Cloning *T. thermophilus* dnaG Gene The DnaG protein sequence from *E. coli* was used to search the *T. thermophilus* genome database at Goettingen Genomics Laboratory. The region of the *T. thermophilus* genome (Feb. 2, 2000 contig working.0.24624, region 42961–48060) containing a putative *T. thermophilus* dnaG gene was identified (using BLAST) and obtained (from Dr. Carsten Jacobi, Goettingen Genomics Laboratory, Institute of Microbiology and Genetics, Grisebachstrasse 8, Goettingen, Germany). Using the crude sequence, two PCR primers were designed to amplify the dnaG gene. The forward/sense primer (ATG primer P161-S1922, 5'-GACTCTGCAG GACGCGGGCCAGGCGGTGGAGCTGA-3') (SEQ ID NO:69) is designed so that the non-complementary portion contains a "GACT" clamp region and a PstI site. The complementary portion of the primer is complementary to the first 25 nt of the dnaG gene beginning at codon 2, so that the first codon (the "ATG" start codon) is excluded. This will allow the PCR product to be inserted into the vector pA1-NB-Avr2(BamH1−) at the PstI site therefore fusing the gene inframe with the N-terminal tagged peptide. The reverse/antisense primer (ATG primer P161-A3714, 5'-GACTACTAGTCTA CTAGGTGGACCAGCCCGAAGGA-3') (SEQ ID NO:70) contains a "GACT" clamp region and a SpeI restriction site in the non-complementary region. The non-complementary region also contains an additional "TAG" (CTA) stop codon that will be adjacent to the native "TAG" stop codon, giving two stop codons in tandem.

The sequence for the *T. thermophilus* dnaG gene is (FIG. 56, SEQ ID NO:71). The start (atg) and the stop (tga) are shown as bold. Also shown is the protein (amino acid) sequence derived from the DNA coding sequence (FIG. 57, SEQ ID NO:72).

The PCR reaction used *T. thermophilus* genomic DNA as a template and yielded a PCR product of 2148 bp in length. This PCR fragment digested with PstI and SpeI was inserted into pA1-NB-Avr2(BamH1−) digested with PstI and SpeI and resulted in the plasmid pA1-NB-TdnaG which contained the entire gene encoding the *T. thermophilus* DnaG primase. PA1-NB-TdnaG was transformed into DH5α bacteria and positive isolates were screened for by plasmid digestion with PstI and SpeI restriction digest yielding 5.6 and 2.15 kb fragments. The plasmids from one positive isolate was selected and the correct sequence of both strands of the DNA were identified by DNA sequencing across the inserted region (ATG SEQ #2022–2031; primers: P161-S2260, P161-S2650, P161-S3056, P161-S3349, P161-A3375, P161-A3048, P161-A2694, P161-A2389, NB-Sseq, p64-A215). The DNA sequence determined here was compared to the crude sequence from Goettingen Genomics Laboratory and no changes were observed. This isolate was stored as a glycerol stock culture (ATG glycerol stock #1173).

Verification of Expression of *T. thermophilus* DnaG Fused to an N-Terminal Peptide that contains Hexahistidine and a Biotinylation Site The pA1-NB-TdnaG plasmid was prepared and transformed into MGC1030 and AP1.L1 bacteria. Three isolates from each tranformation were selected for farther study. The bacterial growths and isolation of total cellular protein were as described Example 2. A small aliquot of supernatant (3 μl) containing total cellular protein from each of the three isolates was loaded onto a 4–20% SDS-polyacrylamide mini-gel (Novex, EC60255; 1 mm thick, with 15 wells/gel) in 25 mM in Tris base, 192 mM glycine, and 0.1% SDS. The mini-gel was stained with Coomassie Blue. Distinct protein bands from all of the isolates corresponding to the predicted migration region of DnaG (approximately 80 kDa) were visualized.

Next, the total protein in each lysate was transferred (blotted) from polyacrylamide gel to nitrocellulose as described in Example 2. Each lane contained 1.5 ul of the supernatant. Proteins on the blotted nitrocellulose were visualized by interactions with phosphatase-conjugated streptavidin. The endogenous *E. coli* biotin-CCP protein, ~20 kDa was detectable in both induced and non-induced samples. A protein band corresponding to the *T. thermophilus* DnaG protein migrated midway between the 70 and 80 kDa molecular weight standard of the Gibco 10 kDa protein ladder. This protein was observed as a very intense band in the induced cultures, but was not observed in the uninduced control lysates. The glycerol stocks of pA1-NB-TdnaG in MGC1030 and AP1.L1 (ATG glycerol stock #1182 and 1183, respectively) were stored at −80° C.

Example 13

*T. thermophilus* PriA—Helicase
Identification and Cloning *T. thermophilus* priA Gene The PriA protein sequence from *E. coli* was used to search the *T. thermophilus* genome database at Goettingen Genomics Laboratory. The region of the *T. thermophilus* genome (Feb. 4, 2000 contig working.0.2196, region 36541–42840) containing a putative *T. thermophilus* priA gene was identified (using BLAST) and obtained (from Dr. Carsten Jacobi, Goettingen Genomics Laboratory, Institute of Microbiology and Genetics, Grisebachstrasse 8, Goettingen, Germany). Unsure of the crude sequence and proper placement of the start and stop codons we decided to sequence the region beginning approximately 200 bp upstream of the putative start codon to approximately 200 bp downstream of the putative stop codon. Using the crude sequence, two PCR primers were designed to amplify the priA gene. The forward/sense primer (ATG primer P162-S963, 5'-CCGAAGAGCCTCTCCAGGAGGGGGAGGAGGGGAA CCA-3') (SEQ ID NO:73) and the reverse/antisense primer (ATG primer P162-A3625, 5'-GGGGCAGCCGCAAGGGGTAAGGGTAGAAAA-3')

(SEQ ID NO:74) using *T. thermophilus* genomic DNA as a substrate yielded a 2676 bp DNA fragment. This DNA fragment was inserted into the T/A cloning site of pGEM-TEasy plasmid per manufacturer instructions creating pT-TpriA. This plasmid was transformed into DH5α bacteria and positive isolates were screened for by plasmid digestion with EcoRI restriction digest yielding 2.7 and 3.0 kb fragments and digestion with HinDIII yielding 0.6 and 5.1 kb fragments. The plasmids from one positive isolate was selected and the sequence of both strands of the DNA were identified by DNA sequencing across the inserted region (ATG SEQ #1969–1982, 2009–2017, and 2042–2043; primers: SP6, T7-Seq2, P162-S1292, P162-S1656, P162-S2026, P162-S2408, P162-S2781, P162-S3173, P162-A3257, P162-A2825, P162-A2446, P162-A2038, P162-A1709, P162-A1243, P162-S963, P162-A1335, P162-S1146). The sequence obtained here was compared to the crude sequence from Goettingen Genomics Laboratory and no descrepancies were discerned. This isolate was stored as a glycerol stock culture (ATG glycerol stock #1155).

The sequence for the *T. thermophilus* priA gene is shown (FIG. 58, SEQ ID NO:75). The start (gtg) and the stop (tag) are shown as bold. Also shown is the protein (amino acid) sequence (FIG. 59, SEQ ID NO:76) derived from the DNA coding sequence.

To insert the *T. thermophilus* gene into the expression vector pA1-NB-AgeI to be expressed as an N-terminal tagged protein a 5' PstI restriction site and a 3' SpeI restriction site was needed. This was accomplished by PCR amplifying the *T. thermophilus* gene using the forward/sense primer (ATG primer P162-S1052, 5'-GACTCTGCAG CGGGTGCTTCAGGTGGCCCTTC-3') (SEQ ID NO:77) designed so that the non-complementary portion contains a "GACT" clamp region and a PstI restriction site. The complementary portion of the primer is complementary to the first 22 nt of the priA gene beginning at codon 2, so that the first codon (the start codon in this case is "GTG") is excluded. The reverse/antisense primer (ATG primer P162-A3180, 5'-CAGTACTAGT CTAGTCCTCCAAAAGCCCCACGA-3') (SEQ ID NO:78) contains a "CAGT" clamp region and a SpeI restriction site in the non-complementary region. This PCR primer can not contain an additional stop codon or it will create an additional SpeI site that will be adjacent to the native "TAG" (cta). The PCR reaction used pT-TpriA as a template and yielded a PCR product of 2130 bp in length. This PCR fragment was digested with PstI and SpeI was inserted into pA1-NB-AgeI digested with PstI and SpeI and resulted in the plasmid pA1-NB-TpriA which contained the entire gene encoding the *T. thermophilus* PriA helicase. pA1-NB-TpriA was transformed into DH5α bacteria and positive isolates were screened for by plasmid digestion with PstI and SpeI restriction digest yielding 5.6 and 2.13 kb fragments. The plasmids from one positive isolate was selected and the correct sequence of both strands of the DNA were identified by DNA sequencing across the inserted region (ATG SEQ #2057–2070; primers: P162-S1146, P162-S1292, P162-S1656, P162-S2026, P162-S2408, P162-S2781, P162-A2825, P162-A2446, P162-A2038, P162-A1709, P162-A1335, P162-A1243, NB-Sseq, p64-A215). This isolate was stored as a glycerol stock culture (ATG glycerol stock #1192).

Verification of Expression of *T. thermophilus* PriA Fused to an N-Terminal Peptide that Contains Hexahistidine and a Biotinylation Site The pA1-NB-TpriA plasmid was prepared and transformed into MGC1030 and AP1.L1 bacteria. Three isolates from each tranformation were selected for farther study. The bacterial growths and isolation of total cellular protein were as described in Example 2. A small aliquot of supernatant (3 µl) containing total cellular protein from each of the three isolates was loaded onto a 4–20% SDS-polyacrylamide mini-gel (Novex, EC60255; 1 mm thick, with 15 wells/gel) in 25 mM in Tris base, 192 mM glycine, and 0.1% SDS. The mini-gel was stained with Coomassie Blue. Distinct protein bands from all of the isolates corresponding to the predicted migration region of PriA (approximately 81.5 kDa) were visualized.

Next, the total protein in each lysate was transferred (blotted) from polyacrylamide gel to nitrocellulose as described in Example 2. Each lane contained 1.5 ul of the supernatant. The endogenous *E. coli* biotin-CCP protein, ~20 kDa was detectable in both induced and non-induced samples. A protein band corresponding to the *T. thermophilus* PriA protein migrated midway between the 80 and 90 kDa molecular weight standard of the Gibco 10 kDa protein ladder. This protein was observed as a very intense band in the induced cultures, but was not observed in the uninduced control lysates. The glycerol stocks of pA1-NB-TpriA in MGC1030 and AP1.L1 (ATG glycerol stock #1196 and 1197, respectively) were stored at −80° C.

Example 14

Cloning *T. thermophilus* dnaQ-2

The ORF encoding *T. thermophilus* dnaQ-2 gene contained two possible start sites that were out of frame with each other. Therefore to determine the correct start codon and to confirm the sequenc the gene encoding the *T. thermophilus* dnaQ-2 gene from *T. thermophilus*, genomic DNA was amplified by PCR using two primers located approximately 200 bp upstream and downstream of the start and stop codon. Using a forward/sense primer (ATG primer #P133-S150, 5'-TGGGGGCGAACCTCACG-3') (SEQ ID NO: 79) and a reverse/antisense primer (ATG primer #P133-A1237, 5'-ACCCCGGCCTTCCAGTCCA-3')(SEQ ID NO: 80) and *T. thermophilus* genomic DNA as a substrate resulted in a 1088 bp PCR product. This PCR fragment was inserted into a pGEM-T Easy plasmid and transformed into DH5α and isolates were selected for by ampicillin-resistance. Plasmids were purified from one isolate and screened by EcoRI digestion of plasmids yielding the expected 1.1 and 3.0 kb fragments. Both DNA strands of the inserted region were sequenced (ATG SEQ #1330–1335; primers, SP6, T7, P133-S456, P133-S894, P133-A896, P133-A527). There was a one base pair descreptancy with the DNA sequence when compared with the crude sequence. There were four "T"s shown in the crude sequence beginning 61 bases downstream of the first GTG start codon. The DNA sequencing by ATG, Inc. indicated and confirmed only three "T"s. This indicated that both possible GTG start codons were in frame and that the first GTG was likely the native start codon. This plasmid was named pT-TQ2 and the isolate was stored as a stock culture (ATG glycerol stock #785).

The DNA coding sequence of the *T. thermophilus* dnaQ-1 gene (SEQ ID:NO:81) is shown in FIG. 60. The two possible start codons (gtg) and the stop codon (tga) are in bold print. Also shown in FIG. 61 is the protein (amino acid) sequence (SEQ ID NO:82) derived from the DNA coding sequence. Construction of a Plasmid (pA1-TQ2) that Expresses *T. thermophilus* dnaQ-2 Gene Expression of *T. thermophilus* dnaQ-2 gene product (ε2-subunit) as a native protein was accomplished. The construction of pA1-TQ2 was performed by insertion of the native *T. thermophilus* dnaQ-2 gene into the pA1-CB-NcoI plasmid. The *T. thermophilus* dnaQ-2 gene was amplified out of *T. thermophilus* genomic DNA using PCR. The forward/sense primer (ATG primer #P133-S442nco; 5-GGATCCA TGGAGCGGGTGGTGCGGCCCCTTCTG-3) (SEQ ID NO:83) used in the PCR reaction was designed to have an upstream NcoI site that overlaps the TGG of the ATG start codon used for the dnaQ-2 gene. The native start codon for the dnaQ-2 gene is GTG, this has been replace in the primer with an ATG start codon to allow for expression in *E. coli*. The reverse/antisense primer (ATG primer #P133-A109kpn; 5-AAGCTAGGTACCTA CTACCTCCCGAGTTCCCAAAG-3) (SEQ ID NO:84) was designed to have an additional stop codon placed in tandem with the native stop codon. This additional stop codon was adjacent to a KpnI restriction site in the non-complementary region of the primer. The PCR product was digested with NcoI and KpnI restriction enzymes. The digested PCR product was inserted into the NcoI/KpnI digested pA1-CB-NcoI plasmid. These plasmids were transformed into DH5α bacteria and positive isolates were selected by ampicillin-resistance. Plasmids were purified from one clone and screened by NcoI/KpnI digest of purified plasmids yielding 0.65 and 5.7 kb fragments. The inserted region in this plasmid was subjected to DNA sequencing to confirm the correct sequence (ATG SEQ #1384–1387, 1404–1405; primers, P38-S5576, P65-A106, P133-S635, and P133-A817). This plasmid was named pA1-TQ2 and the isolate was stored as a stock culture (ATG glycerol stock #815).

Verification of Expression of Plasmid (pA1-TQ2) that Overexpresses *T. thermophilus* dnaQ-2 Gene ($\epsilon$2-Subunit) as a Native Protein from pA1-TQ2/MGC1030 and pA1-TQ2/AP1.L1

The pA1-TQ2 plasmid was prepared and transformed into MGC1030 and AP1.L1 bacteria. Three isolates were selected from pA1-TQ2/MGC1030 (ATG glycerol stock #828, 829, 830) and from pA1-TQ2/AP1.L1 (ATG glycerol stock #847, 848, 849) for further study. The bacterial growths and isolation of total cellular protein were as described in Example 2. A small aliquot (3 μl) of supernatant containing total cellular protein from each of the six isolates, was loaded onto a 4–20% SDS-polyacrylamide mini-gel (Novex, EC60255; 1 mm thick, with 15 wells/gel) in 25 mM in Tris base, 192 mM glycine, and 0.1% SDS. The mini-gel was stained with Coomassie Blue. There were no protein bands that could be resolved from surrounding endogenous *E. coli* from any of the isolates corresponding to the predicted migration region of the $\epsilon$2-subunit.

Construction of a Plasmid (pA1-CB-TQ2) that Overexpress *T. thermophilus* dnaQ-2 ($\epsilon$2-subunit) Fused to a C-Terminal Peptide that Contains Hexahistidine and a Biotinylation Site Since initial attempts to express the native $\epsilon$-subunit failed, a vector was designed to couple the *T. thermophilus* dnaQ-2 gene to a fusion peptide containing a hexahistidine and a biotinylation site. The construction of pA1-CB-TQ2 was also performed by insertion of the *T. thermophilus* dnaQ-2 gene into the pA1-CB-NcoI plasmid. The forward/sense primer was the same used in construction of pA1-TQ2 (ATG primer #P133-S442nco). The *T. thermophilus* genomic DNA was used as the PCR template. The reverse/antisense primer (ATG primer #P133-A1084Spe; 5-CCTCACTAGTCCTCCCGAGTTCCCAAAGCGT-3) (SEQ ID NO:85) was designed so that a SpeI restriction site was adjacent to the penultimate codon (the stop codon was excluded). The SpeI site allowed for the expressed protein to contain two additional amino acids (Thr and Ser) between the C-terminal amino acid of the $\epsilon$2-subunit and the C-terminal fusion peptide. The PCR product was digested with NcoI and SpeI restriction enzymes and inserted into the NcoI/SpeI digested pA1-CB-NcoI plasmid. The plasmid was then transformed into DH5α bacteria and plasmids from positive isolates were selected by ampicillin-resistance. Plasmids were isolated from one positive isolate and screened by digestion with NcoI and SpeI restriction enzymes yielding 0.65 and 5.7 kb fragments. The correct sequence of the inserted region was confirmed by DNA sequencing (ATG SEQ #1388–1391, 1406–1407; primers, P38-S5576, P65-A106, P133-S635 and P133-A817). This plasmid was named pA1-CB-TQ2 and the isolate was stored as a stock culture (ATG glycerol stock #816).

Verification of Expression of Plasmid (pA1-CB-TQ) that Overexpresses *T. thermophilus* dnaQ-2 Gene($\epsilon$2-Subunit) Fused to a C-Terminal Peptide that Contains Hexahistidine and a Biotinylation Site from pA1-CB-TQ/MGC1030

The pA1-CB-TQ2 plasmid was prepared and transformed into MGC1030 and AP1.L1 bacteria. Three isolate was selected from pA1-CB-TQ2/MGC1030 (ATG glycerol stock #831, 832, 833) and from pA1-CB-TQ2/AP1.L1 (ATG glycerol stock #850,851, 852) for further study. The bacterial growths and isolation of total cellular protein were as described in Example 2. A small aliquot (3 μl) of supernatant containing total cellular protein from each of the six isolates was electrophoresed onto a 4–20% SDS-polyacrylamide mini-gel (Novex, EC60255; 1 mm thick, with 15 wells/gel) in 25 mM in Tris base, 192 mM glycine, and 0.1% SDS. The mini-gel was stained with Coomassie Blue. There were no protein bands from any of the isolates that could be resolved from endogenous *E. coli* proteins in the region corresponding to the predicted migration region of the $\epsilon$2-subunit.

Next, the total protein from the lysate was transferred (blotted) from polyacrylamide gel to nitrocellulose as described in Example 2. Proteins on the blotted nitrocellulose were visualized by interactions with phosphatase-conjugated streptavidin. The endogenous *E. coli* biotin-CCP protein, ~20 kDa was detectable in both induced and non-induced samples. A protein band corresponding to the $\epsilon$2-subunit could not be detected. The protein was expressed at levels too low to justify purification attempts.

Having now fully described the present invention in some detail by way of illustration and example for purposes of clarity of understanding, it will be obvious to one of ordinary skill in the art that same can be performed by modifying or changing the invention with a wide and equivalent range of conditions, formulations and other parameters thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. An isolated polypeptide wherein said polypeptide comprises an amino acid sequence having at least 95% sequence identity to the amino acid sequence of SEQ ID NO: 10 (delta subunit), wherein said polypeptide functions as a DNA polymerase III δ subunit by stimulating processive DNA replication.

2. The polypeptide of claim 1 wherein said polypeptide has the amino acid sequence of SEQ ID NO: 10.

3. The isolated polypeptide of claim 1 wherein said polypeptide is a DNA Polymerase delta subunit from *Thermus thermophilus*.

* * * * *